(12) United States Patent
Corti

(10) Patent No.: US 12,304,946 B2
(45) Date of Patent: May 20, 2025

(54) ANTIBODIES THAT NEUTRALIZE HEPATITIS B VIRUS AND USES THEREOF

(71) Applicant: HUMABS BIOMED SA, Bellinzona (CH)

(72) Inventor: Davide Corti, Bellinzona (CH)

(73) Assignee: Humabs BioMed SA, Bellinzona (CH)

( * ) Notice: Subject to any disclaimer, the term of this patent is extended or adjusted under 35 U.S.C. 154(b) by 918 days.

(21) Appl. No.: 17/413,696

(22) PCT Filed: Dec. 18, 2019

(86) PCT No.: PCT/US2019/067216
§ 371 (c)(1),
(2) Date: Jun. 14, 2021

(87) PCT Pub. No.: WO2020/132091
PCT Pub. Date: Jun. 25, 2020

(65) Prior Publication Data
US 2022/0127336 A1    Apr. 28, 2022

Related U.S. Application Data

(60) Provisional application No. 62/860,085, filed on Jun. 11, 2019, provisional application No. 62/782,274, filed on Dec. 19, 2018.

(51) Int. Cl.
| | |
|---|---|
| *C07K 16/08* | (2006.01) |
| *A61K 31/522* | (2006.01) |
| *A61K 39/42* | (2006.01) |
| *C07K 16/10* | (2006.01) |
| *G01N 33/569* | (2006.01) |

(52) U.S. Cl.
CPC .......... *C07K 16/082* (2013.01); *A61K 31/522* (2013.01); *A61K 39/42* (2013.01); *C07K 16/10* (2013.01); *G01N 33/56983* (2013.01); *C07K 2317/732* (2013.01); *C07K 2317/76* (2013.01); *G01N 2333/02* (2013.01); *G01N 2800/26* (2013.01)

(58) Field of Classification Search
None
See application file for complete search history.

(56) References Cited

U.S. PATENT DOCUMENTS

| | | | |
|---|---|---|---|
| 8,802,820 | B2 | 8/2014 | Chamberlain et al. |
| 9,683,029 | B2 | 6/2017 | Kim et al. |
| 10,683,344 | B2 | 6/2020 | Corti |
| 11,390,664 | B2 | 7/2022 | Corti |
| 2015/0166637 | A1 | 6/2015 | Kim et al. |
| 2015/0297745 | A1 | 10/2015 | Cobbold et al. |
| 2015/0299289 | A1 | 10/2015 | Urban et al. |
| 2018/0244756 | A1 | 8/2018 | Graham et al. |
| 2021/0179693 | A1 | 6/2021 | Lazar |
| 2022/0380441 | A1 | 12/2022 | Pang et al. |

FOREIGN PATENT DOCUMENTS

| | | | | |
|---|---|---|---|---|
| WO | WO 9739029 A2 | 10/1997 | | |
| WO | WO 9740164 A1 | 10/1997 | | |
| WO | WO 9829442 A1 | 7/1998 | | |
| WO | WO-0005266 A1 * | 2/2000 | ............. | A61P 31/12 |
| WO | WO 2006076640 A1 | 7/2006 | | |
| WO | WO 2008143954 A2 | 11/2008 | | |
| WO | WO 2009069917 A1 | 6/2009 | | |
| WO | WO 2010132659 A2 | 11/2010 | | |
| WO | WO 2014032176 A1 | 3/2014 | | |
| WO | WO 2015107126 A1 | 7/2015 | | |
| WO | WO 2015112800 A1 | 7/2015 | | |
| WO | WO 2017059878 A1 | 4/2017 | | |
| WO | WO-2017060504 A1 * | 4/2017 | ............. | A61K 39/42 |
| WO | WO 2017106346 A2 | 6/2017 | | |
| WO | WO 2018207023 A2 | 11/2018 | | |
| WO | WO 2019125846 A1 | 6/2019 | | |
| WO | WO 2020132091 A2 | 6/2020 | | |
| WO | WO 2020132346 A1 | 6/2020 | | |

OTHER PUBLICATIONS

Mostafa. J Chromatogr B. 2016. 1032:211-217 (Year: 2016).*
J Pharma Biotech Sci. 2013. 102(6): 1701-1711 (Year: 2013).*
Merriam-Webster. Prevent. Retrieved online on Aug. 14, 2024 from <URL: https://www.merriam-webster.com/dictionary/prevent> (Year: 2024).*
Merriam-Webster. Infect. Retrieved online on Aug. 14, 2024 from <URL: https://www.merriam-webster.com/dictionary/infect> (Year: 2024).*
"EASL 2017 Clinical Practice Guidelines on the management of hepatitis B virus infection," *Journal of Hepatology* 67:370-398, 2017.
Abou-Jaoudé et al., "Entry of Hepatitis Delta Virus Requires the Conserved Cysteine Residues of the Hepatitis B Virus Envelope Protein Antigenic Loop and Is Blocked by Inhibitors of Thiol-Disulfide Exchange," *Journal of Virology* 81(23):13057-13066, Dec. 2007.
Ahmed et al., "Structural Characterization of GASDALIE Fc Bound to the Activiating Fc receptor FcyRIIIa," *J. Struct. Biol.* 194(1):78-89, Apr. 2016.

(Continued)

*Primary Examiner* — Zachary S Skelding
*Assistant Examiner* — Brianna K Swartwout
(74) *Attorney, Agent, or Firm* — Fox Rothschild LLP

(57) ABSTRACT

The present disclosure relates to antibodies, and antigen binding fragments thereof, that can bind to the antigenic loop region of hepatitis B surface antigen (HBsAg) and can neutralize infection of both hepatitis B virus (HBV) and hepatitis delta virus (HDV). The present disclosure also relates to epitopes to which the antibodies and antigen binding fragments bind, as well as to fusion proteins that comprise the antigen binding fragments, and to nucleic acids that encode and cells that produce such antibodies and antibody fragments. In addition, the present disclosure relates to the use of the antibodies and antibody fragments of the present disclosure in the diagnosis, prophylaxis and treatment of hepatitis B and hepatitis D.

28 Claims, 57 Drawing Sheets
Specification includes a Sequence Listing.

(56) References Cited

OTHER PUBLICATIONS

Armour et al., "Recombinant human IgG molecules lacking Fcγ receptor I binding and monocyte triggering activities," *Eur. J. Immunol.* 29:2613-2624, 1999.

Banks et al., "Removal of Cysteinylation from an Upaired Sulfhydryl in the Variable Region of a Recombinant Monoclonal IgG1 Antibody Improves Homogeneity, Stability, and Biological Activity," *Journal of Pharmaceutical Sciences* 97(2):P775-790, Feb. 1, 2008. (abstract only).

Block et al., "Chronic hepatitis B: What should be the goal for new therapies?" *Antiviral Res.* 98(1):27-34, Apr. 2013.

Brüggemann et al., "A repertoire of monoclonal antibodies with human heavy chains from transgenic mice," *PNAS* 86:6709-6713, Sep. 1989.

Bruhns et al., "Specificity and affinity of human Fcγ receptors and their polymorphic variants for human IgG sunglasses," *Blood* 113(16):3716-3725, Apr. 16, 2009.

Bruns et al., "Enhancement of Hepatitis B Virus Infection by Noninfectious Subviral Particles," *J. of Virology* 72(2):1462-1468, Feb. 1998.

Cerino et al., "A Human Monoclonal Antibody against Hepatitis B Surface Antigen with Potent Neutralizing Activity," *PLOS One* 10(4), Apr. 29, 2015. (10 pages).

Chu et al., "Inhibition of B cell receptor-mediated activation of primary human B cells by coengagement of CD19 and FcγRIIb with Fc-engineered antibodies," *Molecular Immunology* 45:3926-3933, 2008.

ClinicalTrials.gov, "Study of VIR-2218 in Healthy Volunteers and Patients With Chronic Hepatitis B," U.S. National Library of Medicine, first posted Sep. 14, 2018, retrieved Apr. 8, 2020, 4 pages.

DiLillo et al., "Differential Fc-Receptor Engagement Drives an Anti-tumor Vaccinal Effect," *Cell* 161(5):1035-1045, May 21, 2015.

Dunbar et al., "ANARCI: antigen receptor numbering and receptor classification," *Bioinformatics* 32(2):298-300, Sep. 30, 2015.

Eren et al., "Preclinical Evaluation of Two Human Anti-Hepatitis B Virus (HBV) Monoclonal Antibodies in the HBV-Trimera Mouse Model and in HBV Chronic Carrier Chimpanzees," *Hepatology* 32(3):588-596, 2000.

Furman et al., "Early Engineering Approaches to Improve Peptide Developability and Manufacturing," *The AAPS Journal* 17(1):111-120, Jan. 2015.

Galun et al., "Clinical Evaluation (Phase I) of a Combination of Two Human Monoclonal Antibodies to HBV: Safety and Antiviral Properties," *Hepatology* 35(3):673-679, Mar. 2002.

Gao et al., "Antibody-mediated immunotherapy against chronic hepatitis B virus infection," *Human Vaccines & Immunotherapeutics* 13(8):1768-1773, 2017.

Hinton et al., "An Engineered Human IgG1 Antibody with Longer Serum Half-Life," *Journal of Immunology* 176:346-356, 2006.

Ho et al., "Generation of monoclonal antibody-producing mammalian cell lines," *Pharm. Bioprocess.* 1(1):71-87, 2013.

International Search Report and Written Opinion, mailed Feb. 1, 2021, for International Application No. PCT/US2019/067216, 27 pages.

International Search Report and Written Opinion, mailed Feb. 8, 2017, for International Application No. PCT/EP2016/074114, 17 pages.

International Search Report and Written Opinion, mailed Jan. 25, 2021, for International Application No. PCT/US2020/048649, 12 pages.

Jaoudé et al., "Role of the Antigenic Loop of the Hepatitis B Virus Envelope Proteins in Infectivity of Hepatitis Delta Virus," *Journal of Virology* 79(16):10460-10466, Aug. 2005.

Krebs et al., "T Cells Expressing a Chimeric Antigen Receptor That Binds Hepatitis B Virus Envelope Proteins Control Virus Replication in Mice," *Gastroenterology* 145:456-465, 2013.

Kuo et al., "Neonatal Fc receptor and IgG-based therapeutics," *mAbs* 3(5):422-430, Sep./Oct. 2011.

Li et al., "A potent human neutralizing antibody Fc-dependently reduces established HBV infections," *eLife* 6(e26738):1-30, Sep. 26, 2017.

Martin et al., "Selection of Ig μ Heavy Chains by Complementarity-Determining Region 3 Length and Amino Acid Composition," *Journal of Immunology* 171:4663-4671, 2003.

Miliotou et al., "CAR T-cell Therapy: A New Era in Cancer Immunotherapy," *Current Pharmaceutical Biotechnology* 19:5-18, 2018.

Mimoto et al., Engineered antibody Fc variant with selectively enhanced FcγRIIb binding over both FcγRIIaR131 and FcγRIIaH131, *Prot. Eng. Des. Sel.* 26(10):589-598, Jun. 5, 2013.

Moore et al., "Accelerated Clearance of IgE In Chimpanzees Is Mediated By Xmab7195, An Fc-Engineered Antibody With Enhanced Affinity For Inhibitory Receptor Fcγriib," *Am. J. Respir. Crit. Care Med.* 189:A4261, 2014.

Nassal, "HBV cccDNA: viral persistence reservoir and key obstacle for a cure of chronic hepatitis B," *Gut* 64:1972-1984, 2015.

Neumann et al., "Novel Mechanism of Antibodies to Hepatitis B Virus in Blocking Viral Particle Release from Cells," *Heptatology* 52:875-885, 2010.

Plath et al., "Characterization of mAb dimers reveals predominant dimer forms common in therapeutic mAbs," *MABS* 8(5):928-940, 2016.

Qiu et al., "Identification and Characterization of a C(K/R)TC Motif as a Common Epitope Present in All Subtypes of Hepatitis B Surface Antigen," *The Journal of Immunology* 156(9):3350-3356, 1996.

Salisse et al., "A Function Essential to Viral Entry Underlies the Hepatitis B Virus "a" Determinant," *Journal of Virology* 83(18):9321-9328, Sep. 2009.

Shields et al., "High Resolution Mapping of the Binding Site of Human IgG1 for FcγRI, FcγRII, FcγRIII, and FcRn and Design of IgG1 Variants with Improved Binding to the FcγR," *J. Biol. Chem.* 276(9):6591-6604, Mar. 2, 2001.

Shirazi et al., "Monoclonal antibodies to various epitopes of hepatitis B surface antigen inhibit hepatitis B virus infection," *Journal of Gastroenterology and Hepatology* 29(5):1083-1091, 2014.

Sureau et al., "Production of Infectious Hepatitis Delta Virus In Vitro and Neutralization with Antibodies Directed against Hepatitis B Virus Pre-S Antigens," *Journal of Virology* 66(2):1241-1245, 1992.

Takaki et al., "Molecular Mechanism to Control Post-Transplantation Hepatitis B Recurrence," *Int. J. Mol. Sci.* 16:17494-17513, 2015.

Thorpe et al., "The Preparation and Cytotoxic Properties of Antibody-Toxin Conjugates," *Immunol. Rev.* 62:119-158, 1982.

Traggiai et al., "An efficient method to make human monoclonal antibodies from memory B cells: potent neutralization of SARS coronavirus," *Nature Medicine* 10(8):871-875, 2004.

Volz et al., "Impaired Intrahepatic Hepatitis B Virus Productivity Contributes to Low Viremia in Most HBeAg-Negative Patients," *Gastroenterology* 133:843-852, 2007.

Wang et al., "IgG Fc engineering to modulate antibody effector functions," *Protein Cell* 9(1):63-73, 2018.

Wedemeyer et al., "Update on the Management of HBV-HDV Coinfection," *Current Hepatitis Reports* 11(2):95-101, 2012.

Wines et al., "The IgG Fc Contains Distinct Fc Receptor (FcR) Binding Sites: The Leukocyte Receptors FcγRI and FcγRIIa Bind to a Region in the Fc Distinct from That Recognized by Neonatal FcR and Protein A1," *J. Immunol.* 164:5313-5318, 2000.

Zubkin et al., "Strategy of Vaccination Against HBV-infection in Hemodialysis Patients with 'Isolated' HBcAb," *International Journal of Infectious Diseases* 10:S42-S43, 2006. (abstract only).

Hong et al., "In Vivo neutralization of hepatitis B Virus infection by an anti-preS1 humanized antibody in chimpanzees," *Virology* 318:134-141, Jan. 2004. (8 pages).

Hong et al., "Recent Progress on Neutralizing Antibodies against Hepatitis B Virus and its Implications," *Infectious Disorders—Drug Targets* 19(3):213-223, Sep. 2019. (11 pages).

ClinicalTrials.gov, "A Phase 1 Study of GC1102 (Recombinant Hepatitis B Immunoglobulin) in Chronic Hepatitis B Patients,"

(56) References Cited

OTHER PUBLICATIONS retrieved from URL=https://clinicaltrials.gov/study/NCT02569372, last updated Oct. 16, 2017, downloaded Oct. 31, 2023. (14 pages).

Tsuge et al., "Antiviral effects of anti-HBs immunoglobulin and vaccine on HBs antigen seroclearance for chronic hepatitis B infection," *Journal of Gastroenterology* 51:1073-1080, Mar. 2016. (9 pages).

Zhang et al., "Prolonged suppression of HBV in mice by a novel antibody that targets a unique epitope on hepatitis B surface antigen," *Gut* 0:1-14, 2015. [Published Online Sep. 2015] (16 pages).

Anonymous, "Conservative replacement," Wikipedia, Mar. 11, 2018, pp. 1-3, XP93121795, retrieved online from <URL: https://en.wikipedia.org/w/index.php?title=Conservative_replacement&oldid=829953914>, Jan. 19, 2024.

Warne, "Development of high concentration protein biopharmaceuticals: The use of platform approaches in formulation development," European Journal of Pharmaceutics and Biopharmaceutics, 78(2), p. 208-212, doi: 10.1016/j.ejpb.2011.03.004, Mar. 13, 2011.

"Hepatitis B," World Health Organization, Jul. 18, 2019, retrieved from https://web.archive.org/web/20191205031400/http://www.who.int/news-room/fact-sheets/detail/hepatitis-b, accessed Mar. 4, 2025, (8 pages).

Buchanan et al., "Engineering a therapeutic IgG molecule to address cysteinylation, aggregation and enhance thermal stability and expression," MAbs 5(2):255-262, Feb. 2013, (9 pages).

Fanning et al., "Therapeutic strategies for hepatitis B virus infection: towards a cure," Nat Rev Drug Discov 18, 827-844, Nov. 2019, (18 pages).

Saxena et al., "Advances in Therapeutic Fe Engineering—Modulation of IgG-Associated Effector Functions and Serum Half-life," Front. Immunol. 7:580, Dec. 2016, (11 pages).

Tanaka, "Hepatitis B Virus Treatment: From "Clinical Healing" to "Functional Healing"," Journal of the Japanese Society of Internal Medicine, 2018, vol. 107(1), pp. 32-37, [with English translation, pp. 32-38], (13 pages).

Tsutsumi et al., "Recent advances in hepatitis B research and drug development," Kanzo, 2017, vol. 58(4), pp. 217-227, [with English translation, (15 pages) ], (26 pages).

UniProt [online database], IgG1 human, https://www.uniprot.org/uniprotkb/P0DOX5/entry, sequence from 2018 (last udpated Jul. 18, 2018), retrieved from the Internet Mar. 17, 2025, (6 pages).

UniProt [online database], IGLC2 Human, https://www.uniprot.org/uniprotkb/P0DOY2/entry, sequence from 2017 (last updated Mar. 15, 2017), retrieved from the Internet Mar. 17, 2025, (8 pages).

* cited by examiner

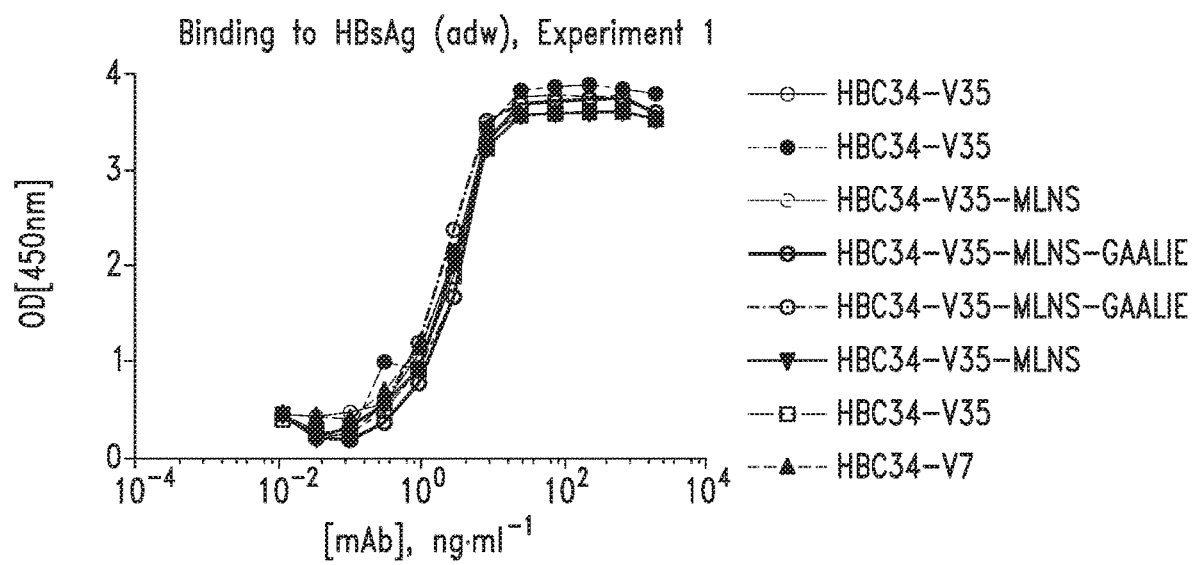
| | EC50 |
|---|---|
| HBC34-V35 | 2.43 |
| HBC34-V35 | 2.799 |
| HBC34-V35-MLNS | 2.565 |
| HBC34-V35-MLNS-GAALIE | 3.186 |
| HBC34-V35-MLNS-GAALIE | 1.982 |
| HBC34-V35-MLNS | 2.309 |
| HBC34-V35 | 2.662 |
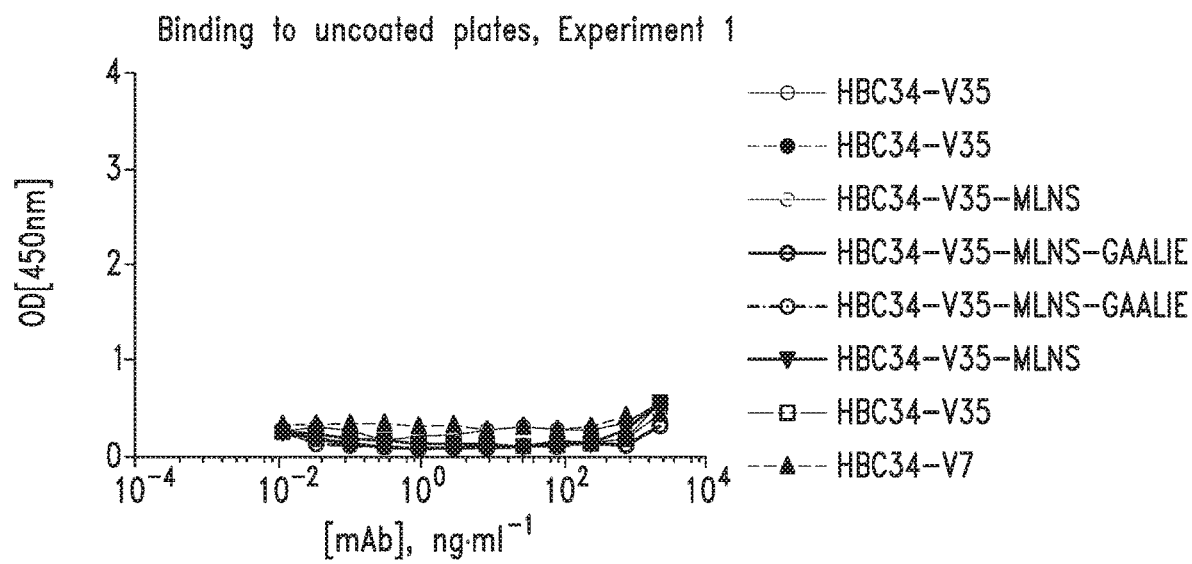
FIG. 3A

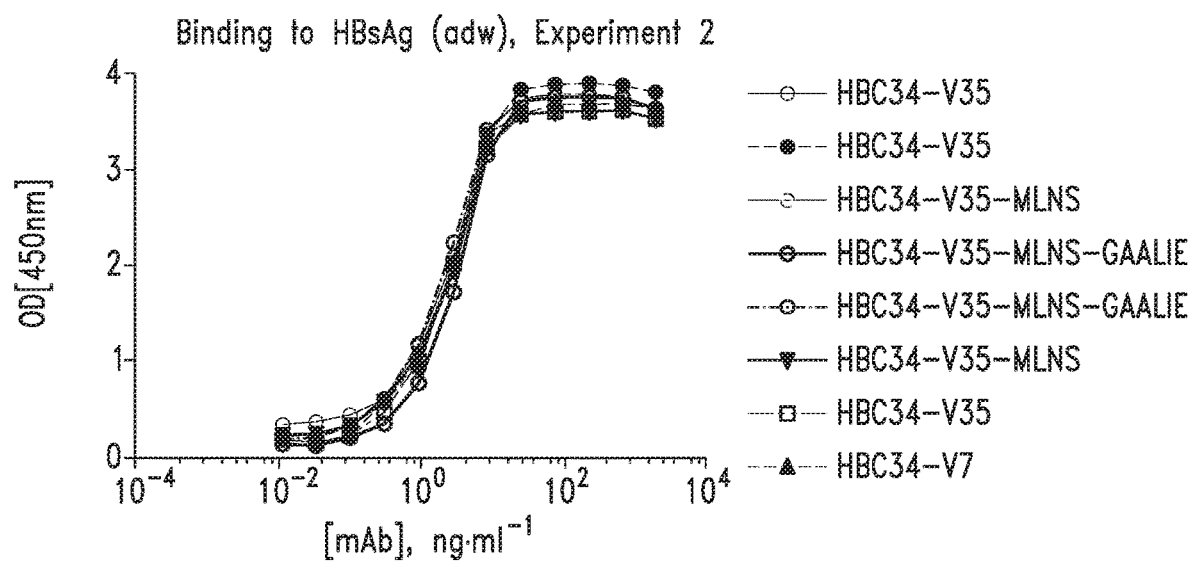
| | EC50 |
|---|---|
| HBC34-V35 | 2.278 |
| HBC34-V35 | 2.651 |
| HBC34-V35-MLNS | 2.484 |
| HBC34-V35-MLNS-GAALIE | 3.018 |
| HBC34-V35-MLNS-GAALIE | 1.958 |
| HBC34-V35-MLNS | 2.174 |
| HBC34-V35 | 2.358 |
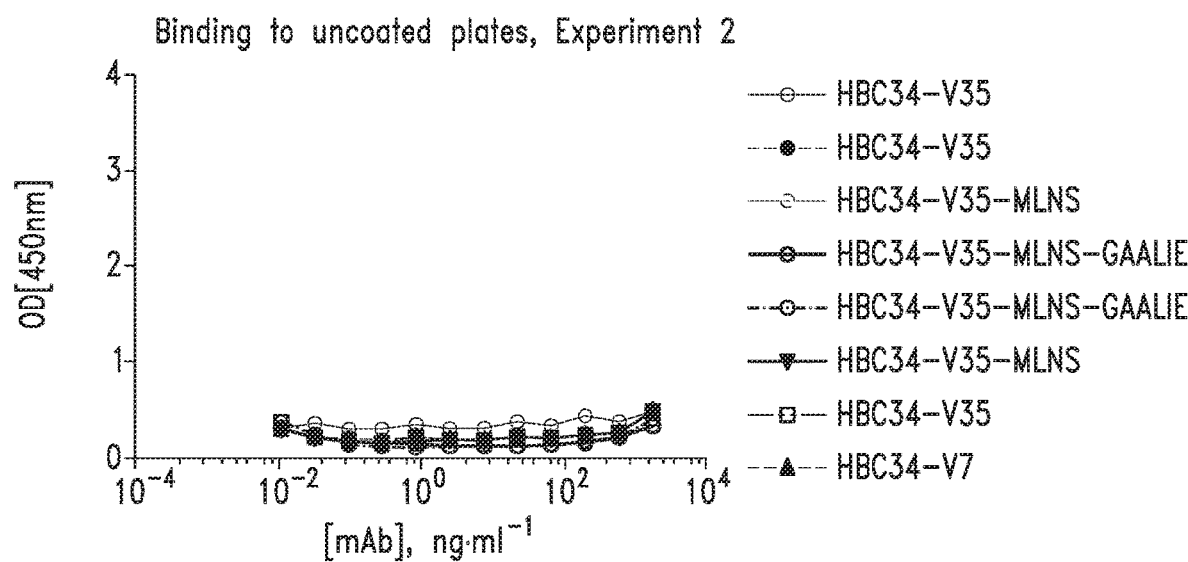
*FIG. 3B*

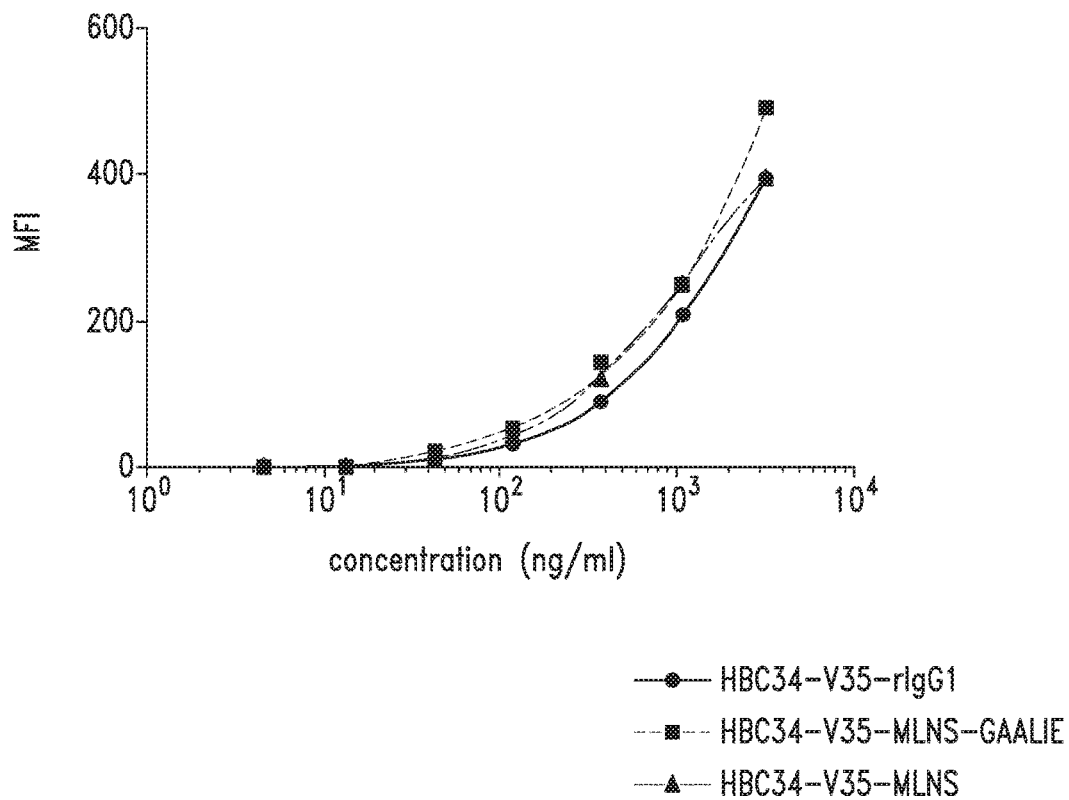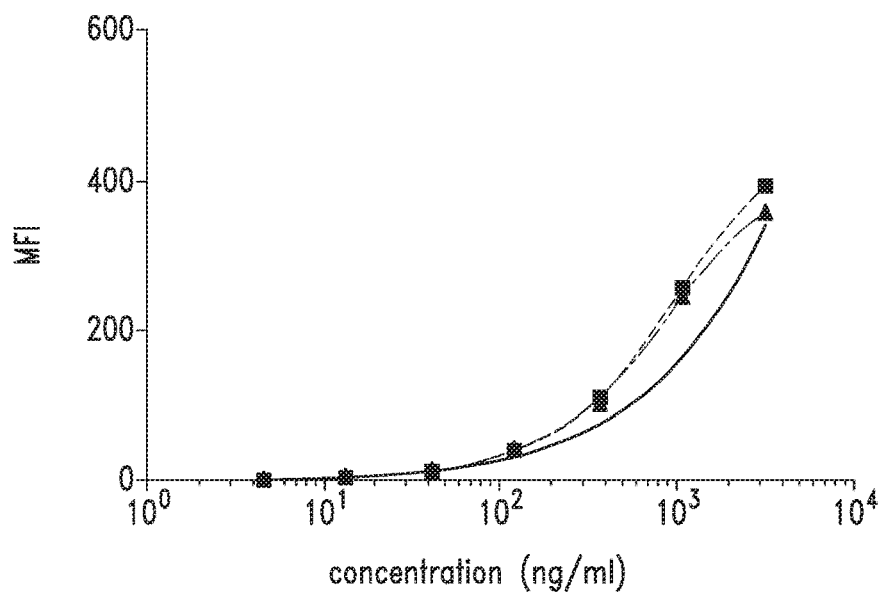
FIG. 3P

| Antibody | HBsAg EC$_{50}$ (ng/mL) | HBeAg EC$_{50}$ (ng/mL) |
|---|---|---|
| HBC34 | 13.64 (12.28–15.15) | 11.67 (11.3–12.05) |
| HBC34-V35 | 17.97 (16.22–19.9) | 12.61 (11.59–13.72) |
| HBC34-V35-MLNS-GAALIE | 12.79 (12.75–12.84) | 10.85 (10.78–10.93) |

FIG. 3T

| Antibody | HBsAg EC$_{50}$ (ng/mL) | HBeAg EC$_{50}$ (ng/mL) |
|---|---|---|
| HBC34-V35-MLNS-GAALIE | 15.12 (13.81–16.56) | 10.64 (10.63–10.66) |
| HBC34-V35-MLNS | 16.56 (12.24–22.41) | 10.49 (10.39–10.60) |
| HBC34-V35 | 14.47 (10.43–20.08) | 13.61 (13.25–13.99) |

The geometric mean and range (in brackets) of EC$_{50}$ values determined in two independent experiments

*FIG. 3V*

| Genotype | $EC_{50}(ng/ml)$ |
|---|---|
| A | 2.34 |
| B | 2.22 |
| C | 0.92 |
| D | 1.10 |
| E | 1.12 |
| F | 1.93 |
| G | 1.43 |
| H | 1.93 |

FIG. 4

Synergy/Antagonism Analysis for HBC34-V35-MLNS-GAALIE in Combination with ETV

| Marker | Synergy [μM 20% ][a] | Antagonism [μM 20% ][a] | Disposition |
|---|---|---|---|
| HBsAg | 4.22 | −12.04 | Additive |
| HBV DNA | 0.19 | −20.28 | Additive | a Results represent the mean of three independent experiments, each incorporating n=3 plates

FIG. 16

SEQUENCE LISTING

<160> NUMBER OF SEQ ID NOS: 139

<210> SEQ ID NO 1
<211> LENGTH: 11
<212> TYPE: PRT
<213> ORGANISM: Hepatitis B virus
<220> FEATURE:
<221> NAME/KEY: VARIANT
<222> LOCATION: (1)...(11)
<223> OTHER INFORMATION: Xaa = any amino acid

<400> SEQUENCE: 1

Xaa Xaa Xaa Thr Cys Xaa Xaa Xaa Ala Xaa Gly
1               5                   10

<210> SEQ ID NO 2
<211> LENGTH: 11
<212> TYPE: PRT
<213> ORGANISM: Hepatitis B Virus
<220> FEATURE:
<221> NAME/KEY: VARIANT
<222> LOCATION: 1
<223> OTHER INFORMATION: Xaa = P, T or S,
<220> FEATURE:
<221> NAME/KEY: VARIANT
<222> LOCATION: 2
<223> OTHER INFORMATION: Xaa = C or S,
<220> FEATURE:
<221> NAME/KEY: VARIANT
<222> LOCATION: 3
<223> OTHER INFORMATION: Xaa = R, K, D or I,
<220> FEATURE:
<221> NAME/KEY: VARIANT
<222> LOCATION: 6
<223> OTHER INFORMATION: Xaa = M or T
<220> FEATURE:
<221> NAME/KEY: VARIANT
<222> LOCATION: 7
<223> OTHER INFORMATION: Xaa = T, A or I
<220> FEATURE:
<221> NAME/KEY: VARIANT
<222> LOCATION: 8
<223> OTHER INFORMATION: Xaa = T, P or L
<220> FEATURE:
<221> NAME/KEY: VARIANT
<222> LOCATION: (10)...(10)
<223> OTHER INFORMATION: Xaa = Q, H or L.

<400> SEQUENCE: 2

Xaa Xaa Xaa Thr Cys Xaa Xaa Xaa Ala Xaa Gly
1               5                   10

<210> SEQ ID NO 3
<211> LENGTH: 226
<212> TYPE: PRT
<213> ORGANISM: Hepatitis B Virus
<220> FEATURE:
<223> OTHER INFORMATION: S domain of HBsAg (GenBank acc. no. J02203)

<400> SEQUENCE: 3

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Pro Gly Tyr Arg Trp Met Cys Leu Arg Arg Phe

```
                65                  70                  75                  80
Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
                100                 105                 110

Ser Ser Thr Thr Ser Thr Gly Pro Cys Arg Thr Cys Met Thr Thr Ala
                115                 120                 125

Gln Gly Thr Ser Met Tyr Pro Ser Cys Cys Thr Lys Pro Ser Asp
                130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
                180                 185                 190

Ser Val Ile Trp Met Met Trp Tyr Trp Gly Pro Ser Leu Tyr Ser Ile
                195                 200                 205

Leu Ser Pro Phe Leu Pro Leu Leu Pro Ile Phe Phe Cys Leu Trp Val
                210                 215                 220

Tyr Ile
225

<210> SEQ ID NO 4
<211> LENGTH: 226
<212> TYPE: PRT
<213> ORGANISM: Hepatits B Virus
<220> FEATURE:
<223> OTHER INFORMATION: S domain of HBsAg (GenBank acc. no. FJ899792)

<400> SEQUENCE: 4

Met Glu Asn Val Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
                20                  25                  30

Asp Ser Trp Trp Thr Ser Leu Asn Phe Leu Gly Gly Thr Thr Val Cys
                35                  40                  45

Leu Gly Gln Asn Ser Gln Ser Pro Thr Ser Asn His Ser Pro Thr Ser
50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
                100                 105                 110

Ser Ser Thr Thr Gly Thr Gly Pro Cys Arg Thr Cys Thr Thr Pro Ala
                115                 120                 125

Gln Gly Thr Ser Met Tyr Pro Ser Cys Cys Cys Thr Lys Pro Ser Asp
                130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
                180                 185                 190

Ser Val Ile Trp Met Met Trp Tyr Trp Gly Pro Ser Leu Tyr Ser Thr
```

```
                195                 200                 205
Leu Ser Pro Phe Leu Pro Leu Leu Pro Ile Phe Phe Cys Leu Trp Val
    210                 215                 220

Tyr Ile
225

<210> SEQ ID NO 5
<211> LENGTH: 72
<212> TYPE: PRT
<213> ORGANISM: Hepatitis B Virus
<220> FEATURE:
<223> OTHER INFORMATION: J02203 (D, ayw3)

<400> SEQUENCE: 5

Gln Gly Met Leu Pro Val Cys Pro Leu Ile Pro Gly Ser Ser Thr Thr
1               5                   10                  15

Ser Thr Gly Pro Cys Arg Thr Cys Met Thr Thr Ala Gln Gly Thr Ser
            20                  25                  30

Met Tyr Pro Ser Cys Cys Cys Thr Lys Pro Ser Asp Gly Asn Cys Thr
        35                  40                  45

Cys Ile Pro Ile Pro Ser Ser Trp Ala Phe Gly Lys Phe Leu Trp Glu
    50                  55                  60

Trp Ala Ser Ala Arg Phe Ser Trp
65                  70

<210> SEQ ID NO 6
<211> LENGTH: 72
<212> TYPE: PRT
<213> ORGANISM: Hepatitis B Virus
<220> FEATURE:
<223> OTHER INFORMATION: FJ899792 (D, adw2)

<400> SEQUENCE: 6

Gln Gly Met Leu Pro Val Cys Pro Leu Ile Pro Gly Ser Ser Thr Thr
1               5                   10                  15

Gly Thr Gly Pro Cys Arg Thr Cys Thr Thr Pro Ala Gln Gly Thr Ser
            20                  25                  30

Met Tyr Pro Ser Cys Cys Cys Thr Lys Pro Ser Asp Gly Asn Cys Thr
        35                  40                  45

Cys Ile Pro Ile Pro Ser Ser Trp Ala Phe Gly Lys Phe Leu Trp Glu
    50                  55                  60

Trp Ala Ser Ala Arg Phe Ser Trp
65                  70

<210> SEQ ID NO 7
<211> LENGTH: 72
<212> TYPE: PRT
<213> ORGANISM: Hepatitis B Virus
<220> FEATURE:
<223> OTHER INFORMATION: AM282986 (A)

<400> SEQUENCE: 7

Gln Gly Met Leu Pro Val Cys Pro Leu Ile Pro Gly Thr Thr Thr Thr
1               5                   10                  15

Ser Thr Gly Pro Cys Lys Thr Cys Thr Thr Pro Ala Gln Gly Asn Ser
            20                  25                  30

Met Phe Pro Ser Cys Cys Cys Thr Lys Pro Ser Asp Gly Asn Cys Thr
        35                  40                  45

Cys Ile Pro Ile Pro Ser Ser Trp Ala Phe Ala Lys Tyr Leu Trp Glu
    50                  55                  60
```

```
Trp Ala Ser Val Arg Phe Ser Trp
65                  70

<210> SEQ ID NO 8
<211> LENGTH: 72
<212> TYPE: PRT
<213> ORGANISM: Hepatitis B Virus
<220> FEATURE:
<223> OTHER INFORMATION: D23678 (B1)

<400> SEQUENCE: 8

Gln Gly Met Leu Pro Val Cys Pro Leu Ile Pro Gly Ser Ser Thr Thr
1               5                   10                  15

Ser Thr Gly Pro Cys Lys Thr Cys Thr Thr Pro Ala Gln Gly Thr Ser
            20                  25                  30

Met Phe Pro Ser Cys Cys Cys Thr Lys Pro Thr Asp Gly Asn Cys Thr
        35                  40                  45

Cys Ile Pro Ile Pro Ser Ser Trp Ala Phe Ala Lys Tyr Leu Trp Glu
    50                  55                  60

Trp Ala Ser Val Arg Phe Ser Trp
65                  70

<210> SEQ ID NO 9
<211> LENGTH: 72
<212> TYPE: PRT
<213> ORGANISM: Hepatitis B Virus
<220> FEATURE:
<223> OTHER INFORMATION: AB117758 (C1)

<400> SEQUENCE: 9

Gln Gly Met Leu Pro Val Cys Pro Leu Leu Pro Gly Thr Ser Thr Thr
1               5                   10                  15

Ser Thr Gly Pro Cys Lys Thr Cys Thr Ile Pro Ala Gln Gly Thr Ser
            20                  25                  30

Met Phe Pro Ser Cys Cys Cys Thr Lys Pro Ser Asp Gly Asn Cys Thr
        35                  40                  45

Cys Ile Pro Ile Pro Ser Ser Trp Ala Phe Ala Arg Phe Leu Trp Glu
    50                  55                  60

Trp Ala Ser Val Arg Phe Ser Trp
65                  70

<210> SEQ ID NO 10
<211> LENGTH: 72
<212> TYPE: PRT
<213> ORGANISM: Hepatitis B Virus
<220> FEATURE:
<223> OTHER INFORMATION: AB205192 (E)

<400> SEQUENCE: 10

Gln Gly Met Leu Pro Val Cys Pro Leu Ile Pro Gly Ser Ser Thr Thr
1               5                   10                  15

Ser Thr Gly Pro Cys Arg Thr Cys Thr Thr Leu Ala Gln Gly Thr Ser
            20                  25                  30

Met Phe Pro Ser Cys Cys Cys Ser Lys Pro Ser Asp Gly Asn Cys Thr
        35                  40                  45

Cys Ile Pro Ile Pro Ser Ser Trp Ala Phe Gly Lys Phe Leu Trp Glu
    50                  55                  60

Trp Ala Ser Ala Arg Phe Ser Trp
65                  70
```

<210> SEQ ID NO 11
<211> LENGTH: 72
<212> TYPE: PRT
<213> ORGANISM: Hepatitis B Virus
<220> FEATURE:
<223> OTHER INFORMATION: X69798 (F4)

<400> SEQUENCE: 11

Gln Gly Met Leu Pro Val Cys Pro Leu Leu Pro Gly Ser Thr Thr Thr
1               5                   10                  15

Ser Thr Gly Pro Cys Lys Thr Cys Thr Thr Leu Ala Gln Gly Thr Ser
                20                  25                  30

Met Phe Pro Ser Cys Cys Cys Ser Lys Pro Ser Asp Gly Asn Cys Thr
            35                  40                  45

Cys Ile Pro Ile Pro Ser Ser Trp Ala Leu Gly Lys Tyr Leu Trp Glu
        50                  55                  60

Trp Ala Ser Ala Arg Phe Ser Trp
65                  70

<210> SEQ ID NO 12
<211> LENGTH: 72
<212> TYPE: PRT
<213> ORGANISM: Hepatitis B Virus
<220> FEATURE:
<223> OTHER INFORMATION: AF160501 (G)

<400> SEQUENCE: 12

Gln Gly Met Leu Pro Val Cys Pro Leu Ile Pro Gly Ser Ser Thr Thr
1               5                   10                  15

Ser Thr Gly Pro Cys Lys Thr Cys Thr Thr Pro Ala Gln Gly Asn Ser
                20                  25                  30

Met Tyr Pro Ser Cys Cys Cys Thr Lys Pro Ser Asp Gly Asn Cys Thr
            35                  40                  45

Cys Ile Pro Ile Pro Ser Ser Trp Ala Phe Ala Lys Tyr Leu Trp Glu
        50                  55                  60

Trp Ala Ser Val Arg Phe Ser Trp
65                  70

<210> SEQ ID NO 13
<211> LENGTH: 72
<212> TYPE: PRT
<213> ORGANISM: Hepatitis B Virus
<220> FEATURE:
<223> OTHER INFORMATION: AY090454 (H)

<400> SEQUENCE: 13

Gln Gly Met Leu Pro Val Cys Pro Leu Leu Pro Gly Ser Thr Thr Thr
1               5                   10                  15

Ser Thr Gly Pro Cys Lys Thr Cys Thr Thr Leu Ala Gln Gly Thr Ser
                20                  25                  30

Met Phe Pro Ser Cys Cys Cys Thr Lys Pro Ser Asp Gly Asn Cys Thr
            35                  40                  45

Cys Ile Pro Ile Pro Ser Ser Trp Ala Phe Gly Lys Tyr Leu Trp Glu
        50                  55                  60

Trp Ala Ser Ala Arg Phe Ser Trp
65                  70

<210> SEQ ID NO 14
<211> LENGTH: 72
<212> TYPE: PRT

```
<213> ORGANISM: Hepatitis B Virus
<220> FEATURE:
<223> OTHER INFORMATION: AF241409 (I)

<400> SEQUENCE: 14

Gln Gly Met Leu Pro Val Cys Pro Leu Ile Pro Gly Ser Ser Thr Thr
1               5                   10                  15

Ser Thr Gly Pro Cys Lys Thr Cys Thr Thr Pro Ala Gln Gly Asn Ser
            20                  25                  30

Met Tyr Pro Ser Cys Cys Cys Thr Lys Pro Ser Asp Gly Asn Cys Thr
        35                  40                  45

Cys Ile Pro Ile Pro Ser Ser Trp Ala Phe Ala Lys Tyr Leu Trp Glu
    50                  55                  60

Trp Ala Ser Ala Arg Phe Ser Trp
65                  70

<210> SEQ ID NO 15
<211> LENGTH: 72
<212> TYPE: PRT
<213> ORGANISM: Hepatitis B Virus
<220> FEATURE:
<223> OTHER INFORMATION: AB486012 (J)

<400> SEQUENCE: 15

Gln Gly Met Leu Pro Val Cys Pro Leu Leu Pro Gly Ser Thr Thr Thr
1               5                   10                  15

Ser Thr Gly Pro Cys Arg Thr Cys Thr Ile Thr Ala Gln Gly Thr Ser
            20                  25                  30

Met Phe Pro Ser Cys Cys Cys Thr Lys Pro Ser Asp Gly Asn Cys Thr
        35                  40                  45

Cys Ile Pro Ile Pro Ser Ser Trp Ala Phe Ala Lys Phe Leu Trp Glu
    50                  55                  60

Trp Ala Ser Val Arg Phe Ser Trp
65                  70

<210> SEQ ID NO 16
<211> LENGTH: 73
<212> TYPE: PRT
<213> ORGANISM: Hepatitis B Virus
<220> FEATURE:
<223> OTHER INFORMATION: HBsAg Y100C/P120T

<400> SEQUENCE: 16

Cys Gln Gly Met Leu Pro Val Cys Pro Leu Ile Pro Gly Ser Ser Thr
1               5                   10                  15

Thr Gly Thr Gly Thr Cys Arg Thr Cys Thr Thr Pro Ala Gln Gly Thr
            20                  25                  30

Ser Met Tyr Pro Ser Cys Cys Cys Thr Lys Pro Ser Asp Gly Asn Cys
        35                  40                  45

Thr Cys Ile Pro Ile Pro Ser Ser Trp Ala Phe Gly Lys Phe Leu Trp
    50                  55                  60

Glu Trp Ala Ser Ala Arg Phe Ser Trp
65                  70

<210> SEQ ID NO 17
<211> LENGTH: 72
<212> TYPE: PRT
<213> ORGANISM: Hepatitis B Virus
<220> FEATURE:
<223> OTHER INFORMATION: HBsAg P120T
```

```
<400> SEQUENCE: 17

Gln Gly Met Leu Pro Val Cys Pro Leu Ile Pro Gly Ser Ser Thr Thr
1               5                   10                  15

Gly Thr Gly Thr Cys Arg Thr Cys Thr Thr Pro Ala Gln Gly Thr Ser
            20                  25                  30

Met Tyr Pro Ser Cys Cys Cys Thr Lys Pro Ser Asp Gly Asn Cys Thr
        35                  40                  45

Cys Ile Pro Ile Pro Ser Ser Trp Ala Phe Gly Lys Phe Leu Trp Glu
    50                  55                  60

Trp Ala Ser Ala Arg Phe Ser Trp
65                  70

<210> SEQ ID NO 18
<211> LENGTH: 72
<212> TYPE: PRT
<213> ORGANISM: Hepatitis B Virus
<220> FEATURE:
<223> OTHER INFORMATION: HBsAg P120T/S143L

<400> SEQUENCE: 18

Gln Gly Met Leu Pro Val Cys Pro Leu Ile Pro Gly Ser Ser Thr Thr
1               5                   10                  15

Gly Thr Gly Thr Cys Arg Thr Cys Thr Thr Pro Ala Gln Gly Thr Ser
            20                  25                  30

Met Tyr Pro Ser Cys Cys Cys Thr Lys Pro Leu Asp Gly Asn Cys Thr
        35                  40                  45

Cys Ile Pro Ile Pro Ser Ser Trp Ala Phe Gly Lys Phe Leu Trp Glu
    50                  55                  60

Trp Ala Ser Ala Arg Phe Ser Trp
65                  70

<210> SEQ ID NO 19
<211> LENGTH: 72
<212> TYPE: PRT
<213> ORGANISM: Hepatitis B Virus
<220> FEATURE:
<223> OTHER INFORMATION: HBsAg C121S

<400> SEQUENCE: 19

Gln Gly Met Leu Pro Val Cys Pro Leu Ile Pro Gly Ser Ser Thr Thr
1               5                   10                  15

Gly Thr Gly Pro Ser Arg Thr Cys Thr Thr Pro Ala Gln Gly Thr Ser
            20                  25                  30

Met Tyr Pro Ser Cys Cys Cys Thr Lys Pro Ser Asp Gly Asn Cys Thr
        35                  40                  45

Cys Ile Pro Ile Pro Ser Ser Trp

-continued

Gly Thr Gly Pro Cys Asp Thr Cys Thr Thr Pro Ala Gln Gly Thr Ser
                20                  25                  30

Met Tyr Pro Ser Cys Cys Cys Thr Lys Pro Ser Asp Gly Asn Cys Thr
            35                  40                  45

Cys Ile Pro Ile Pro Ser Ser Trp Ala Phe Gly Lys Phe Leu Trp Glu
        50                  55                  60

Trp Ala Ser Ala Arg Phe Ser Trp
65                  70

<210> SEQ ID NO 21
<211> LENGTH: 72
<212> TYPE: PRT
<213> ORGANISM: Hepatitis B Virus
<220> FEATURE:
<223> OTHER INFORMATION: HBsAg R122I

<400> SEQUENCE: 21

Gln Gly Met Leu Pro Val Cys Pro Leu Ile Pro Gly Ser Ser Thr Thr
1               5                   10                  15

Gly Thr Gly Pro Cys Ile Thr Cys Thr Thr Pro Ala Gln Gly Thr Ser
20 25 30

Met Tyr Pro Ser Cys Cys Cys Thr Lys Pro Ser Asp Gly Asn Cys Thr
35 40 45

Cys Ile Pro Ile Pro Ser Ser Trp Ala Phe Gly Lys Phe Leu Trp Glu
50 55 60

Trp Ala Ser Ala Arg Phe Ser Trp
65 70

<210> SEQ ID NO 22
<211> LENGTH: 72
<212> TYPE: PRT
<213> ORGANISM: Hepatitis B Virus
<220> FEATURE:
<223> OTHER INFORMATION: HBsAg T123N

<400> SEQUENCE: 22

Gln Gly Met Leu Pro Val Cys Pro Leu Ile Pro Gly Ser Ser Thr Thr
1 5 10 15

Gly Thr Gly Pro Cys Arg Asn Cys Thr Thr Pro Ala Gln Gly Thr Ser
20 25 30

Met Tyr Pro Ser Cys Cys Cys Thr Lys Pro Ser Asp Gly Asn Cys Thr
35 40 45

Cys Ile Pro Ile Pro Ser Ser Trp Ala Phe Gly Lys Phe Leu Trp Glu
50 55 60

Trp Ala Ser Ala Arg Phe Ser Trp
65 70

<210> SEQ ID NO 23
<211> LENGTH: 72
<212> TYPE: PRT
<213> ORGANISM: Hepatitis B Virus
<220> FEATURE:
<223> OTHER INFORMATION: HBsAg Q129H

<400> SEQUENCE: 23

Gln Gly Met Leu Pro Val Cys Pro Leu Ile Pro Gly Ser Ser Thr Thr
1 5 10 15

Gly Thr Gly Pro Cys Arg Thr Cys Thr Thr Pro Ala His Gly Thr Ser
20 25 30

Met Tyr Pro Ser Cys Cys Cys Thr Lys Pro Ser Asp Gly Asn Cys Thr
             35                  40                  45

Cys Ile Pro Ile Pro Ser Ser Trp Ala Phe Gly Lys Phe Leu Trp Glu
 50                  55                  60

Trp Ala Ser Ala Arg Phe Ser Trp
 65                  70

<210> SEQ ID NO 24
<211> LENGTH: 72
<212> TYPE: PRT
<213> ORGANISM: Hepatitis B Virus
<220> FEATURE:
<223> OTHER INFORMATION: HBsAg Q129L

<400> SEQUENCE: 24

Gln Gly Met Leu Pro Val Cys Pro Leu Ile Pro Gly Ser Ser Thr Thr
 1               5                  10                  15

Gly Thr Gly Pro Cys Arg Thr Cys Thr

```
                    50                  55                  60

Trp Ala Ser Ala Arg Phe Ser Trp
 65                  70

<210> SEQ ID NO 27
<211> LENGTH: 72
<212> TYPE: PRT
<213> ORGANISM: Hepatitis B Virus
<220> FEATURE:
<223> OTHER INFORMATION: HBsAg M133T

<400> SEQUENCE: 27

Gln Gly Met Leu Pro Val Cys Pro Leu Ile Pro Gly Ser Ser Thr Thr
  1               5                  10                  15

Gly Thr Gly Pro Cys Arg Thr Cys Thr Thr Pro Ala Gln Gly Thr Ser
                 20                  25                  30

Thr Tyr Pro Ser Cys Cys Cys Thr Lys Pro Ser Asp Gly Asn Cys Thr

<210> SEQ ID NO 30
<211> LENGTH: 72
<212> TYPE: PRT
<213> ORGANISM: Hepatitis B Virus
<220> FEATURE:
<223> OTHER INFORMATION: HBsAg S143K

<400> SEQUENCE: 30

Gln Gly Met Leu Pro Val Cys Pro Leu Ile Pro Gly Ser Ser Thr Thr
1               5                   10                  15

Gly Thr Gly Pro Cys Arg Thr Cys Thr Thr Pro Ala Gln Gly Thr Ser
            20                  25                  30

Met Tyr Pro Ser Cys Cys Cys Th

-continued

```
<212> TYPE: PRT
<213> ORGANISM: Hepatitis B Virus
<220> FEATURE:
<223> OTHER INFORMATION: HBsAg N146A

<400> SEQUENCE: 33

Gln Gly Met Leu Pro Val Cys Pro Leu Ile Pro Gly Ser Ser Thr Thr
1               5                   10                  15

Gly Thr Gly Pro Cys Arg Thr Cys Thr Thr Pro Ala Gln Gly Thr Ser
            20                  25                  30

Met Tyr Pro Ser Cys Cys Cys Thr Lys Pro Ser Asp Gly Ala Cys Thr
        35                  40                  45

Cys Ile Pro Ile Pro Ser Ser Trp Ala Phe Gly Lys Phe Leu Trp Glu
    50                  55                  60

Trp Ala Ser Ala Arg Phe Ser Trp
65                  70

<210> SEQ ID NO 34
<211> LENGTH: 8
<212> TYPE: PRT
<213> ORGANISM: Artificial Sequence
<220> FEATURE:
<223> OTHER INFORMATION: Synthetic sequence HBC34 CDRH1

<400> SEQUENCE: 34

Gly Arg Ile Phe Arg Ser Phe Tyr
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic sequence HBC34 CDRH2

<400> SEQUENCE: 35

Asn Gln Asp Gly Ser Glu Lys
1               5

<210> SEQ ID NO 36
<211> LENGTH: 12
<212> TYPE: PRT
<213> ORGANISM: Artificial Sequence
<220> FEATURE:
<223> OTHER INFORMATION: Synthetic sequence HBC34 CDRH3

<400> SEQUENCE: 36

Ala Ala Trp Ser Gly Asn Ser Gly Gly Met Asp Val
1               5                   10

<210> SEQ ID NO 37
<211> LENGTH: 6
<212> TYPE: PRT
<213> ORGANISM: Artificial Sequence
<220> FEATURE:
<223> OTHER INFORMATION: Synthetic sequence HBC34 CDRL1

<400> SEQUENCE: 37

Lys Leu Gly Asn Lys Asn
1               5

<210> SEQ ID NO 38
<211> LENGTH: 3
<212> TYPE: PRT
<213> ORGANISM: Artificial Sequence
```

```
<220> FEATURE:
<223> OTHER INFORMATION: Synthetic sequence HBC34 CDRL2

<400> SEQUENCE: 38

Glu Val Lys
1

<210> SEQ ID NO 39
<211> LENGTH: 9
<212> TYPE: PRT
<213> ORGANISM: Artificial Sequence
<220> FEATURE:
<223> OTHER INFORMATION: Synthetic sequence HBC34 CDRL2 long

<400> SEQUENCE: 39

Val Ile Tyr Glu Val Lys Tyr Arg Pro
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic sequence HBC34 CDRL3

<400> SEQUENCE: 40

Gln Thr Trp Asp Ser Thr Thr Val Val
1               5

<210> SEQ ID NO 41
<211> LENGTH: 119
<212> TYPE: PRT
<213> ORGANISM: Artificial Sequence
<220> FEATURE:
<223> OTHER INFORMATION: Synthetic sequence HBC34, HBC34-V7, HBC34-V34,
      HBC34-V35 VH

<400> SEQUENCE: 41

Glu Leu Gln Leu Val Glu Ser Gly Gly Gly Trp Val Gln Pro Gly Gly
1               5                   10                  15

Ser Gln Arg Leu Ser Cys Ala Ala Ser Gly Arg Ile Phe Arg Ser Phe
            20                  25                  30

Tyr Met Ser Trp Val Arg Gln Ala Pro Gly Lys Gly Leu Glu Trp Val
        35                  40                  45

Ala Thr Ile Asn Gln Asp Gly Ser Glu Lys Leu Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Asn Leu Arg Val Glu Asp Thr Ala Val Tyr Tyr Cys
                85                  90                  95

Ala Ala Trp Ser Gly Asn Ser Gly Gly Met Asp Val Trp Gly Gln Gly
            100                 105                 110

Thr Thr Val Ser Val Ser Ser
        115

<210> SEQ ID NO 42
<211> LENGTH: 106
<212> TYPE: PRT
<213> ORGANISM: Artificial Sequence
<220> FEATURE:
<223> OTHER INFORMATION: Synthetic sequence HBC34 VL

<400> SEQUENCE: 42
```

-continued

```
Ser Tyr Glu Leu Thr Gln Pro Pro Ser Val Ser Pro Gly Gln
1               5                   10                  15

Thr Val Ser Ile Pro Cys Ser Gly Asp Lys Leu Gly Asn Lys Asn Val
            20                  25                  30

Cys Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Trp Asp Ser Thr Thr Val Val
                85                  90                  95

Phe Gly Gly Gly Thr Arg Leu Thr Val Leu
            100                 105

<210> SEQ ID NO 43
<211> LENGTH: 24
<212> TYPE: DNA
<213> ORGANISM: Artificial Sequence
<220> FEATURE:
<223> OTHER INFORMATION: Synthetic sequence HBC34 CDRH1

<400> SEQUENCE: 43
ggacgcatct ttagaagttt ttac                                      24

<210> SEQ ID NO 44
<211> LENGTH: 24
<212> TYPE: DNA
<213> ORGANISM: Artificial Sequence
<220> FEATURE:
<223> OTHER INFORMATION: Synthetic sequence HBC34 CDRH2

<400> SEQUENCE: 44
ataaaccaag atggaagtga gaaa                                      24

<210> SEQ ID NO 45
<211> LENGTH: 36
<212> TYPE: DNA
<213> ORGANISM: Artificial Sequence
<220> FEATURE:
<223> OTHER INFORMATION: Synthetic sequence HBC34 CDRH3

<400> SEQUENCE: 45
gcggcttgga gcggcaatag tgggggtatg gacgtc                         36

<210> SEQ ID NO 46
<211> LENGTH: 18
<212> TYPE: DNA
<213> ORGANISM: Artificial Sequence
<220> FEATURE:
<223> OTHER INFORMATION: Synthetic sequence HBC34 CDRL1

<400> SEQUENCE: 46
aaattgggga ataaaaat                                             18

<210> SEQ ID NO 47
<211> LENGTH: 9
<212> TYPE: DNA
<213> ORGANISM: Artificial Sequence
<220> FEATURE:
<223> OTHER INFORMATION: Synthetic sequence HBC34 CDRL2

<400> SEQUENCE: 47
``` gaggttaaa                                                              9

<210> SEQ ID NO 48
<211> LENGTH: 27
<212> TYPE: DNA
<213> ORGANISM: Artificial Sequence
<220> FEATURE:
<223> OTHER INFORMATION: Synthetic sequence HBC34 CDRL2 long

<400> SEQUENCE: 48
gtcatctatg aggttaaata ccgcccc                                         27

<210> SEQ ID NO 49
<211> LENGTH: 27
<212> TYPE: DNA
<213> ORGANISM: Artificial Sequence
<220> FEATURE:
<223> OTHER INFORMATION: Synthetic sequence HBC34 CDRL3

<400> SEQUENCE: 49
cagacgtggg acagcaccac tgtggtg                                         27

<210> SEQ ID NO 50
<211> LENGTH: 357
<212> TYPE: DNA
<213> ORGANISM: Artificial Sequence
<220> FEATURE:
<223> OTHER INFORMATION: Synthetic sequence HBC34 VH

<400> SEQUENCE: 50
gaactgcagc tggtggagtc tgggggaggc tgggtccagc cggggggggtc ccagagactg    60 tcctgtgcag cctctggacg catctttaga agtttttaca tgagctgggt ccgccaggcc   120
ccagggaagg ggctggagtg ggtggccact ataaaccaag atggaagtga gaaattatat   180
gtggactctg tgaagggccg attcaccatc tccagagaca acgccaagaa ctcactattt   240
ctgcaaatga acaacctgag agtcgaggac acggccgttt attactgcgc ggcttggagc   300
ggcaatagtg ggggtatgga cgtctgggc caggggacca cggtctccgt ctcctca      357

<210> SEQ ID NO 51
<211> LENGTH: 318
<212> TYPE: DNA
<213> ORGANISM: Artificial Sequence
<220> FEATURE:
<223> OTHER INFORMATION: Synthetic sequence HBC34 VL

<400> SEQUENCE: 51
tcctatgagc tgactcagcc accctcagtg tccgtgtccc caggacagac agtcagcatc     60
ccctgctctg gagataaatt gggaataaa aatgtttgct ggtttcagca taagccaggc   120
cagtcccctg tgttggtcat ctatgaggtt aaataccgcc cctcggggat tcctgagcga   180
ttctctggct ccaactctgg gaacacagcc actctgacca tcagcgggac ccaggctatg   240
gatgaggctg cctatttctg tcagacgtgg gacagcacca ctgtggtgtt cggcggaggg   300
accaggctga ccgtccta                                                  318

<210> SEQ ID NO 52
<211> LENGTH: 33
<212> TYPE: PRT
<213> ORGANISM: Hepatitis B Virus
<220> FEATURE:
<221> NAME/KEY: VARIANT
<222> LOCATION: (1)...(33)
<223> OTHER INFORMATION: Xaa = Any Amino Acid

```
<400> SEQUENCE: 52

Xaa Gly Ser Ser Thr Thr Ser Thr Gly Pro Cys Arg Thr Cys Met Thr
1               5                   10                  15

Xaa Pro Ser Asp Gly Asn Ala Thr Ala Ile Pro Ile Pro Ser Ser Trp
            20                  25                  30

Xaa

<210> SEQ ID NO 53
<211> LENGTH: 15
<212> TYPE: PRT
<213> ORGANISM: Hepatitis B Virus

<400> SEQUENCE: 53

Thr Ser Thr Gly Pro Cys Arg Thr Cys Met Thr Thr Ala Gln Gly
1               5                   10                  15

<210> SEQ ID NO 54
<211> LENGTH: 26
<212> TYPE: PRT
<213> ORGANISM: Hepatitis B Virus

<400> SEQUENCE: 54

Gly Met Leu Pro Val Cys Pro Leu Ile Pro Gly Ser Ser Thr Thr Ser
1               5                   10                  15

Thr Gly Pro Cys Arg Thr Cys Met Thr Thr
            20                  25

<210> SEQ ID NO 55
<211> LENGTH: 33
<212> TYPE: PRT
<213> ORGANISM: Hepatitis B Virus
<220> FEATURE:
<221> NAME/KEY: VARIANT
<222> LOCATION: (1)...(33)
<223> OTHER INFORMATION: Xaa = Any Amino Acid

<400> SEQUENCE: 55

Xaa Ser Met Tyr Pro Ser Ala Ser Ala Thr Lys Pro Ser Asp Gly Asn
1               5                   10                  15

Xaa Thr Gly Pro Cys Arg Thr Cys Met Thr Thr Ala Gln Gly Thr Ser
            20                  25                  30

Xaa

<210> SEQ ID NO 56
<211> LENGTH: 11
<212> TYPE: PRT
<213> ORGANISM: Hepatitis B Virus
<220> FEATURE:
<223> OTHER INFORMATION: amino acids 120 - 130 of the S domain of HBsAg
      (HBV-D J02203)

<400> SEQUENCE: 56

Pro Cys Arg Thr Cys Met Thr Thr Ala Gln Gly
1               5                   10

<210> SEQ ID NO 57
<211> LENGTH: 11
<212> TYPE: PRT
<213> ORGANISM: Hepatitis B Virus
<220> FEATURE:
<221> NAME/KEY: VARIANT
<222> LOCATION: 3
<223> OTHER INFORMATION: Xaa = R or K
```

```
<220> FEATURE:
<221> NAME/KEY: VARIANT
<222> LOCATION: 6
<223> OTHER INFORMATION: Xaa = M or T
<220> FEATURE:
<221> NAME/KEY: VARIANT
<222> LOCATION: 7
<223> OTHER INFORMATION: Xaa = T or I
<220> FEATURE:
<221> NAME/KEY: VARIANT
<222> LOCATION: 8
<223> OTHER INFORMATION: Xaa = T, P or L

<400> SEQUENCE: 57

Pro Cys Xaa Thr Cys Xaa Xaa Xaa Ala Gln Gly
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Synthetic sequence HBC34-V7 CDRL3 and HBC34-V23
      CDRL3

<400> SEQUENCE: 58

Gln Thr Phe Asp Ser Thr Thr Val Val
1               5

<210> SEQ ID NO 59
<211> LENGTH: 106
<212> TYPE: PRT
<213> ORGANISM: Artificial Sequence
<220> FEATURE:
<223> OTHER INFORMATION: Synthetic sequence HBC34-V7 VL

<400> SEQUENCE: 59

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Cys Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Phe Asp Ser Thr Thr Val Val
                85                  90                  95

Phe Gly Gly Gly Thr Arg Leu Thr Val Leu
            100                 105

<210> SEQ ID NO 60
<211> LENGTH: 18
<212> TYPE: DNA
<213> ORGANISM: Artificial Sequence
<220> FEATURE:
<223> OTHER INFORMATION: Synthetic sequence HBC34v7 CDRL1 and HBC-V23
      CDRL1

<400> SEQUENCE: 60
aagctgggga acaaaaat                                                 18

<210> SEQ ID NO 61
<211> LENGTH: 9
```

-continued

```
<212> TYPE: DNA
<213> ORGANISM: Artificial Sequence
<220> FEATURE:
<223> OTHER INFORMATION: Synthetic sequence HBC34-V7 CDRL2 and HBC34v23
      CDRL2

<400> SEQUENCE: 61 gaggtgaaa                                                               9

<210> SEQ ID NO 62
<211> LENGTH: 27
<212> TYPE: DNA
<213> ORGANISM: Artificial Sequence
<220> FEATURE:
<223> OTHER INFORMATION: Synthetic sequence HBC34-V7 CDRL2 long and
      CDRL2 HBC34-V23 long

<400> SEQUENCE: 62
gtcatctacg aggtgaaata tcggcct                                          27

<210> SEQ ID NO 63
<211> LENGTH: 27
<212> TYPE: DNA
<213> ORGANISM: Artificial Sequence
<220> FEATURE:
<223> OTHER INFORMATION: Synthetic sequence CDRL3 HBC34-V7 and CDRL3
      HBC34-V23

<400> SEQUENCE: 63
cagacattcg attccaccac agtggtc                                          27

<210> SEQ ID NO 64
<211> LENGTH: 318
<212> TYPE: DNA
<213> ORGANISM: Artificial Sequence
<220> FEATURE:
<223> OTHER INFORMATION: Synthetic sequence HBC34-V7, HBC34-V34, and
      HBC34-V35 VL

<400> SEQUENCE: 64
tcttacgagc tgacacagcc acctagcgtg tccgtctctc caggacagac cgtgtccatc      60
ccttgctctg gcgacaagct ggggaacaaa atgtctgtt ggttccagca caagccaggg      120
cagagtcccg tgctggtcat ctacgaggtg aaatatcggc cttcaggaat tccagaacgg     180
ttcagcggat caaacagcgg caatactgca accctgacaa ttagcgggac ccaggccatg     240
gacgaagccg cttatttctg ccagacattc gattccacca cagtggtctt ggcgggggga    300
actaggctga ccgtgctg                                                   318

<210> SEQ ID NO 65
<211> LENGTH: 106
<212> TYPE: PRT
<213> ORGANISM: Artificial Sequence
<220> FEATURE:
<223> OTHER INFORMATION: Synthetic sequence HBC34-V23 VL

<400> SEQUENCE: 65

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Asn Ala
            20                  25                  30

Cys Trp Tyr Gln Gln Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
```

```
                50                  55                  60
Asn Ser Gly Asn Thr Ala Thr Leu Thr Ile Ser Gly Thr Gln Ala Met
 65                  70                  75                  80

Asp Glu Ala Asp Tyr Tyr Cys Gln Thr Phe Asp Ser Thr Val Val
                 85                  90                  95

Phe Gly Gly Gly Thr Lys Leu Thr Val Leu
            100                 105
```

<210> SEQ ID NO 66
<211> LENGTH: 8
<212> TYPE: PRT
<213> ORGANISM: Artificial Sequence
<220> FEATURE:
<223> OTHER INFORMATION: Synthetic sequence HBC34wt CDRH2

<400> SEQUENCE: 66

```
Ile Asn Gln Asp Gly Ser Glu Lys
 1               5
```

<210> SEQ ID NO 67
<211> LENGTH: 119
<212> TYPE: PRT
<213> ORGANISM: Artificial Sequence
<220> FEATURE:
<223> OTHER INFORMATION: Synthetic sequence HBC34-V31, HBC34-V32 and
      HBC34-V33 VH

<400> SEQUENCE: 67

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Ile Phe Arg Ser Phe
             20                  25                  30

Tyr Met Ser Trp Val Arg Gln Ala Pro Gly Lys Gly Leu Glu Trp Val
         35                  40                  45

Ala Asn Ile Asn Gln Asp Gly Ser Glu Lys Leu Tyr Val Asp Ser Val
     50                  55                  60

Lys Gly Arg Phe Thr Ile Ser Arg Asp Asn Ala Lys Asn Ser Leu Phe
 65                  70                  75                  80

Leu Gln Met Asn Asn Leu Arg Val Glu Asp Thr Ala Val Tyr Tyr Cys
                 85                  90                  95

Ala Ala Trp Ser Gly Asn Ser Gly Gly Met Asp Val Trp Gly Gln Gly
            100                 105                 110

Thr Thr Val Thr Val Ser Ser
        115
```

<210> SEQ ID NO 68
<211> LENGTH: 357
<212> TYPE: DNA
<213> ORGANISM: Artificial Sequence
<220> FEATURE:
<223> OTHER INFORMATION: Synthetic sequence HBC34-V31, HBC34-V32 and
      HBC34-V33 VH

<400> SEQUENCE: 68

```
gaggtgcagc tggtggaatc cggcggggga ctggtgcagc ctggcggctc actgagactg      60
agctgtgcag cttctggaag aatcttcaga tcttttttaca tgagttgggt gagacaggct    120
cctgggaagg gactggagtg ggtcgcaaac atcaatcagg acggatcaga aaagctgtat    180
gtggatagcg tcaaaggcag gttcactatt tcccgcgaca cgccaaaaa ttctctgttt     240 ctgcagatga acaatctgcg ggtggaggat accgctgtct actattgtgc agcctggtct    300
```
ggcaacagtg gaggcatgga cgtgtgggga cagggaacca cagtgacagt cagctcc    357

<210> SEQ ID NO 69
<211> LENGTH: 318
<212> TYPE: DNA
<213> ORGANISM: Artificial Sequence
<220> FEATURE:
<223> OTHER INFORMATION: Synthetic sequence HBC34v23 VL

<400> SEQUENCE: 69
tcttacgagc tgacacagcc ccctagcgtg tccgtctctc caggccagac agcatccatc    60
acttgctctg gcgacaagct ggggaacaaa aatgcctgtt ggtatcagca gaagccaggg    120
cagagtcccg tgctggtcat ctacgaggtg aaatatcggc cttcaggaat tccagaaaga    180
ttcagtggat caaacagcgg caatactgct accctgacaa ttagcgggac ccaggccatg    240
gacgaagctg attactattg ccagacattc gattccacca cagtggtctt tggcggggga    300
actaagctga ccgtgctg    318

<210> SEQ ID NO 70
<211> LENGTH: 357
<212> TYPE: DNA
<213> ORGANISM: Artificial Sequence
<220> FEATURE:
<223> OTHER INFORMATION: Synthetic sequence HBC34 wt VH codon optimized

<400> SEQUENCE: 70
gaactgcagc tggtcgaatc aggaggaggg tgggtccagc ccggagggag ccagagactg    60
tcttgtgccg catcagggag gatcttcagg agcttctaca tgtcctgggt gcgccaggca    120
ccaggcaagg gactggagtg ggtcgccacc atcaaccagg acggatctga aaagctgtat    180
gtggatagtg tcaaaggccg gttcacaatt agcagagaca cgctaaaaa ttctctgttt    240 ctgcagatga caatctgcg agtggaggat accgccgtct actattgcgc cgcttggtct    300
ggcaacagcg gcgggatgga tgtctggggg cagggcacaa cagtgagcgt ctcttcc    357

<210> SEQ ID NO 71
<211> LENGTH: 318
<212> TYPE: DNA
<213> ORGANISM: Artificial Sequence
<220> FEATURE:
<223> OTHER INFORMATION: Synthetic sequence HBC34 wt VL codon optimized

<400> SEQUENCE: 71
tcatacgaac tgactcagcc tccctccgtc tccgtctcac ctggacagac cgtctcaatc    60
ccctgctccg gcgataaact gggcaacaag aacgtgtgct ggttccagca aaacccggga    120
cagagtcctg tgctggtcat ctacgaggtc aagtatcggc caagcggcat tcccgaaaga    180
ttcagcggct ccaactctgg gaataccgca acactgacta tctctggaac ccaggcaatg    240
gacgaggcag cttactttg ccagacttgg gattcaacta ctgtcgtgtt cggcggcgga    300
actagactga ctgtcctg    318

<210> SEQ ID NO 72
<211> LENGTH: 24
<212> TYPE: DNA
<213> ORGANISM: Artificial Sequence
<220> FEATURE:
<223> OTHER INFORMATION: Synthetic sequence HBC34 wt CDRH1 codon
      optimized

<400> SEQUENCE: 72
gggaggatct tcaggagctt ctac                                           24

<210> SEQ ID NO 73
<211> LENGTH: 24
<212> TYPE: DNA
<213> ORGANISM: Artificial Sequence
<220> FEATURE:
<223> OTHER INFORMATION: Synthetic sequence HBC34 wt CDRH2 codon
      optimized

<400> SEQUENCE: 73
atcaaccagg acggatctga aaag                                           24

<210> SEQ ID NO 74
<211> LENGTH: 36
<212> TYPE: DNA
<213> ORGANISM: Artificial Sequence
<220> FEATURE:
<223> OTHER INFORMATION: Synthetic sequence HBC34 wt CDRH3 codon
      optimized

<400> SEQUENCE: 74
gccgcttggt ctggcaacag cggcgggatg gatgtc                              36

<210> SEQ ID NO 75
<211> LENGTH: 18
<212> TYPE: DNA
<213> ORGANISM: Artificial Sequence
<220> FEATURE:
<223> OTHER INFORMATION: Synthetic sequence HBC34 wt CDRL1 codon
      optimized

<400> SEQUENCE: 75
aaactgggca acaagaac                                                  18

<210> SEQ ID NO 76
<211> LENGTH: 9
<212> TYPE: DNA
<213> ORGANISM: Artificial Sequence
<220> FEATURE:
<223> OTHER INFORMATION: Synthetic sequence HBC34 wt CDRL2 codon
      optimized

<400> SEQUENCE: 76 gaggtcaag                                                             9

<210> SEQ ID NO 77
<211> LENGTH: 27
<212> TYPE: DNA
<213> ORGANISM: Artificial Sequence
<220> FEATURE:
<223> OTHER INFORMATION: Synthetic sequence HBC34 wt CDRL2 long codon
      optimized

<400> SEQUENCE: 77
gtcatctacg aggtcaagta tcggcca                                        27

<210> SEQ ID NO 78
<211> LENGTH: 27
<212> TYPE: DNA
<213> ORGANISM: Artificial Sequence
<220> FEATURE:
<223> OTHER INFORMATION: Synthetic sequence HBC34 wt CDRL3 codon
      optimized

<400> SEQUENCE: 78

```
cagacttggg attcaactac tgtcgtg                                          27
```

<210> SEQ ID NO 79
<211> LENGTH: 5
<212> TYPE: PRT
<213> ORGANISM: Artificial Sequence
<220> FEATURE:
<223> OTHER INFORMATION: Synthetic linker sequence

<400> SEQUENCE: 79

Gly Gly Ser Gly Gly
1               5

<210> SEQ ID NO 80
<211> LENGTH: 7
<212> TYPE: PRT
<213> ORGANISM: Hepatitis B Virus

<400> SEQUENCE: 80

Thr Gly Pro Cys Arg Thr Cys
1               5

<210> SEQ ID NO 81
<211> LENGTH: 7
<212> TYPE: PRT
<213> ORGANISM: Hepatitis B Virus

<400> SEQUENCE: 81

Gly Asn Cys Thr Cys Ile Pro
1               5

<210> SEQ ID NO 82
<211> LENGTH: 25
<212> TYPE: PRT
<213> ORGANISM: Hepatitis B Virus
<220> FEATURE:
<223> OTHER INFORMATION: discontinuous  epitope mimic
<221> NAME/KEY: VARIANT
<222> LOCATION: 2, 21, 24
<223> OTHER INFORMATION: Cysteine coupled to acetamidomethyl

<400> SEQUENCE: 82

Cys Cys Ile Pro Ile Pro Ser Ser Trp Ala Phe Gly Cys Ser Thr Thr
1 5 10 15

Ser Thr Gly Pro Cys Arg Thr Cys Cys
20 25

<210> SEQ ID NO 83
<211> LENGTH: 28
<212> TYPE: PRT
<213> ORGANISM: Hepatitis B Virus
<220> FEATURE:
<223> OTHER INFORMATION: discontinuous epitope mimic
<221> NAME/KEY: VARIANT
<222> LOCATION: 4,6, 24, 27
<223> OTHER INFORMATION: Cys is coupled to acetamidomethyl

<400> SEQUENCE: 83

Cys Gly Asn Cys Thr Cys Ile Pro Ile Pro Ser Ser Trp Ala Phe Cys
1 5 10 15

Ser Thr Thr Ser Thr Gly Pro Cys Arg Thr Cys Cys
20 25

<210> SEQ ID NO 84
<211> LENGTH: 17
<212> TYPE: PRT

```
<213> ORGANISM: Hepatitis B Virus
<220> FEATURE:
<223> OTHER INFORMATION: looped epitope mimic
<221> NAME/KEY: V

```
                35                  40                  45
Glu Val Lys Tyr Arg Pro Ser Gly Ile Pro Glu Arg Phe Ser Gly Ser
         50                  55                  60
Asn Ser Gly Asn Thr Ala Thr Leu Thr Ile Ser Gly Thr Gln Ala Met
 65                  70                  75                  80
Asp Glu Ala Ala Tyr Phe Cys Gln Thr Phe Asp Ser Thr Thr Val Val
                 85                  90                  95
Phe Gly Gly Gly Thr Arg Leu Thr Val Leu
            100                 105

<210> SEQ ID NO 90
<211> LENGTH: 106
<212> TYPE: PRT
<213> ORGANISM: Artificial Sequence
<220> FEATURE:
<223> OTHER INFORMATION: Synthetic sequence HBC34-V34 VL

<400> SEQUENCE: 90

Ser Tyr Glu Leu Thr Gln Pro Pro Ser Val Ser Val Ser Pro Gly Gln
 1               5                  10                  15
Thr Val Ser Ile Pro Cys Ser Gly Asp Lys Leu Gly Asn Lys Asn Val
                20                  25                  30
Ser Trp Phe Gln His Lys Pro Gly Gln Ser Pro Val Leu Val Ile Tyr
            35                  40                  45
Glu Val Lys Tyr Arg Pro Ser Gly Ile Pro Glu Arg Phe Ser Gly Ser
         50                  55                  60
Asn Ser Gly Asn Thr Ala Thr Leu Thr Ile Ser Gly Thr Gln Ala Met
 65                  70                  75                  80
Asp Glu Ala Ala Tyr Phe Cys Gln Thr Phe Asp Ser Thr Thr Val Val
                 85                  90                  95
Phe Gly Gly Gly Thr Arg Leu Thr Val Leu
            100                 105

<210> SEQ ID NO 91
<211> LENGTH: 449
<212> TYPE: PRT
<213> ORGANISM: Artificial Sequence
<220> FEATURE:
<223> OTHER INFORMATION: Synthetic sequence HC of HBC34-V35-MLNS-GAALIE
      and HBC34-V34-MLNS-GAALIE (g1M17, 1)

<400> SEQUENCE: 91

Glu Leu Gln Leu Val Glu Ser Gly Gly Gly Trp Val Gln Pro Gly Gly
 1               5                  10                  15
Ser Gln Arg Leu Ser Cys Ala Ala Ser Gly Arg Ile Phe Arg Ser Phe
                20                  25                  30
Tyr Met Ser Trp Val Arg Gln Ala Pro Gly Lys Gly Leu Glu Trp Val
            35                  40                  45
Ala Thr Ile Asn Gln Asp Gly Ser Glu Lys Leu Tyr Val Asp Ser Val
         50                  55                  60
Lys Gly Arg Phe Thr Ile Ser Arg Asp Asn Ala Lys Asn Ser Leu Phe
 65                  70                  75                  80
Leu Gln Met Asn Asn Leu Arg Val Glu Asp Thr Ala Val Tyr Tyr Cys
                 85                  90                  95
Ala Ala Trp Ser Gly Asn Ser Gly Gly Met Asp Val Trp Gly Gln Gly
            100                 105                 110
Thr Thr Val Ser Val Ser Ser Ala Ser Thr Lys Gly Pro Ser Val Phe
            115                 120                 125
```

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Leu Pro Glu Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Leu His Glu
                420                 425                 430

Ala Leu His Ser His Tyr Thr Gln Lys Ser Leu Ser Leu Ser Pro Gly
            435                 440                 445

Lys

<210> SEQ ID NO 92
<211> LENGTH: 449
<212> TYPE: PRT
<213> ORGANISM: Artificial Sequence
<220> FEATURE:
<223> OTHER INFORMATION: Synthetic sequence HC of HBC34-V35-MLNS and
      HBC34-V34-MLNS (g1M17, 1)

<400> SEQUENCE: 92

Glu Leu Gln Leu Val Glu Ser Gly Gly Gly Trp Val Gln Pro Gly Gly
1               5                   10                  15

Ser Gln Arg Leu Ser Cys Ala Ala Ser Gly Arg Ile Phe Arg Ser Phe
                20                  25                  30

```
Tyr Met Ser Trp Val Arg Gln Ala Pro Gly Lys Gly Leu Glu Trp Val
     35                  40                  45

Ala Thr Ile Asn Gln Asp Gly Ser Glu Lys Leu Tyr Val Asp Ser Val
 50                  55                  60

Lys Gly Arg Phe Thr Ile Ser Arg Asp Asn Ala Lys Asn Ser Leu Phe
 65                  70                  75                  80

Leu Gln Met Asn Asn Leu Arg Val Glu Asp Thr Ala Val Tyr Tyr Cys
             85                  90                  95

Ala Ala Trp Ser Gly Asn Ser Gly Gly Met Asp Val Trp Gly Gln Gly
            100                 105                 110

Thr Thr Val Ser Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Leu His Glu
            420                 425                 430

Ala Leu His Ser His Tyr Thr Gln Lys Ser Leu Ser Leu Ser Pro Gly
            435                 440                 445
```

Lys

<210> SEQ ID NO 93
<211> LENGTH: 212
<212> TYPE: PRT
<213> ORGANISM: Artificial Sequence
<220> FEATURE:
<223> OTHER INFORMATION: Synthetic sequence LC of HBC34-V35

<400> SEQUENCE: 93

```
Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ala Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Phe Asp Ser Thr Thr Val Val
                85                  90                  95

Phe Gly Gly Gly Thr Arg Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210
```

<210> SEQ ID NO 94
<211> LENGTH: 212
<212> TYPE: PRT
<213> ORGANISM: Artificial Sequence
<220> FEATURE:
<223> OTHER INFORMATION: Synthetic sequence LC of HBC34-V34

<400> SEQUENCE: 94

```
Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ser Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80
```

Asp Glu Ala Ala Tyr Phe Cys Gln Thr Phe Asp Ser Thr Thr Val Val
                85                  90                  95

Phe Gly Gly Gly Thr Arg Leu Thr Val Leu Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
            130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
            165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
            195                 200                 205

Thr Glu Cys Ser
        210

<210> SEQ ID NO 95
<211> LENGTH: 128
<212> TYPE: PRT
<213> ORGANISM: Artificial Sequence
<220> FEATURE:
<223> OTHER INFORMATION: Synthetic sequence HBC24 VH

<400> SEQUENCE: 95

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Thr Lys Tyr
            20                  25                  30

Ala Met Ser Trp Val Arg Gln Ala Pro Gly Lys Gly Leu Glu Trp Val
        35                  40                  45

Ala Ser Ile Ser Gly Ser Val Pro Gly Phe Gly Ile Asp Thr Tyr Tyr
    50                  55                  60

Ala Asp Ser Val Lys Gly Arg Phe Thr Ile Ser Arg Asp Thr Ser Lys
65                  70                  75                  80

Asn Thr Leu Tyr Leu Gln Met Asn Ser Leu Arg Ala Glu Asp Thr Ala
                85                  90                  95

Leu Tyr Tyr Cys Ala Lys Asp Val Gly Val Ile Gly Ser Tyr Tyr Tyr
            100                 105                 110

Tyr Ala Met Asp Val Trp Gly Gln Gly Thr Ala Val Thr Val Ser Ser
            115                 120                 125

<210> SEQ ID NO 96
<211> LENGTH: 109
<212> TYPE: PRT
<213> ORGANISM: Artificial Sequence
<220> FEATURE:
<223> OTHER INFORMATION: Synthetic sequence HBC24 VL

<400> SEQUENCE: 96

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Gly Leu Ser Ser Ser
            20                  25                  30

Tyr Leu Ala Trp Tyr Gln Gln Lys Pro Gly Gln Ala Pro Arg Leu Leu
        35                  40                  45

```
Ile Tyr Ser Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Tyr Ser Pro
                85                  90                  95

Arg Trp Thr Phe Gly Gln Gly Thr Lys Val Glu Ile Lys
            100                 105
```

<210> SEQ ID NO 97
<211> LENGTH: 8
<212> TYPE: PRT
<213> ORGANISM: Artificial Sequence
<220> FEATURE:
<223> OTHER INFORMATION: Synthetic sequence CDRH1 of HBC24

<400> SEQUENCE: 97

```
Gly Ser Thr Phe Thr Lys Tyr Ala
1               5
```

<210> SEQ ID NO 98
<211> LENGTH: 8
<212> TYPE: PRT
<213> ORGANISM: Artificial Sequence
<220> FEATURE:
<223> OTHER INFORMATION: Synthetic sequence CDRH2 of HBC24

<400> SEQUENCE: 98

```
Ile Ser Gly Ser Val Pro Gly Phe
1               5
```

<210> SEQ ID NO 99
<211> LENGTH: 21
<212> TYPE: PRT
<213> ORGANISM: Artificial Sequence
<220> FEATURE:
<223> OTHER INFORMATION: Synthetic sequence CDRH3 of HBC24

<400> SEQUENCE: 99

```
Leu Tyr Tyr Cys Ala Lys Asp Val Gly Val Ile Gly Ser Tyr Tyr Tyr
1               5                   10                  15

Tyr Ala Met Asp Val
            20
```

<210> SEQ ID NO 100
<211> LENGTH: 7
<212> TYPE: PRT
<213> ORGANISM: Artificial Sequence
<220> FEATURE:
<223> OTHER INFORMATION: Synthetic sequence CDRL1 of HBC24

<400> SEQUENCE: 100

```
Gln Gly Leu Ser Ser Ser Tyr
1               5
```

<210> SEQ ID NO 101
<211> LENGTH: 3
<212> TYPE: PRT
<213> ORGANISM: Artificial Sequence
<220> FEATURE:
<223> OTHER INFORMATION: Synthetic sequence CDRL2 of HBC24

<400> SEQUENCE: 101

```
Ser Ala Ser
1
```

<210> SEQ ID NO 102
<211> LENGTH: 10
<212> TYPE: PRT
<213> ORGANISM: Artificial Sequence
<220> FEATURE:
<223> OTHER INFORMATION: Synthetic sequence CDRL3 of HBC24

<400> SEQUENCE: 102

Gln Gln Tyr Ala Tyr Ser Pro Arg Trp Thr
1               5                   10

<210> SEQ ID NO 103
<211> LENGTH: 357
<212> TYPE: DNA
<213> ORGANISM: Artificial Sequence
<220> FEATURE:
<223> OTHER INFORMATION: Synthetic sequence VH of HBC34-V7, HBC34-V35,
      and HBC34-V34 (codon optimized)

<400> SEQUENCE: 103
gagctgcagc tggtggagtc cggcggcggc tgggtgcagc ctggcggctc ccagaggctg      60
agctgtgccg cttctggcag gatcttccgg tccttttaca tgtcttgggt gcggcaggct     120
ccaggcaagg gcctggagtg ggtggctacc atcaaccagg acggctccga gaagctgtat     180
gtggatagcg tgaagggcag attcacaatc tctcgcgaca cgccaagaa ctccctgttt      240 ctgcagatga caatctgag ggtggaggat accgccgtgt actattgcgc cgcttggtct      300
ggcaatagcg gcggcatgga cgtgtgggga cagggcacca ccgtgtccgt gtccagc        357

<210> SEQ ID NO 104
<211> LENGTH: 318
<212> TYPE: DNA
<213> ORGANISM: Artificial Sequence
<220> FEATURE:
<223> OTHER INFORMATION: Synthetic sequence HBC34-V34 VL (codon
      optimized)

<400> SEQUENCE: 104
agctacgagc tgacacagcc cccttccgtg tccgtgtccc ctggacagac cgtgtccatc      60
ccatgcagcg gcgacaagct gggcaacaag aacgtgtcct ggtttcagca taagcctggc     120 cagtccccg tgctggtcat ctacgaggtg aagtataggc cagcggcat ccctgagcgg       180 ttctctggct ccaacagcgg caatacagcc accctgacaa tctctggcac acaggctatg     240
gacgaggccg cttatttctg ccagacccttt gattccacca cagtggtgtt cggcggcggc    300
accagactga cagtgctg                                                   318

<210> SEQ ID NO 105
<211> LENGTH: 318
<212> TYPE: DNA
<213> ORGANISM: Artificial Sequence
<220> FEATURE:
<223> OTHER INFORMATION: Synthetic sequence HBC34-V35 VL (codon
      optimized)

<400> SEQUENCE: 105
agctacgagc tgacacagcc cccttccgtg tccgtgtccc ctggacagac cgtgtccatc      60
ccatgcagcg gcgacaagct gggcaacaag aacgtggcct ggtttcagca taagcctggc     120 cagtccccg tgctggtcat ctacgaggtg aagtataggc cagcggcat ccctgagcgg       180 ttctctggct ccaacagcgg caatacagcc accctgacaa tctctggcac acaggctatg     240

```
gacgaggccg cttatttctg ccagacctttt gattccacca cagtggtgtt cggcggcggc    300
accagactga cagtgctg                                                   318
```

<210> SEQ ID NO 106
<211> LENGTH: 360
<212> TYPE: DNA
<213> ORGANISM: Artificial Sequence
<220> FEATURE:
<223> OTHER INFORMATION: Synthetic sequence HBC24 VH (wild type)

<400> SEQUENCE: 106

```
gaggtgcagt tgttggagtc tgggggaggc ttggtacagc ctgggggtc cctgagactc      60 tcctgtgcag cctctggatc cacttttacc aaatatgcca tgagctgggt ccgtcaggct    120
ccagggaagg gctggagtg gtcgcaagt attagtggaa gtgttcctgg tttggtatt       180 gacacatact acgcagactc cgttaagggc cggttcacca tctccagaga cacttccaag    240
aacaccctgt atctgcaaat gaacagcctg agagccgagg acacggcctt atattactgt    300
gcgaaagatg tcggggttat cgggtcatac tattactacg ctatggacgt ctggggtcaa    360
```

<210> SEQ ID NO 107
<211> LENGTH: 327
<212> TYPE: DNA
<213> ORGANISM: Artificial Sequence
<220> FEATURE:
<223> OTHER INFORMATION: Synthetic sequence HBC24 VL (wild type)

<400> SEQUENCE: 107

```
aaattgtgtt gacgcagtct ccaggcaccc tgtctttgtc tccaggggaa agagccaccc     60
tctcctgcag ggccagtcag ggtcttagca gcagttactt agcctggtac agcagaaac    120 ctggccaggc tcccaggctc ctcatctata gtgcgtccac cagggccact ggcatcccag    180
acaggttcag tggcagtggg tctgggacag acttcactct caccatcagc agactggagc    240
ctgaagattt tgcagtgtat tactgtcaac agtatgctta ctcacctcgg tggacgttcg    300
gccaagggac caaggtggag atcaaac                                        327
```

<210> SEQ ID NO 108
<211> LENGTH: 384
<212> TYPE: DNA
<213> ORGANISM: Artificial Sequence
<220> FEATURE:
<223> OTHER INFORMATION: Synthetic sequence HBC24 VH (codon optimized)

<400> SEQUENCE: 108

```
gaggtgcagc tgctggaaag cggcggcggc ctggtgcagc ccggcggctc cctgaggctg     60
tcttgcgccg cctctggcag caccttcaca aagtatgcaa tgtcttgggt cgccaggca    120 ccaggcaagg gcctggagtg ggtggcctcc atctctggca gcgtgcctgg cttcggcatc    180
gacacctact atgccgattc cgtgaagggc cggtttacaa tcagcagaga cacctccaag    240
aacacactgt atctgcagat gaattctctg cgggccgagg acaccgccct gtactattgt    300
gccaaggatg tgggcgtgat cggcagctac tattactatg caatggacgt gtggggacag    360
ggaacagcag tgacagtgag ctcc                                           384
```

<210> SEQ ID NO 109
<211> LENGTH: 327
<212> TYPE: DNA
<213> ORGANISM: Artificial Sequence
<220> FEATURE:

<223> OTHER INFORMATION: Synthetic sequence HBC24 VL (codon optimized)

<400> SEQUENCE: 109

```
gagatcgtgc tgacccagtc tcctggcaca ctgtccctgt ccctggaga gagagccacc    60
ctgtcctgca gagcctctca gggcctgagc tcctcttacc tggcctggta tcagcagaag   120
cctggacagg cccctcggct gctgatctac tctgcctcca ccagagcaac aggcattcct   180
gaccgcttct ccggatctgg aagcggcaca gacttcaccc tgacaatcag ccggctggag   240
cctgaggact tcgccgtgta ctattgtcag cagtacgcct attccccaag gtggaccttt   300
ggccagggca caaaggtgga gatcaag                                       327
```

<210> SEQ ID NO 110
<211> LENGTH: 318
<212> TYPE: DNA
<213> ORGANISM: Artificial Sequence
<220> FEATURE:
<223> OTHER INFORMATION: Synthetic sequence HBC34-V7 VL (codon optimized)

<400> SEQUENCE: 110

```
agctacgagc tgacacagcc cccttccgtg tccgtgtccc ctggacagac cgtgtccatc    60
ccatgcagcg gcgacaagct gggcaacaag aacgtgtgct ggtttcagca taagcctggc   120
cagtcccccg tgctggtcat ctacgaggtg aagtataggc ccagcggcat ccctgagcgg   180
ttctctggct ccaacagcgg caatacagcc accctgacaa tctctggcac acaggctatg   240
gacgaggccg cttatttctg ccagaccttt gattccacca gtggtgtt cggcggcggc     300
accagactga cagtgctg                                                 318
```

<210> SEQ ID NO 111
<211> LENGTH: 106
<212> TYPE: PRT
<213> ORGANISM: Artificial Sequence
<220> FEATURE:
<223> OTHER INFORMATION: Synthetic sequence HBC34v23-L_C40S

<400> SEQUENCE: 111

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Asn Ala
            20                  25                  30

Ser Trp Tyr Gln Gln Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Phe Asp Ser Thr Thr Val Val
                85                  90                  95

Phe Gly Gly Gly Thr Lys Leu Thr Val Leu
            100                 105
```

<210> SEQ ID NO 112
<211> LENGTH: 106
<212> TYPE: PRT
<213> ORGANISM: Artificial Sequence
<220> FEATURE:
<223> OTHER INFORMATION: Synthetic sequence HBC34v23-L_C40A

<400> SEQUENCE: 112

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Asn Ala
            20                  25                  30

Ala Trp Tyr Gln Gln Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Phe Asp Ser Thr Thr Val Val
                85                  90                  95

Phe Gly Gly Gly Thr Lys Leu Thr Val Leu
            100                 105

<210> SEQ ID NO 113
<211> LENGTH: 106
<212> TYPE: PRT
<213> ORGANISM: Artificial Sequence
<220> FEATURE:
<223> OTHER INFORMATION: Synthetic sequence HBC34v31-L_C40S

<400> SEQUENCE: 113

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ser Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Trp Asp Ser Thr Thr Val Val
                85                  90                  95

Phe Gly Gly Gly Thr Arg Leu Thr Val Leu
            100                 105

<210> SEQ ID NO 114
<211> LENGTH: 106
<212> TYPE: PRT
<213> ORGANISM: Artificial Sequence
<220> FEATURE:
<223> OTHER INFORMATION: Synthetic sequence HBC34v31-L_C40A

<400> SEQUENCE: 114

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ala Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Trp Asp Ser Thr Thr Val Val

```
                85                  90                  95

Phe Gly Gly Gly Thr Arg Leu Thr Val Leu
            100                 105

<210> SEQ ID NO 115
<211> LENGTH: 106
<212> TYPE: PRT
<213> ORGANISM: Artificial Sequence
<220> FEATURE:
<223> OTHER INFORMATION: Synthetic sequence HBC34v32-L_C40S

<400> SEQUENCE: 115

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ser Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Phe Asp Ser Thr Thr Val Val
                85                  90                  95

Phe Gly Gly Gly Thr Arg Leu Thr Val Leu
            100                 105

<210> SEQ ID NO 116
<211> LENGTH: 106
<212> TYPE: PRT
<213> ORGANISM: Artificial Sequence
<220> FEATURE:
<223> OTHER INFORMATION: Synthetic sequence HBC34v32-L_C40A

<400> SEQUENCE: 116

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ala Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Trp Asp Ser Thr Thr Val Val
                85                  90                  95

Phe Gly Gly Gly Thr Arg Leu Thr Val Leu
            100                 105

<210> SEQ ID NO 117
<211> LENGTH: 106
<212> TYPE: PRT
<213> ORGANISM: Artificial Sequence
<220> FEATURE:
<223> OTHER INFORMATION: Synthetic sequence HBC34v33-L_C40S

<400> SEQUENCE: 117

Ser Tyr Glu Leu Thr Gln Pro Pro Ser Val Ser Val Ser Pro Gly Gln
1               5                   10                  15
```

Thr Ala Ser Ile Thr Cys Ser Gly Asp Lys Leu Gly Asn Lys Asn Ala
            20                  25                  30

Ser Trp Tyr Gln Gln Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Phe Asp Ser Thr Thr Val Val
                85                  90                  95

Phe Gly Gly Gly Thr Lys Leu Thr Val Leu
            100                 105

<210> SEQ ID NO 118
<211> LENGTH: 106
<212> TYPE: PRT
<213> ORGANISM: Artificial Sequence
<220> FEATURE:
<223> OTHER INFORMATION: Synthetic sequence HBC34v33-L_C40A

<400> SEQUENCE: 118

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Asn Ala
            20                  25                  30

Ala Trp Tyr Gln Gln Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Phe Asp Ser Thr Thr Val Val
                85                  90                  95

Phe Gly Gly Gly Thr Lys Leu Thr Val Leu
            100                 105

<210> SEQ ID NO 119
<211> LENGTH: 106
<212> TYPE: PRT
<213> ORGANISM: Artificial Sequence
<220> FEATURE:
<223> OTHER INFORMATION: Synthetic sequence HBC34-L_C40S

<400> SEQUENCE: 119

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ser Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Trp Asp Ser Thr Thr Val Val
                85                  90                  95

Phe Gly Gly Gly Thr Arg Leu Thr Val Leu

<210> SEQ ID NO 120
<211> LENGTH: 106
<212> TYPE: PRT
<213> ORGANISM: Artificial Sequence
<220> FEATURE:
<223> OTHER INFORMATION: Synthetic sequence HBC34-L_C40A

<400> SEQUENCE: 120

```
Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ala Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Trp Asp Ser Thr Thr Val Val
                85                  90                  95

Phe Gly Gly Gly Thr Arg Leu Thr Val Leu
            100                 105
```

<210> SEQ ID NO 121
<211> LENGTH: 458
<212> TYPE: PRT
<213> ORGANISM: Artificial Sequence
<220> FEATURE:
<223> OTHER INFORMATION: Synthetic sequence HBC24-MLNS

<400> SEQUENCE: 121

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Thr Lys Tyr
            20                  25                  30

Ala Met Ser Trp Val Arg Gln Ala Pro Gly Lys Gly Leu Glu Trp Val
        35                  40                  45

Ala Ser Ile Ser Gly Ser Val Pro Gly Phe Gly Ile Asp Thr Tyr Tyr
    50                  55                  60

Ala Asp Ser Val Lys Gly Arg Phe Thr Ile Ser Arg Asp Thr Ser Lys
65                  70                  75                  80

Asn Thr Leu Tyr Leu Gln Met Asn Ser Leu Arg Ala Glu Asp Thr Ala
                85                  90                  95

Leu Tyr Tyr Cys Ala Lys Asp Val Gly Val Ile Gly Ser Tyr Tyr Tyr
            100                 105                 110

Tyr Ala Met Asp Val Trp Gly Gln Gly Thr Ala Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190
```

```
Leu Ser Ser Val Val Thr Val Pro Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
                260                 265                 270

Val Val Val Asp Val Ser His Glu Asp Pro Glu Val Lys Phe Asn Trp
                275                 280                 285

Tyr Val Asp Gly Val Glu Val His Asn Ala Lys Thr Lys Pro Arg Glu
                290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Asp Glu
                355                 360                 365

Leu Thr Lys Asn Gln Val Ser Leu Thr Cys Leu Val Lys Gly Phe Tyr
                370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
                420                 425                 430

Val Phe Ser Cys Ser Val Leu His Glu Ala Leu His Ser His Tyr Thr
                435                 440                 445

Gln Lys Ser Leu Ser Leu Ser Pro Gly Lys
    450                 455

<210> SEQ ID NO 122
<211> LENGTH: 458
<212> TYPE: PRT
<213> ORGANISM: Artificial Sequence
<220> FEATURE:
<223> OTHER INFORMATION: Synthetic sequence HBC24-MLNS-GAALIE

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Thr Lys Tyr
                20                  25                  30

Ala Met Ser Trp Val Arg Gln Ala Pro Gly Lys Gly Leu Glu Trp Val
            35                  40                  45

Ala Ser Ile Ser Gly Ser Val Pro Gly Phe Gly Ile Asp Thr Tyr Tyr
        50                  55                  60

Ala Asp Ser Val Lys Gly Arg Phe Thr Ile Ser Arg Asp Thr Ser Lys
65                  70                  75                  80

Asn Thr Leu Tyr Leu Gln Met Asn Ser Leu Arg Ala Glu Asp Thr Ala
                85                  90                  95
```

```
Leu Tyr Tyr Cys Ala Lys Asp Val Gly Val Ile Gly Ser Tyr Tyr
                100                 105                 110

Tyr Ala Met Asp Val Trp Gly Gln Gly Thr Ala Val Thr Val Ser Ser
            115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
210                 215                 220

Lys Val Glu Pro Lys Ser Cys Asp Lys Thr His Thr Cys Pro Pro Cys
225                 230                 235                 240

Pro Ala Pro Glu Leu Leu Ala Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Leu Pro Glu Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Leu His Glu Ala Leu His Ser His Tyr Thr
        435                 440                 445

Gln Lys Ser Leu Ser Leu Ser Pro Gly Lys
450                 455
```

<210> SEQ ID NO 123
<211> LENGTH: 449
<212> TYPE: PRT
<213> ORGANISM: Artificial Sequence
<220> FEATURE:
<223> OTHER INFORMATION: Synthetic sequence HBC34-V7-mu (IgG2a) HC

<400> SEQUENCE: 123

-continued

```
Glu Leu Gln Leu Val Glu Ser Gly Gly Gly Trp Val Gln Pro Gly Gly
 1               5                  10                  15

Ser Gln Arg Leu Ser Cys Ala Ala Ser Gly Arg Ile Phe Arg Ser Phe
             20                  25                  30

Tyr Met Ser Trp Val Arg Gln Ala Pro Gly Lys Gly Leu Glu Trp Val
         35                  40                  45

Ala Thr Ile Asn Gln Asp Gly Ser Glu Lys Leu Tyr Val Asp Ser Val
 50                  55                  60

Lys Gly Arg Phe Thr Ile Ser Arg Asp Asn Ala Lys Asn Ser Leu Phe
 65                  70                  75                  80

Leu Gln Met Asn Asn Leu Arg Val Glu Asp Thr Ala Val Tyr Tyr Cys
                 85                  90                  95

Ala Ala Trp Ser Gly Asn Ser Gly Gly Met Asp Val Trp Gly Gln Gly
             100                 105                 110

Thr Thr Val Ser Val Ser Ser Ala Lys Thr Thr Ala Pro Ser Val Tyr
         115                 120                 125

Pro Leu Ala Pro Val Cys Gly Asp Thr Thr Gly Ser Ser Val Thr Leu
130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                 165                 170                 175

Gln Ser Asp Leu Tyr Thr Leu Ser Ser Ser Val Thr Val Thr Ser Ser
             180                 185                 190

Thr Trp Pro Ser Gln Ser Ile Thr Cys Asn Val Ala His Pro Ala Ser
         195                 200                 205

Ser Thr Lys Val Asp Lys Lys Ile Glu Pro Arg Gly Pro Thr Ile Lys
210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                 245                 250                 255

Leu Ser Pro Ile Val Thr Cys Val Val Val Asp Val Ser Glu Asp Asp
             260                 265                 270

Pro Asp Val Gln Ile Ser Trp Phe Val Asn Asn Val Glu Val His Thr
         275                 280                 285

Ala Gln Thr Gln Thr His Arg Glu Asp Tyr Asn Ser Thr Leu Arg Val
290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                 325                 330                 335

Thr Ile Ser Lys Pro Lys Gly Ser Val Arg Ala Pro Gln Val Tyr Val
             340                 345                 350

Leu Pro Pro Pro Glu Glu Glu Met Thr Lys Lys Gln Val Thr Leu Thr
         355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                 405                 410                 415

Lys Asn Trp Val Glu Arg Asn Ser Tyr Ser Cys Ser Val Val His Glu
```

```
                420              425             430
Gly Leu His Asn His Thr Thr Lys Ser Phe Ser Arg Thr Pro Gly
            435              440             445
Lys

<210> SEQ ID NO 124
<211> LENGTH: 212
<212> TYPE: PRT
<213> ORGANISM: Artificial Sequence
<220> FEATURE:
<223> OTHER INFORMATION: Synthetic sequence HBC34-V7-mu (IgG2a) LC

<400> SEQUENCE: 124

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Cys Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Phe Asp Ser Thr Thr Val Val
                85                  90                  95

Phe Gly Gly Gly Thr Arg Leu Thr Val Leu Gly Gln Pro Lys Ser Ser
            100                 105                 110

Pro Ser Val Thr Leu Phe Pro Pro Ser Ser Glu Glu Leu Glu Thr Asn
        115                 120                 125

Lys Ala Thr Leu Val Cys Thr Ile Thr Asp Phe Tyr Pro Gly Val Val
    130                 135                 140

Thr Val Asp Trp Lys Val Asp Gly Thr Pro Val Thr Gln Gly Met Glu
145                 150                 155                 160

Thr Thr Gln Pro Ser Lys Gln Ser Asn Asn Lys Tyr Met Ala Ser Ser
                165                 170                 175

Tyr Leu Thr Leu Thr Ala Arg Ala Trp Glu Arg His Ser Ser Tyr Ser
            180                 185                 190

Cys Gln Val Thr His Glu Gly His Thr Val Glu Lys Ser Leu Ser Arg
        195                 200                 205

Ala Asp Cys Ser
    210

<210> SEQ ID NO 125
<211> LENGTH: 449
<212> TYPE: PRT
<213> ORGANISM: Artificial Sequence
<220> FEATURE:
<223> OTHER INFORMATION: Synthetic sequence HBC34-V35-mu (IgG2a) HC

<400> SEQUENCE: 125

Glu Leu Gln Leu Val Glu Ser Gly Gly Gly Trp Val Gln Pro Gly Gly
1               5                   10                  15

Ser Gln Arg Leu Ser Cys Ala Ala Ser Gly Arg Ile Phe Arg Ser Phe
            20                  25                  30

Tyr Met Ser Trp Val Arg Gln Ala Pro Gly Lys Gly Leu Glu Trp Val
        35                  40                  45

Ala Thr Ile Asn Gln Asp Gly Ser Glu Lys Leu Tyr Val Asp Ser Val
```

```
            50              55              60
Lys Gly Arg Phe Thr Ile Ser Arg Asp Asn Ala Lys Asn Ser Leu Phe
 65              70              75              80

Leu Gln Met Asn Asn Leu Arg Val Glu Asp Thr Ala Val Tyr Tyr Cys
                 85              90              95

Ala Ala Trp Ser Gly Asn Ser Gly Gly Met Asp Val Trp Gly Gln Gly
            100             105             110

Thr Thr Val Ser Val Ser Ser Ala Lys Thr Thr Ala Pro Ser Val Tyr
            115             120             125

Pro Leu Ala Pro Val Cys Gly Asp Thr Thr Gly Ser Ser Val Thr Leu
130             135             140

Gly Cys Leu Val Lys Gly Tyr Phe Pro Glu Pro Val Thr Leu Thr Trp
145             150             155             160

Asn Ser Gly Ser Leu Ser Ser Gly Val His Thr Phe Pro Ala Val Leu
                165             170             175

Gln Ser Asp Leu Tyr Thr Leu Ser Ser Ser Val Thr Val Thr Ser Ser
            180             185             190

Thr Trp Pro Ser Gln Ser Ile Thr Cys Asn Val Ala His Pro Ala Ser
            195             200             205

Ser Thr Lys Val Asp Lys Lys Ile Glu Pro Arg Gly Pro Thr Ile Lys
210             215             220

Pro Cys Pro Pro Cys Lys Cys Pro Ala Pro Asn Leu Leu Gly Gly Pro
225             230             235             240

Ser Val Phe Ile Phe Pro Pro Lys Ile Lys Asp Val Leu Met Ile Ser
            245             250             255

Leu Ser Pro Ile Val Thr Cys Val Val Val Asp Val Ser Glu Asp Asp
            260             265             270

Pro Asp Val Gln Ile Ser Trp Phe Val Asn Asn Val Glu Val His Thr
            275             280             285

Ala Gln Thr Gln Thr His Arg Glu Asp Tyr Asn Ser Thr Leu Arg Val
290             295             300

Val Ser Ala Leu Pro Ile Gln His Gln Asp Trp Met Ser Gly Lys Glu
305             310             315             320

Phe Lys Cys Lys Val Asn Asn Lys Asp Leu Pro Ala Pro Ile Glu Arg
            325             330             335

Thr Ile Ser Lys Pro Lys Gly Ser Val Arg Ala Pro Gln Val Tyr Val
            340             345             350

Leu Pro Pro Pro Glu Glu Glu Met Thr Lys Lys Gln Val Thr Leu Thr
            355             360             365

Cys Met Val Thr Asp Phe Met Pro Glu Asp Ile Tyr Val Glu Trp Thr
370             375             380

Asn Asn Gly Lys Thr Glu Leu Asn Tyr Lys Asn Thr Glu Pro Val Leu
385             390             395             400

Asp Ser Asp Gly Ser Tyr Phe Met Tyr Ser Lys Leu Arg Val Glu Lys
            405             410             415

Lys Asn Trp Val Glu Arg Asn Ser Tyr Ser Cys Ser Val Val His Glu
            420             425             430

Gly Leu His Asn His His Thr Thr Lys Ser Phe Ser Arg Thr Pro Gly
            435             440             445

Lys

<210> SEQ ID NO 126
<211> LENGTH: 212
```

```
<212> TYPE: PRT
<213> ORGANISM: Artificial Sequence
<220> FEATURE:
<223> OTHER INFORMATION: Synthetic sequence HBC34-V35-mu (IgG2a) LC

<400> SEQUENCE: 126

Ser Tyr Glu Leu Thr Gln Pro Pro Ser Val Ser Val Ser Pro Gly Gln
1               5                   10                  15

Thr Val Ser Ile Pro Cys Ser Gly Asp Lys Leu Gly Asn Lys Asn Val
            20                  25                  30

Ala Trp Phe Gln His Lys Pro Gly Gln Ser Pro Val Leu Val Ile Tyr
        35                  40                  45

Glu Val Lys Tyr Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Ala Tyr Phe Cys Gln Thr Phe Asp Ser Thr Thr Val Val
                85                  90                  95

Phe Gly Gly Gly Thr Arg Leu Thr Val Leu Gly Gln Pro Lys Ser Ser
            100                 105                 110

Pro Ser Val Thr Leu Phe Pro Pro Ser Ser Glu Glu Leu Glu Thr Asn
        115                 120                 125

Lys Ala Thr Leu Val Cys Thr Ile Thr Asp Phe Tyr Pro Gly Val Val
130                 135                 140

Thr Val Asp Trp Lys Val Asp Gly Thr Pro Val Thr Gln Gly Met Glu
145                 150                 155                 160

Thr Thr Gln Pro Ser Lys Gln Ser Asn Asn Lys Tyr Met Ala Ser Ser
                165                 170                 175

Tyr Leu Thr Leu Thr Ala Arg Ala Trp Glu Arg His Ser Ser Tyr Ser
            180                 185                 190

Cys Gln Val Thr His Glu Gly His Thr Val Glu Lys Ser Leu Ser Arg
        195                 200                 205

Ala Asp Cys Ser
    210

<210> SEQ ID NO 127
<211> LENGTH: 458
<212> TYPE: PRT
<213> ORGANISM: Artificial Sequence
<220> FEATURE:
<223> OTHER INFORMATION: Synthetic sequence HBC24-mu (IgG2a) HC

<400> SEQUENCE: 127

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Thr Lys Tyr
            20                  25                  30

Ala Met Ser Trp Val Arg Gln Ala Pro Gly Lys Gly Leu Glu Trp Val
        35                  40                  45

Ala Ser Ile Ser Gly Ser Val Pro Gly Phe Gly Ile Asp Thr Tyr Tyr
    50                  55                  60

Ala Asp Ser Val Lys Gly Arg Phe Thr Ile Ser Arg Asp Thr Ser Lys
65                  70                  75                  80

Asn Thr Leu Tyr Leu Gln Met Asn Ser Leu Arg Ala Glu Asp Thr Ala
                85                  90                  95

Leu Tyr Tyr Cys Ala Lys Asp Val Gly Val Ile Gly Ser Tyr Tyr Tyr
            100                 105                 110
```

Tyr Ala Met Asp Val Trp Gly Gln Gly Thr Ala Val Thr Val Ser Ser
            115                 120                 125

Ala Lys Thr Thr Ala Pro Ser Val Tyr Pro Leu Ala Pro Val Cys Gly
    130                 135                 140

Asp Thr Thr Gly Ser Ser Val Thr Leu Gly Cys Leu Val Lys Gly Tyr
145                 150                 155                 160

Phe Pro Glu Pro Val Thr Leu Thr Trp Asn Ser Gly Ser Leu Ser Ser
                165                 170                 175

Gly Val His Thr Phe Pro Ala Val Leu Gln Ser Asp Leu Tyr Thr Leu
            180                 185                 190

Ser Ser Ser Val Thr Val Thr Ser Ser Thr Trp Pro Ser Gln Ser Ile
        195                 200                 205

Thr Cys Asn Val Ala His Pro Ala Ser Ser Thr Lys Val Asp Lys Lys
    210                 215                 220

Ile Glu Pro Arg Gly Pro Thr Ile Lys Pro Cys Pro Pro Cys Lys Cys
225                 230                 235                 240

Pro Ala Pro Asn Leu Leu Gly Gly Pro Ser Val Phe Ile Phe Pro Pro
                245                 250                 255

Lys Ile Lys Asp Val Leu Met Ile Ser Leu Ser Pro Ile Val Thr Cys
            260                 265                 270

Val Val Val Asp Val Ser Glu Asp Asp Pro Asp Val Gln Ile Ser Trp
        275                 280                 285

Phe Val Asn Asn Val Glu Val His Thr Ala Gln Thr Gln Thr His Arg
    290                 295                 300

Glu Asp Tyr Asn Ser Thr Leu Arg Val Val Ser Ala Leu Pro Ile Gln
305                 310                 315                 320

His Gln Asp Trp Met Ser Gly Lys Glu Phe Lys Cys Lys Val Asn Asn
                325                 330                 335

Lys Asp Leu Pro Ala Pro Ile Glu Arg Thr Ile Ser Lys Pro Lys Gly
            340                 345                 350

Ser Val Arg Ala Pro Gln Val Tyr Val Leu Pro Pro Pro Glu Glu Glu
        355                 360                 365

Met Thr Lys Lys Gln Val Thr Leu Thr Cys Met Val Thr Asp Phe Met
    370                 375                 380

Pro Glu Asp Ile Tyr Val Glu Trp Thr Asn Asn Gly Lys Thr Glu Leu
385                 390                 395                 400

Asn Tyr Lys Asn Thr Glu Pro Val Leu Asp Ser Asp Gly Ser Tyr Phe
                405                 410                 415

Met Tyr Ser Lys Leu Arg Val Glu Lys Lys Asn Trp Val Glu Arg Asn
            420                 425                 430

Ser Tyr Ser Cys Ser Val Val His Glu Gly Leu His Asn His His Thr
        435                 440                 445

Thr Lys Ser Phe Ser Arg Thr Pro Gly Lys
    450                 455

<210> SEQ ID NO 128
<211> LENGTH: 215
<212> TYPE: PRT
<213> ORGANISM: Artificial Sequence
<220> FEATURE:
<223> OTHER INFORMATION: Synthetic sequence HBC24-mu (IgG2a) LC

<400> SEQUENCE: 128

Glu Ile Val Leu Thr Gln Ser Pro Gly Thr Leu Ser Leu Ser Pro Gly
1               5                   10                  15

-continued

Glu Arg Ala Thr Leu Ser Cys Arg Ala Ser Gln Gly Leu Ser Ser Ser
            20                  25                  30

Tyr Leu Ala Trp Tyr Gln Gln Lys Pro Gly Gln Ala Pro Arg Leu Leu
        35                  40                  45

Ile Tyr Ser Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Tyr Ser Pro
                85                  90                  95

Arg Trp Thr Phe Gly Gln Gly Thr Lys Val Glu Ile Lys Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
            165                 170                 175

Ser Ser Thr Leu Thr Leu Thr Lys Asp Glu Tyr Glu Arg His Asn Ser
        180                 185                 190

Tyr Thr Cys Glu Ala Thr His Lys Thr Ser Thr Ser Pro Ile Val Lys
    195                 200                 205

Ser Phe Asn Arg Asn Glu Cys
    210                 215

<210> SEQ ID NO 129
<211> LENGTH: 449
<212> TYPE: PRT
<213> ORGANISM: Artificial Sequence
<220> FEATURE:
<223> OTHER INFORMATION: Synthetic sequence HBC34-V7, HBC34-V34,
      HBC34-V35 HC (wild-type)

<400> SEQUENCE: 129

Glu Leu Gln Leu Val Glu Ser Gly Gly Gly Trp Val Gln Pro Gly Gly
1               5                   10                  15

Ser Gln Arg Leu Ser Cys Ala Ala Ser Gly Arg Ile Phe Arg Ser Phe
            20                  25                  30

Tyr Met Ser Trp Val Arg Gln Ala Pro Gly Lys Gly Leu Glu Trp Val
        35                  40                  45

Ala Thr Ile Asn Gln Asp Gly Ser Glu Lys Leu Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Asn Leu Arg Val Glu Asp Thr Ala Val Tyr Tyr Cys
                85                  90                  95

Ala Ala Trp Ser Gly Asn Ser Gly Gly Met Asp Val Trp Gly Gln Gly
            100                 105                 110

Thr Thr Val Ser Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp

```
                145                 150                 155                 160
Asn Ser Gly Ala Leu Thr Ser Gly Val His Thr Phe Pro Ala Val Leu
                    165                 170                 175
Gln Ser Ser Gly Leu Tyr Ser Leu Ser Ser Val Val Thr Val Pro Ser
                    180                 185                 190
Ser Ser Leu Gly Thr Gln Thr Tyr Ile Cys Asn Val Asn His Lys Pro
                    195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                    245                 250                 255
Arg Thr Pro Glu Val Thr Cys Val Val Val Asp Val Ser His Glu Asp
                    260                 265                 270
Pro Glu Val Lys Phe Asn Trp Tyr Val Asp Gly Val Glu Val His Asn
                    275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                    325                 330                 335
Thr Ile Ser Lys Ala Lys Gly Gln Pro Arg Glu Pro Gln Val Tyr Thr
                    340                 345                 350
Leu Pro Pro Ser Arg Asp Glu Leu Thr Lys Asn Gln Val Ser Leu Thr
                    355                 360                 365
Cys Leu Val Lys Gly Phe Tyr Pro Ser Asp Ile Ala Val Glu Trp Glu
                    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                    405                 410                 415
Ser Arg Trp Gln Gln Gly Asn Val Phe Ser Cys Ser Val Met His Glu
                    420                 425                 430
Ala Leu His Asn His Tyr Thr Gln Lys Ser Leu Ser Leu Ser Pro Gly
                    435                 440                 445
Lys
```

<210> SEQ ID NO 130
<211> LENGTH: 990
<212> TYPE: DNA
<213> ORGANISM: Artificial Sequence
<220> FEATURE:
<223> OTHER INFORMATION: Synthetic sequence HBC34-V7, HBC34-V34,
      HBC34-V35 CH1-hinge-CH2-CH3 (codon-optimized)

<400> SEQUENCE: 130

```
gcctccacaa agggcccaag cgtgtttcca ctggctccct cttccaagtc tacctccggc      60
ggcacagccg ctctgggatg tctggtgaag gattacttcc cagagcccgt gaccgtgtct     120
tggaactccg gcgccctgac cagcggagtg catacatttc cagctgtgct gcagagctct     180
ggcctgtact ctctgtccag cgtggtgacc gtgccctctt ccagcctggg cacccagaca     240
tatatctgca acgtgaatca caagccaagc aatacaaagg tggacaagaa ggtggagccc     300
```

| aagtcttgtg ataagaccca tacatgccct ccatgtccag ctccagagct gctgggcggc | 360 |
| ccaagcgtgt tcctgtttcc acccaagcct aaggataccc tgatgatctc cagaaccccc | 420 |
| gaggtgacat gcgtggtggt ggacgtgagc cacgaggatc ctgaggtgaa gttcaactgg | 480 |
| tacgtggacg gcgtggaggt gcataatgct aagaccaagc caggagga gcagtacaac | 540 |
| tctacctatc gggtggtgtc cgtgctgaca gtgctgcacc aggattggct gaacggcaag | 600 |
| gagtataagt gcaaggtgtc taataaggcc ctgcccgctc ctatcgagaa gaccatctcc | 660 |
| aaggccaagg ccagcctag agagccacag gtgtacacac tgcctccatc tcgcgatgag | 720 |
| ctgaccaaga accaggtgtc cctgacatgt ctggtgaagg gcttctatcc ttccgacatc | 780 |
| gctgtggagt gggagagcaa tggccagcca gagaacaatt acaagaccac cccctgtg | 840 |
| ctggacagcg atggctcttt ctttctgtat agcaagctga ccgtggacaa gtctcgctgg | 900 |
| cagcagggca acgtgtttag ctgttctgtg atgcatgagg ccctgcacaa tcattataca | 960 |
| cagaagtccc tgagcctgtc tcctggcaag | 990 |

<210> SEQ ID NO 131
<211> LENGTH: 1417
<212> TYPE: DNA
<213> ORGANISM: Artificial Sequence
<220> FEATURE:
<223> OTHER INFORMATION: Synthetic sequence HBC34-V7, HBC34-V34, HBC34-V35 VH-CH1-hinge-CH2-CH3 (codon-optimized)

<400> SEQUENCE: 131

| gagctgcagc tggtggagtc cggcggcggc tgggtgcagc ctggcggctc ccagaggctg | 60 |
| agctgtgccg cttctggcag gatcttccgg tccttttaca tgtcttgggt gcggcaggct | 120 |
| ccaggcaagg gcctggagtg ggtggctacc atcaaccagg acggctccga gaagctgtat | 180 |
| gtggatagcg tgaagggcag attcacaatc tctcgcgaca cgccaagaa ctcccctgttt | 240 |
| ctgcagatga acaatctgag ggtggaggat accgccgtgt actattgcgc cgcttggtct | 300 |
| ggcaatagcg gcggcatgga cgtgtgggga cagggcacca ccgtgtccgt gtccagcgcc | 360 |
| tccacaaagg gcccaagcgt gtttccactg gctccctctt ccaagtctac ctccggcggc | 420 |
| acagccgctc tgggatgtct ggtgaaggat tacttcccag agcccgtgac cgtgtcttgg | 480 |
| aactccggcg ccctgaccag cggagtgcat acatttccag ctgtgctgca gagctctggc | 540 |
| ctgtactctc tgtccagcgt ggtgaccgtg ccctcttcca gctgggcac ccagacatat | 600 |
| atctgcaacg tgaatcacaa gcccaagcaat acaaggtgg acaagaaggt ggagcccaag | 660 |
| tcttgtgata gacccatac atgccctcca tgtccagctc cagagctgct gggcggccca | 720 |
| agcgtgttcc tgtttccacc caagcctaag ataccctga tgatctccag aacccccgag | 780 |
| gtgacatgcg tggtggtgga cgtgagccac gaggatcctg aggtgaagtt caactggtac | 840 |
| gtggacggcg tggaggtgca taatgctaag accaagccca gggaggagca gtacaactct | 900 |
| acctatcggg tggtgtccgt gctgacagtg ctgcaccagg attggctgaa cggcaaggag | 960 |
| tataagtgca aggtgtctaa taaggccctg cccgctccta tcgagaagac catctccaag | 1020 |
| gccaagggcc agcctagaga gccacaggtg tacacactgc ctccatctcg cgatgagctg | 1080 |
| accaagaacc aggtgtccct gacatgtctg gtgaagggct ctatccttc cgacatcgct | 1140 |
| gtggagtggg agcaatgg ccagccagag acaattaca agaccacacc cctgtgctg | 1200 |
| gacagcgatg gctcttctt tctgtatagc aagctgaccg tggacaagtc tcgctggcag | 1260 |
| cagggcaacg tgtttagctg ttctgtgatg catgaggccc tgcacaatca ttatacacag | 1320 |

```
aagtccctga gcctgtctcc tggcaagtga tgaggtaccg tgcgacggcc ggcaagcccc      1380
cgctccccgg gctctcgcgg tcgtacgagg aaagctt                              1417
```

<210> SEQ ID NO 132
<211> LENGTH: 318
<212> TYPE: DNA
<213> ORGANISM: Artificial Sequence
<220> FEATURE:
<223> OTHER INFORMATION: Synthetic sequence HBC34-V7 CL (codon-
      optimized)

<400> SEQUENCE: 132

```
ggacagccaa aggctgctcc atctgtgacc ctgtttccac cctcttccga ggagctgcag       60
gccaacaagg ccaccctggt gtgcctgatc tctgacttct accctggagc tgtgacagtg      120
gcttggaagg ctgatagctc tcccgtgaag gctggcgtgg agacaacaac ccctagcaag      180
cagtctaaca ataagtacgc cgcttccagc tatctgtctc tgacaccaga gcagtggaag      240
tcccaccgct cttattcctg ccaggtgacc catgagggca gcaccgtgga agacagtgg       300 gcccccaccg agtgttct                                                    318
```

<210> SEQ ID NO 133
<211> LENGTH: 636
<212> TYPE: DNA
<213> ORGANISM: Artificial Sequence
<220> FEATURE:
<223> OTHER INFORMATION: Synthetic sequence HBC34-V7 LC (VL-CL)
      (codon-optimized)

<400> SEQUENCE: 133

```
agctacgagc tgacacagcc cccttccgtg tccgtgtccc ctggacagac cgtgtccatc       60
ccatgcagcg gcgacaagct gggcaacaag aacgtgtgct ggtttcagca taagcctggc      120
cagtcccccg tgctggtcat ctacgaggtg aagtataggc ccagcggcat ccctgagcgg      180
ttctctggct ccaacagcgg caatacagcc accctgacaa tctctggcac acaggctatg      240
gacgaggccg cttatttctg ccagacctt gattccacca cagtggtgtt cggcggcggc      300
accagactga cagtgctggg acagccaaag gctgctccat ctgtgaccct gtttccaccc      360
tcttccgagg agctgcaggc caacaaggcc accctggtgt gcctgatctc tgacttctac      420
cctggagctg tgacagtggc ttggaaggct gatagctctc ccgtgaaggc tggcgtggag      480
acaacaaccc ctagcaagca gtctaacaat aagtacgccg cttccagcta tctgtctctg      540
acaccagagc agtggaagtc ccaccgctct tattcctgcc aggtgaccca tgagggcagc      600
accgtggaga agacagtggc ccccaccgag tgttct                                636
```

<210> SEQ ID NO 134
<211> LENGTH: 318
<212> TYPE: DNA
<213> ORGANISM: Artificial Sequence
<220> FEATURE:
<223> OTHER INFORMATION: Synthetic sequence HBC34-V34, HBC34-V35 CL
      (codon-optimized)

<400> SEQUENCE: 134

```
ggacagccaa aggctgctcc atctgtgacc ctgtttccac cctcttccga ggagctgcag       60
gccaacaagg ccaccctggt gtgcctgatc tctgacttct accctggagc tgtgacagtg      120
gcttggaagg ctgatagctc tcccgtgaag gctggcgtgg agacaacaac ccctagcaag      180
cagtctaaca ataagtacgc cgcttccagc tatctgtctc tgacaccaga gcagtggaag      240
```

```
tcccaccgct cttattcctg ccaggtgacc catgagggca gcaccgtgga agacagtg       300 gcccccaccg agtgttct                                                  318
```

<210> SEQ ID NO 135
<211> LENGTH: 636
<212> TYPE: DNA
<213> ORGANISM: Artificial Sequence
<220> FEATURE:
<223> OTHER INFORMATION: Synthetic sequence HBC34-V34 LC (VL-CL)
    (codon-optimized)

<400> SEQUENCE: 135

```
agctacgagc tgacacagcc cccttccgtg tccgtgtccc ctggacagac cgtgtccatc       60
ccatgcagcg gcgacaagct gggcaacaag aacgtgtcct ggtttcagca taagcctggc     120
cagtcccccg tgctggtcat ctacgaggtg aagtataggc ccagcggcat ccctgagcgg     180
ttctctggct ccaacagcgg caatacagcc accctgacaa tctctggcac acaggctatg     240
gacgaggccg cttatttctg ccagacccttt gattccacca cagtggtgtt cggcggcggc     300
accagactga cagtgctggg acagccaaag gctgctccat ctgtgaccct gtttccaccc     360
tcttccgagg agctgcaggc caacaaggcc accctggtgt gcctgatctc tgacttctac     420
cctggagctg tgacagtggc ttggaaggct gatagctctc ccgtgaaggc tggcgtggag     480
acaacaaccc ctagcaagca gtctaacaat aagtacgccg cttccagcta tctgtctctg     540
acaccagagc agtggaagtc ccaccgctct tattcctgcc aggtgaccca tgagggcagc     600
accgtggaga agacagtggc ccccaccgag tgttct                                636
```

<210> SEQ ID NO 136
<211> LENGTH: 636
<212> TYPE: DNA
<213> ORGANISM: Artificial Sequence
<220> FEATURE:
<223> OTHER INFORMATION: Synthetic sequence HBC34-V35 LC (VL-CL)
    (codon-optimized)

<400> SEQUENCE: 136

```
agctacgagc tgacacagcc cccttccgtg tccgtgtccc ctggacagac cgtgtccatc       60
ccatgcagcg gcgacaagct gggcaacaag aacgtggcct ggtttcagca taagcctggc     120
cagtcccccg tgctggtcat ctacgaggtg aagtataggc ccagcggcat ccctgagcgg     180
ttctctggct ccaacagcgg caatacagcc accctgacaa tctctggcac acaggctatg     240
gacgaggccg cttatttctg ccagaccttt gattccacca cagtggtgtt cggcggcggc     300
accagactga cagtgctggg acagccaaag gctgctccat ctgtgaccct gtttccaccc     360
tcttccgagg agctgcaggc caacaaggcc accctggtgt gcctgatctc tgacttctac     420
cctggagctg tgacagtggc ttggaaggct gatagctctc ccgtgaaggc tggcgtggag     480
acaacaaccc ctagcaagca gtctaacaat aagtacgccg cttccagcta tctgtctctg     540
acaccagagc agtggaagtc ccaccgctct tattcctgcc aggtgaccca tgagggcagc     600
accgtggaga agacagtggc ccccaccgag tgttct                                636
```

<210> SEQ ID NO 137
<211> LENGTH: 217
<212> TYPE: PRT
<213> ORGANISM: Homo sapiens
<220> FEATURE:
<223> OTHER INFORMATION: IgG1
<220> FEATURE:
<223> OTHER INFORMATION: WT hIgG1 Fc

<400> SEQUENCE: 137

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 138
<211> LENGTH: 449
<212> TYPE: PRT
<213> ORGANISM: Artificial Sequence
<220> FEATURE:
<223> OTHER INFORMATION: Synthetic sequence HBC34, HBC34v7, HBC34v23,
    HBC34v34, HBC34v35, HBC34_C40S, HBC34_C40A,
    HBC34v23_C40S, HBC34v23_C40A
    HC with GAALIE mutation in hIgG1 Fc

<400> SEQUENCE: 138

```
Glu Leu Gln Leu Val Glu Ser Gly Gly Gly Trp Val Gln Pro Gly Gly
1               5                   10                  15

Ser Gln Arg Leu Ser Cys Ala Ala Ser Gly Arg Ile Phe Arg Ser Phe
            20                  25                  30

Tyr Met Ser Trp Val Arg Gln Ala Pro Gly Lys Gly Leu Glu Trp Val
        35                  40                  45

Ala Thr Ile Asn Gln Asp Gly Ser Glu Lys Leu Tyr Val Asp Ser Val
50                  55                  60

Lys Gly Arg Phe Thr Ile Ser Arg Asp Asn Ala Lys Asn Ser Leu Phe
65                  70                  75                  80

Leu Gln Met Asn Asn Leu Arg Val Glu Asp Thr Ala Val Tyr Tyr Cys
                85                  90                  95

Ala Ala Trp Ser Gly Asn Ser Gly Gly Met Asp Val Trp Gly Gln Gly
            100                 105                 110
```

-continued

Thr Thr Val Ser Val Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Leu Pro Glu Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys

<210> SEQ ID NO 139
<211> LENGTH: 19
<212> TYPE: PRT
<213> ORGANISM: Artificial Sequence
<220> FEATURE:
<223> OTHER INFORMATION: Chimeric hinge sequence

```
<400> SEQUENCE: 139

Glu Ser Lys Tyr Gly Pro Pro Cys Pro Pro Cys Pro Ala Pro Pro Val
1               5                   10                  15

Ala Gly Pro
```

ANTIBODIES THAT NEUTRALIZE HEPATITIS B VIRUS AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 930485_402USPC_SEQUENCE_LISTING. The text file is 109 KB, was created on Jul. 18, 2021, and is being submitted electronically via EFS-Web.

The present disclosure relates to the field of immunotherapy for hepatitis B virus (HBV) and against hepatitis delta virus (HDV), and uses thereof. Anti-hepatitis B binding proteins described herein, e.g., antibodies and antigen binding fragments thereof, are capable of binding to an epitope located in the antigenic loop region of the S domain of the HBV envelope proteins (HBsAg). In certain embodiments, anti-hepatitis B binding proteins can bind to any or all of the known HBsAg genotypes, as well as HBsAg variants, and can neutralize HBV infection. Nucleic acids that encode, and host cells that express, such binding proteins are also provided herein. In addition, the present disclosure provides methods of using the antibodies and antibody fragments described herein in the diagnosis, prophylaxis, and treatment of diseases, as well as in methods of screening.

By way of background, HBV consists of (i) an envelope containing three related surface proteins (hepatitis B surface antigen, HBsAg) and lipid and (ii) an icosahedral nucleocapsid enclosing the viral DNA genome and DNA polymerase. The HBV capsid is formed in the cytosol of the infected cell during packaging of an RNA pregenome replication complex and gains the ability to bud during synthesis of the viral DNA genome by reverse transcription of the pregenome in the lumen of the particle. The three HBV envelope proteins S-HBsAg, M-HBsAg, and L-HBsAg shape a complex transmembrane fold at the endoplasmic reticulum, and form disulfide-linked homo- and heterodimers. During budding at an intracellular membrane, a short linear domain in the cytosolic preS region interacts with binding sites on the capsid surface. The virions are subsequently secreted into the blood. In addition, the surface proteins can bud in the absence of capsids and form subviral particles (SVPs) which are also secreted in 3-4 log excess over virions. High level of HBsAg can exhaust HBsAg-specific T-cell response, and is proposed as an important factor for viral immunotolerance in patients with chronic hepatitis B (CHB) (Chisari F V, Isogawa M, Wieland S F, Pathologie Biologie, 2010; 58:258-66).

Hepatitis B virus causes potentially life-threatening acute and chronic liver infections. Acute hepatitis B is characterized by viremia, with or without symptoms, with the risk of fulminant hepatitis occurrence (Liang T J, Block T M, McMahon B J, Ghany M G, Urban S, Guo J T, Locarnini S, Zoulim F, Chang K M, Lok A S. Present and future therapies of hepatitis B: From discovery to cure. Hepatology. 2015 Aug. 3. doi: 10.1002/hep.28025. [Epub ahead of print]). Despite an efficacious vaccine against hepatitis B being available since 1982, WHO reports that 240 million people are chronically infected with hepatitis B and more than 780,000 people die every year due to hepatitis B complications. Approximately one third of chronic hepatitis B (CHB) patients develop cirrhosis, liver failure and hepatocellular carcinoma, accounting for 600,000 deaths per year (Liang T J, Block T M, McMahon B J, Ghany M G, Urban S, Guo J T, Locarnini S, Zoulim F, Chang K M, Lok A S. Present and future therapies of hepatitis B: From discovery to cure. Hepatology. 2015 Aug. 3. doi: 10.1002/hep.28025. [Epub ahead of print]).

For patients infected with HBV, severe complications can develop as a result of coinfection or superinfection with HDV. According to the WHO, hepatitis D infects about 15 million people worldwide. HDV is considered a subviral satellite because it can propagate only in the presence of HBV. HDV is one of the smallest known animal viruses (40 nm), whereby its genome is only 1.6 kb and encodes for S and L HDAg. All other proteins needed for genome replication of HDV, including the RNA polymerase, are provided by the host cell, and the HDV envelope is provided by HBV. When introduced into permissive cells, the HDV RNA genome replicates and associates with multiple copies of the HDV-encoded proteins to assemble a ribonucleoprotein (RNP) complex. The RNP is exported from the cell by the HBV envelope proteins, which are able to assemble lipoprotein vesicles that bud into the lumen of a pre-Golgi compartment before being secreted. Moreover, the HBV envelope proteins also provide a mechanism for the targeting of HDV to an uninfected cell, thereby ensuring the spread of HDV.

Complications caused by HDV include a greater likelihood of experiencing liver failure in acute infections and a rapid progression to liver cirrhosis, with an increased chance of developing liver cancer in chronic infections. In combination with hepatitis B virus, hepatitis D has the highest fatality rate of all the hepatitis infections, at 20% (Fattovich G, Giustina G, Christensen E, Pantalena M, Zagni I, Realdi G, Schalm S W. Influence of hepatitis delta virus infection on morbidity and mortality in compensated cirrhosis type B. Gut. 2000 March; 46(3):420-6). The only approved therapy for chronic HDV infection is interferon-alpha. However, treatment of HDV with interferon-alpha is relatively inefficient and is not well-tolerated. Treatment with interferon-alpha results in sustained virological response six months post-treatment in one-fourth of the patients. Also, nucleos(t)ide analogs (NAs) have been widely tested in hepatitis delta, but they appear to be ineffective. Combination treatment using NAs with interferon also proved to be disappointing (Zaigham Abbas, Minaam Abbas Management of hepatitis delta: Need for novel therapeutic Options. World J Gastroenterol 2015 Aug. 28; 21(32): 9461-9465). Accordingly, new therapeutic options are needed.

BRIEF DESCRIPTION OF THE DRAWINGS

The figures provided herein are intended to illustrate subject matter included in the present disclosure in more detail. The figures are not intended to limit the disclosure in any way.

FIGS. 2A-2K show binding of HBC34-V7, HBC34-V34, and HBC34-V35 to all known HBsAg genotypes ((A)-(J), respectively) and to mock control (K). Genotype-representative sequences representing the HBsAg antigenic outer loop, as shown in Example 5 of PCT Publication No. WO 2017/060504, were used. Staining was performed by FACS. Antibody concentrations were as indicated on the x-axis of the graphs.

FIGS. 3A-3V show in vitro binding (3A-3R) and neutralization (3S-3V) of certain HBC antibodies to HBsAg. FIGS. 3A and 3B show binding of HBC34-V7 and HBC34-V35 with wild type or variant Fc regions to HBsAg adw in a direct antigen-based ELISA assay (2 experiments; data from "Experiment 1" is shown in FIG. 3A, and data from "Experiment 2" is shown in FIG. 3B). Antigen-binding curves are shown in the top panel of each Figure. $EC_{50}$ values (determined by fitting the curves using Graphpad prism) are shown in the middle panel of each Figure. Binding to uncoated plates (control) is shown in the bottom panel of each Figure. Fc regions: "HBC34v7" and "HBC34-V35"=wild-type Fc; "HBC34-V35-MLNS"=Fc with M428L/N434S. "HBC34-V35-MLNS-GAALIE"=Fc with M428L/N434S/G236A/A330L/I332E. Three lots of HBC34-V35 were tested. Two lots of HBC34-V35-MLNS, and two lots of HBC34-v35-MLNS-GAALIE were tested. One lot of HBC34-V7 was used. FIGS. 3I-3R show binding of HBC34-V35, HBC34-V35-MLNS, and HBC34-V35-MLNS-GAALIE to Expi293 cells expressing HBsAg from nineteen (19) HBsAg variants or mock control. Binding was determined by flow cytometry. Data are expressed as the mean fluorescence intensity of the transfected populations as defined by gating out the signal obtained with mock-transfected cells. For each HBsAg, serial dilutions of the three test articles were tested (12 points, 1 in 3, starting from 10 μg/ml). Antibody concentration was as shown on the x-axis. FIGS. 3T and 3V show $EC_{50}$ values. The geometric mean and range (in brackets) of $EC_{50}$ values were determined from two independent experiments.

FIG. 4 shows neutralization (EC50 value), by HBC34-V35-MLNS-GAALIE, of individual HBV genotypes using an HDV pseudotyping system.

FIG. 5 shows serum HBV DNA concentration before and after treatment. FIG. 6 shows serum HBsAg concentration before and after treatment. FIG. 7 shows serum HBeAg concentration before and after treatment. FIG. 8 shows serum HBcrAg concentration before and after treatment. "Tmt"=Treament.

In FIG. 13B, the control mAb from FIG. 13A is designated "Ctr mAb1". A second control mAb, designated "Ctr mAb2", is a version of HBC34-V35 including IgG1 Fc with the following mutations that enhance binding to FcγRIIb: G237D/P238D/H268D/P271G/A330R (Mimoto et al., Prot *Eng Des Sel.* 26(10):589-598 (2013)).

FIG. 16 shows results from in vitro drug interaction studies between HBC34-V35-MLNS-GAALIE and polymerase/reverse transcriptase inhibitor Entecavir (ETV).

DETAILED DESCRIPTION

Figure 1:
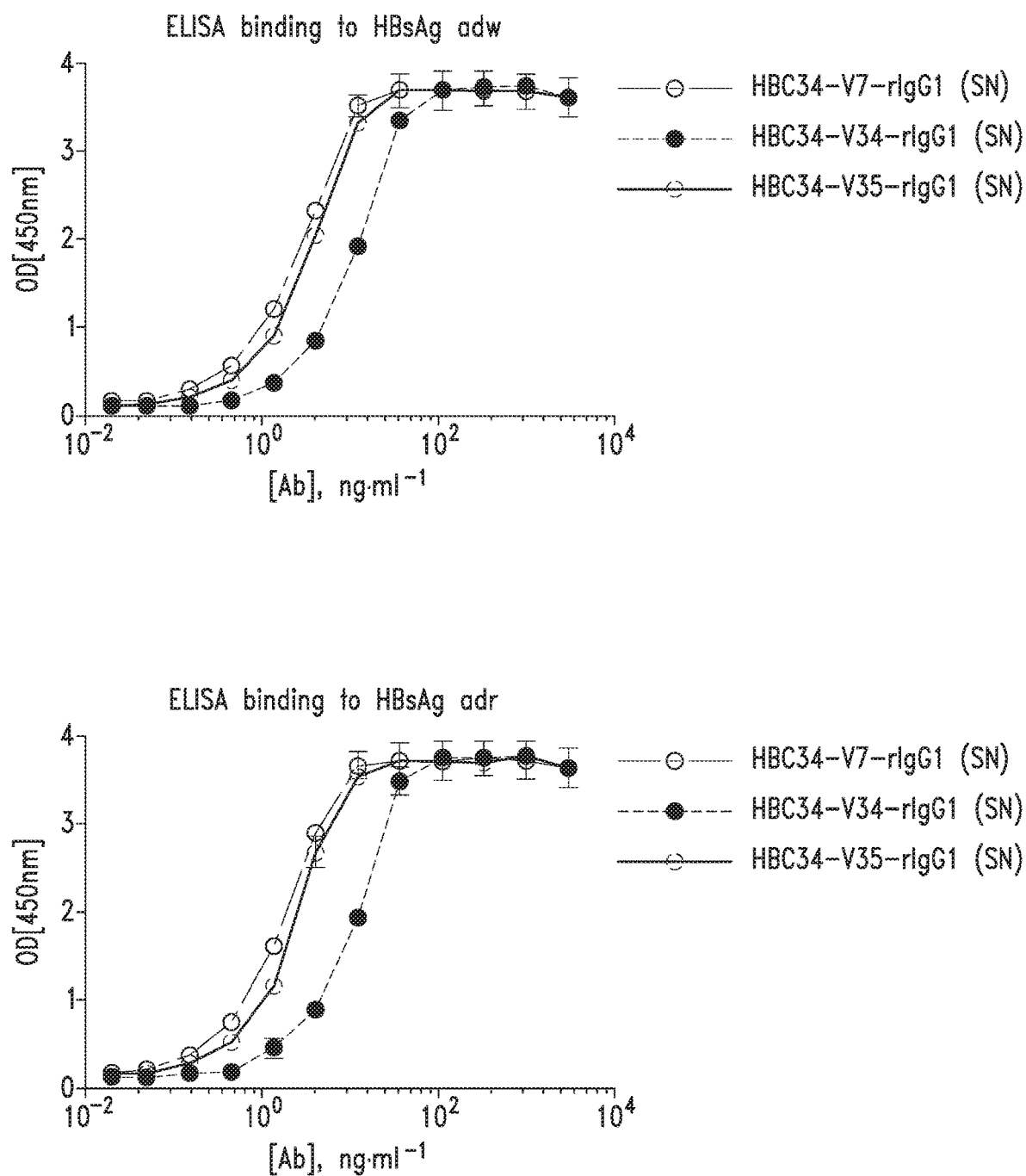
FIG. 1 shows binding of HBC34-V7 and two engineered antibodies of the present disclosure ("HBC34-V34"; "HBC34-V35") at the indicated concentrations to HBsAg adw (top panel) and HBsAg adr (bottom panel), as determined in direct antigen-based ELISA assays. All antibodies were produced as IgG1 (g1m17, 1 allotype).
Figure 2A:
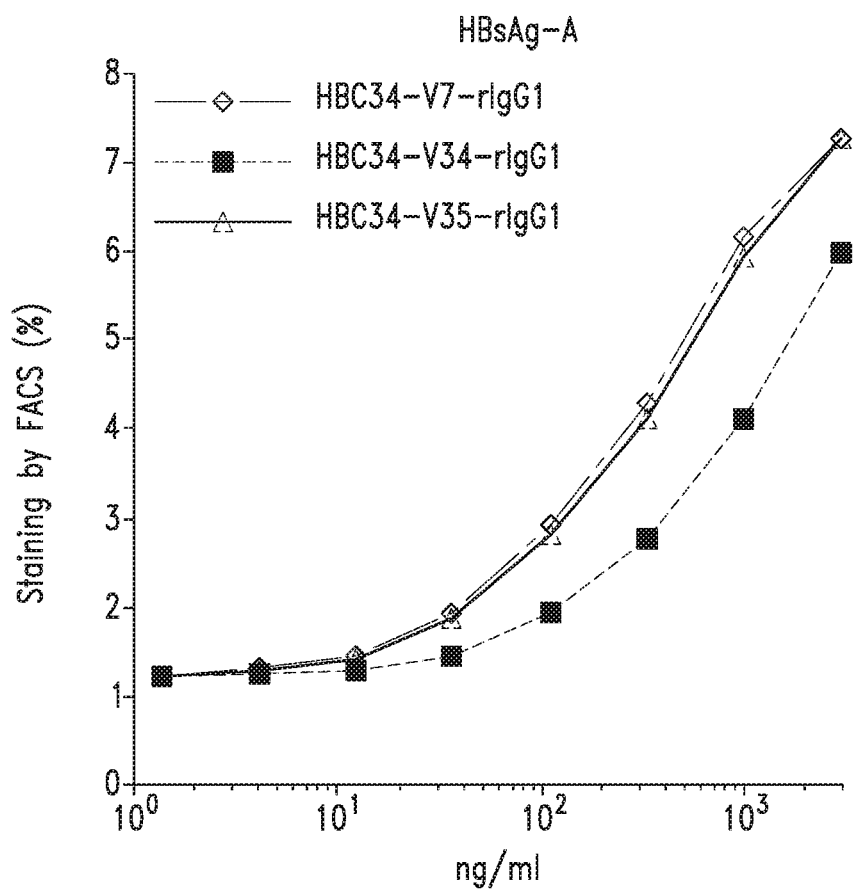
Figure 2B:
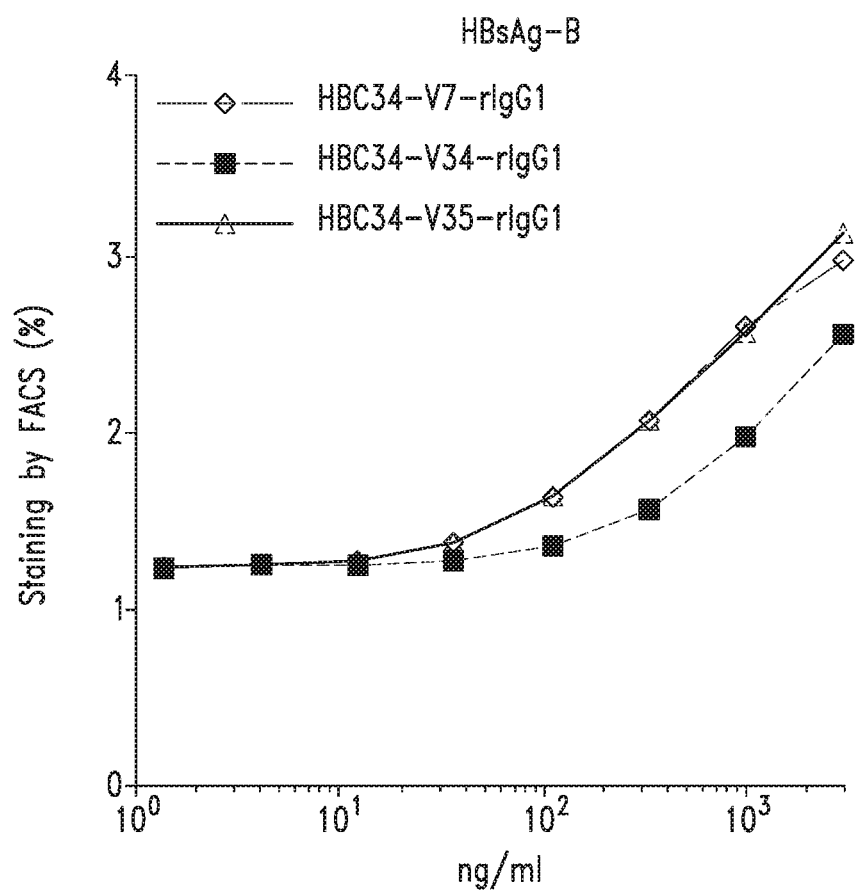
Figure 2C:
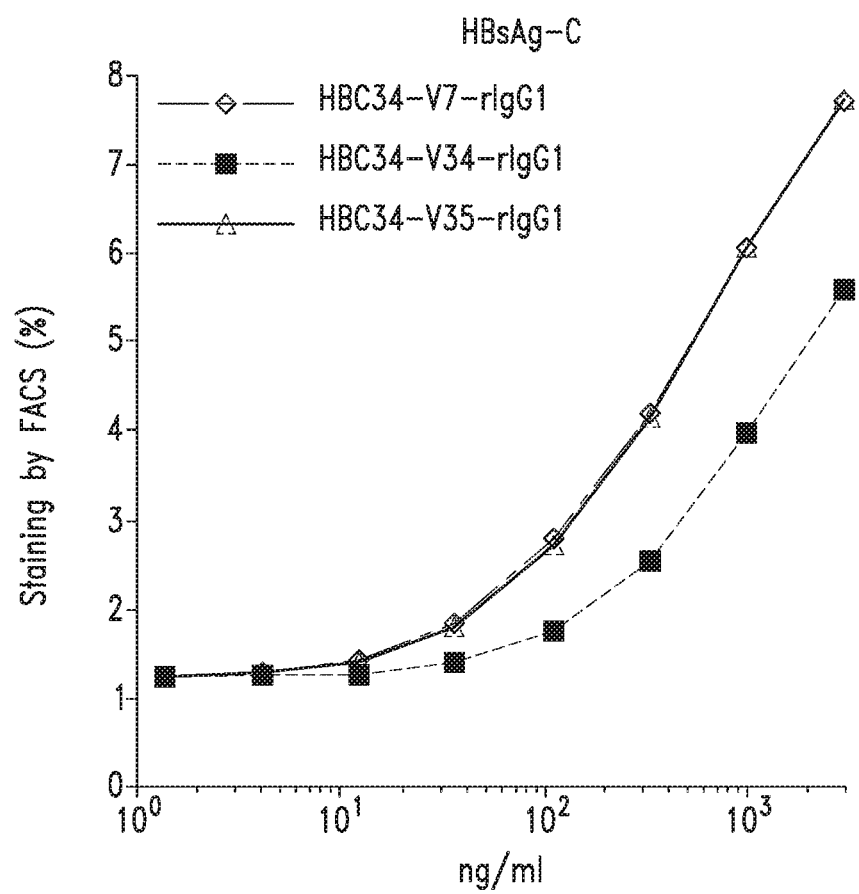
Figure 2D:
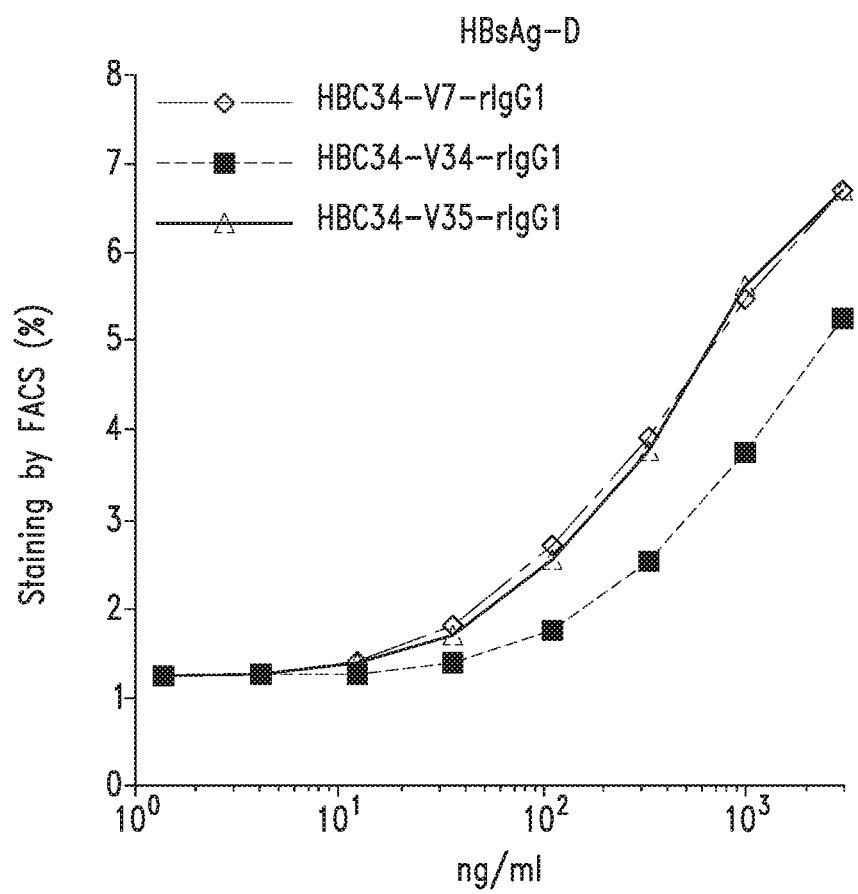
Figure 2E:
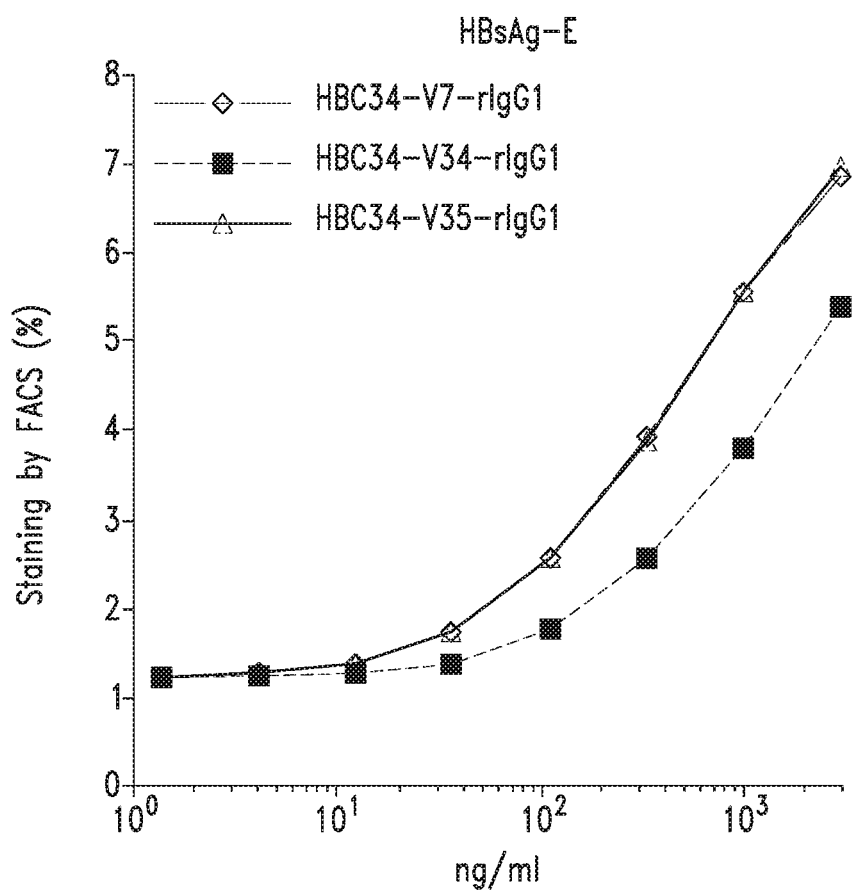
Figure 2F:
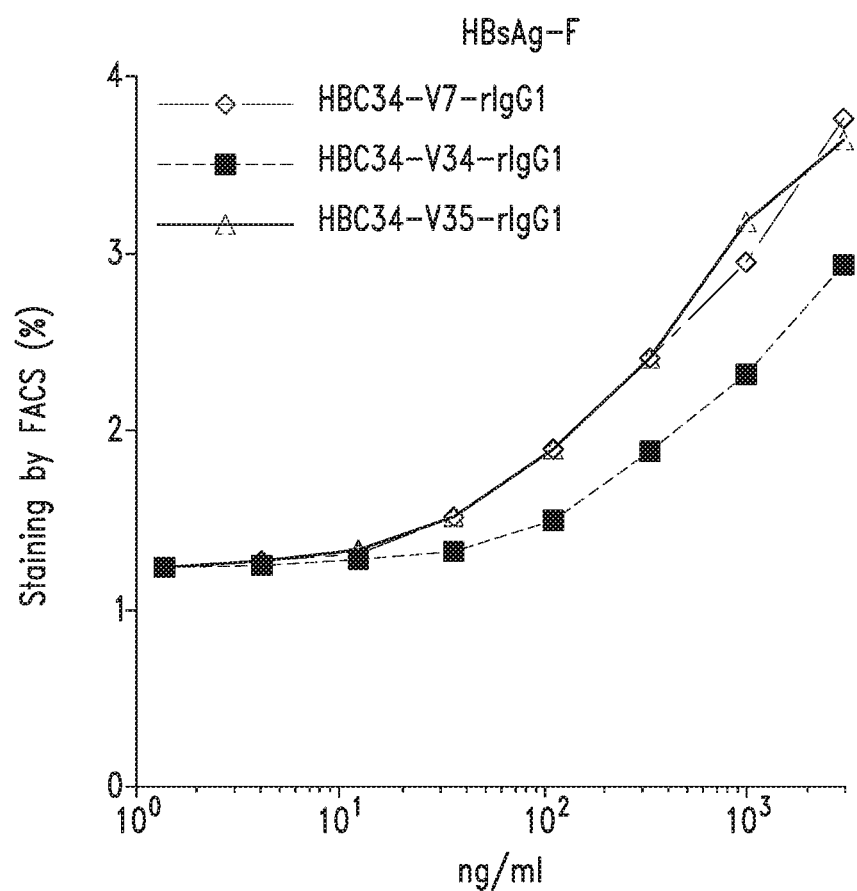
Figure 2G:
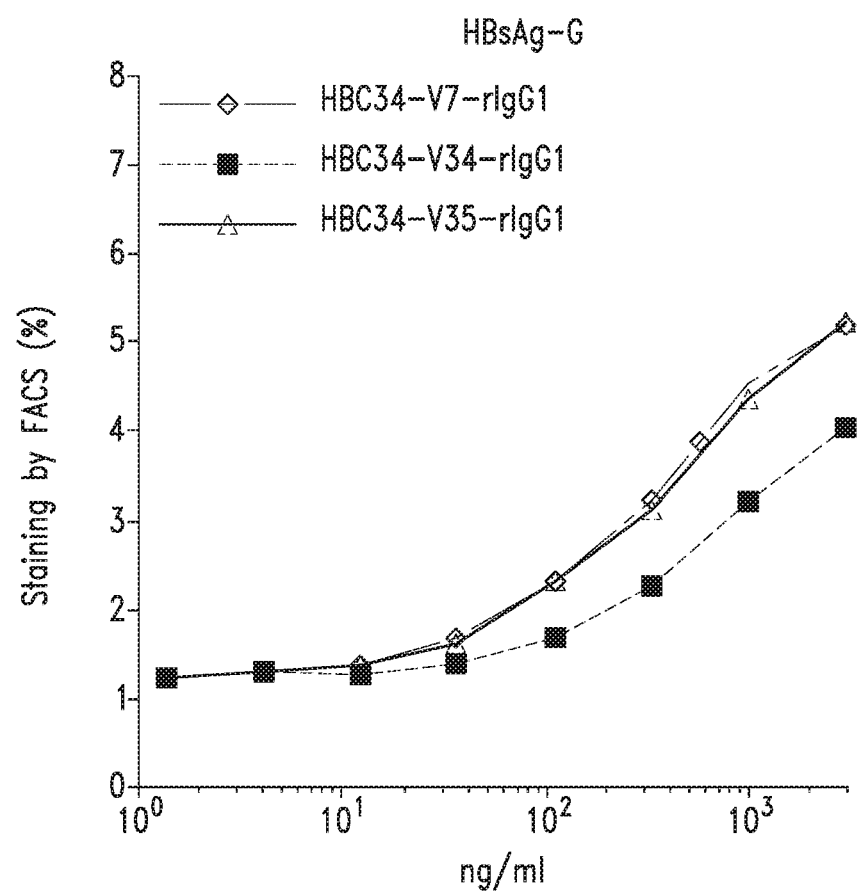
Figure 2H:
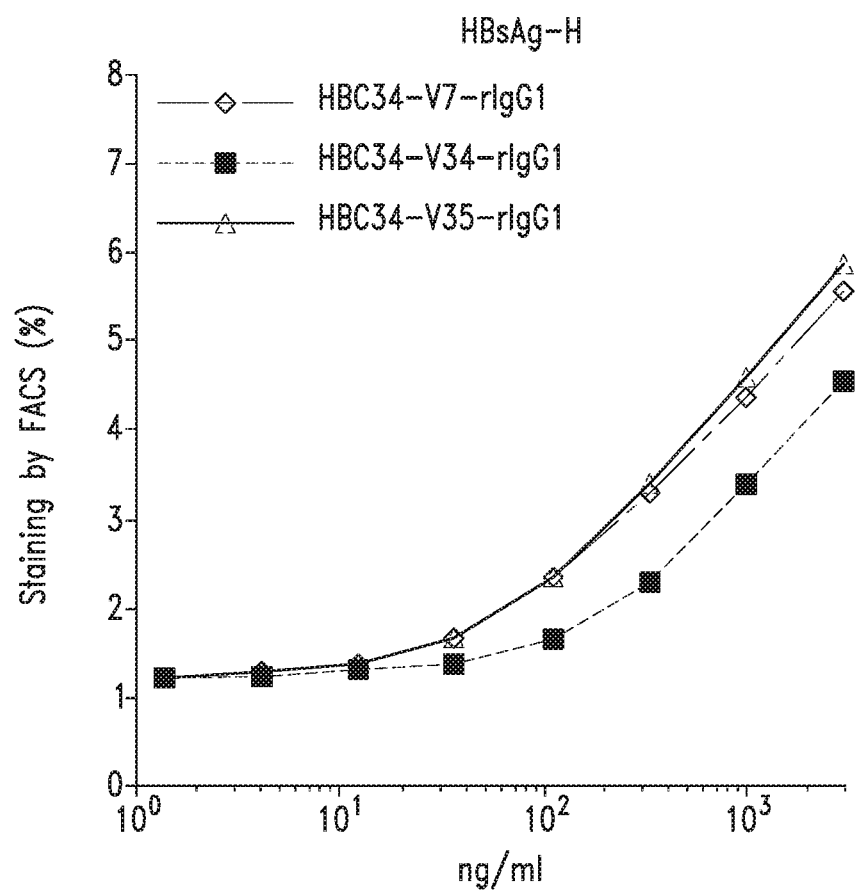
Figure 21:
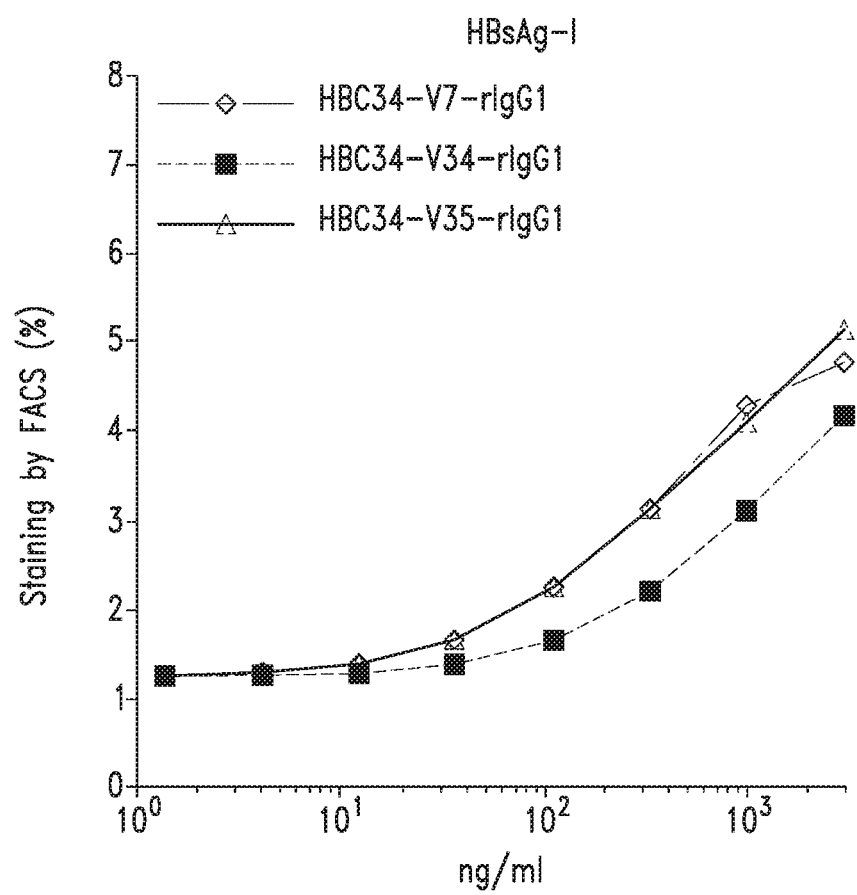
Figure 2J:
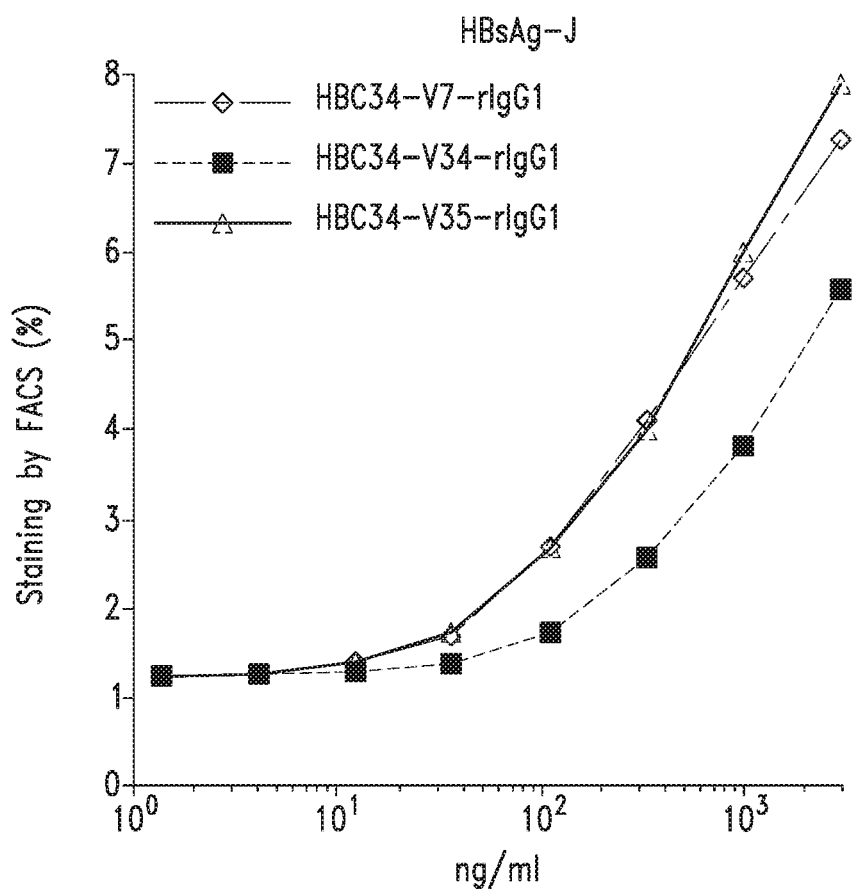
Figure 2K:
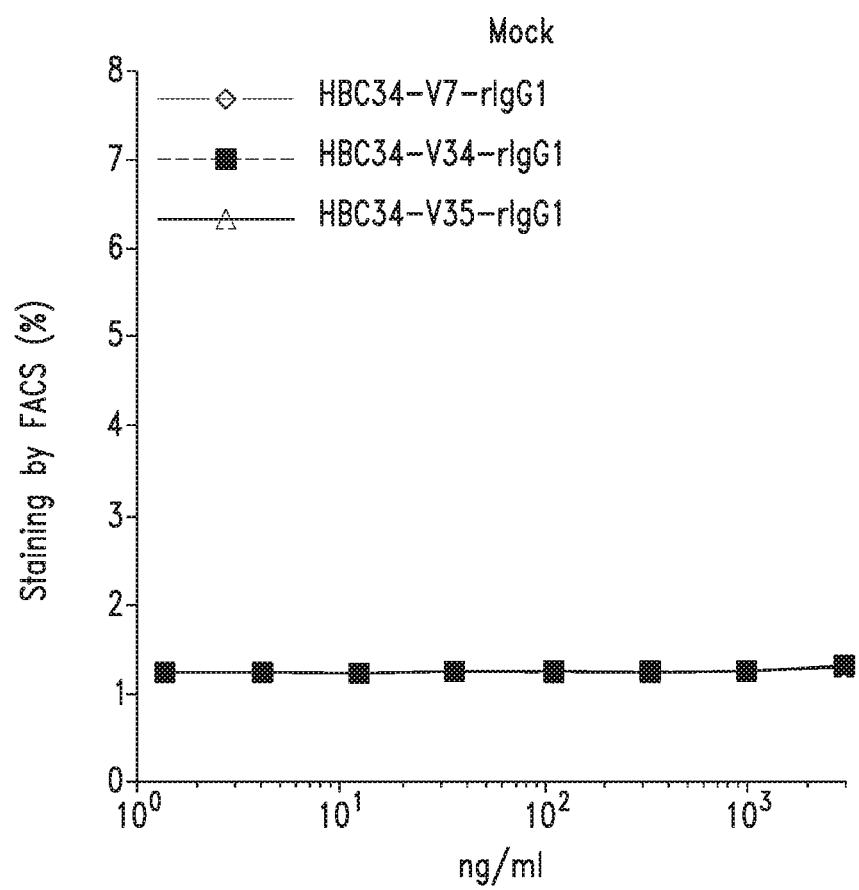

Unless defined otherwise, all technical and scientific terms used herein have the same meaning as commonly understood by one of ordinary skill in the art.

Throughout this disclosure, unless the context requires otherwise, the term "comprise," and variations thereof, such as "comprises," and "comprising," is used synonymously with, e.g. "having," "has," "including," "includes," or the like, and will be understood to imply the inclusion of a stated member, ratio, integer (including, where appropriate, a fraction thereof; e.g., one tenth and one hundredth of an integer), concentration, or step but not the exclusion of any other non-stated member, ratio, integer, concentration, or step. Any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. The term "consists of" refers to an embodiment of the term "comprise," wherein any other non-stated member, integer or step is excluded. In the context of the present disclosure, the term "comprise" encompasses the term "consist of". The term "consisting essentially of" is not equivalent to "comprising" and refers to the specified materials or steps of a claim, or to those that do not materially affect the basic characteristics of a claimed subject matter.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

The terms "a" and "an" and "the" and similar reference used in the context of describing the disclosure (including in the context of the claims) are to be construed to cover both the singular and the plural, unless otherwise indicated herein or clearly contradicted by context. The use of the alternative (e.g., "or") should be understood to mean either one, both, or any combination of the alternatives. Recitation of ranges of values herein is intended to serve as a shorthand method of referring individually to each separate value falling within the range. Unless otherwise indicated herein, each individual value is incorporated into the disclosure as if it were individually recited herein. No language in the specification should be construed as indicating any non-claimed element as essential to the practice of the subject matter disclosed herein.

The word "substantially" does not exclude "completely"; e.g., a composition which is "substantially free" from Y may be completely free from Y. In certain embodiments, "substantially" refers to a given amount, effect, or activity of a composition, method, or use of the present disclosure as compared to that of a reference composition, method, or use, and describes a reduction in the amount, effect, or activity of no more than 50%, such as no more than 40%, 30%, 25%, 20%, 15%, 10%, 5%, or 1%, or less, of the amount, effect, or activity of the reference composition, method, or use.

As used herein, the term "about" means±20% of the indicated range, value, or structure, unless otherwise indicated.

"Optional" or "optionally" means that the subsequently described element, component, event, or circumstance may or may not occur, and that the description includes instances in which the element, component, event, or circumstance occurs and instances in which they do not.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the affected human or animal to have a reduced duration or quality of life.

As used herein, reference to "treatment" of a subject or patient is intended to include prevention, prophylaxis, attenuation, amelioration and therapy. Benefits of treatment include improved clinical outcome; lessening or alleviation of symptoms associated with a disease; decreased occurrence of symptoms; improved quality of life; longer disease-free status; diminishment of extent of disease; stabilization of disease state; delay of disease progression; remission; survival; prolonged survival; or any combination thereof. The terms "subject" or "patient" are used interchangeably herein to mean all mammals, including humans. Examples of subjects include humans, cows, dogs, cats, horses, goats, sheep, pigs, and rabbits. In one embodiment, the patient is a human.

As used herein, "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid.

As used herein, the terms "peptide," "polypeptide," and "protein," and variations of these terms, refer to a molecule that comprises at least two amino acids joined to each other by a (normal or modified) peptide bond. For example, a peptide, polypeptide or protein may comprise or be composed of a plurality of amino acids selected from the 20 amino acids defined by the genetic code or an amino acid analog or mimetic, each being linked to at least one other by a peptide bond. A peptide, polypeptide or protein can comprise or be composed of L-amino acids and/or D-amino acids (or analogs or mimetics thereof). The terms "peptide", "polypeptide," "protein" also include "peptidomimetics" which are defined as peptide analogs containing non-peptidic structural elements, which peptides are capable of mimicking or antagonizing the biological action(s) of a natural parent peptide. In certain embodiments, a peptidomimetic lacks characteristics such as enzymatically scissile peptide bonds.

A peptide, polypeptide or protein may comprise amino acids other than the 20 amino acids defined by the genetic code in addition to these amino acids, or it can be composed of amino acids other than the 20 amino acids defined by the genetic code. In certain embodiments, a peptide, polypeptide or protein in the context of the present disclosure can comprise amino acids that are modified by natural processes, such as post-translational maturation processes, or by chemical processes (e.g., synthetic processes), which are known in the art and include those described herein. Such modifications can appear anywhere in the polypeptide; e.g., in the peptide skeleton; in the amino acid chain; or at the carboxy- or amino-terminal ends. A peptide or polypeptide can be branched, such as following an ubiquitination, or may be cyclic, with or without branching. The terms "peptide", "polypeptide", and "protein" also include modified peptides, polypeptides and proteins. For example, peptide, polypeptide or protein modifications can include acetylation, acylation, ADP-ribosylation, amidation, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, glycosylation including pegylation, hydroxylation, iodization, methylation, myristoylation, oxidation, proteolytic processes, phosphorylation, prenylation, racemization, seneloylation, sulfatation, amino acid addition such as arginylation or ubiquitination. Such modifications have been described in the literature (see Proteins Structure and Molecular Properties (1993) 2nd Ed., T. E. Creighton, New York; Post-translational Covalent Modifications of Proteins (1983) B. C. Johnson, Ed., Academic Press, New York; Seifter et al. (1990) Analysis for protein modifications and nonprotein cofactors, Meth. Enzymol. 182: 626-646 and Rattan et al., (1992) Protein Synthesis: Post-translational Modifications and Aging, Ann NY Acad Sci, 663: 48-62). Accordingly, the terms "peptide", "polypeptide", "protein" can include for example lipopeptides, lipoproteins, glycopeptides, glycoproteins and the like. Variants of proteins, peptides, and polypeptides of this disclosure are also contemplated. In certain embodiments, variant proteins, peptides, and polypeptides comprise or consist of an amino acid sequence that is at least 70%, 75%, 80%, 85%, 90%, 91%, 92%, 93%, 94%, 95%, 96%, 97%, 98%, 99%, or 99.9% identical to an amino acid sequence of a defined or reference amino acid sequence as described herein.

As used herein, "(poly)peptide" and "protein" may be used interchangeably in reference to a polymer of amino acid residues, such as a plurality of amino acid monomers linked by peptide bonds.

"Nucleic acid molecule" or "polynucleotide" or "nucleic acid" refers to a polymeric compound including covalently linked nucleotides, which can be made up of natural subunits (e.g., purine or pyrimidine bases) or non-natural subunits (e.g., morpholine ring). Purine bases include adenine, guanine, hypoxanthine, and xanthine, and pyrimidine bases include uracil, thymine, and cytosine. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, or the like.

Nucleic acid molecules include polyribonucleic acid (RNA), polydeoxyribonucleic acid (DNA), which includes cDNA, genomic DNA, and synthetic DNA, any of which may be single or double-stranded. If single-stranded, the nucleic acid molecule may be the coding strand or non-coding (anti-sense strand). Polynucleotides (including oligonucleotides), and fragments thereof may be generated, for example, by polymerase chain reaction (PCR) or by in vitro translation, or generated by any of ligation, scission, endonuclease action, or exonuclease action.

A nucleic acid molecule encoding an amino acid sequence includes all nucleotide sequences that encode the same amino acid sequence. Some versions of the nucleotide sequences may also include intron(s) to the extent that the intron(s) may be removed through co- or post-transcriptional mechanisms. Different nucleotide sequences may encode the same amino acid sequence as the result of the redundancy or degeneracy of the genetic code, or by splicing, or both.

Variants of nucleic acid molecules of this disclosure are also contemplated. Variant nucleic acid molecules are at least 70%, 75%, 80%, 85%, 90%, 95%, 96%, 97%, 98%, 99%, or 99.9% identical a nucleic acid molecule of a defined or reference polynucleotide as described herein, or that hybridize to a polynucleotide under stringent hybridization conditions of 0.015M sodium chloride, 0.0015M sodium citrate at about 65-68° C. or 0.015M sodium chloride, 0.0015M sodium citrate, and 50% formamide at about 42° C. Nucleic acid molecule variants retain the capacity to encode a fusion protein or a binding domain thereof having a functionality described herein, such as specifically binding a target molecule.

As used herein, the term "sequence variant" refers to any sequence having one or more alterations in comparison to a reference sequence, whereby a reference sequence is any published sequence and/or of the sequences listed in the "Table of Sequences and SEQ ID Numbers" (sequence listing), i.e. SEQ ID NO: 1 to SEQ ID NO: 139. Thus, the term "sequence variant" includes nucleotide sequence variants and amino acid sequence variants. In certain embodiments, a sequence variant in the context of a nucleotide sequence, the reference sequence is also a nucleotide sequence, whereas in certain embodiments for a sequence variant in the context of an amino acid sequence, the reference sequence is also an amino acid sequence. A "sequence variant" as used herein can be at least 80%, at least 85%, at least 90%, at least 91%, at least 92%, at least 93%, at least 94%, at least 95%, at least 96%, at least 97%, at least 98%, or at least 99% identical to the reference sequence.

"Percent sequence identity" refers to a relationship between two or more sequences, as determined by comparing the sequences. Methods to determine sequence identity can be designed to give the best match between the sequences being compared. For example, the sequences may be aligned for optimal comparison purposes (e.g., gaps can be introduced in one or both of a first and a second amino acid or nucleic acid sequence for optimal alignment). Further, non-homologous sequences may be disregarded for comparison purposes. The percent sequence identity referenced herein is calculated over the length of the reference sequence, unless indicated otherwise. Methods to determine sequence identity and similarity can be found in publicly available computer programs. Sequence alignments and percent identity calculations may be performed using a BLAST program (e.g., BLAST 2.0, BLASTP, BLASTN, or BLASTX). The mathematical algorithm used in the BLAST programs can be found in Altschul et al., Nucleic Acids Res. 25:3389-3402, 1997. Within the context of this disclosure, it will be understood that where sequence analysis software is used for analysis, the results of the analysis are based on the "default values" of the program referenced. "Default values" mean any set of values or parameters which originally load with the software when first initialized.

A "sequence variant" in the context of a nucleic acid (nucleotide) sequence has an altered sequence in which one or more of the nucleotides in the reference sequence is deleted, or substituted, or one or more nucleotides are inserted into the sequence of the reference nucleotide sequence. Nucleotides are referred to herein by the standard one-letter designation (A, C, G, or T). Due to the degeneracy of the genetic code, a "sequence variant" of a nucleotide sequence can either result in a change in the respective reference amino acid sequence, i.e. in an amino acid "sequence variant" or not. In certain embodiments, a nucleotide sequence variant does not result in an amino acid sequence variant (e.g., a silent mutation). In some embodiments, a nucleotide sequence variant that results in one or more "non-silent" mutation is contemplated. In some embodiments, a nucleotide sequence variant of the present disclosure encodes an amino acid sequence that is at least 80%, at least 85%, at least 90%, at least 91%, at least 92%, at least 93%, at least 94%, at least 95%, at least 96%, at least 97%, at least 98%, or at least 99% identical to a reference amino acid sequence. Nucleotide and amino sequences as disclosed herein refer also to codon-optimized versions of a reference or wild-type nucleotide or amino acid sequence. In any of the embodiments described herein, a polynucleotide of the present disclosure may be codon-optimized for a host cell containing the polynucleotide (see, e.g., Scholten et al., Clin. Immunol. 119:135-145 (2006). Codon optimization can be performed using known techniques and tools, e.g., using the GenScript® OptimumGene™ tool, or the GeneArt Gene Synthesis Tool (Thermo Fisher Scientific). Codon-optimized sequences include sequences that are partially codon-optimized (i.e., at least one codon is optimized for expression in the host cell) and those that are fully codon-optimized.

A "sequence variant" in the context of an amino acid sequence has an altered sequence in which one or more of the amino acids is deleted, substituted, or inserted in comparison to a reference amino acid sequence. As a result of the alterations, such a sequence variant has an amino acid sequence which is at least 80%, at least 85%, at least 90%, at least 91%, at least 92%, at least 93%, at least 94%, at least 95%, at least 96%, at least 97%, at least 98%, or at least 99% identical to the reference amino acid sequence. For example, per 100 amino acids of the reference sequence a variant sequence that has no more than 10 alterations, i.e. any combination of deletions, insertions or substitutions, is "at least 90% identical" to the reference sequence.

A "conservative substitution" refers to amino acid substitutions that do not significantly affect or alter binding characteristics of a particular protein. Generally, conservative substitutions are ones in which a substituted amino acid residue is replaced with an amino acid residue having a similar side chain. Conservative substitutions include a substitution found in one of the following groups: Group 1: Alanine (Ala or A), Glycine (Gly or G), Serine (Ser or S), Threonine (Thr or T); Group 2: Aspartic acid (Asp or D), Glutamic acid (Glu or Z); Group 3: Asparagine (Asn or N), Glutamine (Gln or Q); Group 4: Arginine (Arg or R), Lysine (Lys or K), Histidine (His or H); Group 5: Isoleucine (Ile or I), Leucine (Leu or L), Methionine (Met or M), Valine (Val or V); and Group 6: Phenylalanine (Phe or F), Tyrosine (Tyr or Y), Tryptophan (Trp or W). Additionally or alternatively, amino acids can be grouped into conservative substitution groups by similar function, chemical structure, or composition (e.g., acidic, basic, aliphatic, aromatic, or sulfur-containing). For example, an aliphatic grouping may include, for purposes of substitution, Gly, Ala, Val, Leu, and Ile. Other conservative substitutions groups include: sulfur-containing: Met and Cysteine (Cys or C); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information can be found in Creighton (1984) *Proteins*, W. H. Freeman and Company.

Amino acid sequence insertions can include amino- and/or carboxyl-terminal fusions ranging in length from one residue to polypeptides containing a hundred or more residues, as well as intrasequence insertions of single or multiple amino acid residues. Examples of terminal insertions include the fusion to the N- or C-terminus of an amino acid sequence to a reporter molecule or an enzyme.

In general, alterations in the sequence variants do not abolish or significantly reduce a desired functionality of the respective reference sequence. For example, it is preferred that a variant sequence of the present disclosure does not significantly reduce or completely abrogate the functionality of a sequence of an antibody, or antigen binding fragment thereof, to bind to the same epitope and/or to sufficiently neutralize infection of HBV and HDV as compared to antibody or antigen binding fragment having (or encoded by) the reference sequence. Guidance in determining which nucleotides and amino acid residues, respectively, may be substituted, inserted or deleted without abolishing a desired structure or functionality can be found by using, e.g., known computer programs.

As used herein, a nucleic acid sequence or an amino acid sequence "derived from" a designated nucleic acid, peptide, polypeptide or protein refers to the origin of the nucleic acid, peptide, polypeptide or protein. A nucleic acid sequence or amino acid sequence which is derived from a particular sequence may have an amino acid sequence that is essentially identical to that sequence or a portion thereof, from which it is derived, whereby "essentially identical" includes sequence variants as defined above. A nucleic acid sequence or amino acid sequence which is derived from a particular peptide or protein, may be derived from the corresponding domain in the particular peptide or protein. In this context, "corresponding" refers to possession of a same functionality or characteristic of interest. For example, an "extracellular domain" corresponds to another "extracellular domain" (of another protein), or a "transmembrane domain" corresponds to another "transmembrane domain" (of another protein). "Corresponding" parts of peptides, proteins and nucleic acids are thus easily identifiable to one of ordinary skill in the art. Likewise, a sequence "derived from" another (e.g., "source") sequence can be identified by one of ordinary skill in the art as having its origin in the source sequence.

A nucleic acid sequence or an amino acid sequence derived from another nucleic acid, peptide, polypeptide or protein may be identical to the starting nucleic acid, peptide, polypeptide or protein (from which it is derived). However, a nucleic acid sequence or an amino acid sequence derived from another nucleic acid, peptide, polypeptide or protein may also have one or more mutations relative to the starting nucleic acid, peptide, polypeptide or protein (from which it is derived), in particular a nucleic acid sequence or an amino acid sequence derived from another nucleic acid, peptide, polypeptide or protein may be a functional sequence variant as described above of the starting nucleic acid, peptide, polypeptide or protein (from which it is derived). For example, in a peptide/protein, one or more amino acid residues may be substituted with other amino acid residues, or one or more amino acid residue insertions or deletions may occur.

As used herein, the term "mutation" relates to a change in a nucleic acid sequence and/or in an amino acid sequence in comparison to a reference sequence, e.g. a corresponding genomic, wild type, or reference sequence. A mutation, e.g. in comparison to a reference genomic sequence, may be, for example, a (naturally occurring) somatic mutation, a spontaneous mutation, an induced mutation, e.g. induced by enzymes, chemicals or radiation, or a mutation obtained by site-directed mutagenesis (molecular biology methods for making specific and intentional changes in the nucleic acid sequence and/or in the amino acid sequence). Thus, the terms "mutation" or "mutating" shall be understood to also include physically making or inducing a mutation, e.g. in a nucleic acid sequence or in an amino acid sequence. A mutation includes substitution, deletion and insertion of one or more nucleotides or amino acids as well as inversion of several successive nucleotides or amino acids. To achieve a mutation in an amino acid sequence, a mutation may be introduced into the nucleotide sequence encoding said amino acid sequence in order to express a (recombinant) mutated polypeptide. A mutation may be achieved, for example, by altering (e.g., by site-directed mutagenesis) a codon (e.g., by alterning one, two, or three nucleotide bases therein) of a nucleic acid molecule encoding one amino acid to provide a codon that encodes a different amino acid, or that encodes a same amino acid, or by synthesizing a sequence variant.

The term "introduced" in the context of inserting a nucleic acid molecule into a cell, means "transfection", or "transformation" or "transduction" and includes reference to the incorporation of a nucleic acid molecule into a eukaryotic or prokaryotic cell wherein the nucleic acid molecule may be incorporated into the genome of a cell (e.g., chromosome, plasmid, plastid, or mitochondrial DNA), converted into an autonomous replicon, or transiently expressed (e.g., transfected mRNA).

The term "recombinant", as used herein (e.g. a recombinant antibody, a recombinant protein, a recombinant nucleic acid, or the like, refers to any molecule (antibody, protein, nucleic acid, or the like) which is prepared, expressed, created or isolated by recombinant means, and which is not naturally occurring. "Recombinant" can be used synonymously with "engineered" or "non-natural" and can refer to to an organism, microorganism, cell, nucleic acid molecule, or vector that includes at least one genetic alteration or has been modified by introduction of an exogenous nucleic acid molecule, wherein such alterations or modifications are introduced by genetic engineering (i.e., human intervention). Genetic alterations include, for example, modifications introducing expressible nucleic acid molecules encoding proteins, fusion proteins or enzymes, or other nucleic acid molecule additions, deletions, substitutions or other functional disruption of a cell's genetic material. Additional modifications include, for example, non-coding regulatory regions in which the modifications alter expression of a polynucleotide, gene or operon.

As used herein, "heterologous" or "non-endogenous" or "exogenous" refers to any gene, protein, compound, nucleic acid molecule, or activity that is not native to a host cell or a subject, or any gene, protein, compound, nucleic acid molecule, or activity native to a host cell or a subject that has been altered. Heterologous, non-endogenous, or exogenous includes genes, proteins, compounds, or nucleic acid molecules that have been mutated or otherwise altered such that the structure, activity, or both is different as between the native and altered genes, proteins, compounds, or nucleic acid molecules. In certain embodiments, heterologous, non-endogenous, or exogenous genes, proteins, or nucleic acid molecules may not be endogenous to a host cell or a subject, but instead nucleic acids encoding such genes, proteins, or nucleic acid molecules may have been added to a host cell by conjugation, transformation, transfection, electroporation, or the like, wherein the added nucleic acid molecule may integrate into a host cell genome or can exist as extra-chromosomal genetic material (e.g., as a plasmid or other self-replicating vector). The term "homologous" or "homolog" refers to a gene, protein, compound, nucleic acid molecule, or activity found in or derived from a host cell, species, or strain. For example, a heterologous or exogenous polynucleotide or gene encoding a polypeptide may be homologous to a native polynucleotide or gene and encode a homologous polypeptide or activity, but the polynucleotide or polypeptide may have an altered structure, sequence, expression level, or any combination thereof. A non-endogenous polynucleotide or gene, as well as the encoded polypeptide or activity, may be from the same species, a different species, or a combination thereof.

As used herein, the term "endogenous" or "native" refers to a polynucleotide, gene, protein, compound, molecule, or activity that is normally present in a host cell or a subject.

As used herein, the terms "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same or substantially the same function, phenotype, or biological activity as screened for in the originally transformed cell are included. Where distinct designations are intended, it will be clear from the context.

The present disclosure provides, in part, on antibodies, antigen binding fragments, and fusion proteins that are capable of neutralizing hepatitis B and hepatitis delta viruses. Embodiments of the antibodies, antigen binding fragments, and fusion proteins according to the present description may be used in methods of preventing, treating, or attenuating, or diagnosing HBV and HDV. In particular embodiments, the antibodies, antigen binding fragments, and fusion proteins described herein bind to two or more different genotypes of hepatitis B virus surface antigen and to two or more different infectious mutants of hepatitis B virus surface antigen. In specific embodiments, the antibodies, antigen binding fragments, and fusion proteins described herein bind to all known genotypes of hepatitis B virus surface antigen and to all known infectious mutants of hepatitis B virus surface antigen.

Antibodies and Antigen-Binding Fragments

In one aspect, the present disclosure provides an isolated antibody, or an antigen binding fragment thereof, that is capable of binding to the antigenic loop region of HBsAg and is capable of neutralizing infection with hepatitis B virus and hepatitis delta virus.

As used herein, and unless the context clearly indicates otherwise, "antibody" refers to an intact antibody comprising at least two heavy (H) chains and two light (L) chains inter-connected by disulfide bonds (though it will be understood that heavy chain antibodies, which lack light chains, are still encompassed by the term "antibody"), as well as any antigen-binding portion or fragment of an intact antibody that has or retains the ability to bind to the antigen target molecule recognized by the intact antibody, such as, for example, a scFv, Fab, or F(ab')2 fragment. Thus, the term "antibody" herein is used in the broadest sense and includes polyclonal and monoclonal antibodies, including intact antibodies and functional (antigen-binding) antibody fragments thereof, including fragment antigen-binding (Fab) fragments, F(ab')2 fragments, Fab' fragments, FIT fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class thereof, including IgG and sub-classes thereof, IgM, IgE, IgA, and IgD.

As used herein, the terms "antigen binding fragment," "fragment," and "antibody fragment" are used interchangeably to refer to any fragment of an antibody of the disclosure that retains the antigen-binding activity of the antibody. Examples of antibody fragments include, but are not limited to, a single chain antibody, Fab, Fab', F(ab')$_2$, Fv or scFv.

Human antibodies are known (e.g., van Dijk, M. A., and van de Winkel, J. G., *Curr. Opin. Chem. Biol.* 5 (2001) 368-374). Human antibodies can be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., *Proc. Natl. Acad. Sci. USA* 90 (1993) 2551-2555; Jakobovits, A., et al., Nature 362 (1993) 255-258; Bruggemann, M., et al., *Year Immunol.* 7 (1993) 3340). Human antibodies can also be produced in phage display libraries (Hoogenboom, H. R., and Winter, G., *J. Mol. Biol.* 227 (1992) 381-388; Marks, J. D., et al., *J. Mol. Biol.* 222 (1991) 581-597). The techniques of Cole et al. and Boerner et al. are also available for the preparation of human monoclonal antibodies (Cole et al., *Monoclonal Antibodies and Cancer Therapy*, Alan R. Liss, p. 77 (1985); and Boerner, P., et al., J. Immunol. 147 (1991) 86-95). Human monoclonal antibodies may be prepared by using improved EBV-B cell immortalization as described in Traggiai E, Becker S, Subbarao K, Kolesnikova L, Uematsu Y, Gismondo M R, Murphy B R, Rappuoli R, Lanzavecchia A. (2004): An efficient method to make human monoclonal antibodies from memory B cells: potent neutralization of SARS coronavirus. Nat Med. 10(8):871-5. The term "human antibody" as used herein also comprises such antibodies which are modified, e.g., in the variable region, to generate properties according to the antibodies and antibody fragments of the present disclosure.

As used herein, the term "variable region" (variable region of a light chain ($V_L$), variable region of a heavy chain ($V_H$)) denotes each variable region polypeptide of the pair of light and heavy chains which, in most instances, is involved directly in binding the antibody to the antigen.

Antibodies according to the present disclosure can be of any isotype (e.g., IgA, IgG, IgM, IgE, IgD; i.e., comprising a α, γ, μ, ε, or δ heavy chain). Within the IgG isotype, for example, antibodies may be IgG1, IgG2, IgG3 or IgG4 subclass. In specific embodiments, an antibody of the present disclosure is an IgG1 antibody. Antibodies or antigen binding fragments provided herein may include a κ or a λ light chain. In certain embodiments, HBsAg-specific antibodies described herein are of the IgG isotype and may block the release of HBV and HBsAg from infected cells. Accordingly, in certain embodiments, an antibody according to the present description can bind intracellularly and thereby block the release of HBV virions and HBsAg.

The terms "VL" and "VH" refer to the variable binding region from an antibody light and heavy chain, respectively. The variable binding regions are made up of discrete, well-defined sub-regions known as "complementarity determining regions" (CDRs) and "framework regions" (FRs). The terms "complementarity determining region" and "CDR" are synonymous with "hypervariable region" or "HVR," and are known in the art to refer to sequences of amino acids within TCR or antibody variable regions, which confer antigen specificity and/or binding affinity and are separated by framework sequence. In general, there are three CDRs in each variable region of an immunoglobulin binding protein; e.g., for antibodies, the VH and VL regions comprise six CDRs HCDR1, HCDR2, HCDR3; LCDR1, LCDR2, LCDR3; also referred to herein as CDRH1, CDRH2, CDRH3, CDRL1, CDRL2, and CDRL3, respectively). As used herein, a "variant" of a CDR refers to a functional variant of a CDR sequence having up to 1-3 amino acid substitutions, deletions, or combinations thereof.

Immunoglobulin sequences can be aligned to a numbering scheme (e.g., Kabat, E U, International Immunogenetics Information System (IMGT) and Aho), which can allow equivalent residue positions to be annotated and for different molecules to be compared using Antigen receptor Numbering And Receptor Classification (ANARCI) software tool (2016, Bioinformatics 15:298-300). It will be understood that in certain embodiments, an antibody or antigen binding fragment of the present disclosure can comprise all or part of a heavy chain (HC), a light chain (LC), or both. For example, a full-length intact IgG antibody monomer typically includes a VH, a CH1, a CH2, a CH3, a VL, and a CL. Fc components are described further herein. In certain embodiments, an antibody or antigen binding fragment of the present disclosure comprises a CDRH1, a CDRH2, a CDRH3, a CDRL1, a CDRL2, and a CDRL3 according to any one of the presently disclosed VH and VL sequences, respectively.

Table 1 shows the amino acid sequences of heavy chain variable regions (VH), light chain variable regions (VL), CDRs, heavy chains (HC), and light chains (LC) of certain exemplary antibodies according to the present disclosure.

| Antibody sequence description | SEQ ID NO: | Amino acid sequence |
|---|---|---|
| HBC34-V35 VH,<br>HBC34-V34 VH,<br>HBC23-LC40A VH,<br>HBC23-LC40S VH,<br>HBC34-LC40A VH,<br>HBC34-LC40S VH | 41 | ELQLVESGGGWVQPGGSQRLSCAAS<br>GRIFRSFYMSWVRQAPGKGLEWVATI<br>NQDGSEKLYVDSVKGRFTISRDNAKN<br>SLFLQMNNLRVEDTAVYYCAAWSGN<br>SGGMDVWGQGTTVSVSS |
| HBC34v31_LC40A VH<br>HBC34v31_LC40S VH<br>HBC34v32_LC40A VH<br>HBC34v32_LC40S VH<br>HBC34v33_LC40A VH<br>HBC34v32_LC40S VH | 67 | EVQLVESGGGLVQPGGSLRLSCAASG<br>RIFRSFYMSWVRQAPGKGLEWVANIN<br>QDGSEKLYVDSVKGRFTISRDNAKNS<br>LFLQMNNLRVEDTAVYYCAAWSGNS<br>GGMDVWGQGTTVTVSS |
| HBC34-V35 VL | 89 | SYELTQPPSVSVSPGQTVSIPCSGDKL<br>GNKNVAWFQHKPGQSPVLVIYEVKY<br>RPSGIPERFSGSNSGNTATLTISGTQA<br>MDEAAYFCQTFDSTTVVFGGGTRLTV<br>L |
| HBC34-V34 VL | 90 | SYELTQPPSVSVSPGQTVSIPCSGDKL<br>GNKNVSWFQHKPGQSPVLVIYEVKY<br>RPSGIPERFSGSNSGNTATLTISGTQA<br>MDEAAYFCQTFDSTTVVFGGGTRLTV<br>L |
| HBC34-V23-VL_C40S | 110 | SYELTQPPSVSVSPGQTASITCSGDKL<br>GNKNASWYQQKPGQSPVLVIYEVKY<br>RPSGIPERFSGSNSGNTATLTISGTQA<br>MDEADYYCQTFDSTTVVFGGGTKLT<br>VL |
| HBC34-V23-VL_C40A | 111 | SYELTQPPSVSVSPGQTASITCSGDKL<br>GNKNAAWYQQKPGQSPVLVIYEVKY<br>RPSGIPERFSGSNSGNTATLTISGTQA<br>MDEADYYCQTFDSTTVVFGGGTKLT<br>VL |
| HBC34-V31-VL_C40S | 112 | SYELTQPPSVSVSPGQTVSIPCSGDKL<br>GNKNVSWFQHKPGQSPVLVIYEVKY<br>RPSGIPERFSGSNSGNTATLTISGTQA<br>MDEAAYFCQTWDSTTVVFGGGTRLT<br>VL |
| HBC34-V31-VL_C40A | 113 | SYELTQPPSVSVSPGQTVSIPCSGDKL<br>GNKNVAWFQHKPGQSPVLVIYEVKY<br>RPSGIPERFSGSNSGNTATLTISGTQA<br>MDEAAYFCQTWDSTTVVFGGGTRLT<br>VL |
| HBC34-V32-VL_C40S | 114 | SYELTQPPSVSVSPGQTVSIPCSGDKL<br>GNKNVSWFQHKPGQSPVLVIYEVKY<br>RPSGIPERFSGSNSGNTATLTISGTQA |

-continued

| Antibody sequence description | SEQ ID NO: | Amino acid sequence |
|---|---|---|
| | | MDEAAYFCQTFDSTTVVFGGGTRLTV L |
| HBC34-V32-VL_C40A | 115 | SYELTQPPSVSVSPGQTVSIPCSGDKL GNKNVAWFQHKPGQSPVLVIYEVKY RPSGIPERFSGSNSGNTATLTISGTQA MDEAAYFCQTFDSTTVVFGGGTRLTV L |
| HBC34-V33-VL_C40S | 116 | SYELTQPPSVSVSPGQTASITCSGDKL GNKNASWYQQKPGQSPVLVIYEVKY RPSGIPERFSGSNSGNTATLTISGTQA MDEADYYCQTFDSTTVVFGGGTKLT VL |
| HBC34-V33-VL_C40A | 117 | SYELTQPPSVSVSPGQTASITCSGDKL GNKNAAWYQQKPGQSPVLVIYEVKY RPSGIPERFSGSNSGNTATLTISGTQA MDEADYYCQTFDSTTVVFGGGTKLT VL |
| HBC34-VL_C40S | 118 | SYELTQPPSVSVSPGQTVSIPCSGDKL GNKNVSWFQHKPGQSPVLVIYEVKY RPSGIPERFSGSNSGNTATLTISGTQA MDEAAYFCQTWDSTTVVFGGGTRLT VL |
| HBC34-VL_C40A | 119 | SYELTQPPSVSVSPGQTVSIPCSGDKL GNKNVAWFQHKPGQSPVLVIYEVKY RPSGIPERFSGSNSGNTATLTISGTQA MDEAAYFCQTWDSTTVVFGGGTRLT VL |
| HBC34-V35 CDRH1, HBC34-V34 CDRH1, HBC34-V23_LC40S CDRH1, HBC34-V23_LC40A CDRH1, HBC34-V31_LC40S CDRH1, HBC34-V31_LC40A CDRH1, HBC34-V32_LC40S CDRH1, HBC34-V32_LC40A CDRH1, HBC34-V33_LC40S CDRH1, HBC34-V3_LC40A CDRH1, HBC34_LC40S CDRH1, HBC34_LC40A CDRH1 | 34 | GRIFRSFY |
| HBC34-V35 CDRH2, HBC34-V34 CDRH2, HBC34-V23_LC40S CDRH2, HBC34-V23_LC40A CDRH2, HBC34-V31_LC40S CDRH2, HBC34-V31_LC40A CDRH2, HBC34-V32_LC40S CDRH2, HBC34-V32_LC40A CDRH2, HBC34-V33_LC40S CDRH2, HBC34-V33_LC40A CDRH2, HBC34_LC40S CDRH2, HBC34_LC40A CDRH2 (short CDRH2) | 35 | NQDGSEK |
| HBC34-V35 CDRH2, HBC34-V34 CDRH2, HBC34-V23_LC40S CDRH2, HBC34-V23_LC40A CDRH2, HBC34-V31_LC40S CDRH2, HBC34-V31_LC40A CDRH2, HBC34-V32_LC40S CDRH2, HBC34-V32_LC40A CDRH2, HBC34-V33_LC40S CDRH2, HBC34-V33_LC40A CDRH2, HBC34_LC40S CDRH2, HBC34_LC40A CDRH2 (long CDRH2) | 66 | INQDGSEK |
| HBC34-V35 CDRH3, HBC34-V34 CDRH3, | 36 | AAWSGNSGGMDV |

-continued

| Antibody sequence description | SEQ ID NO: | Amino acid sequence |
|---|---|---|
| HBC34-V23_LC40S CDRH3,<br>HBC34-V23_LC40A CDRH3,<br>HBC34-V31_LC40S CDRH3,<br>HBC34-V31_LC40A CDRH3,<br>HBC34-V32_LC40S CDRH3,<br>HBC34-V32_LC40A CDRH3,<br>HBC34-V33_LC40S CDRH3,<br>HBC34-V33_LC40A CDRH3,<br>HBC34_LC40S CDRH3,<br>HBC34_LC40A CDRH3 | | |
| HBC34-V35 CDRL1,<br>HBC34-V34 CDRL1,<br>HBC34-V23_LC40S CDRL1,<br>HBC34-V23_LC40A CDRL1,<br>HBC34-V31_LC40S CDRL1,<br>HBC34-V31_LC40A CDRL1,<br>HBC34-V32_LC40S CDRL1,<br>HBC34-V32_LC40A CDRL1,<br>HBC34-V33_LC40S CDRL1,<br>HBC34-V33_LC40A CDRL1,<br>HBC34_LC40S CDRL1,<br>HBC34_LC40A CDRL1 | 37 | KLGNKN |
| HBC34-V35 CDRL2,<br>HBC34-V34 CDRL2,<br>HBC34-V23_LC40S CDRL2,<br>HBC34-V23_LC40A CDRL2,<br>HBC34-V31_LC40S CDRL2;<br>HBC34-V31_LC40A CDRL2;<br>HBC34-V32_LC40S CDRL2;<br>HBC34-V32_LC40A CDRL2;<br>HBC34-V33_LC40S CDRL2;<br>HBC34-V33_LC40A CDRL2;<br>HBC34_LC40S CDRL2;<br>HBC34_LC40A CDRL2<br>(short CDRL2) | 38 | EVK |
| HBC34-V35 CDRL2;<br>HBC34-V34 CDRL2;<br>HBC34-V23_LC40S CDRL2;<br>HBC34-V23_LC40A CDRL2;<br>HBC34-V31_LC40S CDRL2;<br>HBC34-V31_LC40A CDRL2;<br>HBC34-V32_LC40S CDRL2;<br>HBC34-V32_LC40A CDRL2;<br>HBC34-V33_LC40S CDRL2;<br>HBC34-V33_LC40A CDRL2;<br>HBC34_LC40S CDRL2;<br>HBC34_LC40A CDRL2<br>(long LCDR2) | 39 | VIYEVKYRP |
| HBC34-V35 CDRL3;<br>HBC34-V34 CDRL3;<br>HBC34-V23_LC40S CDRL3;<br>HBC34-V23_LC40A CDRL3;<br>HBC34-V32_LC40S CDRL3;<br>HBC34-V32_LC40A CDRL3;<br>HBC34-V33_LC40S CDRL3;<br>HBC34-V33_LC40A CDRL3; | 58 | QTFDSTTVV |
| HBC34_LC40S CDRL3;<br>HBC34_LC40A CDRL3;<br>HBC34-V31_LC40S CDRL3;<br>HBC34-V31_LC40A CDRL3; | 40 | QTWDSTTVV |
| HC of HBC34-V35-MLNS-<br>GAALIE and HBC34-V34-<br>MLNS-GAALIE (g1M17, 1) | 91 | ELQLVESGGGWVQPGGSQRLSCAAS<br>GRIFRSFYMSWVRQAPGKGLEWVATI<br>NQDGSEKLYVDSVKGRFTISRDNAKN<br>SLFLQMNNLRVEDTAVYYCAAWSGN<br>SGGMDVWGQGTTVSVSSASTKGPSV<br>FPLAPSSKSTSGGTAALGCLVKDYFPE<br>PVTVSWNSGALTSGVHTFPAVLQSSG<br>LYSLSSVVTVPSSSLGTQTYICNVNHK<br>PSNTKVDKKVEPKSCDKTHTCPPCPA<br>PELLAGPSVFLFPPKPKDTLMISRTPEV |

-continued

| Antibody sequence description | SEQ ID NO: | Amino acid sequence |
|---|---|---|
| | | TCVVVDVSHEDPEVKFNWYVDGVEV HNAKTKPREEQYNSTYRVVSVLTVLH QDWLNGKEYKCKVSNKALPLPEEKTI SKAKGQPREPQVYTLPPSRDELTKNQ VSLTCLVKGFYPSDIAVEWESNGQPE NNYKTTPPVLDSDGSFFLYSKLTVDK SRWQQGNVFSCSVLHEALHSHYTQKS LSLSPGK |
| HC of HBC34-V35-MLNS and HBC34-V34-MLNS | 92 | ELQLVESGGGWVQPGGSQRLSCAAS GRIFRSFYMSWVRQAPGKGLEWVATI NQDGSEKLYVDSVKGRFTISRDNAKN SLFLQMNNLRVEDTAVYYCAAWSGN SGGMDVWGQGTTVSVSSASTKGPSV FPLAPSSKSTSGGTAALGCLVKDYFPE PVTVSWNSGALTSGVHTFPAVLQSSG LYSLSSVVTVPSSSLGTQTYICNVNHK PSNTKVDKKVEPKSCDKTHTCPPCPA PELLGGPSVFLFPPKPKDTLMISRTPEV TCVVVDVSHEDPEVKFNWYVDGVEV HNAKTKPREEQYNSTYRVVSVLTVLH QDWLNGKEYKCKVSNKALPAPIEKTI SKAKGQPREPQVYTLPPSRDELTKNQ VSLTCLVKGFYPSDIAVEWESNGQPE NNYKTTPPVLDSDGSFFLYSKLTVDK SRWQQGNVFSCSVLHEALHSHYTQKS LSLSPGK |
| LC of HBC34-V35 | 93 | SYELTQPPSVSVSPGQTVSIPCSGDKL GNKNVAWFQHKPGQSPVLVIYEVKY RPSGIPERFSGSNSGNTATLTISGTQA MDEAAYFCQTFDSTTVVFGGGTRLTV LGQPKAAPSVTLFPPSSEELQANKATL VCLISDFYPGAVTVAWKADSSPVKAG VETTTPSKQSNNKYAASSYLSLTPEQ WKSHRSYSCQVTHEGSTVEKTVAPTE CS |
| LC of HBC34-V34 | 94 | SYELTQPPSVSVSPGQTVSIPCSGDKL GNKNVSWFQHKPGQSPVLVIYEVKY RPSGIPERFSGSNSGNTATLTISGTQA MDEAAYFCQTFDSTTVVFGGGTRLTV LGQPKAAPSVTLFPPSSEELQANKATL VCLISDFYPGAVTVAWKADSSPVKAG VETTTPSKQSNNKYAASSYLSLTPEQ WKSHRSYSCQVTHEGSTVEKTVAPTE CS |
| HBC24 VH | 95 | EVQLLESGGGLVQPGGSLRLSCAASG STFTKYAMSWVRQAPGKGLEWVASI SGSVPGFGIDTYYADSVKGRFTISRDT SKNTLYLQMNSLRAEDTALYYCAKD VGVIGSYYYYAMDVWGQGTAVTVSS |
| HBC24 VL | 96 | EIVLTQSPGTLSLSPGERATLSCRASQ GLSSSYLAWYQQKPGQAPRLLIYSAS TRATGIPDRFSGSGSGTDFTLTISRLEP EDFAVYYCQQYAYSPRWTFGQGTKV EIK |
| HBC24 CDRH1 | 97 | GSTFTKYA |
| HBC24 CDRH2 | 98 | ISGSVPGF |
| HBC24 CDRH3 | 99 | LYYCAKDVGVIGSYYYYAMDV |
| HBC24 CDRL1 | 100 | QGLSSSY |
| HBC24 CDRL2 | 101 | SAS |
| HBC24 CDRL3 | 102 | QQYAYSPRWT |
| HBC34-V7, HBC34-V34, HBC34-V35 HC (VH-hinge-CH1-CH2-CH3) (wild-type) | 129 | ELQLVESGGGWVQPGGSQRLSCAAS GRIFRSFYMSWVRQAPGKGLEWVATI NQDGSEKLYVDSVKGRFTISRDNAKN SLFLQMNNLRVEDTAVYYCAAWSGN SGGMDVWGQGTTVSVSSASTKGPSV |

| Antibody sequence description | SEQ ID NO: | Amino acid sequence |
|---|---|---|
| | | FPLAPSSKSTSGGTAALGCLVKDYFPE
PVTVSWNSGALTSGVHTFPAVLQSSG
LYSLSSVVTVPSSSLGTQTYICNVNHK
PSNTKVDKKVEPKSCDKTHTCPPCPA
PELLGGPSVFLFPPKPKDTLMISRTPEV
TCVVVDVSHEDPEVKFNWYVDGVEV
HNAKTKPREEQYNSTYRVVSVLTVLH
QDWLNGKEYKCKVSNKALPAPIEKTI
SKAKGQPREPQVYTLPPSRDELTKNQ
VSLTCLVKGFYPSDIAVEWESNGQPE
NNYKTTPPVLDSDGSFFLYSKLTVDK
SRWQQGNVFSCSVMHEALHNHYTQK
SLSLSPGK |
| WT hIgG1 Fc | 137 | APELLGGPSVFLFPPKPKDTLMISRTPE
VTCVVVDVSHEDPEVKFNWYVDGVE
VHNAKTKPREEQYNSTYRVVSVLTVL
HQDWLNGKEYKCKVSNKALPAPIEK
TISKAKGQPREPQVYTLPPSRDELTKN
QVSLTCLVKGFYPSDIAVEWESNGQP
ENNYKTTPPVLDSDGSFFLYSKLTVD
KSRWQQGNVFSCSVMHEALHNHYTQ
KSLSLSPGK |
| HBC34-V7,
HBC34-V23,
HBC34-V34,
HBC34-V35,
HBC34_C40S,
HBC34_C40A,
HBC34-V23_C40S,
HBC34-V23_C40A
HC with GAALIE mutation in hIgG1 Fc | 138 | ELQLVESGGGWVQPGGSQRLSCAAS
GRIFRSFYMSWVRQAPGKGLEWVATI
NQDGSEKLYVDSVKGRFTISRDNAKN
SLFLQMNNLRVEDTAVYYCAAWSGN
SGGMDVWGQGTTVSVSSASTKGPSV
FPLAPSSKSTSGGTAALGCLVKDYFPE
PVTVSWNSGALTSGVHTFPAVLQSSG
LYSLSSVVTVPSSSLGTQTYICNVNHK
PSNTKVDKKVEPKSCDKTHTCPPCPA
PELLAGPSVFLFPPKPKDTLMISRTPEV
TCVVVDVSHEDPEVKFNWYVDGVEV
HNAKTKPREEQYNSTYRVVSVLTVLH
QDWLNGKEYKCKVSNKALPLPEEKTI
SKAKGQPREPQVYTLPPSRDELTKNQ
VSLTCLVKGFYPSDIAVEWESNGQPE
NNYKTTPPVLDSDGSFFLYSKLTVDK
SRWQQGNVFSCSVMHEALHNHYTQK
SLSLSPGK |

Fragments of the antibodies described herein can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. The present disclosure encompasses single-chain Fv fragments (scFv) derived from the heavy and light chains of an antibody as described herein, including, for example, an scFv comprising the CDRs from an antibody according to the present description, heavy or light chain monomers and dimers, single domain heavy chain antibodies, single domain light chain antibodies, as well as single chain antibodies, in which the heavy and light chain variable domains are joined by a peptide linker.

In certain embodiments, an antibody according to the present disclosure, or an antigen binding fragment thereof, comprises a purified antibody, a monoclonal antibody, a single chain antibody, Fab, Fab', F(ab')2, Fv or scFv.

Antibodies and antigen binding fragments of the present disclosure may, in embodiments, be multispecific (e.g., bispecific, trispecific, tetraspecific, or the like), and may be provided in any multispecific format, as disclosed herein. In certain embodiments, an antibody or antigen-binding fragment of the present disclosure is a multispecific antibody, such as a bispecific or trispecific antibody. Formats for bispecific antibodies are disclosed in, for example, Spiess et al., Mol. Immunol. 67(2):95 (2015), and in Brinkmann and Kontermann, mAbs 9(2):182-212 (2017), which bispecific formats and methods of making the same are incorporated herein by reference and include, for example, Bispecific T cell Engagers (BiTEs), DARTs, Knobs-Into-Holes (KIH) assemblies, scFv-CH3-KIH assemblies, KIH Common Light-Chain antibodies, TandAbs, Triple Bodies, TriBi Minibodies, Fab-scFv, scFv-CH-CL-scFv, F(ab')2-scFv2, tetravalent HCabs, Intrabodies, CrossMabs, Dual Action Fabs (DAFs) (two-in-one or four-in-one), DutaMabs, DT-IgG, Charge Pairs, Fab-arm Exchange, SEEDbodies, Triomabs, LUZ-Y assemblies, Fcabs, κλ-bodies, orthogonal Fabs, DVD-IgGs, IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, Zybody, and DVI-IgG (four-in-one). A bispecific or multispecific antibody may comprise a HBV- and/or HDV-specific binding domain of the instant disclosure in combination with another HBV- and/or HDV-specific binding domain of the instant disclosure, or in combination with a different binding domain that specifically binds to HBV and/or HDV (e.g., at a same or a different epitope), or with a binding domain that specifically binds to a different antigen.

Antibody fragments of the disclosure may impart monovalent or multivalent interactions and be contained in a variety of structures as described above. For instance, scFv molecules may be synthesized to create a trivalent "triabody" or a tetravalent "tetrabody". The scFv molecules may include a domain of the Fc region resulting in bivalent minibodies. In addition, the sequences of the disclosure may be a component of multispecific molecules in which the sequences of the disclosure target the epitopes of the disclosure and other regions of the molecule bind to other targets. Exemplary molecules include, but are not limited to, bispecific Fab2, trispecific Fab3, bispecific scFv, and diabodies (Holliger and Hudson, 2005, *Nature Biotechnology* 9: 1126-1136).

Antibodies or antigen-binding fragments thereof such as those described herein, including but not limited to scFv, may, in certain embodiments, be comprised in a fusion protein that is capable of specifically binding to an antigen as described herein. As used herein, "fusion protein" refers to a protein that, in a single chain, has at least two distinct domains or motifs, wherein the domains or motifs are not naturally found together, or in the given arrangement, in a protein. A polynucleotide encoding a fusion protein may be constructed using PCR, recombinantly engineered, or the like, or such fusion proteins can be synthesized.

In some embodiments, a fusion protein is capable of expression at a surface of a host cell, e.g., a T cell, NK cell, or NK-T cell. In certain embodiments, a fusion protein comprises (i) an extracellular component comprising the antibody or antigen binding fragment thereof (e.g., a scFv); (ii) a transmembrane component (e.g., a transmembrane domain from CD4, CD8, CD27, CD28, or a functional variant or portion thereof, or any combination thereof); and (iii) an intracellular component comprising a signaling domain from a costimulatory protein, or a functional variant or portion thereof (e.g., a signaling domain from from CD27, CD28, 4-1BB (CD137), OX40 (CD134), CD2, CD5, ICAM-1 (CD54), LFA-1 (CD11a/CD18), ICOS (CD278), GITR, CD30, CD40, BAFF-R, HVEM, LIGHT, MKG2C, SLAMF7, NKp80, CD160, B7-H3, a ligand that specifically binds with CD83, or a functional variant thereof, or any combination thereof), and/or an effector domain (e.g., from CD3ε, CD3δ, CD3ζ, CD25, CD79A, CD79B, CARD11, DAP10, FcRα, FcRβ, FcRγ, Fyn, HVEM, ICOS, Lck, LAG3, LAT, LRP, NKG2D, NOTCH1, NOTCH2, NOTCH3, NOTCH4, Wnt, ROR2, Ryk, SLAMF1, Slp76, pTα, TCRα, TCRβ, TRIM, Zap70, PTCH2, or any combination thereof).

In certain embodiments, a fusion protein comprising an antibody or antigen binding fragment comprises a chimeric antigen receptor molecule (CAR), which may be expressed on a cell surface of a host cell such as a T cell, a NK cell, or a NK-T cell for use in a cellular immunotherapy. CAR molecules and principles of design are described in, for example: Sadelain et al., Cancer Discov., 3(4):388 (2013); Harris and Kranz, Trends Pharmacol. Sci., 37(3):220 (2016); Stone et al., Cancer Immunol. Immunother., 63(11):1163 (2014); Xu et al., 2018 Oncotarget 9:13991; Androulla et al., 2018 Curr. Pharm. Biotechnol. Volume 19 (April 2018); Wu et al., 2016 Expert Opin. Biol. Ther. 16:1469; Ren et al., 2017 Protein Cell 8:634; which CAR molecules, CAR designs, and CAR design principles are herein incorporated by reference in their entirety.

Throughout this disclosure, antibodies, antigen binding fragments thereof, and fusion proteins may individually or collectively (e.g., in any combination) be referred to as "binding proteins"

Binding proteins according to the present disclosure may be provided in purified form. For example, an antibody may be present in a composition that is substantially free of other polypeptides e.g., where less than 90% (by weight), usually less than 60% and more usually less than 50% of the composition is made up of other polypeptides.

Binding proteins according to the present disclosure may be immunogenic in human and/or in non-human (or heterologous) hosts; e.g., in mice. For example, an antibody may have an idiotype that is immunogenic in non-human hosts, but not in a human host. Antibodies of the disclosure for human use include those that are not typically isolated from hosts such as mice, goats, rabbits, rats, non-primate mammals, or the like, and in some instances are not obtained by humanization or from xeno-mice. Also contemplated herein are variant forms of the disclosed antibodies, which are engineered so as to reduce known or potential immunogenicity and/or other potential liabilities, or to confer a desired structure and/or functionality of the antibody in a non-human animal, such as a mouse (e.g., a "murinized" antibody wherein one or more human amino acid residue, sequence, or motif is replaced by a residue, sequence, or motif that has reduced or abrogated immunogenicity or other liability, or has a desired structure and/or function, in a mouse; e.g., for model studies using a mouse).

Amino acid sequences of exemplary murinized antibodies of the present disclosure are provided in Table 2.

| Murinized antibody sequence description | SEQ ID NO. | Amino acid sequence |
|---|---|---|
| HBC34-V7-mu (IgG2a) HC | 122 | ELQLVESGGGWVQPGGSQRLSCAASGRIFRSFY MSWVRQAPGKGLEWVATINQDGSEKLYVDSV KGRFTISRDNAKNSLFLQMNNLRVEDTAVYYC AAWSGNSGGMDVWGQGTTVSVSSAKTTAPSV YPLAPVCGDTTGSSVTLGCLVKGYFPEPVTLT WNSGSLSSGVHTFPAVLQSDLYTLSSSVTVTSS TWPSQSITCNVAHPASSTKVDKKIEPRGPTIKPC PPCKCPAPNLLGGPSVFIFPPKIKDVLMISLSPIV TCVVVDVSEDDPDVQISWFVNNVEVHTAQTQT HREDYNSTLRVVSALPIQHQDWMSGKEFKCKV NNKDLPAPIERTISKPKGSVRAPQVYVLPPPEEE MTKKQVTLTCMVTDFMPEDIYVEWTNNGKTE LNYKNTEPVLDSDGSYFMYSKLRVEKKNWVE RNSYSCSVVHEGLHNHHTTKSFSRTPGK |
| HBC34-V7-mu (IgG2a) LC | 123 | SYELTQPPSVSVSPGQTVSIPCSGDKLGNKNVC WFQHKPGQSPVLVIYEVKYRPSGIPERFSGSNS GNTATLTISGTQAMDEAAYFCQTFDSTTVVFG GGTRLTVLGQPKSSPSVTLFPPSSEELETNKATL |

-continued

| Murinized antibody sequence description | SEQ ID NO. | Amino acid sequence |
|---|---|---|
| | | VCTITDFYPGVVTVDWKVDGTPVTQGMETTQP SKQSNNKYMASSYLTLTARAWERHSSYSCQVT HEGHTVEKSLSRADCS |
| HBC34-V35-mu (IgG2a) HC | 124 | ELQLVESGGGWVQPGGSQRLSCAASGRIFRSFY MSWVRQAPGKGLEWVATINQDGSEKLYVDSV KGRFTISRDNAKNSLFLQMNNLRVEDTAVYYC AAWSGNSGGMDVWGQGTTVSVSSAKTTAPSV YPLAPVCGDTTGSSVTLGCLVKGYFPEPVTLT WNSGSLSSGVHTFPAVLQSDLYTLSSSVTVTSS TWPSQSITCNVAHPASSTKVDKKIEPRGPTIKPC PPCKCPAPNLLGGPSVFIFPPKIKDVLMISLSPIV TCVVVDVSEDDPDVQISWFVNNVEVHTAQTQT HREDYNSTLRVVSALPIQHQDWMSGKEFKCKV NNKDLPAPIERTISKPKGSVRAPQVYVLPPPEEE MTKKQVTLTCMVTDFMPEDIYVEWTNNGKTE LNYKNTEPVLDSDGSYFMYSKLRVEKKNWVE RNSYSCSVVHEGLHNHHTTKSFSRTPGK |
| HBC34-V35-mu (IgG2a) LC | 125 | SYELTQPPSVSVSPGQTVSIPCSGDKLGNKNVA WFQHKPGQSPVLVIYEVKYRPSGIPERFSGSNS GNTATLTISGTQAMDEAAYFCQTFDSTTVVFG GGTRLTVLGQPKSSPSVTLFPPSSEELETNKATL VCTITDFYPGVVTVDWKVDGTPVTQGMETTQP SKQSNNKYMASSYLTLTARAWERHSSYSCQVT HEGHTVEKSLSRADCS |
| HBC24-mu (IgG2a) HC | 126 | EVQLLESGGGLVQPGGSLRLSCAASGSTFTKYA MSWVRQAPGKGLEWVASISGSVPGFGIDTYYA DSVKGRFTISRDTSKNTLYLQMNSLRAEDTAL YYCAKDVGVIGSYYYYAMDVWGQGTAVTVS SAKTTAPSVYPLAPVCGDTTGSSVTLGCLVKG YFPEPVTLTWNSGSLSSGVHTFPAVLQSDLYTL SSSVTVTSSTWPSQSITCNVAHPASSTKVDKKIE PRGPTIKPCPPCKCPAPNLLGGPSVFIFPPKIKDV LMISLSPIVTCVVVDVSEDDPDVQISWFVNNVE VHTAQTQTHREDYNSTLRVVSALPIQHQDWMS GKEFKCKVNNKDLPAPIERTISKPKGSVRAPQV YVLPPPEEEMTKKQVTLTCMVTDFMPEDIYVE WTNNGKTELNYKNTEPVLDSDGSYFMYSKLR VEKKNWVERNSYSCSVVHEGLHNHHTTKSFSR TPGK |
| HBC24-mu (IgG2a) LC | 127 | EIVLTQSPGTLSLSPGERATLSCRASQGLSSSYL AWYQQKPGQAPRLLIYSASTRATGIPDRFSGSG SGTDFTLTISRLEPEDFAVYYCQQYAYSPRWTF GQGTKVEIKADAAPTVSIFPPSSEQLTSGGASV VCFLNNFYPKDINVKWKIDGSERQNGVLNSWT DQDSKDSTYSMSSTLTLTKDEYERHNSYTCEA THKTSTSPIVKSFNRNEC |

As used herein, a "neutralizing antibody" (or antigen binding fragment, or fusion protein) is one that can neutralize, i.e., prevent, inhibit, reduce, impede or interfere with, the ability of a pathogen to initiate and/or perpetuate an infection in a host (e.g., host organism or host cell). The terms "neutralizing antibody" and "an antibody that neutralizes" or "antibodies that neutralize" are used interchangeably herein. These antibodies can be used alone, or in combination (e.g., two or more of the presently disclosed antibodies in a combination, or an antibody of the present disclosure in combination with another agent, which may or may not be an antibody agent, including an antibody that is capable of neutralizing an HBV B and/or D infection), as prophylactic or therapeutic agents upon appropriate formulation, in association with active vaccination, as a diagnostic tool, or as a production tool as described herein.

As used herein, "specifically binds" or "specific for" refers to an association or union of a binding protein (e.g., an antibody or antigen binding fragment thereof) or a binding domain to a target molecule with an affinity or Ka (i.e., an equilibrium association constant of a particular binding interaction with units of 1/M) equal to or greater than $10^5$ $M^{-1}$ (which equals the ratio of the on-rate [$K_{on}$] to the off rate [Koff] for this association reaction), while not significantly associating or uniting with any other molecules or components in a sample. Binding proteins or binding domains may be classified as "high-affinity" binding proteins or binding domains or as "low-affinity" binding proteins or binding domains. "High-affinity" binding proteins or binding domains refer to those binding proteins or binding domains having a Ka of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low-affinity" binding proteins or binding domains refer to those binding proteins or binding domains having a Ka of up to $10^7$ $M^{-1}$, up to $10^6$ $M^{-1}$, or up to $10^5$ $M^{-1}$. Alternatively, affinity may be defined as an equilibrium dissociation constant (Kd) of a particular binding interaction with units of M (e.g., $10^{-5}$ M to $10^{-13}$ M). The terms "binding" and "specifically binding" and similar references do not encompass non-specific sticking.

Binding of a binding protein can be determined or assessed using an appropriate assay, such as, for example, Surface Plasmon Resonance (SPR) methods, e.g., a Biacore™ system; kinetic exclusion assays such as KinExA®; and BioLayer interferometry (e.g., using the ForteBio® Octet platform); isothermal titration calorimetry (ITC), or the like, an antigen-binding ELISA (e.g., direct or indirect) with imaging by, e.g., optical density at 450 nm, or by flow cytometry, or the like.

In certain embodiments, binding proteins according to the present disclosure can bind to the antigenic loop region of HBsAg. The envelope of the hepatitis B virus generally contains three "HBV envelope proteins" (also known as "HBsAg", "hepatitis B surface antigen"): S protein (for "small", also referred to as S-HBsAg), M protein (for "middle", also referred to as M-HBsAg) and L protein (for "large", also referred to as L-HBsAg). S-HBsAg, M-HBsAg and L-HBsAg share the same C-terminal extremity (also referred to as "S domain", 226 amino acids), which corresponds to the S protein (S-HBsAg) and which is crucial for virus assembly and infectivity. S-HBsAg, M-HBsAg and L-HBsAg are synthesized in the endoplasmic reticulum (ER), assembled, and secreted as particles through the Golgi apparatus. The S domain comprises four predicted transmembrane (TM) domains, whereby both the N-terminus as well as the C-terminus of the S domain are exposed to the lumen. The transmembrane domains TM1 and TM2 are both believed necessary for cotranslational protein integration into the ER membrane and the transmembrane domains TM3 and TM4 are located in the C-terminal third of the S domain. The "antigenic loop region" of HBsAg is located between the predicted TM3 and TM4 transmembrane domains of the S domain of HBsAg, whereby the antigenic loop region comprises amino acids 101-172 of the S domain, which contains 226 amino acids in total (Salisse J. and Sureau C., 2009, Journal of Virology 83: 9321-9328). A determinant of infectivity resides in the antigenic loop region of HBV envelope proteins. In particular, residues between 119 and 125 of the HBsAg contain a CXXC motif, which is considered to be important for the infectivity of HBV and HDV (Jaoude G A, Sureau C, Journal of Virology, 2005; 79:10460-6).

When positions in the amino acid sequence of the S domain of HbsAg are referred to herein, such positions are made with reference to the amino acid sequence as set forth in SEQ ID NO: 3 (shown below) or to natural or artificial sequence variants thereof.

```
MENITSGFLGPLLVLQAGFFLLTRILTIPQSLDSWWTSLNFLGGTTVCL

GQNSQSPTSNHSPTSCPPTCPGYRWMCLRRFIIFLFILLLCLIFLLVLL

DYQGMLPVCPLIPGSSTTSTGPCRTCMTTAQGTSMYPSCCCTKPSDGNC

TCIPIPSSWAFGKFLWEWASARFSWLSLLVPFVQWFVGLSPTVWLSVIW

MMWYWGPSLYSILSPFLPLLPIFFCLWVYI
(SEQ ID NO: 3; amino acids 101-172 are shown underlined)
```

For example, the expression "amino acids 101-172 of the S domain" refers to the amino acid residues from positions 101-172 of the polypeptide according to SEQ ID NO: 3. However, a person skilled in the art understands that mutations or variations (including, but not limited to, substitution, deletion and/or addition, for example, HBsAg of a different genotype or a different HBsAg mutant as described herein) may occur naturally in the amino acid sequence of the S domain of HBsAg or be introduced artificially into the amino acid sequence of the S domain of HBsAg without affecting its biological properties. Therefore, as used herein, the term "S domain of HBsAg" encompasses all such polypeptides including, for example, the polypeptide according to SEQ ID NO: 3 and its natural or artificial mutants. In addition, when sequence fragments of the S domain of HBsAg are described herein (e.g. amino acids 101-172 or amino acids 120-130 of the S domain of HBsAg), they include not only the corresponding sequence fragments of SEQ ID NO: 3, but also the corresponding sequence fragments of its natural or artificial mutants. For example, the phrase "amino acid residues from positions 101-172 of the S domain of HBsAg" encompasses amino acid residues from positions 101-172 of SEQ ID NO: 3 and the corresponding fragments of its mutants (natural or artificial mutants). As used herein, the phrases "corresponding sequence fragments" and "corresponding fragments" refer to fragments that are located in equal positions of sequences when the sequences are subjected to optimized alignment, namely, the sequences are aligned to obtain a highest percentage of identity.

The M protein (M-HBsAg) corresponds to the S protein extended by an N-terminal domain of 55 amino acids called "pre-S2". The L protein (L-HBsAg) corresponds to the M protein extended by an N-terminal domain of 108 amino acids called "pre-S1" (genotype D). The pre-S1 and pre-S2 domains of the L protein can be present either at the inner face of viral particles (on the cytoplasmic side of the ER), and is believed to play a crucial role in virus assembly, or on the outer face (on the luminal side of the ER), available for the interaction with target cells and important for viral infectivity. Moreover, HBV surface proteins (HBsAgs) are not only incorporated into virion envelopes but also can spontaneously bud from ER-Golgi intermediate compartment membranes to form empty "subviral particles" (SVPs) that are released from the cell by secretion.

In some embodiments, an antibody, antigen binding fragment, or fusion protein binds to the antigenic loop region of HBsAg, and is capable of binding to all of S-HBsAg, M-HBsAg and L-HBsAg.

In some embodiments, an antibody, an antigen binding fragment, or fusion protein neutralizes infection with hepatitis B virus and hepatitis delta virus. In some embodiments, the antibody, or the antigen binding fragment thereof, reduces viral infectivity of hepatitis B virus and hepatitis delta virus.

To study and quantitate virus infectivity (or "neutralization") in the laboratory, standard "neutralization assays" may be utilized. For a neutralization assay, animal viruses are typically propagated in cells and/or cell lines. A neutralization assay wherein cultured cells are incubated with a fixed amount of HBV or HDV in the presence (or absence) of the antibody (or antigen-binding fragment or fusion protein) to be tested may be used. In such an assay, the levels of hepatitis B surface antigen (HBsAg) or hepatitis B e antigen (HBeAg) secreted into the cell culture supernatant may be used and/or HBcAg staining may be assessed to provide a readout. For HDV, for example, delta antigen immunofluorescence staining may be assessed.

In a particular embodiment of an HBV neutralization assay, cultured cells, for example HepaRG cells, such as differentiated HepaRG cells, are incubated with a fixed amount of HBV in the presence or absence of the antibody to be tested. In such and embodiment, incubation may be carried out, for example, for 16 hours at 37° C. That incubation may be performed in a medium (e.g. supplemented with 4% PEG 8000). After incubation, cells may be washed and further cultivated. To measure virus infectivity, the levels of hepatitis B surface antigen (HBsAg) and hepatitis B e antigen (HBeAg) secreted into the culture supernatant, e.g. from day 7 to day 11 post-infection, may be determined by enzyme-linked immunosorbent assay (ELISA). Additionally, HBcAg staining may be assessed in an immunofluorescence assay. In an embodiment of a HDV neutralization assay, essentially the same assay as for HBV may be used, with the difference that sera from HDV carriers may be used as HDV infection inoculum on differentiated HepaRg cells (instead of HBV). For detection, delta antigen immunofluorescence staining may be used as a readout.

Embodiments of the binding proteins of the disclosure have high neutralizing potency. In certain embodiments, the concentration of an antibody as described herein required for 50% neutralization of hepatitis B virus (HBV) and hepatitis delta virus (HDV), is, for example, about 10 µg/ml or less. In other embodiments, the concentration of a binding protein required for 50% neutralization of HBV and HDV is about 5 µg/ml. In other embodiments, the concentration of a binding protein as described herein required for 50% neutralization of HBV and HDV is about 1 µg/ml. In still other embodiments, the concentration of a binding protein required for 50% neutralization of HBV and HDV is about 750 ng/ml. In yet further embodiments, the concentration of a binding protein as described herein required for 50% neutralization of HBV and HDV is 500 ng/ml or less. In such embodiments, the concentration of abinding protein as described herein required for 50% neutralization of HBV and HDV may be selected from 450 ng/ml or less, 400 ng/ml or less, 350 ng/ml or less, 300 ng/ml or less, 250 ng/ml or less, 200 ng/ml or less, 175 ng/ml or less, 150 ng/ml or less, 125 ng/ml or less, 100 ng/ml or less, 90 ng/ml or less, 80 ng/ml or less, 70 ng/ml or less, 60 ng/ml or less or 50 ng/ml or less.

Antibodies or antigen binding fragments according to the present disclosure, which can neutralize both HBV and HDV, are useful in the prevention and treatment of hepatitis B and hepatitis D. Infection with HDV typically occurs simultaneously with or subsequent to infection by HBV (e.g., inoculation with HDV in the absence of HBV does not cause hepatitis D since HDV requires the support of HBV for its own replication) and hepatitis D is typically observed in chronic HBV carriers.

Embodiments of the disclosed binding proteins promote clearance of HBsAg and HBV. In particular embodiments, binding proteins promote clearance of both HBV and subviral particles of hepatitis B virus (SVPs). Clearance of HBsAg or of subviral particles may be assessed by measuring the level of HBsAg for example in a blood sample, e.g. from a hepatitis B patient. Similarly, clearance of HBV may be assessed by measuring the level of HBV for example in a blood sample, e.g. from a hepatitis B patient.

In the sera of patients infected with HBV, in addition to infectious particles (HBV), there is typically an excess (typically 1,000- to 100,000-fold) of empty subviral particles (SVP) composed solely of HBV envelope proteins (HBsAg) in the form of relatively smaller spheres and filaments of variable length. Subviral particles have been shown to strongly enhance intracellular viral replication and gene expression of HBV (Bruns M. et al. 1998 J Virol 72(2): 1462-1468). This is also relevant in the context of infectivity of sera containing HBV, since the infectivity depends not only on the number of viruses but also on the number of SVPs (Bruns M. et al. 1998 J Virol 72(2): 1462-1468). Moreover, an excess of subviral particles can serve as a decoy by absorbing neutralizing antibodies and therefore delay the clearance of infection. Achievement of hepatitis B surface antigen (HBsAg) loss is considered in some instances to be an ideal endpoint of treatment and the closest outcome to cure chronic hepatitis B (CHB).

Embodiments of binding proteins of the present disclosure may promote clearance of HbsAg. In certain embodiments, the binding proteins may promote clearance of subviral particles of hepatitis B virus. In some embodiments, the binding proteins may be used to treat chronic hepatitis B.

In any of the presently disclosed embodiments, a binding protein of the present disclosure is capable of binding an HBsAg of a genotype selected from the HBsAg genotypes A, B, C, D, E, F, G, H, I, and J, or any combination thereof.

In certain embodiments, binding proteins of the present disclosure are capable of binding to 1, 2, 3, 4, 5, 6, 7, 8, 9 or 10 of the HBsAg genotypes A, B, C, D, E, F, G, H, I, and J. Examples of different HBsAg genotypes of include the following: GenBank accession number J02203 (HBV-D, ayw3); GenBank accession number FJ899792.1 (HBV-D, adw2); GenBank accession number AM282986 (HBV-A); GenBank accession number D23678 (HBV-B1 Japan); GenBank accession number AB117758 (HBV-C1 Cambodia); GenBank accession number AB205192 (HBV-E Ghana); GenBank accession number X69798 (HBV-F4 Brazil); GenBank accession number AF160501 (HBV-G USA); GenBank accession number AY090454 (HBV-H Nicaragua); GenBank accession number AF241409 (HBV-I Vietnam); and GenBank accession number AB486012 (HBV-J Borneo). Exemplary amino acid sequences of the antigenic loop region of the S domain of HBsAg of different genotypes are described herein (e.g., SEQ ID NOs: 5-15).

In some embodiments, a binding protein is capable of binding to one or more, and in some cases at least 6 of the 10 HBsAg genotypes A, B, C, D, E, F, G, H, I, and J. In certain embodiments, a binding protein is capable of binding to at least 8 of the 10 HBsAg genotypes A, B, C, D, E, F, G, H, I, and J. In some embodiments, a binding protein is capable of binding to all 10 of the 10 HBsAg genotypes A, B, C, D, E, F, G, H, I, and J. HBV is differentiated into several genotypes, according to genome sequence. To date, eight well-known genotypes (A-H) of the HBV genome have been defined. Moreover, two other genotypes, I and J, have also been identified (Sunbul M., 2014, World J Gastroenterol 20(18): 5427-5434). The genotype is known to affect the progression of the disease and differences between genotypes in response to antiviral treatment have been determined.

In some embodiments, a binding protein according to the present disclosure is capable of binding to 1, 2, 3, 4, 5, 6, 7, 8, 9, 10, 11, 12, 13, 14, 15, 16, 17 or 18 of the HBsAg mutants having mutations in the antigenic loop region, with such mutant(s) being selected from one ore more of HBsAg Y100C/P120T, HBsAg P120T, HBsAg P120T/S143L, HBsAg C121S, HBsAg R122D, HBsAg R122I, HBsAg T123N, HBsAg Q129H, HBsAg Q129L, HBsAg M133H, HBsAg M133L, HBsAg M133T, HBsAg K141E, HBsAg P142S, HBsAg S143K, HBsAg D144A, HBsAg G145R and HBsAg N146A. These mutants are naturally occurring mutants based on the S domain of HBsAg Genotype D, Genbank accession no. FJ899792 (SEQ ID NO: 4). The mutated amino acid residue(s) in each of the mutants noted herein are indicated in the name.

SEQ ID NO: 4:
MENVTSGFLGPLLVLQAGFFLLTRILTIPQSLDSWWTSLNFLGGTTVCL

GQNSQSPTSNHSPTSCPPTCPGYRWMCLRRFIIFLFILLLCLIFLLVLL

DYQGMLPVCPLIPGSSTTGTGPCRTCTTPAQGTSMYPSCCCTKPSDGNC

TCIPIPSSWAFGKFLWEWASARFSWLSLLVPFVQWFVGLSPTVWLSVIW

MMWYWGPSLYSTLSPFLPLLPIFFCLWVYI
(the antigenic loop region, i.e. amino acids 101-172, is shown underlined).

Amino acid sequences of the antigenic loop region of the S domain of HBsAg of different mutants are shown in SEQ ID NOs: 16-33.

In certain embodiments, a binding protein as disclosed herein is capable of binding to at one or more, and in some cases at least 12 infectious HBsAg mutants selected from HBsAg Y100C/P120T, HBsAg P120T, HBsAg P120T/S143L, HBsAg C121S, HBsAg R122D, HBsAg R122I, HBsAg T123N, HBsAg Q129H, HBsAg Q129L, HBsAg M133H, HBsAg M133L, HBsAg M133T, HBsAg K141E, HBsAg P142S, HBsAg S143K, HBsAg D144A, HBsAg G145R and HBsAg N146A. In some such embodiments, a binding protein is capable of binding to at least 15 infectious HBsAg mutants selected from HBsAg Y100C/P120T, HBsAg P120T, HBsAg P120T/S143L, HBsAg C121S, HBsAg R122D, HBsAg R122I, HBsAg T123N, HBsAg Q129H, HBsAg Q129L, HBsAg M133H, HBsAg M133L, HBsAg M133T, HBsAg K141E, HBsAg P142S, HBsAg S143K, HBsAg D144A, HBsAg G145R and HBsAg N146A. In some embodiments, a binding protein is capable of binding to each of the following infectious HBsAg mutants: HBsAg Y100C/P120T; HBsAg P120T; HBsAg P120T/S143L; HBsAg C121S; HBsAg R122D; HBsAg R122I; HBsAg T123N; HBsAg Q129H; HBsAg Q129L; HBsAg M133H; HBsAg M133L; HBsAg M133T; HBsAg K141E; HBsAg P142S; HBsAg S143K; HBsAg D144A; HBsAg G145R; and HBsAg N146A.

In certain embodiments, the binding protein (e.g., including an antibody or antigen binding fragment thereof) is capable of reducing a serum concentration of HBV DNA in a mammal having an HBV infection. In certain embodiments, the binding protein is capable of reducing a serum concentration of HBsAg in a mammal having an HBV infection. In certain embodiments, binding protein is capable of reducing a serum concentration of HBeAg in a mammal having an HBV infection. In certain embodiments, the binding protein is capable of reducing a serum concentration of HBcrAg in a mammal having an HBV infection. In some embodiments, the binding protein is capable of reducing the serum concentration of HBV DNA, HBsAg, HBeAg, and/or HBcrAg in the mammal for about 10, 11, 12, 13, 14, 15, 16, 17, 18, 19, 20, or more days following a single administration of the binding protein.

The term "epitope" or "antigenic epitope" includes any molecule, structure, amino acid sequence, or protein determinant that is recognized and specifically bound by a cognate binding molecule, such as an immunoglobulin, chimeric antigen receptor, or other binding molecule, domain or protein. Epitopic determinants generally contain chemically active surface groupings of molecules, such as amino acids or sugar side chains, and can have specific three dimensional structural characteristics, as well as specific charge characteristics.

In some embodiments, a binding protein is capable of binding to an epitope comprising at least one, at least two, at least three, or at least four amino acids of the antigenic loop region of HbsAg. In certain embodiments, a binding protein is capable of binding at least two amino acids selected from amino acids 115-133 of the S domain of HbsAg, amino acids 120-133 of the S domain of HbsAg, or amino acids 120-130 of the S domain of HbsAg. In certain embodiments, a binding protein is capable of binding at least three amino acids selected from amino acids 115-133 of the S domain of HbsAg, amino acids 120-133 of the S domain of HbsAg, or amino acids 120-130 of the S domain of HbsAg. In some embodiments, a binding protein is capable of binding at least four amino acids selected from amino acids 115-133 of the S domain of HbsAg, amino acids 120-133 of the S domain of HbsAg, or amino acids 120-130 of the S domain of HbsAg. As used herein, the position of the amino acids (e.g. 115-133, 120-133, 120-130) refers to the S domain of HBsAg as described above, which is present in all three HBV envelope proteins S-HBsAg, M-HBsAg, and L-HBsAg, whereby 5-HBsAg typically corresponds to the S domain of HBsAg.

The term "formed by" as used herein in the context of an epitope, means that the epitope to which binding protein binds to may be linear (continuous) or conformational (discontinuous). A linear or a sequential epitope is an epitope that is recognized by an antibody according to its linear sequence of amino acids, or primary structure. A conformational epitope may be recognized according to a three-dimensional shape and protein structure. Accordingly, if the epitope is a linear epitope and comprises more than one amino acid located at positions selected from amino acid positions 115-133 or from amino acid positions 120-133 of the S domain of HBsAg, the amino acids comprised by the epitope may be located in adjacent positions of the primary structure (e.g., are consecutive amino acids in the amino acid sequence). In the case of a conformational epitope (3D structure), the amino acid sequence typically forms a 3D structure as epitope and, thus, the amino acids forming the epitope may be or may be not located in adjacent positions of the primary structure (i.e. may be or may be not consecutive amino acids in the amino acid sequence).

In certain embodiments, an epitope to which a binding protein binds to a conformational epitope. In some embodiments, a binding protein binds to an epitope comprising at least two amino acids of the antigenic loop region of HBsAg, wherein the at least two amino acids are selected from amino acids 120-133 or from from amino acids 120-130, of the S domain of HbsAg, and wherein the at least two amino acids are not located in adjacent positions (of the primary structure). In certain embodiments, a binding protein binds to an epitope comprising at least three amino acids of the antigenic loop region of HBsAg, wherein the at least three amino acids are selected from amino acids 120-133 or from from amino acids 120-130, of the S domain of HbsAg, and wherein at least two of the three amino acids are not located in adjacent positions (of the primary structure). In some embodiments, a binding protein binds to an epitope comprising at least four amino acids of the antigenic loop region of HBsAg, wherein the at least four amino acids are selected from amino acids 120-133 or from from amino acids 120-130, of the S domain of HbsAg, and wherein at least two of the four amino acids are not located in adjacent positions (of the primary structure).

Amino acids to which a presently disclosed antibody, antigen binding fragment, or fusion protein binds (i.e. the amino acids forming the epitope), which are not located in adjacent positions of the primary structure, are in some cases spaced apart by one or more amino acids, to which the antibody, antigen binding fragment, or fusion protein does not bind. In some embodiments, at least one, at least two, at least three, at least four, or at least five amino acids may be located between two of the amino acids not located in adjacent positions comprised by the epitope.

In certain embodiments, a binding protein binds to an epitope comprising at least amino acids P120, C121, R122 and C124 of the S domain of HBsAg. In other embodiments, a binding protein of the present disclosure binds to an epitope comprising an amino acid sequence according to SEQ ID NO: 88:

PCRXC wherein X is any amino acid or no amino acid; X is any amino acid; X is T, Y, R, S, or F; X is T, Y or R; or X is T or R.

In other embodiments, a binding protein of the present disclosure binds to an epitope comprising an amino acid sequence according to SEQ ID NO: 80:

TGPCRTC or to an amino acid sequence sharing at least 80%, at least 90%, or at least 95% sequence identity with SEQ ID NO: 80.

In other embodiments, a binding protein of the present disclosure binds to an epitope comprising an amino acid sequence according to SEQ ID NO: 85:

STTSTGPCRTC or to an amino acid sequence sharing at least 80%, at least 90% or at least 95% sequence identity with SEQ ID NO: 85.

In certain embodiments, a binding protein of the present disclosure binds to an epitope comprising an amino acid sequence comprising at least amino acids 145-151 of the S domain of HBsAg:

GNCTCIP. (SEQ ID NO: 81)

In still other embodiments, a binding protein of the present disclosure binds to an epitope comprising an amino acid sequence according to SEQ ID NO: 80 and an amino acid sequence according to SEQ ID NO: 81.

In other embodiments, a binding protein of the present disclosure binds to an epitope comprising an amino acid sequence according to SEQ ID NO: 85 and/or an amino acid sequence according to SEQ ID NO: 87.

As described above, an epitope to which a binding protein of the present disclosure binds may be linear (continuous) or conformational (discontinuous). In some embodiments, a binding protein of the disclosure binds to a conformational epitope, and in certain such embodiments, the conformational epitope is present only under non-reducing conditions.

In certain embodiments, binding protein of the present disclosure, binds to a linear epitope. In certain such embodiments, the the linear epitope is present under both, non-reducing conditions and reducing conditions.

In particular embodiments, a binding protein of the present disclosure binds to an epitope in the antigenic loop of HBsAg formed by an amino acid sequence according to SEQ ID NO: 1:

$X_1$ $X_2$ $X_3$ TC $X_4$ $X_5$ $X_6$A $X_7$G wherein $X_1$, $X_2$, $X_3$, $X_4$, $X_5$, $X_6$ and $X_7$ may be any amino acid (SEQ ID NO: 1).

In some embodiments, $X_1$, $X_2$, $X_3$, $X_4$, $X_5$, $X_6$ and $X_7$ are amino acids, which are conservatively substituted in comparison to amino acids 120-130 of SEQ ID NO: 3. In some embodiments, $X_1$, $X_2$, $X_3$, $X_4$, $X_5$, $X_6$ and $X_7$ are amino acids, which are conservatively substituted in comparison to amino acids 20-30 of any of SEQ ID NOs 5-33.

In specific embodiments, $X_1$ of SEQ ID NO: 1 $X_1$ is a small amino acid. A "small" amino acid, as used herein, refers to any amino acid selected from the group consisting of alanine, aspartic acid, asparagine, cysteine, glycine, proline, serine, threonine and valine. In certain such embodiments, $X_1$ is proline, serine or threonine.

In certain embodiments, $X_2$ of SEQ ID NO: 1 $X_2$ is a small amino acid. In certain embodiments, $X_2$ may be selected from cystein or threonine.

In some embodiments, $X_3$ of SEQ ID NO: 1 is a charged amino acid or an aliphatic amino acid. A "charged" amino acid, as used herein, refers to any amino acid selected from the group consisting of arginine, lysine, aspartic acid, glutamic acid and histidine. A "aliphatic" amino acid, as used herein, refers to any amino acid selected from the group consisting of alanine, glycine, isoleucine, leucine, and valine. In certain embodiments, $X_3$ is selected from arginine, lysine, aspartic acid or isoleucine.

In some embodiments, $X_4$ of SEQ ID NO: 1 is a small amino acid and/or a hydrophobic amino acid. A "hydrophobic" amino acid, as used herein, refers to any amino acid selected from the group consisting of alanine, isoleucine, leucine, phenylalanine, valine, tryptophan, tyrosine, methionine, proline and glycine. In certain embodiments, $X_4$ is selected from methionine or threonine.

In some embodiments, $X_5$ of SEQ ID NO: 1 $X_5$ is a small amino acid and/or a hydrophobic amino acid. In certain embodiments, $X_5$ is selected from threonine, alanine or isoleucine.

In some embodiments, $X_6$ of SEQ ID NO: 1 $X_6$ is a small amino acid and/or a hydrophobic amino acid. In certain embodiments, $X_6$ is selected from threonine, proline or leucine.

In some embodiments, $X_7$ of SEQ ID NO: 1 is a polar amino acid or an aliphatic amino acid. A "polar" amino acid, as used herein, refers to any amino acid selected from the group consisting of aspartic acid, asparagine, arginine, glutamic acid, histidine, lysine, glutamine, tryptophan, tyrosine, serine, and threonine. In certain such embodiments, $X_7$ is glutamine, histidine or leucine.

In some embodiments, abinding protein according to the present disclosure binds to an epitope in the antigenic loop of HBsAg formed by an amino acid sequence according to SEQ ID NO: 2:

$X_1$ $X_2$ $X_3$ TC $X_4$ $X_5$ $X_6$A $X_7$G wherein $X_1$ is P, T or S,
$X_2$ is C or S,
$X_3$ is R, K, D or I,
$X_4$ is M or T,
$X_5$ is T, A or I,
$X_6$ is T, P or L, and
$X_7$ is Q, H or L
(SEQ ID NO: 2).

With regard to the epitopes formed by the amino acid sequences according to SEQ ID NO: 1 or 2, it is noted that the term "formed by" as used herein is not intended to imply that a disclosed binding protein necessarily binds to each and every amino acid of SEQ ID NO: 1 or 2. In particular, a binding protein may bind only to some of the amino acids of SEQ ID NO: 1 or 2, whereby other amino acid residues may act as "spacers".

In particular embodiments, a binding protein according to the present disclosure binds to an epitope in the antigenic loop of HBsAg formed by one or more, two or more, three or more, or four or more amino acids of an amino acid sequence selected from SEQ ID NOs 5-33 shown below in Table 3.

In some embodiments, binding protein according to the present disclosure binds to an antigenic loop region of HBsAg having an amino acid sequence according to any one or more of SEQ ID NOs 5-33 shown below in Table 3, or to a sequence variant thereof. In certain embodiments, a binding protein according to the present disclosure binds to all of the antigenic loop variants of HBsAg having an amino acid sequence according to any of SEQ ID NOs 5-33 shown below in Table 3.

TABLE 3

Exemplary amino acid sequences of the antigenic loop region of the S domain of HBsAg (residues 101-172 of the S domain of HBsAg-except for SEQ ID NO: 16, which refers to residues 100-172 of the S domain of HBsAg in order to include the relevant mutation) of the different genotypes and mutants as used herein.

| Name | SEQ ID NO. | Amino acid sequence |
|---|---|---|
| J02203 (D, ayw3) | 5 | QGMLPVCPLIPGSSTTSTGPCRTCMTTAQGTS MYPSCCCTKPSDGNCTCIPIPSSWAFGKFLWE WASARFSW |
| FJ899792 (D, adw2) | 6 | QGMLPVCPLIPGSSTTGTGPCRTCTTP AQGTSMYPSCCCTKPSDGNCTCIPIPS SWAFGKFLWEWASARFSW |
| AM282986 (A) | 7 | QGMLPVCPLIPGTTTTSTGPCKTCTTPAQGNS MFPSCCCTKPSDGNCTCIPIPSSWAFAKYLWE WASVRFSW |
| D23678 (B1) | 8 | QGMLPVCPLIPGSSTTSTGPCKTCTTPAQGTS MFPSCCCTKPTDGNCTCIPIPSSWAFAKYLWE WASVRFSW |
| AB117758 (C1) | 9 | QGMLPVCPLLPGTSTTSTGPCKTCTIPAQGTS MFPSCCCTKPSDGNCTCIPIPSSWAFARFLWE WASVRFSW |
| AB205192 (E) | 10 | QGMLPVCPLIPGSSTTSTGPCRTCTTLAQGTS MFPSCCCSKPSDGNCTCIPIPSSWAFGKFLWE WASARFSW |
| X69798 (F4) | 11 | QGMLPVCPLLPGSTTTSTGPCKTCTTLAQGTS MFPSCCCSKPSDGNCTCIPIPSSWALGKYLWE WASARFSW |
| AF160501 (G) | 12 | QGMLPVCPLIPGSSTTSTGPCKTCTTPAQGNS MYPSCCCTKPSDGNCTCIPIPSSWAFAKYLWE WASVRFSW |
| AY090454 (H) | 13 | QGMLPVCPLLPGSTTTSTGPCKTCTTLAQGTS MFPSCCCTKPSDGNCTCIPIPSSWAFGKYLWE WASARFSW |
| AF241409 (I) | 14 | QGMLPVCPLIPGSSTTSTGPCKTCTTPAQGNS MYPSCCCTKPSDGNCTCIPIPSSWAFAKYLWE WASARFSW |
| AB486012 (J) | 15 | QGMLPVCPLLPGSTTTSTGPCRTCTITAQGTS MFPSCCCTKPSDGNCTCIPIPSSWAFAKFLWE WASVRFSW |
| HBsAg Y100C/P120T | 16 | CQGMLPVCPLIPGSSTTGTGTCRTCTTPAQGT SMYPSCCCTKPSDGNCTCIPIPSSWAFGKFLW EWASARFSW |
| HBsAg P120T | 17 | QGMLPVCPLIPGSSTTGTGTCRTCTTPAQGTS MYPSCCCTKPSDGNCTCIPIPSSWAFGKFLWE WASARFSW |
| HBsAg P120T/S143L | 18 | QGMLPVCPLIPGSSTTGTGTCRTCTTPAQGTS MYPSCCCTKPLDGNCTCIPIPSSWAFGKFLWE WASARFSW |

TABLE 3-continued

Exemplary amino acid sequences of the antigenic loop region of the S domain of HBsAg (residues 101-172 of the S domain of HBsAg-except for SEQ ID NO: 16, which refers to residues 100-172 of the S domain of HBsAg in order to include the relevant mutation) of the different genotypes and mutants as used herein.

| Name | SEQ ID NO. | Amino acid sequence |
|---|---|---|
| HBsAg C121S | 19 | QGMLPVCPLIPGSSTTGTGPSRTCTTPAQGTS MYPSCCCTKPSDGNCTCIPIPSSWAFGKFLWE WASARFSW |
| HBsAg R122D | 20 | QGMLPVCPLIPGSSTTGTGPCDTCTTPAQGTS MYPSCCCTKPSDGNCTCIPIPSSWAFGKFLWE WASARFSW |
| HBsAg R122I | 21 | QGMLPVCPLIPGSSTTGTGPCITCTTPAQGTSM YPSCCCTKPSDGNCTCIPIPSSWAFGKFLWEW ASARFSW |
| HBsAg T123N | 22 | QGMLPVCPLIPGSSTTGTGPCRNCTTPAQGTS MYPSCCCTKPSDGNCTCIPIPSSWAFGKFLWE WASARFSW |
| HBsAg Q129H | 23 | QGMLPVCPLIPGSSTTGTGPCRTCTTPAHGTS MYPSCCCTKPSDGNCTCIPIPSSWAFGKFLWE WASARFSW |
| HBsAg Q129L | 24 | QGMLPVCPLIPGSSTTGTGPCRTCTTPALGTS MYPSCCCTKPSDGNCTCIPIPSSWAFGKFLWE WASARFSW |
| HBsAg M133H | 25 | QGMLPVCPLIPGSSTTGTGPCRTCTTPAQGTS HYPSCCCTKPSDGNCTCIPIPSSWAFGKFLWE WASARFSW |
| HBsAg M133L | 26 | QGMLPVCPLIPGSSTTGTGPCRTCTTPAQGTSL YPSCCCTKPSDGNCTCIPIPSSWAFGKFLWEW ASARFSW |
| HBsAg M133T | 27 | QGMLPVCPLIPGSSTTGTGPCRTCTTPAQGTST YPSCCCTKPSDGNCTCIPIPSSWAFGKFLWEW ASARFSW |
| HBsAg K141E | 28 | QGMLPVCPLIPGSSTTGTGPCRTCTTPAQGTS MYPSCCCTEPSDGNCTCIPIPSSWAFGKFLWE WASARFSW |
| HBsAg P142S | 29 | QGMLPVCPLIPGSSTTGTGPCRTCTTPAQGTS MYPSCCCTKSSDGNCTCIPIPSSWAFGKFLWE WASARFSW |
| HBsAg S143K | 30 | QGMLPVCPLIPGSSTTGTGPCRTCTTPAQGTS MYPSCCCTKPKDGNCTCIPIPSSWAFGKFLWE WASARFSW |
| HBsAg D144A | 31 | QGMLPVCPLIPGSSTTGTGPCRTCTTPAQGTS MYPSCCCTKPSAGNCTCIPIPSSWAFGKFLWE WASARFSW |
| HBsAg G145R | 32 | QGMLPVCPLIPGSSTTGTGPCRTCTTPAQGTS MYPSCCCTKPSDRNCTCIPIPSSWAFGKFLWE WASARFSW |
| HBsAg N146A | 33 | QGMLPVCPLIPGSSTTGTGPCRTCTTPAQGTS MYPSCCCTKPSDGACTCIPIPSSWAFGKFLWE WASARFSW |

In certain aspects, the present disclosure provides an isolated antibody, or an antigen binding fragment thereof, comprising: (i) a heavy chain variable region ($V_H$) comprising at least 90% (i.e., 90%, 91%, 92%, 93%, 94%, 95%, 96%, 97%, 98%, 99%, or more) identity to the amino acid sequence according to SEQ ID NO:41 or 67; and (ii) a light chain variable region ($V_L$) comprising at least 90% identity to the amino acid sequence according to any one of SEQ ID NOs:42; 59; 65; 89, 90, or 111-120, provided that the amino acid at position 40 of the VL according to IMGT numbering is not a cysteine, wherein the antibody or antigen binding fragment thereof binds to the antigenic loop region of HBsAg and neutralizes infection with hepatitis B virus and hepatitis delta virus.

In further embodiments, (i) the $V_H$ comprises at least 95% identity to the amino acid sequence according to SEQ ID NO:41 or 67; and/or (ii) the $V_L$ comprises at least 95% identity to the amino acid sequence according to any one of SEQ ID NOs:42, 59, 65, 89, 90, or 111-120.

In certain embodiments, the amino acid at position 40 of the $V_L$ is alanine. In other embodiments, the amino acid at position 40 of the $V_L$ is serine. In still other embodiments, the amino acid at position 40 of the $V_L$ is glycine.

In any of the embodiments disclosed herein, the antibody or antigen binding fragment can comprise CDRH1, CDRH2, CDRH3, CDRL1, CDRL2, and CDRL3 sequences according to SEQ ID NOs: (i) 34-36, 37, 38, and 40, respectively; (ii) 34, 66, 36, 37, 38, and 40, respectively; (iii) 34-36, 37, 39, and 40, respectively; (iv) 34, 66, 36, 37, 39, and 40, respectively; (v) 34-36, 37, 38, and 58, respectively; (vi) 34, 66, 36, 37, 38, and 58, respectively; (vii) 34-36, 37, 39, and 58, respectively; or (vii) 34, 66, 36, 37, 39, and 58, respectively.

In some embodiments, the $V_L$ of the antibody or antigen binding fragment comprises or consists of the amino acid sequence according to SEQ ID NO:89. In some embodiments, the $V_L$ of the antibody or antigen binding fragment comprises or consists of the amino acid sequence according to SEQ ID NO:90. In other embodiments, the $V_L$ of the antibody or antigen binding fragment comprises or consists of the amino acid sequence according to any one of SEQ ID NOs: 111-120. In certain embodiments, the $V_H$ comprises or consists of the amino acid sequence according to SEQ ID NO:41. In other embodiments, the $V_H$ comprises or consists of the amino acid sequence according to SEQ ID NO:67.

In particular embodiments, the $V_H$ comprises or consists of the amino acid sequence according to SEQ ID NO:41 and the $V_L$ comprises or consists of the amino acid sequence according to SEQ ID NO:89. In other embodiments, the $V_H$ comprises or consists of the amino acid sequence according to SEQ ID NO:41 and the $V_L$ comprises or consists of the amino acid sequence according to SEQ ID NO:90. In certain embodiments, the the $V_H$ comprises or consists of the amino acid sequence according to SEQ ID NO:41 and the $V_L$ comprises or consists of the amino acid sequence according to any one of SEQ ID NOs:111-120. In other embodiments, the the $V_H$ comprises or consists of the amino acid sequence according to SEQ ID NO:67 and the $V_L$ comprises or consists of the amino acid sequence according to any one of SEQ ID NOs:89, 90, and 111-120.

In another aspect, the present disclosure provides an isolated antibody, or an antigen binding fragment thereof, comprising: (i) a heavy chain variable region ($V_H$) comprising at least 90% identity to the amino acid sequence according to SEQ ID NO:95; and (ii) a light chain variable region ($V_L$) comprising at least 90% identity to the amino acid sequence according to SEQ ID NO:96, wherein the antibody or antigen binding fragment thereof binds to the antigenic loop region of HBsAg and neutralizes infection with hepatitis B virus and hepatitis delta virus.

In further embodiments, (i) the $V_H$ comprises at least 95% identity to the amino acid sequence according to SEQ ID NO:95; and/or (ii) the $V_L$ comprises at least 95% identity to the amino acid sequence according to SEQ ID NO:96.

In certain embodiments, the antibody or antigen binding fragment comprises CDRH1, CDRH2, CDRH3, CDRL1, CDRL2, and CDRL3 sequences according to SEQ ID NOs: 97-102, respectively.

In particular embodiments, the $V_H$ comprises or consists of the amino acid sequence according to SEQ ID NO:95; and the $V_L$ comprises or consists of the amino acid sequence according to SEQ ID NO:96.

Fc Moiety

In some embodiments, a binding protein (e.g., antibody or an antigen binding fragment thereof) of the present disclosure comprises an Fc moiety. In certain embodiments, the Fc moiety may be derived from human origin, e.g., from human IgG1, IgG2, IgG3, and/or IgG4, or from another Ig class or isotype. In specific embodiments, an antibody or antigen binding fragments can comprise an Fc moiety derived from human IgG1.

As used herein, the term "Fc moiety" refers to a sequence comprising, consisting, consisting essentially of, or derived from a portion of an immunoglobulin heavy chain beginning in the hinge region just upstream of the papain cleavage site (e.g., residue 216 in native IgG, taking the first residue of heavy chain constant region to be 114) and ending at the C-terminus of the immunoglobulin heavy chain. Accordingly, an Fc moiety may be a complete Fc moiety or a portion (e.g., a domain) thereof. In certain embodiments, a complete Fc moiety comprises a hinge domain, a CH2 domain, and a CH3 domain (e.g., EU amino acid positions 216-446). An additional lysine residue (K) is sometimes present at the extreme C-terminus of the Fc moiety, but is often cleaved from a mature antibody. Amino acid positions within an Fc moiety have been numbered according to the EU numbering system of Kabat, see e.g., Kabat et al., "Sequences of Proteins of Immunological Interest", U.S. Dept. Health and Human Services, 1983 and 1987. Amino acid positions of an Fc moiety can also be numbered according to the IMGT numbering system (including unique numbering for the C-domain and exon numbering) and the Kabat numbering system.

In some embodiments, an Fc moiety comprises at least one of: a hinge (e.g., upper, middle, and/or lower hinge region) domain, a CH2 domain, a CH3 domain, or a variant, portion, or fragment thereof. In some embodiments, an Fc moiety comprises at least a hinge domain, a CH2 domain or a CH3 domain. In further embodiments, the Fc moiety is a complete Fc moiety. The amino acid sequence of an exemplary Fc moiety of human IgG1 isotype is provided in SEQ ID NO:137. The Fc moiety may also comprise one or more amino acid insertions, deletions, or substitutions relative to a naturally occurring Fc moiety. For example, at least one of a hinge domain, CH2 domain, or CH3 domain, or a portion thereof, may be deleted. For example, an Fc moiety may comprise or consist of: (i) hinge domain (or a portion thereof) fused to a CH2 domain (or a portion thereof), (ii) a hinge domain (or a portion thereof) fused to a CH3 domain (or a portion thereof), (iii) a CH2 domain (or a portion thereof) fused to a CH3 domain (or a portion thereof), (iv) a hinge domain (or a portion thereof), (v) a CH2 domain (or a portion thereof), or (vi) a CH3 domain or a portion thereof.

An Fc moiety of the present disclosure may be modified such that it varies in amino acid sequence from the complete Fc moiety of a naturally occurring immunoglobulin molecule, while retaining or enhancing at least one desirable function conferred by the naturally occurring Fc moiety, and/or reducing an undesired function of a naturally occurring Fc moiety. Such functions include, for example, Fc receptor (FcR) binding, antibody half-life modulation (e.g., by binding to FcRn), ADCC function, protein A binding, protein G binding, and complement binding. Portions of naturally occurring Fc moieties which are involved with such functions have been described in the art.

For example, to activate the complement cascade, the C1q protein complex can bind to at least two molecules of IgG1 or one molecule of IgM when the immunoglobulin molecule(s) is attached to the antigenic target (Ward, E. S., and Ghetie, V., *Ther. Immunol.* 2 (1995) 77-94). Burton, D. R., described (*Mol. Immunol.* 22 (1985) 161-206) that the heavy chain region comprising amino acid residues 318 to 337 is involved in complement fixation. Duncan, A. R., and Winter, G. (*Nature* 332 (1988) 738-740), using site directed mutagenesis, reported that Glu318, Lys320 and Lys322 form the binding site to C1q. The role of Glu318, Lys320 and Lys 322 residues in the binding of C1q was confirmed by the ability of a short synthetic peptide containing these residues to inhibit complement mediated lysis.

For example, FcR binding can be mediated by the interaction of the Fc moiety (of an antibody) with Fc receptors (FcRs), which are specialized cell surface receptors on cells including hematopoietic cells. Fc receptors belong to the immunoglobulin superfamily, and shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC; Van de Winkel, J. G., and Anderson, C. L., *J. Leukoc. Biol.* 49 (1991) 511-524). FcRs are defined by their specificity for immunoglobulin classes; Fc receptors for IgG antibodies are referred to as FcγR, for IgE as FcεR, for IgA as FcαR and so on and neonatal Fc receptors are referred to as FcRn. Fc receptor binding is described for example in Ravetch, J. V., and Kinet, J. P., *Annu. Rev. Immunol.* 9 (1991) 457-492; Capel, P. J., et al., *Immunomethods* 4 (1994) 25-34; de Haas, M., et al., *J Lab. Clin. Med.* 126 (1995) 330-341; and Gessner, J. E., et al., *Ann. Hematol.* 76 (1998) 231-248.

Cross-linking of receptors by the Fc domain of native IgG antibodies (FcγR) triggers a wide variety of effector functions including phagocytosis, antibody-dependent cellular cytotoxicity, and release of inflammatory mediators, as well as immune complex clearance and regulation of antibody production. Fc moieties providing cross-linking of receptors (e.g., FcγR) are contemplated herein. In humans, three classes of FcγR have been characterized to-date, which are: (i) FcγRI (CD64), which binds monomeric IgG with high affinity and is expressed on macrophages, monocytes, neutrophils and eosinophils; (ii) FcγRII (CD32), which binds complexed IgG with medium to low affinity, is widely expressed, in particular on leukocytes, is believed to be a central player in antibody-mediated immunity, and which can be divided into FcγRIIA, FcγRIIB and FcγRIIC, which perform different functions in the immune system, but bind with similar low affinity to the IgG-Fc, and the ectodomains of these receptors are highly homologous; and (iii) FcγRIII (CD16), which binds IgG with medium to low affinity and has been found in two forms: FcγRIIIA, which has been found on NK cells, macrophages, eosinophils, and some monocytes and T cells, and is believed to mediate ADCC; and FcγRIIIB, which is highly expressed on neutrophils.

FcγRIIA is found on many cells involved in killing (e.g. macrophages, monocytes, neutrophils) and seems able to activate the killing process. FcγRIIB seems to play a role in inhibitory processes and is found on B-cells, macrophages and on mast cells and eosinophils. Importantly, it has been shown that 75% of all FcγRIIB is found in the liver (Ganesan, L. P. et al., 2012: "FcγRIIb on liver sinusoidal endothelium clears small immune complexes," Journal of Immunology 189: 4981-4988), FcγRIIB is abundantly expressed on Liver Sinusoidal Endothelium, called LSEC, and in Kupffer cells in the liver and LSEC are the major site of small immune complexes clearance (Ganesan, L. P. et al., 2012: FcγRIIb on liver sinusoidal endothelium clears small immune complexes. Journal of Immunology 189: 4981-4988).

In some embodiments, the antibodies disclosed herein and the antigen binding fragments thereof comprise an Fc moiety for binding to FcγRIIb, in particular an Fc region, such as, for example IgG-type antibodies. Moreover, it is possible to engineer the Fc moiety to enhance FcγRIIB binding by introducing the mutations S267E and L328F as described by Chu, S. Y. et al., 2008: Inhibition of B cell receptor-mediated activation of primary human B cells by coengagement of CD19 and FcgammaRIIb with Fc-engineered antibodies. Molecular Immunology 45, 3926-3933. Thereby, the clearance of immune complexes can be enhanced (Chu, S., et al., 2014: Accelerated Clearance of IgE In Chimpanzees Is Mediated By Xmab7195, An Fc-Engineered Antibody With Enhanced Affinity For Inhibitory Receptor FcγRIIb. Am J Respir Crit, American Thoracic Society International Conference Abstracts). In some embodiments, the antibodies of the present disclosure, or the antigen binding fragments thereof, comprise an engineered Fc moiety with the mutations S267E and L328F, in particular as described by Chu, S. Y. et al., 2008: Inhibition of B cell receptor-mediated activation of primary human B cells by coengagement of CD19 and FcgammaRIIb with Fc-engineered antibodies. Molecular Immunology 45, 3926-3933.

On B cells, FcγRIIB seems to function to suppress further immunoglobulin production and isotype switching to, for example, the IgE class. On macrophages, FcγRIIB is thought to inhibit phagocytosis as mediated through FcγRIIA. On eosinophils and mast cells, the B form may help to suppress activation of these cells through IgE binding to its separate receptor.

Regarding FcγRI binding, modification in native IgG of at least one of E233-G236, P238, D265, N297, A327 and P329 reduces binding to FcγRI. IgG2 residues at positions 233-236, substituted into corresponding positions IgG1 and IgG4, reduces binding of IgG1 and IgG4 to FcγRI by $10^3$-fold and eliminated the human monocyte response to antibody-sensitized red blood cells (Armour, K. L., et al. *Eur. J. Immunol.* 29 (1999) 2613-2624).

Regarding FcγRII binding, reduced binding for FcγRIIA is found, e.g., for IgG mutation of at least one of E233-G236, P238, D265, N297, A327, P329, D270, Q295, A327, R292 and K414.

Two allelic forms of human FcγRIIA are the "H131" variant, which binds to IgG1 Fc with high affinity, and the "R131" variant, which binds to IgG1 Fc with low affinity. See, e.g., Bruhns et al., *Blood* 113:3716-3725 (2009).

Regarding FcγRIII binding, reduced binding to FcγRIIIA is found, e.g., for mutation of at least one of E233-G236, P238, D265, N297, A327, P329, D270, Q295, A327, S239, E269, E293, Y296, V303, A327, K338 and D376. Mapping of the binding sites on human IgG1 for Fc receptors, the above-mentioned mutation sites, and methods for measuring binding to FcγRT and FcγRIIA, are described in Shields, R. L., et al., *J. Biol. Chem.* 276 (2001) 6591-6604.

Two allelic forms of human FcγRIIIA are the "F158" variant, which binds to IgG1 Fc with low affinity, and the "V158" variant, which binds to IgG1 Fc with high affinity. See, e.g., Bruhns et al., *Blood* 113:3716-3725 (2009).

Regarding binding to FcγRII, two regions of native IgG Fc appear to be involved in interactions between FcγRIIs and IgGs, namely (i) the lower hinge site of IgG Fc, in particular amino acid residues L, L, G, G (234-237, EU numbering), and (ii) the adjacent region of the CH2 domain of IgG Fc, in particular a loop and strands in the upper CH2 domain adjacent to the lower hinge region, e.g. in a region of P331 (Wines, B. D., et al., J. Immunol. 2000; 164: 5313-5318). Moreover, FcγRT appears to bind to the same site on IgG Fc, whereas FcRn and Protein A bind to a different site on IgG Fc, which appears to be at the CH2-CH3 interface (Wines, B. D., et al., J. Immunol. 2000; 164: 5313-5318).

Also contemplated are mutations that increase binding affinity of an Fc moiety of the present disclosure to a (i.e., one or more) Fcγ receptor (e.g., as compared to a reference Fc moiety or antibody containing the same that does not comprise the mutation(s)). See, e.g., Delillo and Ravetch, Cell 161(5):1035-1045 (2015) and Ahmed et al., J. Struc. Biol. 194(1):78 (2016), the Fc mutations and techniques of which are incorporated herein by reference.

In any of the herein disclosed embodiments, a binding protein can comprise a Fc moiety comprising a mutation selected from G236A; S239D; A330L; and I332E; or a combination comprising any two or more of the same; e.g., S239D/I332E; S239D/A330L/I332E; G236A/S239D/I332E; G236A/A330L/I332E (also referred to herein as "GAALIE"); or G236A/S239D/A330L/I332E. In some embodiments, the Fc moiety does not comprise S239D.

In certain embodiments, the Fc moiety may comprise or consist of at least a portion of an Fc moiety that is involved in binding to FcRn binding. In certain embodiments, the Fc moiety comprises one or more amino acid modifications that improve binding affinity for (e.g., enhance binding to) FcRn (e.g., at a pH of about 6.0) and, in some embodiments, thereby extend in vivo half-life of a molecule comprising the Fc moiety (e.g., as compared to a reference Fc moiety or antibody that is otherwise the same but does not comprise the modification(s)). In certain embodiments, the Fc moiety comprises or is derived from a IgG Fc and a half-life-extending mutation comprises any one or more of: M428L; N434S; N434H; N434A; N434S; M252Y; S254T; T256E; T250Q; P257I Q311I; D376V; T307A; E380A (EU numbering). In certain embodiments, a half-life-extending mutation comprises M428L/N434S (also referred to herein as "MLNS"). In certain embodiments, a half-life-extending mutation comprises M252Y/S254T/T256E. In certain embodiments, a half-life-extending mutation comprises T250Q/M428L. In certain embodiments, a half-life-extending mutation comprises P257I/Q311I. In certain embodiments, a half-life-extending mutation comprises P257I/N434H. In certain embodiments, a half-life-extending mutation comprises D376V/N434H. In certain embodiments, a half-life-extending mutation comprises T307A/E380A/N434A.

In some embodiments, a binding protein includes a Fc moiety that comprises the substitution mutations M428L/N434S. In some embodiments, a binding protein includes a Fc moiety that comprises the substitution mutations G236A/A330L/I332E. In certain embodiments, a binding protein includes a (e.g., IgG) Fc moiety that comprises a G236A mutation, an A330L mutation, and a I332E mutation (GAALIE), and does not comprise a S239D mutation (e.g., comprises a native S at position 239).

In particular embodiments, a binding protein includes an Fc moiety that comprises the substitution mutations: M428L/N434S and G236A/A330L/I332E, and optionally does not comprise S239D. In certain embodiments, a binding protein includes a Fc moiety that comprises the substitution mutations: M428L/N434S and G236A/S239D/A330L/I332E.

In certain embodiments, a binding protein of the present disclosure comprises: CDRs and/or a variable domain and/or a heavy chain and/or a light chain according to any one of the exemplary anti-HBV antibodies disclosed herein and/or in PCT Publication No. WO 2017/060504 (including antibodies HBC34, HBC34-V7, HBC34-V23, HBC34-V31, HBC34-V32, HBC34-V33, HBC34-V34, HBC34-V35, (including herein disclosed variants of HBC antibodies which comprise a substitution mutation at position 40 in the light chain (e.g., a substitution of a native cysteine with an alanine, a serine, or the like) and HBC24); and a Fc moiety comprising a G236A mutation, an A330L mutation, and a I332E (GAALIE) mutation, wherein the Fc moiety optionally further comprises a M428L/N434S (MLNS) mutation. In certain embodiments, the Fc moiety does not comprise S239D.

In certain embodiments, a binding protein comprises: a CDRH1 amino acid sequence according to SEQ ID NO:34, a CDRH2 amino acid sequence according to SEQ ID NO:35 or 66, a CDRH3 amino acid sequence according to SEQ ID NO:36, a CDRL1 acid sequence according to SEQ ID NO:37, a CDRL2 acid sequence according to SEQ ID NO:38 or 39, and CDRL3 amino acid sequence according to SEQ ID NO:58 or 40; and a Fc moiety comprising a GAALIE mutation. In certain embodiments, the Fc moiety does not comprise a S239D mutation. In certain embodiments, the Fc moiety further comprises a MLNS mutation.

In certain embodiments, a binding protein comprises: a heavy chain variable domain (VH) amino acid sequence according to any one of SEQ ID NOs:41 or 67 and a light chain variable domain (VL) amino acid sequence according to any one of SEQ ID NOs:42, 59, 65, 89, 90, and 111-120; and a Fc moiety comprising a GAALIE mutation. In certain embodiments, the Fc moiety further comprises a MLNS mutation.

In certain embodiments, a binding protein comprises a heavy chain amino acid sequence according to SEQ ID NO:138 or 91 or 92 and/or a light chain amino acid sequences according to any one of SEQ ID NOs:93 or 94. In certain embodiments, a binding protein comprises a heavy chain amino acid sequence according to SEQ ID NO: 91 and a light chain amino acid sequences according to SEQ ID NOs:93. In certain embodiments, a binding protein comprises a heavy chain amino acid sequence according to SEQ ID NO: 91 and a light chain amino acid sequences according to SEQ ID NOs:94. In certain embodiments, a binding protein comprises a heavy chain amino acid sequence according to SEQ ID NO: 92 and a light chain amino acid sequences according to SEQ ID NOs:93. In certain embodiments, a binding protein comprises a heavy chain amino acid sequence according to SEQ ID NO: 92 and a light chain amino acid sequences according to SEQ ID NOs:94.

In certain embodiments, a binding protein comprises: a CDRH1 amino acid sequence according to SEQ ID NO:97, a CDRH2 amino acid sequence according to SEQ ID NO:98, a CDRH3 amino acid sequence according to SEQ ID NO:99, a CDRL1 acid sequence according to SEQ ID NO:100, a CDRL2 acid sequence according to SEQ ID NO:100, and CDRL3 amino acid sequence according to SEQ ID NO:102; and a Fc moiety comprising a GAALIE mutation. In certain embodiments, the Fc moiety further comprises a MLNS mutation.

In certain embodiments, a binding protein comprises: a heavy chain variable domain (VH) amino acid sequence according to SEQ ID NO:95 and a light chain variable domain (VL) amino acid sequence according to SEQ ID NO:96; and a Fc moiety comprising a GAALIE mutation. In certain embodiments, the Fc moiety further comprises a MLNS mutation.

In any of the presently disclosed embodiments, a binding protein of the present disclosure includes a Fc moiety comprising a GAALIE mutation and has enhanced binding to a human FcγRIIa and/or a human FcγRIIIa, as compared to a reference polypeptide (i.e., a polypeptide, which may be a binding protein, that includes a Fc moiety that does not comprise the GAALIE mutation).

In certain embodiments, the reference polypeptide includes a Fc moiety that is a wild-type Fc moiety (e.g., of the same isotype) or is a Fc moiety that comprises one or more substitution mutation (or insertion or deletion), provided that the substitution mutation is not or does not comprise GAALIE. In certain embodiments, a binding protein comprises HBC34-V35 antibody with a GAALIE mutation (and optionally other substitution mutations, such as, for example, MLNS), and a reference polypeptide is HBC34-V35 (including a wild-type Fc moiety). In certain embodiments, the reference polypeptide does not comprise a substitution mutation that is known or believed to affect binding to a human FcγRIIa and/or to a human FcγRIIIa.

Binding between polypeptides, such as binding between a Fc moiety (or a binding protein comprising the same) and a human Fcγ Receptor, such as human FcγRIIA, human FcγRIIIA, or human Fc FcγRIIB, or a complement protein, such as C1q, can be determined or detected using methods known in the art. For example, a biolayer interferometry (BLI) assay can be performed using an Octet® RED96 (FortéBio, Fremont, California USA) instrument according to manufacturer's instructions to determine real-time association and dissociation between a first polypeptide of interest (e.g., HBC34v35 comprising a GAALIE mutation) and a second polypeptide of interest (e.g., a FcγRIIA (H131), a FcγRIIA (R131), a FcγRIIIA (F158), a FcγRIIIA (V158), or a FcγRIIb) that is captured on a sensor substrate.

In certain embodiments, a binding protein includes a Fc moiety comprising a GAALIE mutation and has enhanced binding to a human FcγRIIA (H131), a human FcγRIIA (R131), a human FcγRIIIA (F158), a human FcγRIIIA (V158), or any combination thereof, as compared to a reference polypeptide that includes a Fc moiety that does not comprise the GAALIE mutation. In certain embodiments, enhanced binding is determined by an increase (e.g., one or more of: a higher peak signal; a greater rate of association; a slower rate of dissociation; a greater area under the curve) in signal shift versus the reference binding protein in a BLI assay. In certain embodiments, the BLI assay comprises use of Octet® RED96 (FortéBio, Fremont, California USA) instrument. In further embodiments, the BLI assay comprises a tagged human FcγR captured onto an anti-penta-tag sensor and exposed to the binding protein. In some embodiments, the binding protein comprises a IgG Fab and the BLI assay further comprises exposing the captured human FcγR to the binding protein in the presence of an anti-IgG Fab binding fragment to cross-link the binding proteins through the Fab fragment.

In certain embodiments, a binding protein includes a Fc moiety comprising a GAALIE mutation and has enhanced binding to a human FcγRIIA (H131), a human FcγRIIA (R131), a human FcγRIIIA (F158), and/or a human FcγRIIIA (V158) as compared to a reference polypeptide, wherein the enhanced binding can comprise a signal shift (nanometers) in a BLI assay of 1.5, 2, 2.5, 3, or more times greater than the signal shift observed using the reference binding protein.

In certain embodiments, a binding protein includes a Fc moiety comprising a GAALIE mutation and has enhanced binding to a human FcγRIIA (H131), a human FcγRIIA (R131), a human FcγRIIIA (F158), and a human FcγRIIIA (V158), as compared to a reference polypeptide.

In any of the presently disclosed embodiments, a binding protein includes a Fc moiety comprising a GAALIE mutation and has reduced binding to a human FcγRIIB, as compared to a reference polypeptide. In certain embodiments, a binding protein includes a Fc moiety comprising a GAALIE mutation and does not bind to a human FcγRIIB, as determined, for example, by the absence of a statistically significant signal shift versus baseline in a BLI assay.

In any of the presently disclosed embodiments, a binding protein includes a Fc moiety comprising a GAALIE mutation and has reduced binding to a human C1q (complement protein), as compared to a reference polypeptide. In certain embodiments, a binding protein includes a Fc moiety comprising a GAALIE mutation and does not bind to a human C1q, as determined by the absence of a statistically significant signal shift versus baseline in a BLI assay.

In any of the presently disclosed embodiments, a binding protein includes a Fc moiety comprising a GAALIE mutation and activates a human FcγRIIA, a human FcγRIIIA, or both, to a greater degree than does a reference polypeptide. (i.e., a polypeptide, which may be a HbsAg-specific binding protein, that includes a Fc moiety that does not comprise the GAALIE mutation). In certain embodiments, the reference polypeptide includes a Fc moiety that is a wild-type Fc moiety or that comprises one or more substitution mutation, provided that the substitution mutation is not GAALIE. In certain embodiments, a binding protein comprises HBC34-V35 antibody with a GAALIE mutation (and optionally other substitution mutations, such as, for example, MLNS), and a reference polypeptide is HBC34-V35 with a wild-type Fc moiety.

Activation of a human FcγR can be determined or detected using methods known in the art. For example, a well-validated, commercially available bioreporter assay involves incubating a HBsAg-specific binding protein with a recombinant HBsAg (Engerix B, GlaxoSmithKline) in the presence of Jurkat effector cells (Promega; Cat. no: G9798) stably expressing (i) a FcγR of interest and (ii) firefly luciferase reporter under the control of a NFAT response element. Binding of Fc to cell surface-expressed FcγR drives NFAT-mediated expression of luciferase reporter gene. Luminescence is then measured with a luminometer (e.g., Bio-Tek) using the Bio-Glo-™ Luciferase Assay Reagent (Promega) according to the manufacturer's instructions. Activation is expressed as the average of relative luminescence units (RLU) over the background by applying the following formula: (RLU at concentration [x] of binding protein (e.g., mAbs)—RLU of background).

In certain embodiments, a binding protein includes a Fc moiety comprising a GAALIE mutation activates a human FcγRIIA (H131), a human FcγRIIA (R131), a human FcγRIIIA (F158), and/or a human FcγRIIIA (V158) to a greater degree than does a reference polypeptide. In certain embodiments, a greater degree of activation refers to a higher peak luminescence and/or a greater luminescence area under the curve, as determined using a luminescence bioreporter assay as described herein. In certain embodiments, a binding protein includes a Fc moiety comprising a GAALIE mutation and activates a human FcγRIIA (H131), a human FcγRIIA (R131), and a human FcγRIIIA (F158) to a greater degree than does a reference polypeptide, wherein the greater degree of activation comprises to a peak RLU that is 1.5, 2, 2.5, 3, or more times greater than the peak RLU observed using the reference binding protein.

In any of the presently disclosed embodiments, a binding protein includes a Fc moiety comprising a GAALIE mutation does not activate a human FcγRIIB, as determined by the absence of a statistically significant and/or measurable RLU in a luminescence bioreporter assay as described above.

In any of the presently disclosed embodiments, a binding protein includes a Fc moiety comprising a GAALIE mutation and activates a human natural killer (NK) cell in the presence of HBsAg to a greater degree than does a reference polypeptide. In certain embodiments, activation of a NK cell is determined by CD107a expression (e.g., by flow cytometry). In certain embodiments, the NK cell comprises a cell that comprises V158/V158 homozygous, a F158/F158 homozygous, or a V158/F158 heterozygous FcγRIIIa genotype.

It will be appreciated that any binding protein including a Fc moiety comprising a GAALIE mutation according to the present disclosure can perform or possess any one or more of the features described herein; e.g., enhanced binding to a human FcγRIIA and/or a human FcγRIIIA as compared to a reference polypeptide; reduced binding to a human FcγRIIB as compared to a reference polypeptide (and/or no binding to a human FcγRIIB); reduced binding to a human C1q as compared to a reference polypeptide (and/or no binding to a human C1q); activates a FcγRIIA, a human FcγRIIIA, or both, to a greater degree than does a reference polypeptide; does not activate a human FcγRIIB; and/or activates a human natural killer (NK) cell in the presence of HBsAg to a greater degree than does a reference polypeptide (e.g., an antibody that is specific for HBsAg and includes a Fc moiety that does not comprise a GAALIE mutation).

In certain embodiments, a binding protein of the present disclosure includes a Fc moiety comprising a GAALIE mutation and: (i) has enhanced binding to a human FcγRIIA, a human FcγRIIIA, or both, as compared to a reference polypeptide that includes a Fc moiety that does not comprise G236A/A330L/I332E, wherein the human FcγRIIA is optionally H131 or R131, and/or the human FcγRIIIA is optionally F158 or V158; (ii) has reduced binding to a human FcγRIIB, as compared to a reference polypeptide that includes a Fc moiety that does not comprise G236A/A330L/I332E; (iii) does not bind to a human FcγRIIB; (iv) has reduced binding to a human C1q, as compared to a reference polypeptide that includes a Fc moiety that does not comprise G236A/A330L/I332E; (v) does not bind to a human C1q; (vi) activates a FcγRIIA, a human FcγRIIIA, or both, to a greater degree than does a reference polypeptide that includes a Fc moiety that does not comprise G236A/A330L/I332E, wherein the human FcγRIIA is optionally H131 or R131, and/or the human FcγRIIIA is optionally F158 or V158; (vii) does not activate a human FcγRIIB; (viii) activates a human natural killer (NK) cell in the presence of HBsAg to a greater degree than does a reference polypeptide that includes a Fc moiety that does not comprise G236A/A330L/I332E, wherein the reference polypeptide is optionally an antibody that binds to an HB Ag, optionally an HBsAg; (ix) has an HBsAg $EC_{50}$ of from about 12.75 ng/mL to about 19.9 ng/mL, or from about 12.75 ng/mL to about 12.84 ng/mL, or about 12.79 ng/mL, or from about 16.22 ng/mL to about 19.9 ng/mL, or about 17.97 ng/mL, and/or (b) has an HBeAg $EC_{50}$ about from about 10.78 ng/mL to about 13.72 ng/mL, or from about 10.78 ng/mL to about 10.93 ng/mL, or about 10.85 ng/mL, or from about 11.59 ng/mL to about 13.72 ng/mL, or about 12.61 ng/mL, wherein the HBV is optionally HBV Genotype D, and wherein the $EC_{50}$ is optionally determined in vitro by measuring HBsAg or HBeAg, respectively, secreted by HepG2 cells overexpressing NTCP and infected with the HBV, at day 7 following administration of the antibody or antigen binding fragment to the HepG2 cells; (x) has an HBsAg $EC_{50}$ of from about 10.43 ng/mL to about 22.41 ng/mL, or about 13.81 ng/mL to about 16.56 ng/mL, or about 15.12 ng/mL, or from about 12.24 ng/mL to about 22.41 ng/mL, or about 16.56 ng/mL, or from about 10.43 ng/mL to about 20.08 ng/mL, or about 14.47 ng/mL, n and/or (b) has an HBeAg $EC_{50}$ about from about 10.39 ng/mL to about 13.99 ng/mL, or from about 10.63 ng/mL to about 10.66 ng/mL, or about 10.64 ng/mL, or from about 10.39 ng/mL to about 10.60 ng/mL, or about 10.49 ng/mL, or from about 13.25 ng/mL to about 13.99 ng/mL, or about 13.61 ng/mL, wherein the HBV is optionally HBV Genotype D, and wherein the $EC_{50}$ is optionally determined in vitro by measuring HBsAg or HBeAg, respectively, secreted by HepG2 cells overexpressing NTCP and infected with the HBV, at day 7 following administration of the antibody or antigen binding fragment to the HepG2 cells; (xi) is capable of binding to an HBsAg variant comprising HBsAg-Y100C/P120T, HBsAg-P120T, HBsAg-P120S/S143L, HBsAg-C121S, HBsAg-R122D, HBsAg-R122I, HBsAg-T123N, HBsAg-Q129H, HBsAg-Q129L, HBsAg-M133H, HBsAg-M133L, HBsAg-M133T, HBsAg-K141E, HBsAg-P142S, HBsAg-S143K, HBsAg-D144A, HBsAg-G145R, HBsAg-N146A, or any combination thereof; (xii) has improved binding to an HBsAg variant comprising HBsAg-Y100C/P120T, HBsAg-P120T, HBsAg-P120S/S143L, HBsAg-C121S, HBsAg-R122D, HBsAg-R122I, HBsAg-T123N, HBsAg-Q129H, HBsAg-Q129L, HBsAg-M133H, HBsAg-M133L, HBsAg-M133T, HBsAg-K141E, HBsAg-P142S, HBsAg-S143K, HBsAg-D144A, HBsAg-G145R, HBsAg-N146A, or any combination thereof, as compared to a reference antibody or antigen binding fragment that binds to HBsAg and that includes a Fc moiety that does not comprise G236A/A330L/I332E; and/or (xiii) is capable of neutralizing (a) an HBV of genotype A with an $EC_{50}$ of about 2.34 ng/mL; (b) an HBV of genotype B with an $EC_{50}$ of about 2.22 ng/mL; (c) an HBV of genotype C with an $EC_{50}$ of about 0.92 ng/mL; (d) an HBV of genotype D with an $EC_{50}$ of about 1.10 ng/mL; (e) an HBV of genotype E with an $EC_{50}$ of about 1.12 ng/mL; (f) an HBV of genotype F with an $EC_{50}$ of about 1.93 ng/mL; (g) an HBV of genotype G with an $EC_{50}$ of about 1.43 ng/mL; and/or (h) an HBV of genotype H with an $EC_{50}$ of about 1.93 ng/mL, wherein the $EC_{50}$ is optionally determined using a recombinant HDV engineered to express an HBsAg of the HBV genotype.

Alternatively or additionally, the Fc moiety of a binding protein of the disclosure can comprise at least a portion known in the art to be required for Protein A binding; and/or the Fc moiety of an antibody of the disclosure comprises at least the portion of an Fc molecule known in the art to be required for protein G binding. In some embodiments, a retained function comprises the clearance of HBsAg and HBVg. Accordingly, in certain embodiments, an Fc moiety comprises at least a portion known in the art to be required for FcγR binding. As outlined above, an Fc moiety may thus at least comprise (i) the lower hinge site of native IgG Fc, in particular amino acid residues L, L, G, G (234-237, EU numbering), and (ii) the adjacent region of the CH2 domain of native IgG Fc, in particular a loop and strands in the upper CH2 domain adjacent to the lower hinge region, e.g. in a region of P331, for example a region of at least 3, 4, 5, 6, 7, 8, 9, or 10 consecutive amino acids in the upper CH2 domain of native IgG Fc around P331, e.g. between amino acids 320 and 340 (EU numbering) of native IgG Fc.

In some embodiments, a binding protein according to the present disclosure comprises an Fc region. As used herein, the term "Fc region" refers to the portion of an immunoglobulin formed by two or more Fc moieties of antibody heavy chains. For example, an Fc region may be monomeric or "single-chain" Fc region (i.e., a scFc region). Single chain Fc regions are comprised of Fc moieties linked within a single polypeptide chain (e.g., encoded in a single contiguous nucleic acid sequence). Exemplary scFc regions are disclosed in WO 2008/143954 A2, and are incorporated by reference herein. The Fc region can be or comprise a dimeric Fc region. A "dimeric Fc region" or "dcFc" refers to the dimer formed by the Fc moieties of two separate immunoglobulin heavy chains. The dimeric Fc region may be a homodimer of two identical Fc moieties (e.g., an Fc region of a naturally occurring immunoglobulin) or a heterodimer of two non-identical Fc moieties (e.g., one Fc monomer of the dimeric Fc region comprises at least one amino acid modification (e.g., substitution, deletion, insertion, or chemical modification) that is not present in the other Fc monomer, or one Fc monomer may be truncated as compared to the other).

Particular embodiments include those antibodies and antigen binding fragments having a heavy chain (e.g., VH-hinge-CH1-CH2-CH3) according to SEQ ID NO:91 or SEQ ID NO:92 or SEQ ID NO:138, and those having a light chain (i.e., VL-CL) according to SEQ ID NO:93 or SEQ ID NO:94. In certain embodiments, an antibody or antigen binding fragment comprises a heavy chain according to SEQ ID NO:91 and a light chain according to SEQ ID NO:93. In other embodiments, an antibody or antigen binding fragment comprises a heavy chain according to SEQ ID NO:92 and a light chain according to SEQ ID NO:94. In other embodiments, an antibody or antigen binding fragment comprises a heavy chain according to SEQ ID NO:91 and a light chain according to SEQ ID NO:94. In other embodiments, an antibody or antigen binding fragment comprises a heavy chain according to SEQ ID NO:92 and a light chain according to SEQ ID NO:93. In some embodiments, an antibody or antigen binding fragment comprises or consists of a heavy chain according to SEQ ID NO:129. In some embodiments, an antibody or antigen binding fragment comprises or consists of a heavy chain according to SEQ ID NO:138, and optionally a light chain according to any one of SEQ ID NOs:93 or 94. These sequences are provided in the Sequence Listing.

Presently disclosed Fc moieties may comprise Fc sequences or regions of the same or different class and/or subclass. For example, Fc moieties may be derived from an immunoglobulin (e.g., a human immunoglobulin) of an IgG1, IgG2, IgG3 or IgG4 subclass, or from any combination thereof. In certain embodiments, the Fc moieties of Fc region are of the same class and subclass. However, the Fc region (or one or more Fc moieties of an Fc region) may also be chimeric, whereby a chimeric Fc region may comprise Fc moieties derived from different immunoglobulin classes and/or subclasses. For example, at least two of the Fc moieties of a dimeric or single-chain Fc region may be from different immunoglobulin classes and/or subclasses. In certain embodiments, a dimeric Fc region can comprise sequences from two or more different isotypes or subclasses; e.g., a SEEDbody ("strand-exchange engineered domains"), see Davis el al, Protein Eng. Des. Sel. 23(4):195 (2010).

Additionally or alternatively, chimeric Fc regions may comprise one or more chimeric Fc moieties. For example, the chimeric Fc region or moiety may comprise one or more portions derived from an immunoglobulin of a first subclass (e.g., an IgG1, IgG2, or IgG3 subclass) while the remainder of the Fc region or moiety is of a different subclass. For example, an Fc region or moiety of an Fc polypeptide may comprise a CH2 and/or CH3 domain derived from an immunoglobulin of a first subclass (e.g., an IgG1, IgG2 or IgG4 subclass) and a hinge region from an immunoglobulin of a second subclass (e.g., an IgG3 subclass). For example, the Fc region or moiety may comprise a hinge and/or CH2 domain derived from an immunoglobulin of a first subclass (e.g., an IgG4 subclass) and a CH3 domain from an immunoglobulin of a second subclass (e.g., an IgG1, IgG2, or IgG3 subclass). For example, the chimeric Fc region may comprise an Fc moiety (e.g., a complete Fc moiety) from an immunoglobulin for a first subclass (e.g., an IgG4 subclass) and an Fc moiety from an immunoglobulin of a second subclass (e.g., an IgG1, IgG2 or IgG3 subclass). For example, the Fc region or moiety may comprise a CH2 domain from an IgG4 immunoglobulin and a CH3 domain from an IgG1 immunoglobulin. For example, the Fc region or moiety may comprise a CH1 domain and a CH2 domain from an IgG4 molecule and a CH3 domain from an IgG1 molecule. For example, the Fc region or moiety may comprise a portion of a CH2 domain from a particular subclass of antibody, e.g., EU positions 292-340 of a CH2 domain. For example, an Fc region or moiety may comprise amino acids a positions 292-340 of CH2 derived from an IgG4 moiety and the remainder of CH2 derived from an IgG1 moiety (alternatively, 292-340 of CH2 may be derived from an IgG1 moiety and the remainder of CH2 derived from an IgG4 moiety).

It will also be appreciated that any antibody, antigen-binding fragment, or Fc region or moiety of the present disclosure can be of any allotype and/or haplotype. For example, human Immunoglobulin G allotypes include those disclosed in Jefferis and LeFranc, mAbs 1(4):1-7 (2009), which allotypes (including G1m (1(a); 2(x); 3(f); and 17(z)); G2m (23(n)); G3m (21(g1); 28(g5); 11(b0); 5(b2); 13(b3); 14(b4); 10(b5); 15(s); 16(t); 6(c3); 24(c5); 26(u); and 27(v)); A2m (1 and 2); and Km (1; 2; and 3) and haplotypes, and resultant amino acid sequences, and combinations thereof, are incorporated herein by reference. In certain embodiments, an antibody, antigen-binding fragment, or Fc region or moiety of the present disclosure comprises a IgG1 allotype g1m17, k1.

Moreover, an Fc region or moiety may (additionally or alternatively) for example comprise a chimeric hinge region. For example, the chimeric hinge may be derived, e.g. in part, from an IgG1, IgG2, or IgG4 molecule (e.g., an upper and lower middle hinge sequence) and, in part, from an IgG3 molecule (e.g., an middle hinge sequence). In another example, an Fc region or moiety may comprise a chimeric hinge derived, in part, from an IgG1 molecule and, in part, from an IgG4 molecule. In another example, the chimeric hinge may comprise upper and lower hinge domains from an IgG4 molecule and a middle hinge domain from an IgG1 molecule. Such a chimeric hinge may be made, for example, by introducing a proline substitution (Ser228Pro) at EU position 228 in the middle hinge domain of an IgG4 hinge region. In another embodiment, the chimeric hinge can comprise amino acids at EU positions 233-236 are from an IgG2 antibody and/or the Ser228Pro mutation, wherein the remaining amino acids of the hinge are from an IgG4 antibody (e.g., a chimeric hinge of the sequence ESKY-GPPCPPCPAPPVAGP). Further chimeric hinges which may be used in the Fc moiety of the antibody according to the present disclosure are described in US 2005/0163783 A1.

In some embodiments of the binding proteins disclosed herein, the Fc moiety, or the Fc region, comprises or consists of an amino acid sequence derived from a human immunoglobulin sequence (e.g., from an Fc region or Fc moiety from a human IgG molecule). However, polypeptides may comprise one or more amino acids from another mammalian species. For example, a primate Fc moiety or a primate binding site may be included in the subject polypeptides. Alternatively, one or more murine amino acids may be present in the Fc moiety or in the Fc region.

Nucleic Acid Molecule

In another aspect, the disclosure provides a nucleic acid molecule comprising a polynucleotide encoding an antibody, antigen binding fragment, or fusion protein according to the present disclosure Table 4 shows exemplary $V_H$-, $V_L$-, CH-, CL-, HC-, and LC-encoding nucleotide sequences according to the present disclosure:

| Antibody nucleotide acid sequence description | SEQ ID NO: | nucleotide sequence |
|---|---|---|
| V$_H$ of HBC34-V7, HBC34-V35, and HBC34-V34 (codon optimized) | 103 | GAGCTGCAGCTGGTGGAGTCCGGCGGC<br>GGCTGGGTGCAGCCTGGCGGCTCCCAGA<br>GGCTGAGCTGTGCCGCTTCTGGCAGGAT<br>CTTCCGGTCCTTTTACATGTCTTGGGTGC<br>GGCAGGCTCCAGGCAAGGGCCTGGAGT<br>GGGTGGCTACCATCAACCAGGACGGCTC<br>CGAGAAGCTGTATGTGGATAGCGTGAA<br>GGGCAGATTCACAATCTCTCGCGACAAC<br>GCCAAGAACTCCCTGTTTCTGCAGATGA<br>ACAATCTGAGGGTGGAGGATACCGCCGT<br>GTACTATTGCGCCGCTTGGTCTGGCAAT<br>AGCGGCGGCATGGACGTGTGGGGACAG<br>GGCACCACCGTGTCCGTGTCCAGC |
| HBC34-V34 V$_L$ (codon optimized) | 104 | AGCTACGAGCTGACACAGCCCCCTTCCG<br>TGTCCGTGTCCCCTGGACAGACCGTGTC<br>CATCCCATGCAGCGGCGACAAGCTGGGC<br>AACAAGAACGTGTCCTGGTTTCAGCATA<br>AGCCTGGCCAGTCCCCCGTGCTGGTCAT<br>CTACGAGGTGAAGTATAGGCCCAGCGG<br>CATCCCTGAGCGGTTCTCTGGCTCCAAC<br>AGCGGCAATACAGCCACCCTGACAATCT<br>CTGGCACACAGGCTATGGACGAGGCCG<br>CTTATTTCTGCCAGACCTTTGATTCCACC<br>ACAGTGGTGTTCGGCGGCGGCACCAGAC<br>TGACAGTGCTG |
| HBC34-V35 V$_L$ (codon optimized) | 105 | AGCTACGAGCTGACACAGCCCCCTTCCG<br>TGTCCGTGTCCCCTGGACAGACCGTGTC<br>CATCCCATGCAGCGGCGACAAGCTGGGC<br>AACAAGAACGTGGCCTGGTTTCAGCATA<br>AGCCTGGCCAGTCCCCCGTGCTGGTCAT<br>CTACGAGGTGAAGTATAGGCCCAGCGG<br>CATCCCTGAGCGGTTCTCTGGCTCCAAC<br>AGCGGCAATACAGCCACCCTGACAATCT<br>CTGGCACACAGGCTATGGACGAGGCCG<br>CTTATTTCTGCCAGACCTTTGATTCCACC<br>ACAGTGGTGTTCGGCGGCGGCACCAGAC<br>TGACAGTGCTG |
| HBC34-V7 V$_L$ (codon optimized) | 110 | AGCTACGAGCTGACACAGCCCCCTTCCG<br>TGTCCGTGTCCCCTGGACAGACCGTGTC<br>CATCCCATGCAGCGGCGACAAGCTGGGC<br>AACAAGAACGTGTGCTGGTTTCAGCATA<br>AGCCTGGCCAGTCCCCCGTGCTGGTCAT<br>CTACGAGGTGAAGTATAGGCCCAGCGG<br>CATCCCTGAGCGGTTCTCTGGCTCCAAC<br>AGCGGCAATACAGCCACCCTGACAATCT<br>CTGGCACACAGGCTATGGACGAGGCCG<br>CTTATTTCTGCCAGACCTTTGATTCCACC<br>ACAGTGGTGTTCGGCGGCGGCACCAGAC<br>TGACAGTGCTG |
| HBC24 V$_H$ (wild type) | 106 | gaggtgcagttgttggagtctgggggaggcttggtacagcctgg<br>ggggtccctgagactctcctgtgcagcctctGGATCCACT<br>TTTACCAAATATGCCatgagctgggtccgtcaggct<br>ccagggaaggggctggagtgggtcgcaagtATTAGTGG<br>AAGTgttectggtfttGGTATTGACACAtactacgca<br>gactccgttaagggccggttcaccatctccagagacacttccaag<br>aacaccctgtatctgcaaatgaacagcctgagagccgaggacac<br>ggccttatattactgtGCGAAAGATGTCGGGGTTA<br>TCGGGTCATACTATTACTACGCTATGGA<br>CGTCtggggtcaa |
| HBC24 V$_L$ (wild type) | 107 | aaattgtgttgacgcagtctccaggcaccctgtctttgtctccaggg<br>gaaagagccaccctctcctgcagggccagtCAGGGTCTT<br>AGCAGCAGTTACttagcctggtaccagcagaaacctg<br>gccaggctcccaggctcctcatctatAGTGCGTCCaccag<br>ggccactggcatcccagacaggttcagtggcagtgggtctggga<br>cagacttcactctcaccatcagcagactggagcctgaagattttgc<br>agtgtattactgtCAACAGTATGCTTACTCACCT<br>CGGTGGACGtteggccaagggaccaaggtggagatcaa<br>ac |
| HBC24 V$_H$ (codon optimized) | 108 | GAGGTGCAGCTGCTGGAAAGCGGCGGC<br>GGCCTGGTGCAGCCCGGCGGCTCCCTGA<br>GGCTGTCTTGCGCCGCCTCTGGCAGCAC<br>CTTCACAAAGTATGCAATGTCTTGGGTG |

-continued

| Antibody nucleotide acid sequence description | SEQ ID NO: | nuclecotide sequence |
|---|---|---|
| | | CGCCAGGCACCAGGCAAGGGCCTGGAG<br>TGGGTGGCCTCCATCTCTGGCAGCGTGC<br>CTGGCTTCGGCATCGACACCTACTATGC<br>CGATTCCGTGAAGGGCCGGTTTACAATC<br>AGCAGAGACACCTCCAAGAACACACTG<br>TATCTGCAGATGAATTCTCTGCGGGCCG<br>AGGACACCGCCCTGTACTATTGTGCCAA<br>GGATGTGGGCGTGATCGGCAGCTACTAT<br>TACTATGCAATGGACGTGTGGGGACAGG<br>GAACAGCAGTGACAGTGAGCTCC |
| HBC24 V$_L$<br>(codon optimized) | 109 | GAGATCGTGCTGACCCAGTCTCCTGGCA<br>CACTGTCCCTGTCCCCTGGAGAGAGAGC<br>CACCCTGTCCTGCAGAGCCTCTCAGGGC<br>CTGAGCTCCTCTTACCTGGCCTGGTATC<br>AGCAGAAGCCTGGACAGGCCCCTCGGCT<br>GCTGATCTACTCTGCCTCCACCAGAGCA<br>ACAGGCATTCCTGACCGCTTCTCCGGAT<br>CTGGAAGCGGCACAGACTTCACCCTGAC<br>AATCAGCCGGCTGGAGCCTGAGGACTTC<br>GCCGTGTACTATTGTCAGCAGTACGCCT<br>ATTCCCCAAGGTGGACCTTTGGCCAGGG<br>CACAAAGGTGGAGATCAAG |
| HBC34-V7, HBC34-V34,<br>HBC34-V35<br>CH1-hinge-CH2-CH3<br>(codon-optimized) | 130 | GCCTCCACAAAGGGCCCAAGCGTGTTTC<br>CACTGGCTCCCTCTTCCAAGTCTACCTCC<br>GGCGGCACAGCCGCTCTGGGATGTCTGT<br>TGAAGGATTACTTCCCAGAGCCCGTGAC<br>CGTGTCTTGGAACTCCGGCGCCCTGACC<br>AGCGGAGTGCATACATTTCCAGCTGTGC<br>TGCAGAGCTCTGGCCTGTACTCTCTGTC<br>CAGCGTGGTGACCGTGCCCTCTTCCAGC<br>CTGGGCACCCAGACATATATCTGCAACG<br>TGAATCACAAGCCAAGCAATACAAAGG<br>TGGACAAGAAGGTGGAGCCCAAGTCTT<br>GTGATAAGACCCATACATGCCCTCCATG<br>TCCAGCTCCAGAGCTGCTGGGCGGCCCA<br>AGCGTGTTCCTGTTTCCACCCAAGCCTA<br>AGGATACCCTGATGATCTCCAGAACCCC<br>CGAGGTGACATGCGTGGTGGTGGACGTG<br>AGCCACGAGGATCCTGAGGTGAAGTTCA<br>ACTGGTACGTGGACGGCGTGGAGGTGC<br>ATAATGCTAAGACCAAGCCCAGGGAGG<br>AGCAGTACAACTCTACCTATCGGGTGGT<br>GTCCGTGCTGACAGTGCTGCACCAGGAT<br>TGGCTGAACGGCAAGGAGTATAAGTGC<br>AAGGTGTCTAATAAGGCCCTGCCCGCTC<br>CTATCGAGAAGACCATCTCCAAGGCCAA<br>GGGCCAGCCTAGAGAGCCACAGGTGTA<br>CACACTGCCTCCATCTCGCGATGAGCTG<br>ACCAAGAACCAGGTGTCCCTGACATGTC<br>TGGTGAAGGGCTTCTATCCTTCCGACAT<br>CGCTGTGGAGTGGGAGAGCAATGGCCA<br>GCCAGAGAACAATTACAAGACCACACC<br>CCCTGTGCTGGACAGCGATGGCTCTTTC<br>TTTCTGTATAGCAAGCTGACCGTGGACA<br>AGTCTCGCTGGCAGCAGGGCAACGTGTT<br>TAGCTGTTCTGTGATGCATGAGGCCCTG<br>CACAATCATTATACACAGAAGTCCCTGA<br>GCCTGTCTCCTGGCAAG |
| HBC34-V7, HBC34-V34,<br>HBC34-V35<br>HC (VH-CH1-hinge-CH2-<br>CH3) (codon-optimized) | 131 | GAGCTGCAGCTGGTGGAGTCCGGCGGC<br>GGCTGGGTGCAGCCTGGCGGCTCCCAGA<br>GGCTGAGCTGTGCCGCTTCTGGCAGGAT<br>CTTCCGGTCCTTTTACATGTCTTGGGTGC<br>GGCAGGCTCCAGGCAAGGGCCTGGAGT<br>GGGTGGCTACCATCAACCAGGACGGCTC<br>CGAGAAGCTGTATGTGGATAGCGTGAA<br>GGGCAGATTCACAATCTCTCGCGACAAC<br>GCCAAGAACTCCCTGTTTCTGCAGATGA<br>ACAATCTGAGGGTGGAGGATACCGCCGT<br>GTACTATTGCGCCGCTTGGTCTGGCAAT<br>AGCGGCGGCATGGACGTGTGGGGACAG<br>GGCACCACCGTGTCCGTGTCCAGCGCCT<br>CCACAAAGGGCCCAAGCGTGTTTCCACT<br>GGCTCCCTCTTCCAAGTCTACCTCCGGC |

-continued

| Antibody nucleotide acid sequence description | SEQ ID NO: | nuclecotide sequence |
|---|---|---|
| | | GGCACAGCCGCTCTGGGATGTCTGGTGA AGGATTACTTCCCAGAGCCCGTGACCGT GTCTTGGAACTCCGGCGCCCTGACCAGC GGAGTGCATACATTTCCAGCTGTGCTGC AGAGCTCTGGCCTGTACTCTCTGTCCAG CGTGGTGACCGTGCCCTCTTCCAGCCTG GGCACCCAGACATATATCTGCAACGTGA ATCACAAGCCAAGCAATACAAAGGTGG ACAAGAAGGTGGAGCCCAAGTCTTGTG ATAAGACCCATACATGCCCTCCATGTCC AGCTCCAGAGCTGCTGGGCGGCCCAAGC GTGTTCCTGTTTCCACCCAAGCCTAAGG ATACCCTGATGATCTCCAGAACCCCCGA GGTGACATGCGTGGTGGTGGACGTGAGC CACGAGGATCCTGAGGTGAAGTTCAACT GGTACGTGGACGGCGTGGAGGTGCATA ATGCTAAGACCAAGCCCAGGGAGGAGC AGTACAACTCTACCTATCGGGTGGTGTC CGTGCTGACAGTGCTGCACCAGGATTGG CTGAACGGCAAGGAGTATAAGTGCAAG GTGTCTAATAAGGCCCTGCCCGCTCCTA TCGAGAAGACCATCTCCAAGGCCAAGG GCCAGCCTAGAGAGCCACAGGTGTACA CACTGCCTCCATCTCGCGATGAGCTGAC CAAGAACCAGGTGTCCCTGACATGTCTG GTGAAGGGCTTCTATCCTTCCGACATCG CTGTGGAGTGGGAGAGCAATGGCCAGC CAGAGAACAATTACAAGACCACACCCC CTGTGCTGGACAGCGATGGCTCTTTCTTT CTGTATAGCAAGCTGACCGTGGACAAGT CTCGCTGGCAGCAGGGCAACGTGTTTAG CTGTTCTGTGATGCATGAGGCCCTGCAC AATCATTATACACAGAAGTCCCTGAGCC TGTCTCCTGGCAAGTGATGAGGTACCGT GCGACGGCCGGCAAGCCCCCGCTCCCCG GGCTCTCGCGGTCGTACGAGGAAAGCTT |
| HBC34-V7 CL (codon-optimized) | 132 | GGACAGCCAAAGGCTGCTCCATCTGTGA CCCTGTTTCCACCCTCTTCCGAGGAGCT GCAGGCCAACAAGGCCACCCTGGTGTGC CTGATCTCTGACTTCTACCCTGGAGCTGT GACAGTGGCTTGGAAGGCTGATAGCTCT CCCGTGAAGGCTGGCGTGGAGACAACA ACCCCTAGCAAGCAGTCTAACAATAAGT ACGCCGCTTCCAGCTATCTGTCTCTGAC ACCAGAGCAGTGGAAGTCCCACCGCTCT TATTCCTGCCAGGTGACCCATGAGGGCA GCACCGTGGAGAAGACAGTGGCCCCCA CCGAGTGTTCT |
| HBC34-V7 LC (VL-CL) (codon-optimized) | 133 | AGCTACGAGCTGACACAGCCCCCTTCCG TGTCCGTGTCCCCTGGACAGACCGTGTC CATCCCATGCAGCGGCGACAAGCTGGGC AACAAGAACGTGTGCTGGTTTCAGCATA AGCCTGGCCAGTCCCCCGTGCTGGTCAT CTACGAGGTGAAGTATAGGCCCAGCGG CATCCCTGAGCGGTTCTCTGGCTCCAAC AGCGGCAATACAGCCACCCTGACAATCT CTGGCACACAGGCTATGGACGAGGCCG CTTATTTCTGCCAGACCTTTGATTCCACC ACAGTGGTGTTCGGCGGCGGCACCAGAC TGACAGTGCTGGGACAGCCAAAGGCTG CTCCATCTGTGACCCTGTTTCCACCCTCT TCCGAGGAGCTGCAGGCCAACAAGGCC ACCCTGGTGTGCCTGATCTCTGACTTCTA CCCTGGAGCTGTGACAGTGGCTTGGAAG GCTGATAGCTCTCCCGTGAAGGCTGGCG TGGAGACAACAACCCCTAGCAAGCAGT CTAACAATAAGTACGCCGCTTCCAGCTA TCTGTCTCTGACACCAGAGCAGTGGAAG TCCCACCGCTCTTATTCCTGCCAGGTGA CCCATGAGGGCAGCACCGTGGAGAAGA CAGTGGCCCCCACCGAGTGTTCT |
| HBC34-V34, HBC34-V35 | 134 | GGACAGCCAAAGGCTGCTCCATCTGTGA CCCTGTTTCCACCCTCTTCCGAGGAGCT |

| Antibody nucleotide acid sequence description | SEQ ID NO: | nuclecotide sequence |
|---|---|---|
| CL (codon-optimized) | | GCAGGCCAACAAGGCCACCCTGGTGTGC CTGATCTCTGACTTCTACCCTGGAGCTGT GACAGTGGCTTGGAAGGCTGATAGCTCT CCCGTGAAGGCTGGCGTGGAGACAACA ACCCCTAGCAAGCAGTCTAACAATAAGT ACGCCGCTTCCAGCTATCTGTCTCTGAC ACCAGAGCAGTGGAAGTCCCACCGCTCT TATTCCTGCCAGGTGACCCATGAGGGCA GCACCGTGGAGAAGACAGTGGCCCCCA CCGAGTGTTCT |
| HBC34-V34 LC (VL-CL) (codon-optimized) | 135 | AGCTACGAGCTGACACAGCCCCCTTCCG TGTCCGTGTCCCCTGGACAGACCGTGTC CATCCCATGCAGCGGCGACAAGCTGGGC AACAAGAACGTGTCCTGGTTTCAGCATA AGCCTGGCCAGTCCCCCGTGCTGGTCAT CTACGAGGTGAAGTATAGGCCCAGCGG CATCCCTGAGCGGTTCTCTGGCTCCAAC AGCGGCAATACAGCCACCCTGACAATCT CTGGCACACAGGCTATGGACGAGGCCG CTTATTTCTGCCAGACCTTTGATTCCACC ACAGTGGTGTTCGGCGGCGGCACCAGAC TGACAGTGCTGGGACAGCCAAAGGCTG CTCCATCTGTGACCCTGTTTCCACCCTCT TCCGAGGAGCTGCAGGCCAACAAGGCC ACCCTGGTGTGCCTGATCTCTGACTTCTA CCCTGGAGCTGTGACAGTGGCTTGGAAG GCTGATAGCTCTCCCGTGAAGGCTGGCG TGGAGACAACAACCCCTAGCAAGCAGT CTAACAATAAGTACGCCGCTTCCAGCTA TCTGTCTCTGACACCAGAGCAGTGGAAG TCCCACCGCTCTTATTCCTGCCAGGTGA CCCATGAGGGCAGCACCGTGGAGAAGA CAGTGGCCCCCACCGAGTGTTCT |
| HBC34-V35 LC (VL-CL) (codon-optimized) | 136 | AGCTACGAGCTGACACAGCCCCCTTCCG TGTCCGTGTCCCCTGGACAGACCGTGTC CATCCCATGCAGCGGCGACAAGCTGGGC AACAAGAACGTGGCCTGGTTTCAGCATA AGCCTGGCCAGTCCCCCGTGCTGGTCAT CTACGAGGTGAAGTATAGGCCCAGCGG CATCCCTGAGCGGTTCTCTGGCTCCAAC AGCGGCAATACAGCCACCCTGACAATCT CTGGCACACAGGCTATGGACGAGGCCG CTTATTTCTGCCAGACCTTTGATTCCACC ACAGTGGTGTTCGGCGGCGGCACCAGAC TGACAGTGCTGGGACAGCCAAAGGCTG CTCCATCTGTGACCCTGTTTCCACCCTCT TCCGAGGAGCTGCAGGCCAACAAGGCC ACCCTGGTGTGCCTGATCTCTGACTTCTA CCCTGGAGCTGTGACAGTGGCTTGGAAG GCTGATAGCTCTCCCGTGAAGGCTGGCG TGGAGACAACAACCCCTAGCAAGCAGT CTAACAATAAGTACGCCGCTTCCAGCTA TCTGTCTCTGACACCAGAGCAGTGGAAG TCCCACCGCTCTTATTCCTGCCAGGTGA CCCATGAGGGCAGCACCGTGGAGAAGA CAGTGGCCCCCACCGAGTGTTCT |

Due to the redundancy of the genetic code, the present disclosure also comprises sequence variants of these nucleic acid sequences and in particular such sequence variants, which encode the same amino acid sequences.

In certain embodiments, a polynucleotide or nucleic acid molecule comprises a nucleotide sequence sharing at least 80% identity to the nucleotide sequence according to any one of SEQ ID NOs: 103-110 and 130-136, wherein the nucleotide sequence is codon optimized for expression by a host cell.

In particular embodiments, a nucleic acid molecule according to the present disclosure comprises or consists of a nucleic acid sequence according to any one of SEQ ID NOs: 103-110 and 130-136.

In certain embodiments, a polynucleotide comprises a $V_H$-encoding nucleotide sequence according to SEQ ID NO:103 and a $V_L$-encoding nucleotide sequence according to SEQ ID NO:105. In other embodiments, a polynucleotide comprises a $V_H$-encoding nucleotide sequence according to SEQ ID NO:103, and a $V_L$-encoding nucleotide sequence according to SEQ ID NO:104. In other embodiments, a polynucleotide comprises a $V_H$-encoding nucleotide sequence according to SEQ ID NO: 108, and a $V_L$-encoding nucleotide sequence according to SEQ ID NO: 109.

Also provided herein are polynucleotides that encode an antibody or antigen binding fragment, wherein the polynucleotide comprises or consists of a $V_H$-encoding nucleotide sequence according to SEQ ID NO:103 and a $V_L$- encoding nucleotide sequence according to SEQ ID NO:110, wherein the encoded antibody or antigen binding fragment binds to the antigenic loop region of HBsAg and neutralizes infection with hepatitis B virus and hepatitis delta virus.

In any of the presently disclosed embodiments, a polynucleotide can comprise a CH1-hinge-CH2-CH3-encoding nucleotide sequence according to SEQ ID NO:130, and/or comprises a HC (VH-CH1-hinge-CH3-CH3)-encoding nucleotide sequence according to SEQ ID NO:131. In some embodiments, a polynucleotide comprises a CL-encoding nucleotide sequence according to SEQ ID NO:132 and/or comprises a LC (VL-CL)-encoding nucleotide sequence according to SEQ ID NO:133. In other embodiments, a polynucleotide comprises a CL-encoding nucleotide sequence according to SEQ ID NO:134 and/or comprises a LC (VL-CL)-encoding nucleotide sequence according to SEQ ID NO:135 or SEQ ID NO:136.

Vectors

Further included within the scope of the disclosure are vectors, for example, expression vectors, that comprise a nucleic acid molecule according to the present disclosure.

The term "vector" refers to a construct comprising a nucleic acid molecule. A vector in the context of the present disclosure is suitable for incorporating or harboring a desired nucleic acid sequence. Such vectors may be storage vectors, expression vectors, cloning vectors, transfer vectors etc. A storage vector is a vector which allows the convenient storage of a nucleic acid molecule. Thus, the vector may comprise a sequence corresponding, e.g., to a desired antibody or antibody fragment thereof according to the present description.

As used herein, "expression vector" refers to a DNA construct containing a nucleic acid molecule that is operably linked to a suitable control sequence capable of effecting the expression of the nucleic acid molecule in a suitable host. Such control sequences include a promoter (e.g., a heterologous promoter) to effect transcription, an optional operator sequence to control such transcription, a sequence encoding suitable mRNA ribosome binding sites, and sequences which control termination of transcription and translation. Any of the elements of an expression vector that contribute to transcription of a nucleic acid molecule of interest may be heterologous to the vector. The vector may be a plasmid, a phage particle, a virus, or simply a potential genomic insert. Once transformed into a suitable host, the vector may replicate and function independently of the host genome, or may, in some instances, integrate into the genome itself. In the present specification, "plasmid," "expression plasmid," "virus" and "vector" are often used interchangeably.

A cloning vector is typically a vector that contains a cloning site, which may be used to incorporate nucleic acid sequences into the vector. A cloning vector may be, e.g., a plasmid vector or a bacteriophage vector.

A transfer vector may be a vector which is suitable for transferring nucleic acid molecules into cells or organisms, for example, viral vectors. A vector in the context of the present disclosure may be, e.g., an RNA vector or a DNA vector. A vector may be a DNA molecule. For example, a vector in the sense of the present application comprises a cloning site, a selection marker, such as an antibiotic resistance factor, and a sequence suitable for multiplication of the vector, such as an origin of replication. In some embodiments, a vector in the context of the present application is a plasmid vector. In certain such embodiments, a vector comprises a lentiviral vector or a retroviral vector.

Cells

In a further aspect, the present disclosure also provides a cell (also referred to as a "host cell") expressing an antibody, antigen binding fragment, or fusion protein according to the present disclosure; or comprising a vector or polynucleotide according the present disclosure.

Examples of such cells include but are not limited to, eukaryotic cells, e.g., yeast cells, animal cells, insect cells, plant cells; and prokaryotic cells, including E. coli. In some embodiments, the cells are mammalian cells. In certain such embodiments, the cells are a mammalian cell line such as CHO cells (e.g., DHFR-CHO cells (Urlaub et al., PNAS 77:4216 (1980), CHO-KSV), human embryonic kidney cells (e.g., HEK293T cells), PER.C6 cells, Y0 cells, Sp2/0 cells. NS0 cells, human liver cells, e.g. Hepa R G cells, myeloma cells or hybridoma cells. Other examples of mammalian host cell lines include mouse sertoli cells (e.g., TM4 cells); monkey kidney CV1 line transformed by SV40 (COS-7); baby hamster kidney cells (BHK); African green monkey kidney cells (VERO-76); monkey kidney cells (CV1); human cervical carcinoma cells (HELA); human lung cells (W138); human liver cells (Hep G2); canine kidney cells (MDCK; buffalo rat liver cells (BRL 3A); mouse mammary tumor (MMT 060562); TRI cells; MRC 5 cells; and FS4 cells. Mammalian host cell lines suitable for antibody production also include those described in, for example, Yazaki and Wu, Methods in Molecular Biology, Vol. 248 (B. K. C. Lo, ed., Humana Press, Totowa, N.J.), pp. 255-268 (2003).

In certain embodiments, a host cell is a prokaryotic cell, such as an E. coli. The expression of peptides in prokaryotic cells such as E. coli is well established (see, e.g., Pluckthun, A. Bio/Technology 9:545-551 (1991). For example, antibodies may be produced in bacteria, in particular when glycosylation and Fc effector function are not needed. For expression of antibody fragments and polypeptides in bacteria, see, e.g., U.S. Pat. Nos. 5,648,237; 5,789,199; and 5,840,523.

Insect cells useful expressing a binding protein of the present disclosure are known in the art and include, for example, Spodoptera frugipera Sf9 cells, Trichoplusia ni BTI-TN5B1-4 cells, and Spodoptera frugipera SfSWT01 "Mimic™" cells. See, e.g., Palmberger et al., J. Biotechnol. 153(3-4):160-166 (2011). Numerous baculoviral strains have been identified which may be used in conjunction with insect cells, particularly for transfection of Spodoptera frugiperda cells.

Eukaryotic microbes such as filamentous fungi or yeast are also suitable hosts for cloning or expressing protein-encoding vectors, and include fungi and yeast strains with "humanized" glycosylation pathways, resulting in the production of an antibody with a partially or fully human glycosylation pattern. See Gerngross, Nat. Biotech. 22:1409-1414 (2004); Li et al., Nat. Biotech. 24:210-215 (2006).

Plant cells can also be utilized as hosts for expressing a binding protein of the present disclosure. For example, PLANTIBODIES™ technology (described in, for example, U.S. Pat. Nos. 5,959,177; 6,040,498; 6,420,548; 7,125,978; and 6,417,429) employs transgenic plants to produce antibodies.

In some embodiments, a fusion protein is expressed at a cell surface by an immune cell, e.g., a T cell, NK cell, or NK-T cell, or any subtype thereof.

Any protein expression system compatible with the disclosure may be used to produce the disclosed binding proteins. Suitable expression systems include transgenic animals described in Gene Expression Systems, Academic Press, eds. Fernandez et al., 1999.

In particular embodiments, the cell may be transfected with a vector according to the present description with an expression vector. The term "transfection" refers to the introduction of nucleic acid molecules, such as DNA or RNA (e.g. mRNA) molecules, into cells, such as into eukaryotic cells. In the context of the present description, the term "transfection" encompasses any method known to the skilled person for introducing nucleic acid molecules into cells, such as into eukaryotic cells, including into mammalian cells. Such methods encompass, for example, electroporation, lipofection, e.g., based on cationic lipids and/or liposomes, calcium phosphate precipitation, nanoparticle based transfection, virus based transfection, or transfection based on cationic polymers, such as DEAE-dextran or polyethylenimine etc. In certain embodiments, the introduction is non-viral.

Moreover, cells of the present disclosure may be transfected stably or transiently with the vector according to the present description, e.g. for expressing an antibody, or an antigen binding fragment thereof, according to the present description. In such embodiments, the cells are stably transfected with the vector as described herein encoding a binding protein. Alternatively, cells may be transiently transfected with a vector according to the present disclosure encoding a binding protein according to the present description. In any of the presently disclosed embodiments, a polynucleotide may be heterologous to the host cell.

In a related aspect, the present disclosure provides methods for producing an antibody, antigen binding fragment, or fusion protein, wherein the methods comprise culturing a host cell of the present disclosure under conditions and for a time sufficient to produce the antibody, antigen binding fragment, or fusion protein.

Accordingly, the present disclosure also provides recombinant host cells that heterologously express an antibody, antigen binding fragment, or fusion protein of the present disclosure. For example, the cell may be of a species that is different to the species from which the antibody was fully or partially obtained (e.g., CHO cells expressing a human antibody or an engineered human antibody). In some embodiments, the cell type of the host cell does not express the antibody or antigen binding fragment in nature. Moreover, the host cell may impart a post-translational modification (PTM; e.g., glysocylation or fucosylation) on the antibody or antigen binding fragment that is not present in a native state of the antibody or antigen binding fragment (or in a native state of a parent antibody from which the antibody or antigen binding fragment was engineered or derived). Such a PTM may result in a functional difference (e.g., reduced immunogenicity). Accordingly, an antibody or antigen binding fragment of the present disclosure that is produced by a host cell as disclosed herein may include one or more post-translational modification that is distinct from the antibody (or parent antibody) in its native state (e.g., a human antibody produced by a CHO cell can comprise a more post-translational modification that is distinct from the antibody when isolated from the human and/or produced by the native human B cell or plasma cell, Optional Additional Features of the Antibodies, Antigen Binding Fragments, or Fusion Proteins Antibodies, antigen binding fragments, and fusion proteins of the disclosure may be coupled, for example, to a drug for delivery to a treatment site or coupled to a detectable label to facilitate imaging of a site comprising cells of interest. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody (or antigen binding fragment or fusion protein) of the disclosure and an epitope of interest on HBsAg, in particular on the antigenic loop region of HBsAg, can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include 125I, 131I, 35S, or 3H. Such labeled reagents may be used in a variety of well-known assays, such as radioimmunoassays, enzyme immunoassays, e.g., ELISA, fluorescent immunoassays, and the like. Labeled antibodies, antigen binding fragments, and fusion proteins according to the present disclosure may be thus be used in such assays for example as described in U.S. Pat. Nos. 3,766,162; 3,791,932; 3,817,837; and 4,233,402.

An antibody, antigen binding fragment, or fusion protein according to the present disclosure may be conjugated to a therapeutic moiety such as a cytotoxin, a therapeutic agent, or a radioactive metal ion or radioisotope. Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, *Pseudomonas* exotoxin, or diphtheria toxin.

Techniques for conjugating such therapeutic moiety to antibodies are well known. See, for example, Arnon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; Thorpe (1985) "Antibody Carriers of Cytotoxic Agents in Cancer Therapy: A Review," in Monoclonal Antibodies '84: Biological and Clinical Applications, ed. Pinchera et al. pp. 475-506 (Editrice Kurtis, Milano, Italy, 1985); "Analysis, Results, and Future Prospective of the Therapeutic Use of Radiolabeled Antibody in Cancer Therapy," in Monoclonal Antibodies for Cancer Detection and Therapy, ed. Baldwin et al. (Academic Press, New York, 1985), pp. 303-316; and Thorpe et al. (1982) Immunol. Rev. 62:119-158.

Alternatively, an antibody, antibody fragment, or fusion protein, can be conjugated to a second antibody, or antibody fragment thereof, (or second fusion protein) to form a heteroconjugate as described in U.S. Pat. No. 4,676,980. In addition, linkers may be used between the labels and the antibodies of the description, e.g., as described in U.S. Pat. No. 4,831,175. Antibodies, antigen-binding fragments, and fusion proteins may be directly labeled with radioactive iodine, indium, yttrium, or other radioactive particle known in the art, e.g., as described in U.S. Pat. No. 5,595,721. Treatment may consist of a combination of treatment with conjugated and non-conjugated antibodies, antigen binding fragments, and/or fusion proteins, administered simultaneously or subsequently e.g., as described in WO00/52031; WO00/52473.

Antibodies, antigen binding fragments, and fusion proteins as described herein may also be attached to a solid support. Additionally, the antibodies of the present disclosure, functional antibody fragments thereof, or fusion proteins, can be chemically modified by covalent conjugation to a polymer to, for example, increase their circulating half-life. Examples of polymers, and methods to attach them to peptides, are shown in U.S. Pat. Nos. 4,766,106; 4,179,337; 4,495,285 and 4,609,546. In some embodiments, the polymers may be selected from polyoxyethylated polyols and polyethylene glycol (PEG). PEG is soluble in water at room temperature and has the general formula: $R(O—CH_2—CH_2)_nO—R$, wherein R can be hydrogen, or a protective group such as an alkyl or alkanol group. In certain embodiments, the protective group may have between 1 and 8 carbons. For example, the protective group may be methyl. The symbol n is a positive integer. In one embodiment, n is between 1 and 1,000. In another embodiment n is between 2 and 500. In some embodiments, the PEG has an average molecular weight selected from between 1,000 and 40,000, between 2,000 and 20,000, and between 3,000 and 12,000. Furthermore, PEG may have at least one hydroxy group, for example the PEG may have a terminal hydroxy group. For example, it is the terminal hydroxy group which is activated to react with a free amino group on the inhibitor. However, it will be understood that the type and amount of the reactive groups may be varied to achieve a covalently conjugated PEG/antibody of the present description.

Water-soluble polyoxyethylated polyols may also be utilized in the context of the antibodies and antigen binding fragments described herein. They include polyoxyethylated sorbitol, polyoxyethylated glucose, polyoxyethylated glycerol (POG), and the like. In one embodiment, POG is used. Without being bound by any theory, because the glycerol backbone of polyoxyethylated glycerol is the same backbone occurring naturally in, for example, animals and humans in mono-, di-, triglycerides, this branching would not necessarily be seen as a foreign agent in the body. POG may have a molecular weight in the same range as PEG. Another drug delivery system that can be used for increasing circulatory half-life is the liposome. Methods of preparing liposome delivery systems are known to one of skill in the art. Other drug delivery systems are known in the art and are described in, for example, referenced in Poznansky et al. (1980) and Poznansky (1984).

Antibodies, antigen binding fragments, and fusion proteins of the disclosure may be provided in purified form. Typically, the antibody, binding fragment, or fusion protein will be present in a composition that is substantially free of other polypeptides e.g., where less than 90% (by weight), usually less than 60% and more usually less than 50% of the composition is made up of other polypeptides.

Antibodies, fusion proteins, or antigen binding fragments of the disclosure may be immunogenic in non-human (or heterologous) hosts e.g., in mice. In particular, the antibodies, antigen binding fragments, or fusion proteins may have an idiotope that is immunogenic in non-human hosts, but not in a human host. In particular, such molecules of the disclosure for human use include those that cannot be easily isolated from hosts such as mice, goats, rabbits, rats, non-primate mammals, etc. and cannot generally be obtained by humanization or from xeno-mice.

Production of Antibodies, Antigen Binding Fragments, and Fusion Proteins

Antibodies, antigen binding fragments, and fusion proteins according to the disclosure can be made by any method known in the art. For example, the general methodology for making monoclonal antibodies using hybridoma technology is well known (Kohler, G. and Milstein, C., 1975; Kozbar et al. 1983). In one embodiment, the alternative EBV immortalization method described in WO2004/076677 is used.

In one embodiment, antibodies are produced using a method described in WO 2004/076677. In such methods, B cells producing the antibody are transformed with EBV and a polyclonal B cell activator. Additional stimulants of cellular growth and differentiation may optionally be added during the transformation step to further enhance the efficiency. These stimulants may be cytokines such as IL-2 and IL-15. In one aspect, IL-2 is added during the immortalization step to further improve the efficiency of immortalization, but its use is not essential. The immortalized B cells produced using these methods can then be cultured using methods known in the art and antibodies isolated therefrom.

Another method for producing antibodies is described in WO 2010/046775. In such a method, plasma cells are cultured in limited numbers, or as single plasma cells in microwell culture plates. Antibodies can be isolated from the plasma cell cultures. Further, from the plasma cell cultures, RNA can be extracted and PCR can be performed using methods known in the art. The VH and VL regions of the antibodies can be amplified by RT-PCR (reverse transcriptase PCR), sequenced and cloned into an expression vector that is then transfected into HEK293T cells or other host cells. The cloning of nucleic acid in expression vectors, the transfection of host cells, the culture of the transfected host cells and the isolation of the produced antibody can be done using any methods known to one of skill in the art.

The antibodies may be further purified, if desired, using filtration, centrifugation and various chromatographic methods such as HPLC or affinity chromatography. Techniques for purification of antibodies, e.g., monoclonal antibodies, including techniques for producing pharmaceutical-grade antibodies, are well known in the art.

Standard techniques of molecular biology may be used to prepare DNA sequences encoding the antibodies, antibody fragments, or fusion proteins of the present description. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody or fusion protein molecules of the present disclosure or fragments thereof. Bacterial, for example *E. coli*, and other microbial systems may be used, in part, for expression of antibody fragments such as Fab and F(ab')2 fragments, and especially Fv fragments and single chain antibody fragments, for example, single chain Fvs. Eukaryotic, e.g., mammalian, host cell expression systems may be used for production of larger antibody molecules, including complete antibody molecules. Suitable mammalian host cells include, but are not limited to, those exemplary host cells and cell lines disclosed herein.

The present disclosure also provides a process for the production of an antibody, antigen binding fragment, or fusion protein molecule according to the present disclosure comprising culturing a host cell comprising a vector encoding a nucleic acid of the present disclosure under conditions suitable for expression of protein from DNA encoding the antibody molecule of the present description, and isolating the antibody molecule.

An antibody molecule or antibody fragment may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Alternatively, antibodies, antigen binding fragments, and fusion proteins according to the disclosure may be produced by (i) expressing a nucleic acid sequence according to the disclosure in a host cell, e.g. by use of a vector according to the present description, and (ii) isolating the expressed desired product. Additionally, the method may include (iii) purifying the isolated antibody, antigen binding fragment, or fusion protein. Transformed B cells and cultured plasma cells may be screened for those producing antibodies, antigen binding fragments, or fusion proteins of the desired specificity or function.

Screening may be carried out by any immunoassay, e.g., ELISA, by staining of tissues or cells (including transfected cells), by neutralization assay or by one of a number of other methods known in the art for identifying desired specificity or function. The assay may select on the basis of simple recognition of one or more antigens, or may select on the additional basis of a desired function e.g., to select neutralizing antibodies rather than just antigen-binding antibodies, to select antibodies that can change characteristics of targeted cells, such as their signaling cascades, their shape, their growth rate, their capability of influencing other cells, their response to the influence by other cells or by other reagents or by a change in conditions, their differentiation status, or the like.

Individual transformed B cell clones may then be produced from the positive transformed B cell culture. The cloning step for separating individual clones from the mixture of positive cells may be carried out using limiting dilution, micromanipulation, single cell deposition by cell sorting or another method known in the art.

Nucleic acid from the cultured plasma cells can be isolated, cloned and expressed in HEK293T cells or other known host cells using methods known in the art.

The immortalized B cell clones or the transfected host-cells of described herein can be used in various ways e.g., as a source of monoclonal antibodies, as a source of nucleic acid (DNA or mRNA) encoding a monoclonal antibody of interest, for research, etc.

Pharmaceutical Compositions

The present disclosure also provides a pharmaceutical composition comprising an antibody, antigen binding fragment, or fusion protein, according to the present disclosure, a nucleic acid according to the present disclosure, a vector according to the present disclosure and/or a cell according to the present disclosure.

Pharmaceutical compositions may also contain a pharmaceutically acceptable carrier, diluent and/or excipient. Although the carrier or excipient may facilitate administration, it should not itself induce the production of antibodies harmful to the individual receiving the composition. Nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles. In general, pharmaceutically acceptable carriers in a pharmaceutical composition according to the present disclosure may be active components or inactive components.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in a pharmaceutical composition may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the subject.

Pharmaceutical compositions of the disclosure may be prepared in various forms. For example, the compositions may be prepared as injectables, either as liquid solutions or suspensions. Solid forms suitable for solution in, or suspension in, liquid vehicles prior to injection can also be prepared (e.g., a lyophilized composition, similar to Synagis™ and Herceptin™, for reconstitution with sterile water containing a preservative). The composition may be prepared for topical administration e.g., as an ointment, cream or powder. The composition may be prepared for oral administration e.g., as a tablet or capsule, as a spray, or as a syrup (optionally flavored). The composition may be prepared for pulmonary administration e.g., as an inhaler, using a fine powder or a spray. The composition may be prepared as a suppository or pessary. The composition may be prepared for nasal, aural or ocular administration e.g., as drops. The composition may be in kit form, designed such that a combined composition is reconstituted just prior to administration to a subject. For example, a lyophilized antibody may be provided in kit form with sterile water or a sterile buffer.

In particular embodiments, the active ingredient in a composition according to the present disclosure is an antibody molecule, an antibody fragment or variant or derivative thereof, in particular the active ingredient in the composition is an antibody, an antibody fragment, a fusion protein, or variants and derivatives thereof, as described herein. As such, it may be susceptible to degradation in the gastrointestinal tract. Thus, if the composition is to be administered by a route using the gastrointestinal tract, the composition may contain agents which protect the antibody from degradation but which release the antibody once it has been absorbed from the gastrointestinal tract.

A thorough discussion of pharmaceutically acceptable carriers is available in Gennaro (2000) Remington: The Science and Practice of Pharmacy, 20th edition, ISBN: 0683306472.

Pharmaceutical compositions of the disclosure may have a pH between 5.5 and 8.5, and in some embodiments this may be between 6 and 8. In other embodiments, the pH of a pharmaceutical composition as described herein may be about 7. The pH may be maintained by the use of a buffer. The composition may be sterile and/or pyrogen free. The composition may be isotonic with respect to humans. In certain embodiments, pharmaceutical compositions of the disclosure are supplied in hermetically sealed containers.

Within the scope of the disclosure are compositions present in several forms of administration; the forms include, but are not limited to, those forms suitable for parenteral administration, e.g., by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody molecule may be in dry form, for reconstitution before use with an appropriate sterile liquid. A vehicle is typically understood to be a material that is suitable for storing, transporting, and/or administering a compound, such as a pharmaceutically active compound, in particular the antibodies according to the present description. For example, the vehicle may be a physiologically acceptable liquid, which is suitable for storing, transporting, and/or administering a pharmaceutically active compound, in particular the antibodies according to the present description. Once formulated, the compositions of the present disclosure can be administered directly to the subject. In one embodiment the compositions are adapted for administration to mammalian, e.g., human subjects.

The pharmaceutical compositions described herein may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions of the description. In specific embodiments, the pharmaceutical composition may be prepared for oral administration, e.g. as tablets, capsules and the like, for topical administration, or as injectable, e.g. as liquid solutions or suspensions. Solid forms suitable for solution in, or suspension in, liquid vehicles prior to injection may also be utilized, e.g. that the pharmaceutical composition is in lyophilized form.

For injection, e.g. intravenous, cutaneous or subcutaneous injection, or injection at the site of affliction, the active ingredient can be provided be in the form of a parenterally acceptable aqueous solution which is pyrogen-free and has suitable pH, isotonicity and stability. Preservatives, stabilizers, buffers, antioxidants and/or other additives may be included, as required.

Whether it is a polypeptide, peptide, or nucleic acid molecule, cell, or other pharmaceutically useful compound according to the present disclosure that is to be given to an individual, administration is generally in a "prophylactically effective amount" or a "therapeutically effective amount" or an "effective amount" (as the case may be), this being sufficient to show a benefit to the individual (e.g., improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; or prolonged survival in a statistically significant manner). The actual amount administered, and rate and time-course of administration, will depend on the nature and severity of what is being treated. For injection, the pharmaceutical composition according to the present disclosure may be provided for example in a pre-filled syringe.

Pharmaceutical compositions as disclosed herein may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient, i.e. the inventive transporter cargo conjugate molecule as defined above, is combined with emulsifying and suspending agents. If desired, certain sweetening, flavoring or coloring agents may also be added.

The pharmaceutical compositions according to the present description may also be administered topically, especially when the target of treatment includes areas or organs readily accessible by topical application, e.g., including diseases of the skin or of any other accessible epithelial tissue. Suitable topical formulations are readily prepared for each of these areas or organs. For topical applications, the pharmaceutical composition may be formulated in a suitable ointment, containing the inventive pharmaceutical composition, particularly its components as defined above, suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the pharmaceutical composition can be formulated in a suitable lotion or cream. In the context of the present description, suitable carriers include, but are not limited to, mineral oil, sorbitan monostearate, polysorbate 60, cetyl esters wax, cetearyl alcohol, 2-octyldodecanol, benzyl alcohol and water.

Doses may be expressed in relation to the bodyweight. Thus, a dose which is expressed as [g, mg, or other unit]/kg (or g, mg etc.) usually refers to [g, mg, or other unit] "per kg (or g, mg etc.) bodyweight", even if the term "bodyweight" is not explicitly mentioned. In specific embodiments, in a single dose, e.g. a daily, weekly or monthly dose, the amount of the antibody, or the antigen binding fragment thereof, in the pharmaceutical composition does not exceed 1 g. In certain such embodiments, the single dose does not exceed a dose selected from 500 mg, 250 mg, 100 mg, and 50 mg.

In some embodiments, a composition or kit as described herein further comprises (i) a polymerase inhibitor, wherein the polymerase inhibitor optionally comprises Lamivudine, Adefovir, Entecavir, Telbivudine, Tenofovir, or any combination thereof; (ii) an interferon, wherein the interferon optionally comprises IFNbeta and/or IFNalpha; (iii) a checkpoint inhibitor, wherein the checkpoint inhibitor optionally comprises an anti-PD-1 antibody or antigen binding fragment thereof, an anti-PD-L1 antibody or antigen binding fragment thereof, and/or an anti-CTLA4 antibody or antigen binding fragment thereof; (iv) an agonist of a stimulatory immune checkpoint molecule; or (v) any combination of (i)-(iv). In some embodiments, a kit comprises a composition or combination as described herein, and further comprises instructions for using the component to prevent, treat, attenuate, and/or diagnose a hepatitis B infection and/or a hepatitis D infection.

In certain embodiments, a composition of the present disclosure (e.g., antibody, antigen-binding fragment, host cell, nucleic acid, vector, or pharmaceutical composition) is used in combination with a PD-1 inhibitor, for example a PD-1-specific antibody or binding fragment thereof, such as pidilizumab, nivolumab, pembrolizumab, MEDI0680 (formerly AMP-514), AMP-224, BMS-936558 or any combination thereof.

In certain embodiments, a composition of the present disclosure is used in combination with a PD-L1 specific antibody or binding fragment thereof, such as BMS-936559, durvalumab (MEDI4736), atezolizumab (RG7446), avelumab (MSB0010718C), MPDL3280A, or any combination thereof.

In certain embodiments, a composition of the present disclosure is used in combination with a LAG3 inhibitor, such as LAG525, IMP321, IMP701, 9H12, BMS-986016, or any combination thereof.

In certain embodiments, a composition of the present disclosure is used in combination with an inhibitor of CTLA4. In particular embodiments, a composition of the present disclosure is used in combination with a CTLA4 specific antibody or binding fragment thereof, such as ipilimumab, tremelimumab, CTLA4-Ig fusion proteins (e.g., abatacept, belatacept), or any combination thereof.

In certain embodiments, a composition of the present disclosure is used in combination with a B7-H3 specific antibody or binding fragment thereof, such as enoblituzumab (MGA271), 376.96, or both. A B7-H3 antibody binding fragment may be a scFv or fusion protein thereof, as described in, for example, Dangaj et al., Cancer Res. 73:4820, 2013, as well as those described in U.S. Pat. No. 9,574,000 and PCT Patent Publication Nos. WO/201640724A1 and WO 2013/025779A1.

In certain embodiments, a composition of the present disclosure is used in combination with an inhibitor of CD244.

In certain embodiments, a composition of the present disclosure is used in combination with an inhibitor of BLTA, HVEM, CD160, or any combination thereof. Anti CD-160 antibodies are described in, for example, PCT Publication No. WO 2010/084158.

In certain embodiments, a composition of the present disclosure is used in combination with an inhibitor of TIM3.

In certain embodiments, a composition of the present disclosure is used in combination with an inhibitor of Ga19.

In certain embodiments, a composition of the present disclosure is used in combination with an inhibitor of adenosine signaling, such as a decoy adenosine receptor.

In certain embodiments, a composition of the present disclosure is used in combination with an inhibitor of A2aR.

In certain embodiments, a composition of the present disclosure is used in combination with an inhibitor of KIR, such as lirilumab (BMS-986015).

In certain embodiments, a composition of the present disclosure is used in combination with an inhibitor of an inhibitory cytokine (typically, a cytokine other than TGFβ) or Treg development or activity.

In certain embodiments, a composition of the present disclosure is used in combination with an IDO inhibitor, such as levo-1-methyl tryptophan, epacadostat (INCB024360; Liu et al., Blood 115:3520-30, 2010), ebselen (Terentis et al., Biochem. 49:591-600, 2010), indoximod, NLG919 (Mautino et al., American Association for Cancer Research 104th Annual Meeting 2013; Apr. 6-10, 2013), 1-methyl-tryptophan (1-MT)-tira-pazamine, or any combination thereof.

In certain embodiments, a composition of the present disclosure is used in combination with an arginase inhibitor, such as N(omega)-Nitro-L-arginine methyl ester (L-NAME), N-omega-hydroxy-nor-1-arginine (nor-NOHA), L-NOHA, 2(S)-amino-6-boronohexanoic acid (ABH), S-(2-boronoethyl)-L-cysteine (BEC), or any combination thereof.

In certain embodiments, a composition of the present disclosure is used in combination with an inhibitor of VISTA, such as CA-170 (Curis, Lexington, Mass.).

In certain embodiments, a composition of the present disclosure is used in combination with an inhibitor of TIGIT such as, for example, COM902 (Compugen, Toronto, Ontario Canada), an inhibitor of CD155, such as, for example, COM701 (Compugen), or both.

In certain embodiments, a composition of the present disclosure is used in combination with an inhibitor of PVRIG, PVRL2, or both. Anti-PVRIG antibodies are described in, for example, PCT Publication No. WO 2016/134333. Anti-PVRL2 antibodies are described in, for example, PCT Publication No. WO 2017/021526.

In certain embodiments, a composition of the present disclosure is used in combination with a LAIR1 inhibitor.

In certain embodiments a composition of the present disclosure is used in combination with an inhibitor of CEACAM-1, CEACAM-3, CEACAM-5, or any combination thereof.

In certain embodiments, a composition of the present disclosure is used in combination with an agent that increases the activity (i.e., is an agonist) of a stimulatory immune checkpoint molecule. For example, a composition of the present disclosure can be used in combination with a CD137 (4-1BB) agonist (such as, for example, urelumab), a CD134 (OX-40) agonist (such as, for example, MEDI6469, MEDI6383, or MEDI0562), lenalidomide, pomalidomide, a CD27 agonist (such as, for example, CDX-1127), a CD28 agonist (such as, for example, TGN1412, CD80, or CD86), a CD40 agonist (such as, for example, CP-870,893, rhuCD40L, or SGN-40), a CD122 agonist (such as, for example, IL-2) an agonist of GITR (such as, for example, humanized monoclonal antibodies described in PCT Patent Publication No. WO 2016/054638), an agonist of ICOS (CD278) (such as, for example, GSK3359609, mAb 88.2, JTX-2011, Icos 145-1, Icos 314-8, or any combination thereof). In any of the embodiments disclosed herein, a method may comprise administering a composition of the present disclosure with one or more agonist of a stimulatory immune checkpoint molecule, including any of the foregoing, singly or in any combination.

An antibody, antigen binding fragment, or fusion protein according to the present disclosure can be present either in the same pharmaceutical composition as the additional active component or, the antibody, antigen binding fragment, or fusion protein according to the present disclosure may be included in a first pharmaceutical composition and the additional active component may be included in a second pharmaceutical composition different from the first pharmaceutical composition.

Uses

In a further aspect, the present disclosure provides methods for the use of an antibody, an antigen binding fragment, a fusion protein, a nucleic acid, a vector, a cell or a pharmaceutical composition, or kit according to the present disclosure in the (i) prophylaxis, treatment or attenuation of hepatitis B and/or hepatitis D; or in (ii) diagnosis of hepatitis B and/or hepatitis D (e.g., in a human subject).

Methods of diagnosis (e.g., in vitro, ex vivo) may include contacting an antibody, antibody fragment (e.g., antigen binding fragment), or fusion protein with a sample. Such samples may be isolated from a subject, for example an isolated tissue sample taken from, for example, nasal passages, sinus cavities, salivary glands, lung, liver, pancreas, kidney, ear, eye, placenta, alimentary tract, heart, ovaries, pituitary, adrenals, thyroid, brain, skin or blood. The methods of diagnosis may also include the detection of an antigen/antibody or antigen/fusion protein complex, in particular following the contacting of an antibody, antibody fragment, or fusion protein with a sample. Such a detection step is typically performed at the bench, i.e. without any contact to the human or animal body. Examples of detection methods are well-known to the person skilled in the art and include, e.g., ELISA (enzyme-linked immunosorbent assay).

The disclosure also provides the use of (i) an antibody, an antibody fragment, fusion protein, or variants and derivatives thereof according to the disclosure, (ii) host cell (which can be an immortalized B cell) according to the disclosure, (iii) a nucleic acid or a vector according to the present disclosure or (iv) a pharmaceutical composition of the disclosure in (a) the manufacture of a medicament for the prevention, treatment or attenuation of hepatitis B and/or hepatitis D or for (b) diagnosis of hepatitis B and/or hepatitis D.

The disclosure also provides an antibody, antigen binding fragment, or fusion protein according to the present disclosure, a nucleic acid according to the present disclosure, a vector according to the present disclosure, a cell according to the present disclosure or the pharmaceutical composition according to the present disclosure for use as a medicament for the prevention or treatment of hepatitis B and/or hepatitis D. It also provides the use of an antibody, antigen binding fragment, or fusion protein of the disclosure in the manufacture of a medicament for treatment of a subject and/or diagnosis in a subject. It also provides a method for treating a subject (e.g., a human subject), comprising administering to the subject an effective amount of a composition as described herein. In some embodiments, the subject may be a human. One way of checking efficacy of therapeutic treatment involves monitoring disease symptoms after administration of the composition. Treatment can be a single dose schedule or a multiple dose schedule.

In one embodiment, an antibody, antibody fragment, fusion protein, host cell (e.g., immortalized B cell clone, or T cell, NK-T cell, or NK cell that expresses a fusion protein), or pharmaceutical composition according to the disclosure is administered to a subject in need of such treatment. Such a subject includes, but is not limited to, one who is particularly at risk of or susceptible to hepatitis B and/or hepatitis D.

Antibodies, antigen binding fragments, fusion proteins, polynucleotides, vectors, host cells, pharmaceutical compositions, and combinations of the same, according to the present disclosure may also be used in a kit for the prevention, treatment, attenuation, and/or diagnosis of hepatitis B and/or hepatitis D. In some embodiments, a kit further comprises instructions for using the component to prevent, treat, attenuate, and/or diagnose a hepatitis B infection and/or a hepatitis D infection. Further, the epitope in the antigenic loop region of HBsAg, which is capable of binding an antibody, antigen binding fragment, or fusion protein of the disclosure as described herein may be used in a kit for monitoring the efficacy of application procedures by detecting the presence or determining the titer of protective anti-HBV antibodies.

In certain embodiments, a composition or a kit of this disclosure further comprises: a polymerase inhibitor, wherein the polymerase inhibitor optionally comprises Lamivudine, Adefovir, Entecavir, Telbivudine, Tenofovir, or any combination thereof; (ii) an interferon, wherein the interferon optionally comprises IFNbeta and/or IFNalpha; (iii) a checkpoint inhibitor, wherein the checkpoint inhibitor optionally comprises an anti-PD-1 antibody or antigen binding fragment thereof, an anti-PD-L1 antibody or antigen binding fragment thereof, and/or an anti-CTLA4 antibody or antigen binding fragment thereof; (iv) an agonist of a stimulatory immune checkpoint molecule; or (v) any combination of (viii)-(xii).

In some embodiments, an antibody, an antigen binding fragment, or fusion protein according to the present disclosure, a nucleic acid according to the present disclosure, the vector according to the present disclosure, the cell according to the present disclosure or the pharmaceutical composition according to the present disclosure is used in treatment or attenuation of chronic hepatitis B infection.

In particular embodiments, an antibody, antigen binding fragment, or fusion protein according to the present disclosure (i) neutralizes HBV infection, (ii) binds to L-HBsAg (the large HBV envelope protein, which is present in infectious HBV particles), thereby preventing spreading of HBV, (iii) binds to S-HBsAg, thereby promoting clearance of subviral particles (SVP) and/or (iv) can induce seroconversion, i.e. an active immune response to the virus.

In particular embodiments, antibody, antigen binding fragment, or fusion protein according to the present disclosure, a nucleic acid according to the present disclosure, a vector according to the present disclosure, a cell according to the present disclosure, or a pharmaceutical composition according to the present disclosure, may be used in prevention of hepatitis B (re-)infection after liver transplantation in particular for hepatitis B induced liver failure.

In further embodiments an antibody, antigen binding fragment thereof, or fusion protein according to the present disclosure, a nucleic acid according to the present disclosure, a vector according to the description provided herein, a cell according to the present disclosure, or a pharmaceutical composition according to the present disclosure, may be used in prevention/prophylaxis of hepatitis B in non-immunized subjects. This is for example in case of (an assumed) accidental exposure to HBV (post-exposure prophylaxis). The term "non-immunized subjects" includes subjects, who never received a vaccination and are, thus, not immunized, and subjects, who did not show an immune response (e.g., no measurable anti-hepatitis B antibodies) after vaccination.

In some embodiments, an antibody, antigen binding fragment, or fusion protein according to the present disclosure, the nucleic acid according to the present disclosure, a vector according to the present disclosure, a cell according to the present disclosure, or a pharmaceutical composition according to the present disclosure, is used in prophylaxis of hepatitis B in haemodialysed patients.

In some embodiments, an antibody, an antigen binding fragment, or fusion protein according to the present disclosure, a nucleic acid according to the present disclosure, a vector according to the present disclosure, a cell according to the present disclosure or a pharmaceutical composition according to the present disclosure is used in prevention of hepatitis B in a newborn. In such embodiments, an antibody, or an antigen binding fragment thereof, according to the present disclosure, a nucleic acid according to the present disclosure, a vector according to the present disclosure, a cell according to the present disclosure or a pharmaceutical composition according to the present disclosure may be administered at birth or as soon as possible after birth. The administration may be repeated until seroconversion following vaccination.

Moreover, the present disclosure also provides the use of an antibody, antigen binding fragment, or fusion protein according to the present disclosure, a nucleic acid according to the present disclosure, a vector according to the present disclosure, a cell according to the present disclosure or a pharmaceutical composition according to the present disclosure in the diagnosis (e.g. in vitro, ex vivo, or in vivo) of hepatitis B and/or hepatitis D.

In addition, the use of an antibody, antigen binding fragment, or fusion protein according to the present disclosure, a nucleic acid according to the present disclosure, a vector according to the present disclosure, a cell according to the present disclosure or a pharmaceutical composition according to the present disclosure in determining whether an isolated blood sample is infected with hepatitis B virus and/or hepatitis delta virus is provided.

As described above, methods of diagnosis may include contacting an antibody, antibody fragment, or fusion protein with a sample. Such samples may be isolated from a subject, for example an isolated tissue sample taken from, for example, nasal passages, sinus cavities, salivary glands, lung, liver, pancreas, kidney, ear, eye, placenta, alimentary tract, heart, ovaries, pituitary, adrenals, thyroid, brain, skin or blood. The methods of diagnosis may also include the detection of an antigen/antibody complex, in particular following the contacting of an antibody or an antibody fragment with a sample. Such a detection step is typically performed at the bench, i.e. without any contact to the human or animal body. Examples of detection methods are well-known to the person skilled in the art and include, e.g., ELISA (enzyme-linked immunosorbent assay).

The present disclosure also provides a method of treating, preventing and/or attenuating hepatitis B and/or hepatitis D in a subject, wherein the method comprises administering to the subject an antibody, antigen binding fragment, or fusion protein according to the present disclosure, a nucleic acid according to the present disclosure, a vector according to the present disclosure, a cell according to the present disclosure or a pharmaceutical composition according to the present disclosure. In certain embodiments, a method further comprises administering to the subject one or more of: (vii) a polymerase inhibitor, wherein the polymerase inhibitor optionally comprises Lamivudine, Adefovir, Entecavir, Telbivudine, Tenofovir, or any combination thereof; (viii) an interferon, wherein the interferon optionally comprises IFN-beta and/or IFNalpha; (ix) a checkpoint inhibitor, wherein the checkpoint inhibitor optionally comprises an anti-PD-1 antibody or antigen binding fragment thereof, an anti-PD-L1 antibody or antigen binding fragment thereof, and/or an anti-CTLA4 antibody or antigen binding fragment thereof; (x) an agonist of a stimulatory immune checkpoint molecule; or (xi) any combination of (vii)-(x).

In some embodiments, the hepatitis B infection is a chronic hepatitis B infection. In some embodiments, the subject has received a liver transplant. In some embodiments, the subject is non-immunized against hepatitis B. In certain embodiments, the subject is a newborn. In some embodiments, the subject is undergoing or has undergone hemodialysis.

The present disclosure also provides a method of treating a subject who has received a liver transplant comprising administering to the subject who has received the liver transplant an effective amount of an antibody, an antigen binding fragment, or fusion protein according to the present disclosure, a nucleic acid according to the present disclosure, a vector according to the present disclosure, a cell according to the present disclosure or a pharmaceutical composition according to the present disclosure.

Also provided herein are methods for detecting the presence or absence of an epitope in a correct conformation in an anti-hepatitis-B and/or an anti-hepatitis-D vaccine, wherein the methods comprise: (i) contacting the vaccine with an antibody, antigen-binding fragment, or fusion protein of any one of the present disclosure; and (ii) determining whether a complex comprising an antigen and the antibody, or comprising an antigen and the antigen binding fragment, or comprising an antigen and the fusion protein, has been formed.

The term "vaccine" as used herein is typically understood to be a prophylactic or therapeutic material providing at least one antigen, such as an immunogen. The antigen or immunogen may be derived from any material that is suitable for vaccination. For example, the antigen or immunogen may be derived from a pathogen, such as from bacteria particles, virus particles, a tumor (including a solid or liquid tumor), or other cancerous tissue. The antigen or immunogen stimulates the body's adaptive immune system to provide an adaptive immune response. In certain embodiments, an "antigen" or an "immunogen" refers to a substance which may be recognized by the immune system, e.g. by the adaptive immune system, and which is capable of triggering an antigen-specific immune response, e.g. by formation of antibodies and/or antigen-specific T cells as part of an adaptive immune response. In some embodiments, an antigen may be or may comprise a peptide or protein which may be presented by an MHC complex (e.g., MHC class I; MHC class II) to T cells. In certain embodiments, the antigen comprises a HBV and/or HBD antigen; e.g., an HBsAg antigen.

In some instances, elements of the of the antibodies, antibody fragments, fusion proteins, nucleic acids, cells, compositions, uses, and methods provided herein are described or listed with reference to embodiments or examples. However, it should be understood that the examples and embodiments described herein may be combined in various ways to create additional embodiments.

EXAMPLES

In the following, particular examples illustrating various embodiments and aspects of the disclosure are presented. However, the present disclosure shall not to be limited in scope by the specific embodiments described herein.

Example 1: Generation and Testing of Engineered Antibodies

Analysis of some HBC34 antibody variants from PCT Publication No. WO 2017/060504 revealed a cysteine amino acid at position 40 (IMGT numbering) in the light chain variable region that is unpaired and represents a potential liability. Without wishing to be bound by theory, unpaired cysteine residues are potentially reactive and can potentially trigger aggregation through intramolecular scrambling or intermolecular disulfide formation. Variants of HBC34-V7 (WO 2017/060504) were engineered in which the cysteine amino acid at position 40 of the light chain variable region was substituted with a serine (thereby generating "HBC34-V34") or with an alanine (thereby generating "HBC34-V35"). The nucleotide sequences encoding these additional variant antibodies were codon-optimized, and antibodies were expressed as IgG1 (g1m17, 1 allotype) in ExpiCHO™ cells (ThermoFisher). Codon-optimized nucleotide sequences encoding the VH and VL domains of HBC34-V35 are provided in SEQ ID NOS: 103 and 104, respectively.

The ability of HBC34-V34 and HBC34-V35 to bind antigen was investigated using a direct antigen-binding ELISA. HBC34-V7 was used as a comparator. As shown in FIG. 1, both HBC34-V34 and HBC34-V35 bound effectively to two recombinant HBsAg antigens ("adw", top panel; "adr", bottom panel), and HBC34-V35 had very similar binding as the parent HBC34-V7.

The variant antibodies were examined for binding to all known HBsAg genotypes ((A)-(J)). Briefly, human epithelial cells (Hep2 cells) were transfected with plasmids expressing the HBsAg of each of the 10 HBV genotypes A, B, C, D, E, F, G, H, I, and J. All antibodies were tested at multiple concentrations for staining of transiently transfected permeabilized cells. Two days after transfection, Hep2 cells were collected, fixed and permeabilized with saponin for immunostaining with HBC34 and the five selected variants. HBC34-V7 was included as a comparator. Binding of antibodies to transfected cells was analysed using a Becton Dickinson FACSCanto2™ (BD Biosciences) with FlowJo software (TreeStar). As shown in FIGS. 2A-2J, HBC34-V34 and HBC34-V35 recognized all 10 HBV HBsAg genotypes. HBC34-V35 showed somewhat stronger staining than HBC34-V34.

These data show that the antibody variants HBC34-V34 and HBC34-V35 broadly recognize and bind to HBsAG at levels comparable to HBC34-V7.

Example 2: Anti-HBsAg Antibodies with Modified Fc Regions Efficiently Bind to Antigen Modifications in the Fc region may provide advantages to a therapeutic antibody. HBC34-V35 was expressed as IgG1 with wild-type Fc, or with Fc containing a "MLNS" mutation (M428L/N434S) or with Fc containing MLNS in combination with a "GAALIE" mutation (G239A/A330L/I332E). Each construct was tested for binding to recombinant HBsAg (adw) in two separate antigen-binding ELISA experiments. Three (3) lots of HBC34-v35 (wild-type Fc) were tested. Two (2) lots of HBC34-V35-MLNS and two (2) lots of HBC34-V35-MLNS-GAALIE were tested. HBC34v7 (one lot) was tested as a comparator.

Figure 3C:
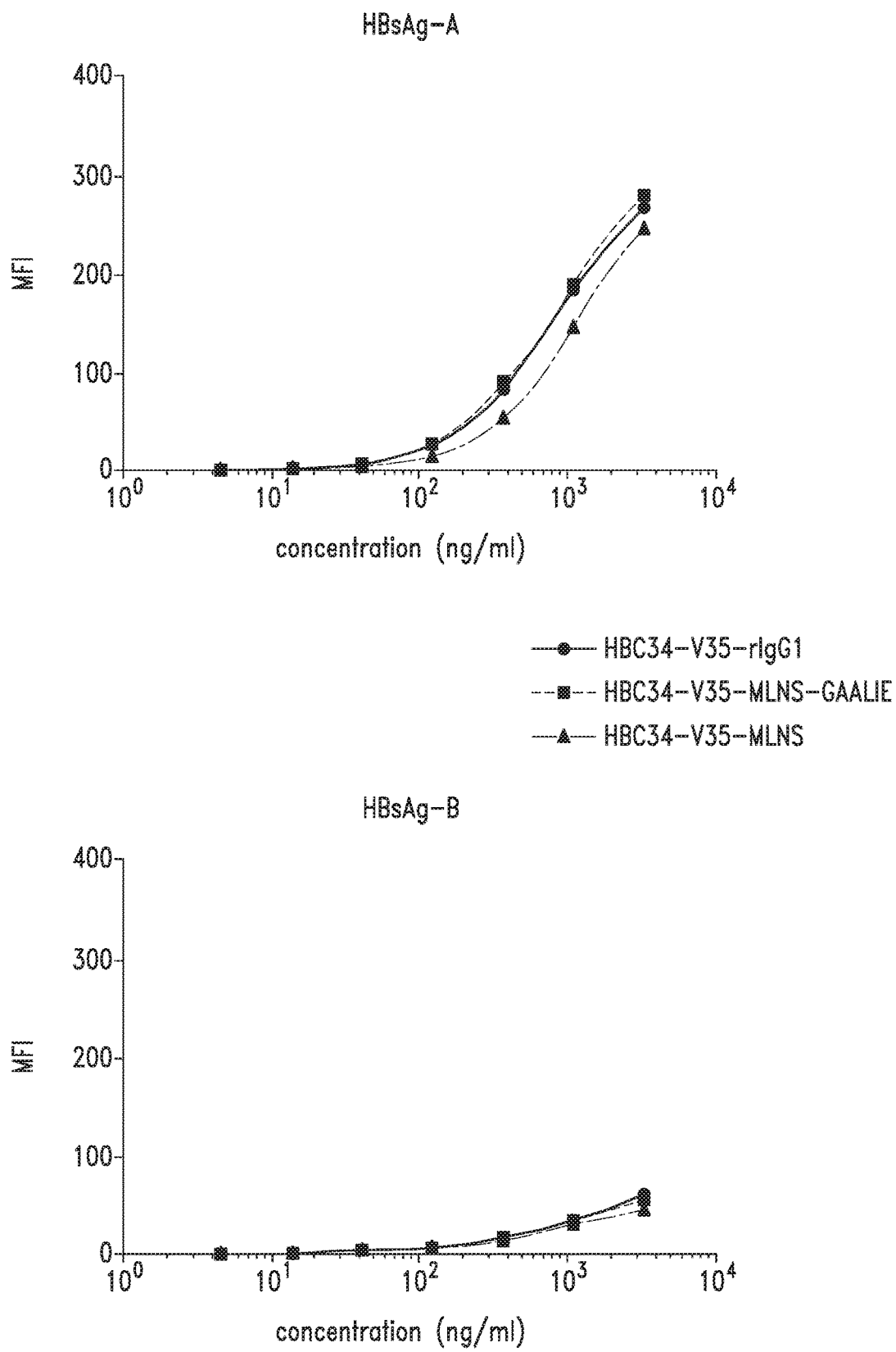
FIGS. 3C-3H show binding of HBC34-V35, HBC34-V35-MLNS, and HBC34-V35-MLNS-GAALIE to Expi293 cells expressing HBsAg from all ten known HBV genotypes or mock control. Binding was determined by flow cytometry. Data are expressed as the mean fluorescence intensity (y-axis) of the transfected populations as defined by gating out the signal obtained with mock-transfected cells. For each HbsAg, serial dilutions of the three test articles were tested (12 points, 1 in 3, starting from 10 μg/ml).
Figure 3D:
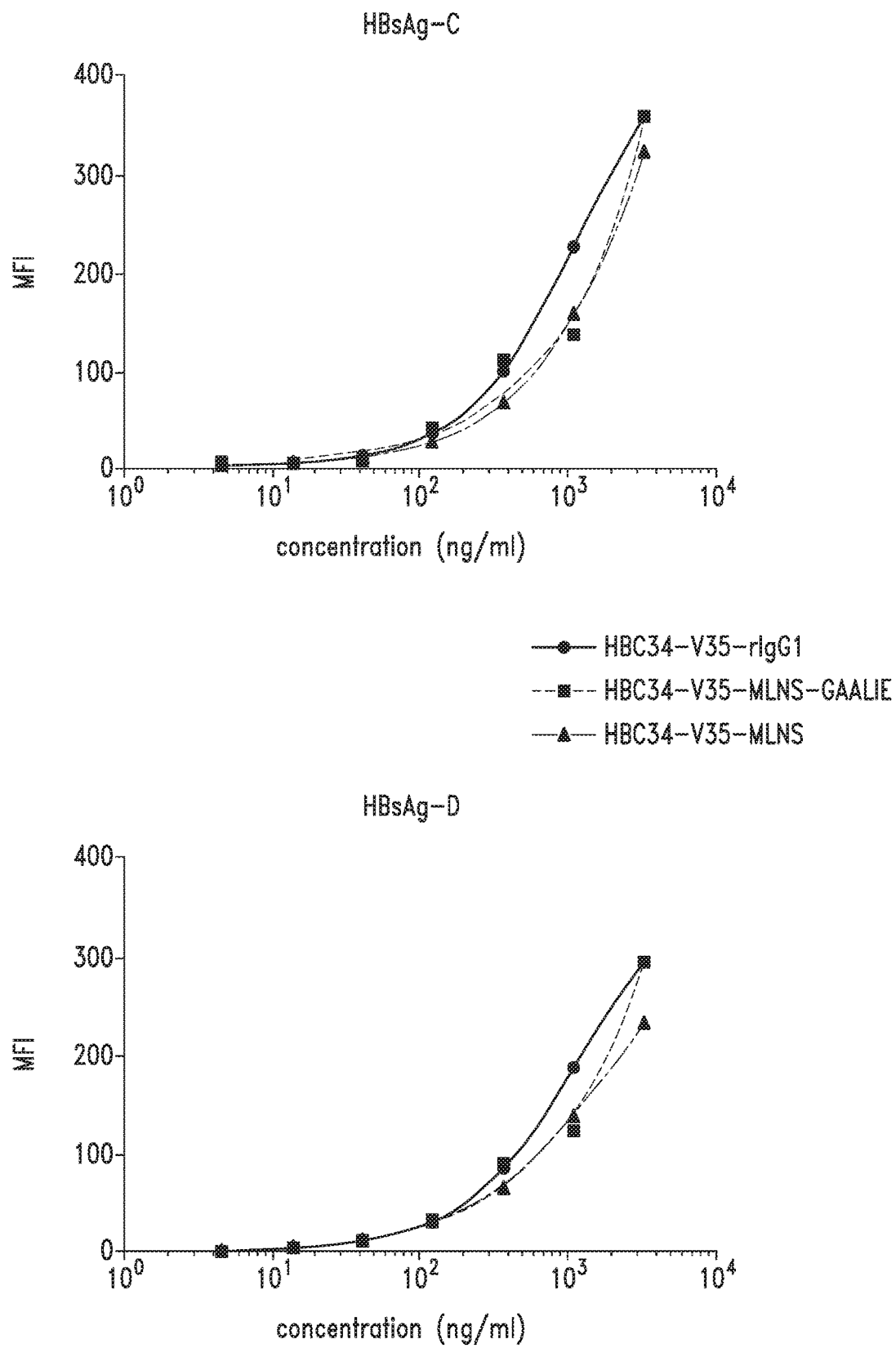
Figure 3E:
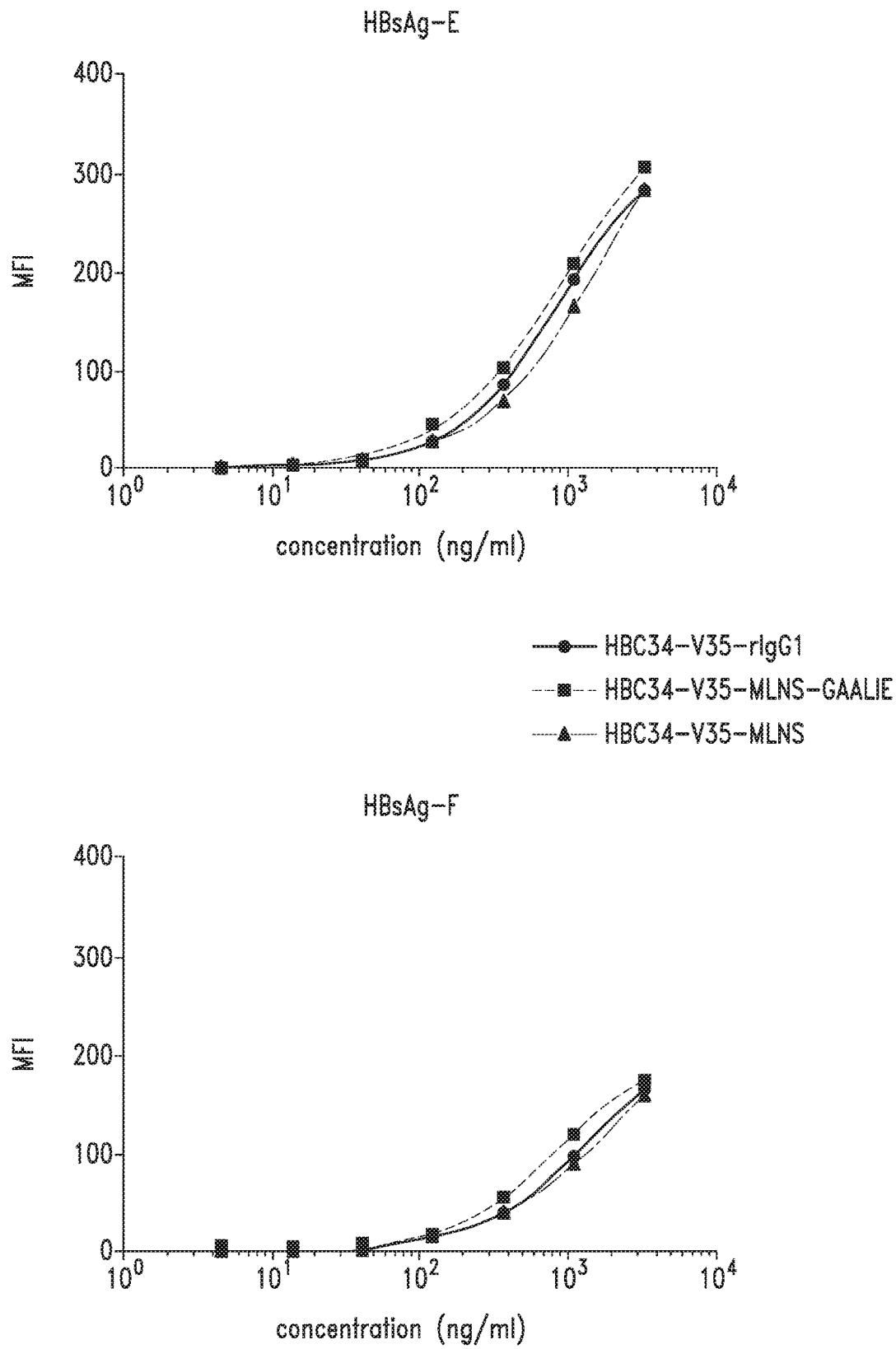
Figure 3F:
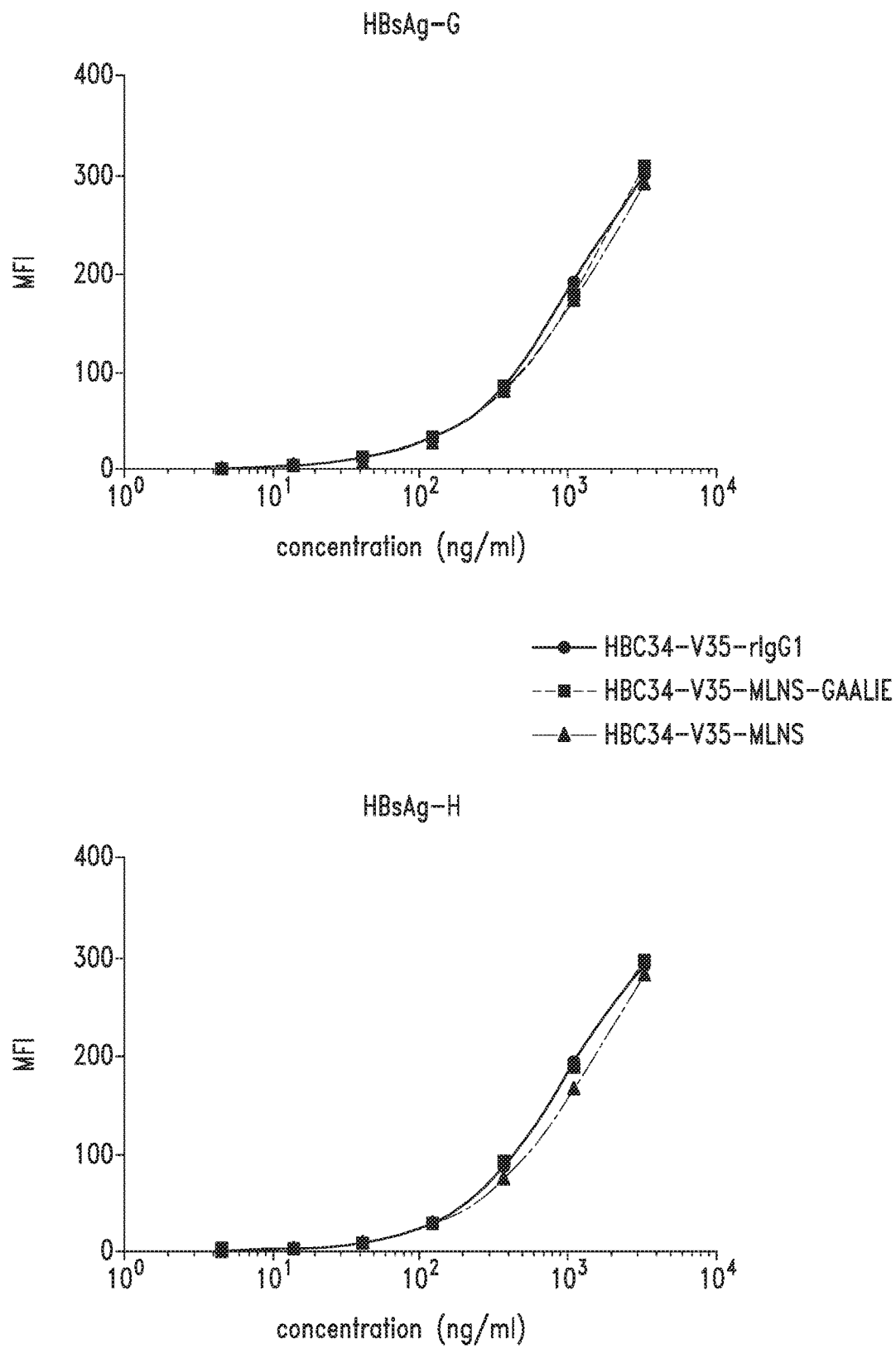
Figure 3G:
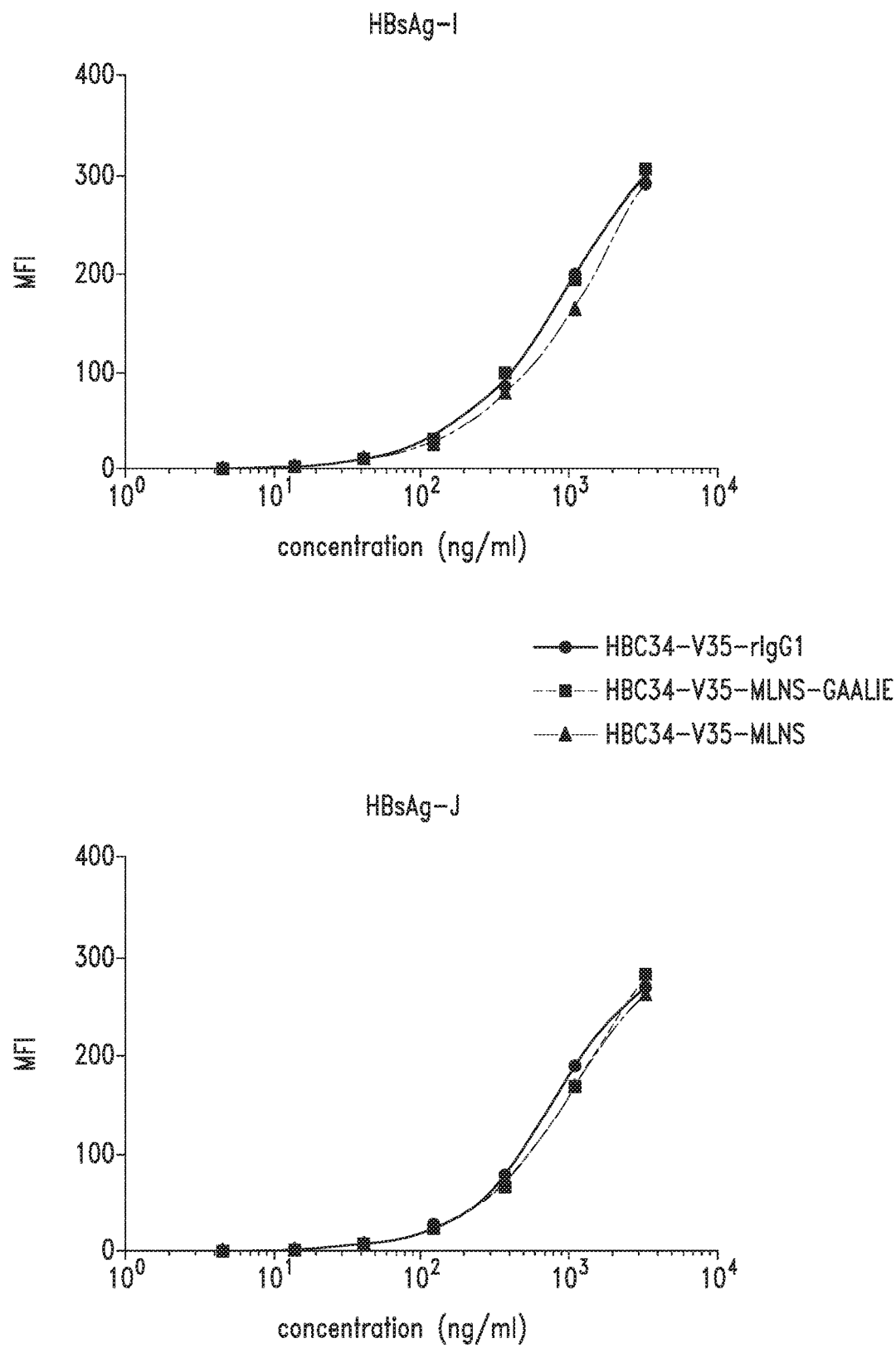
Figure 3H:
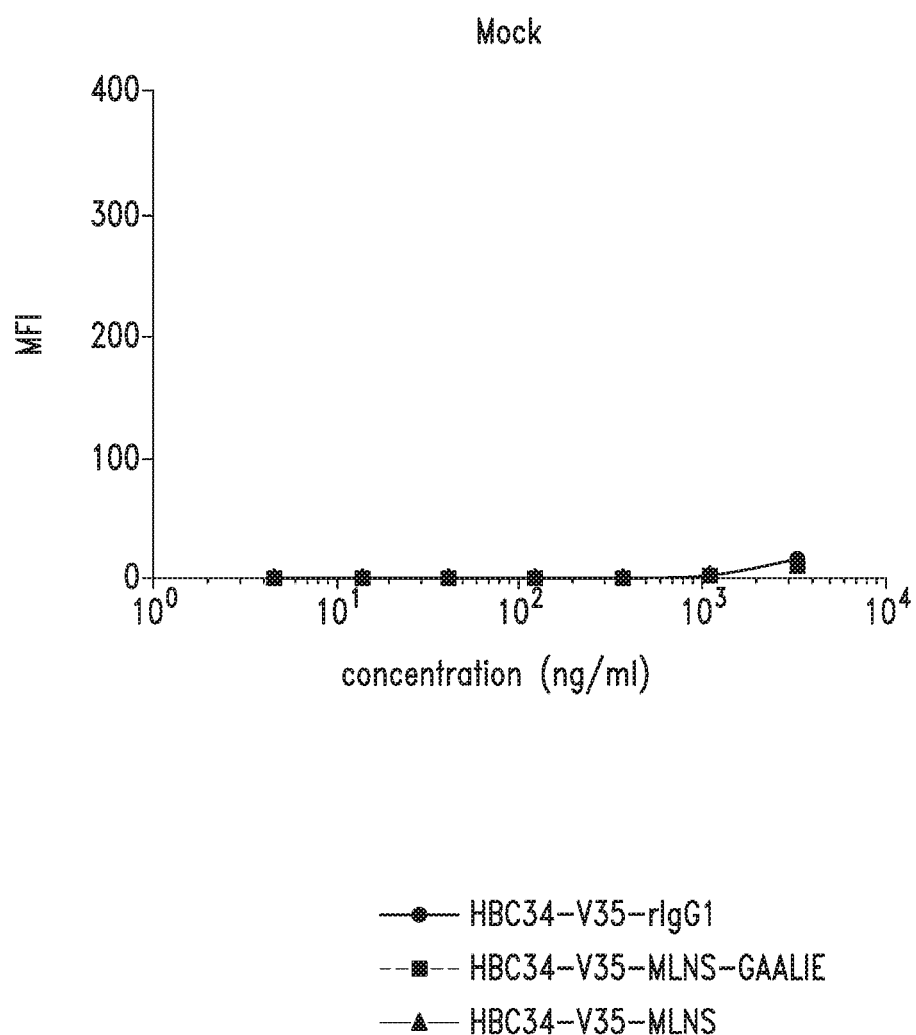
Figure 3I:
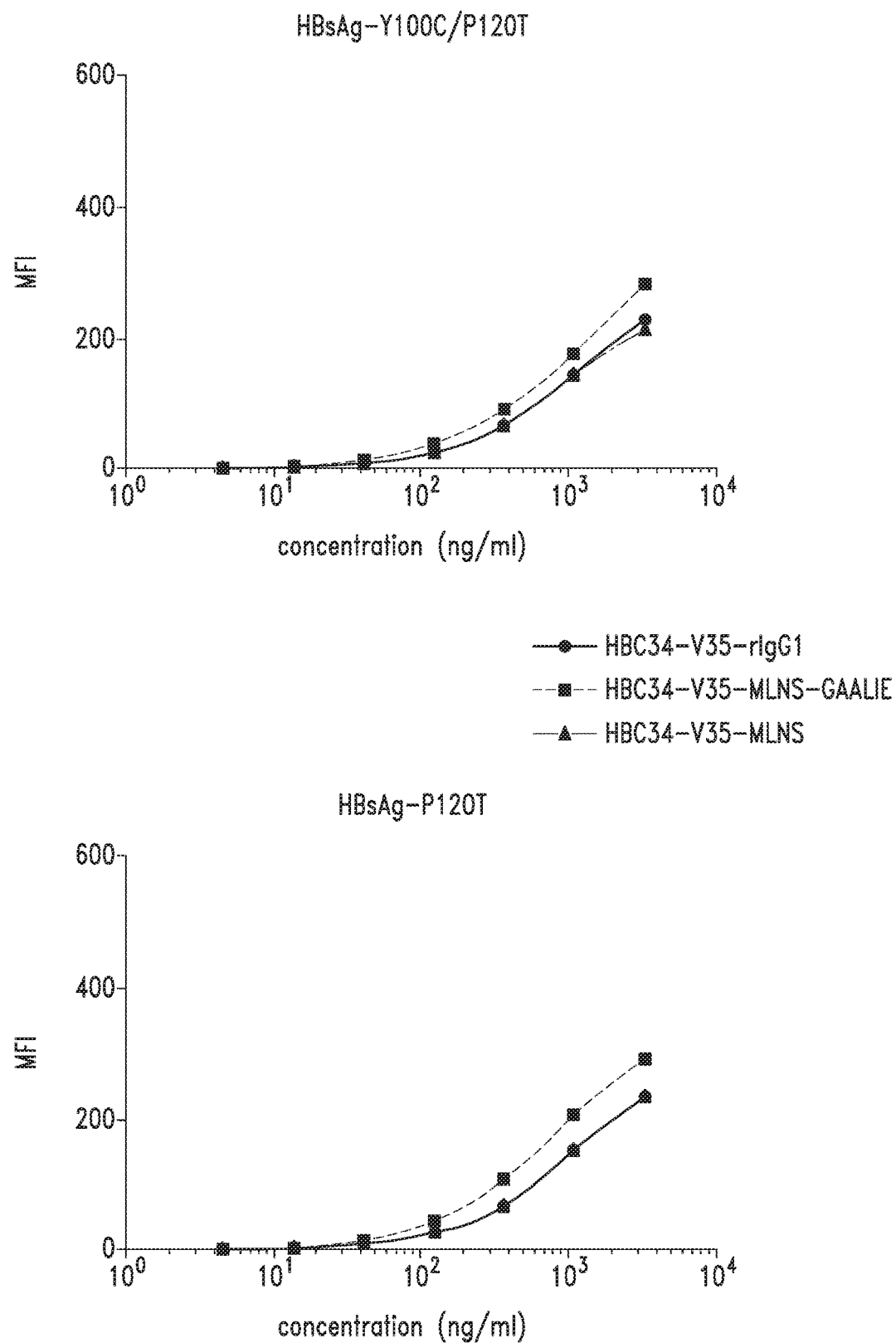
Figure 3J:
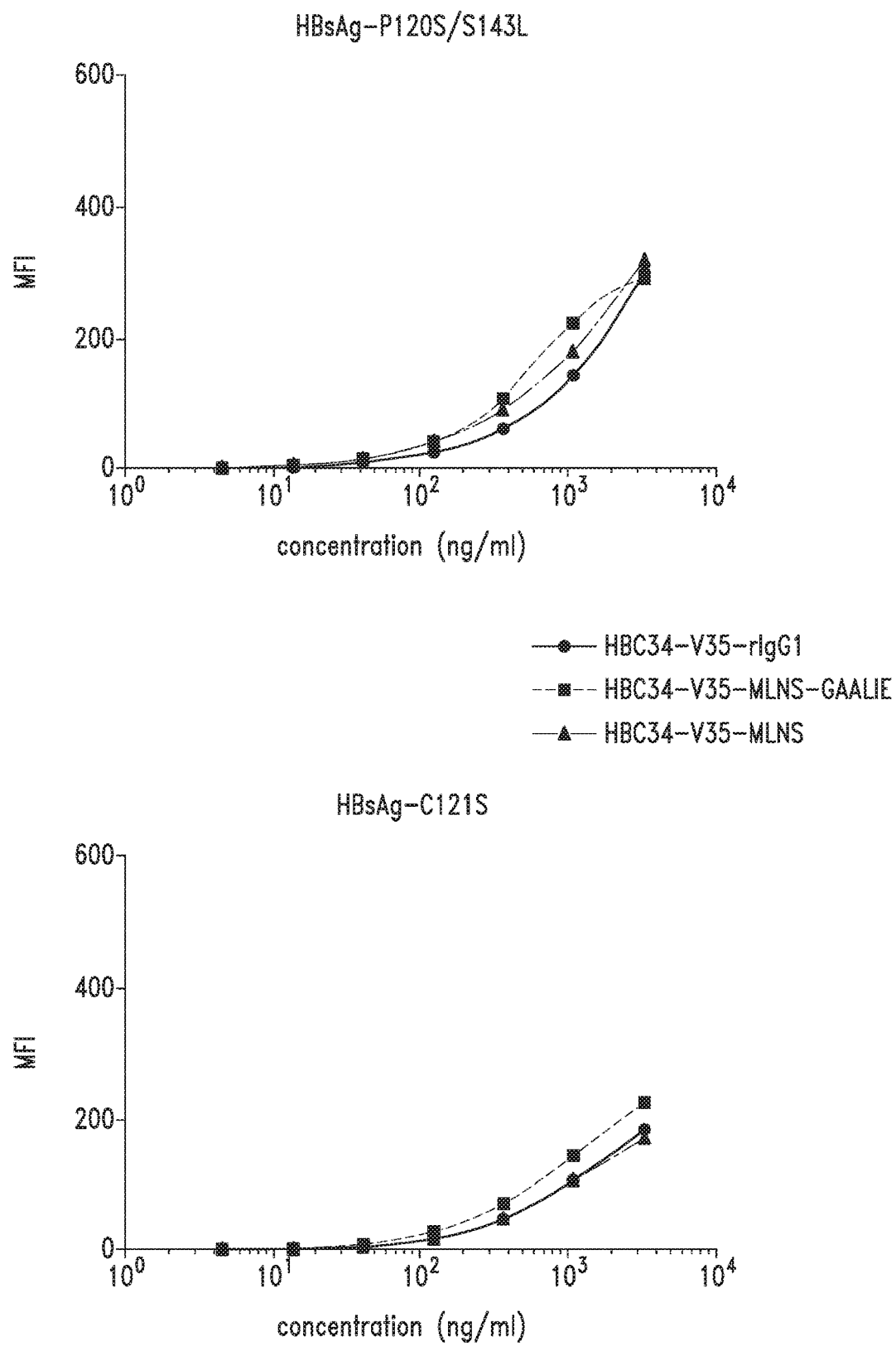
Figure 3K:
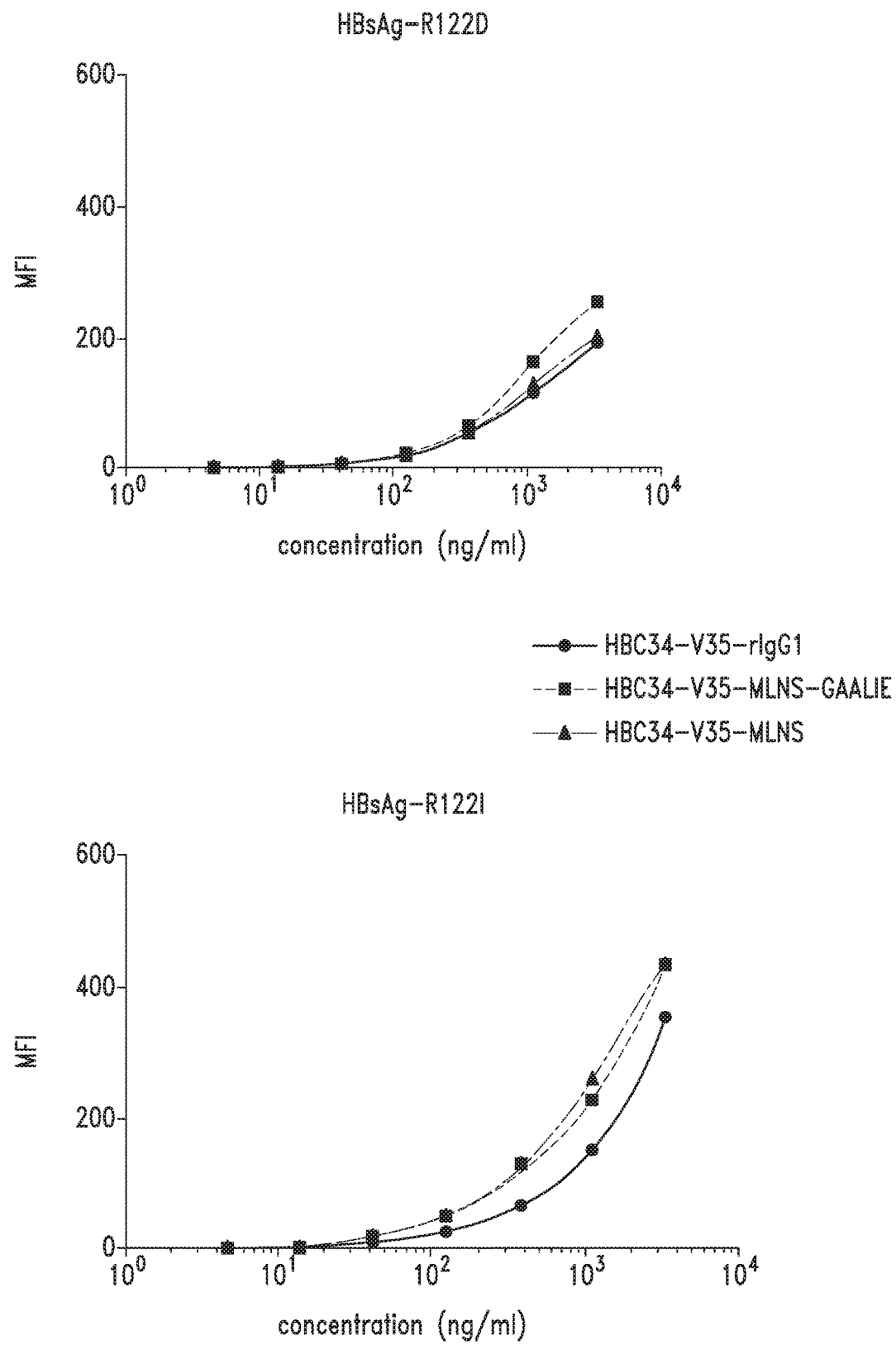
Figure 3L:
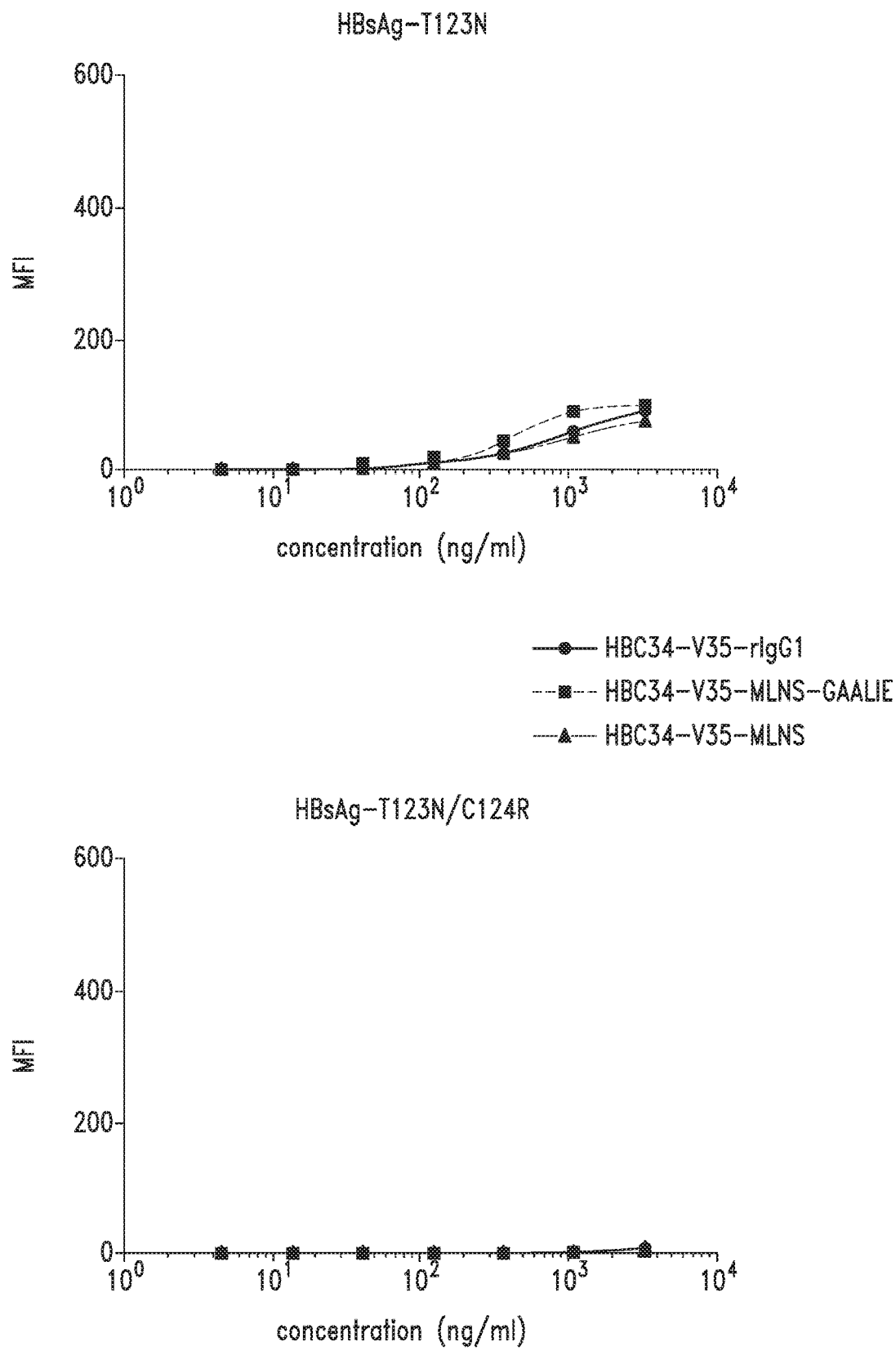
Figure 3M:
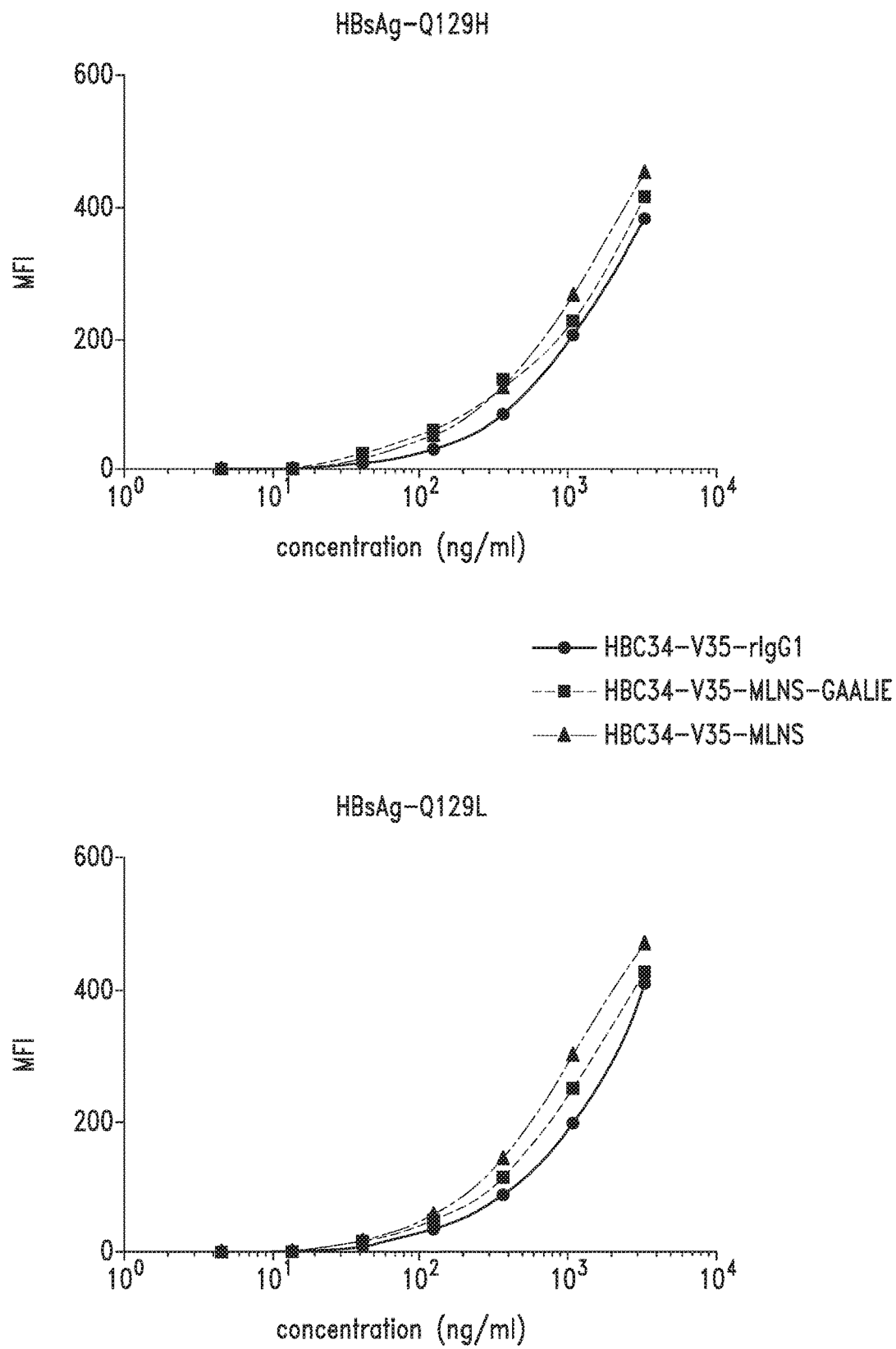
Figure 3N:
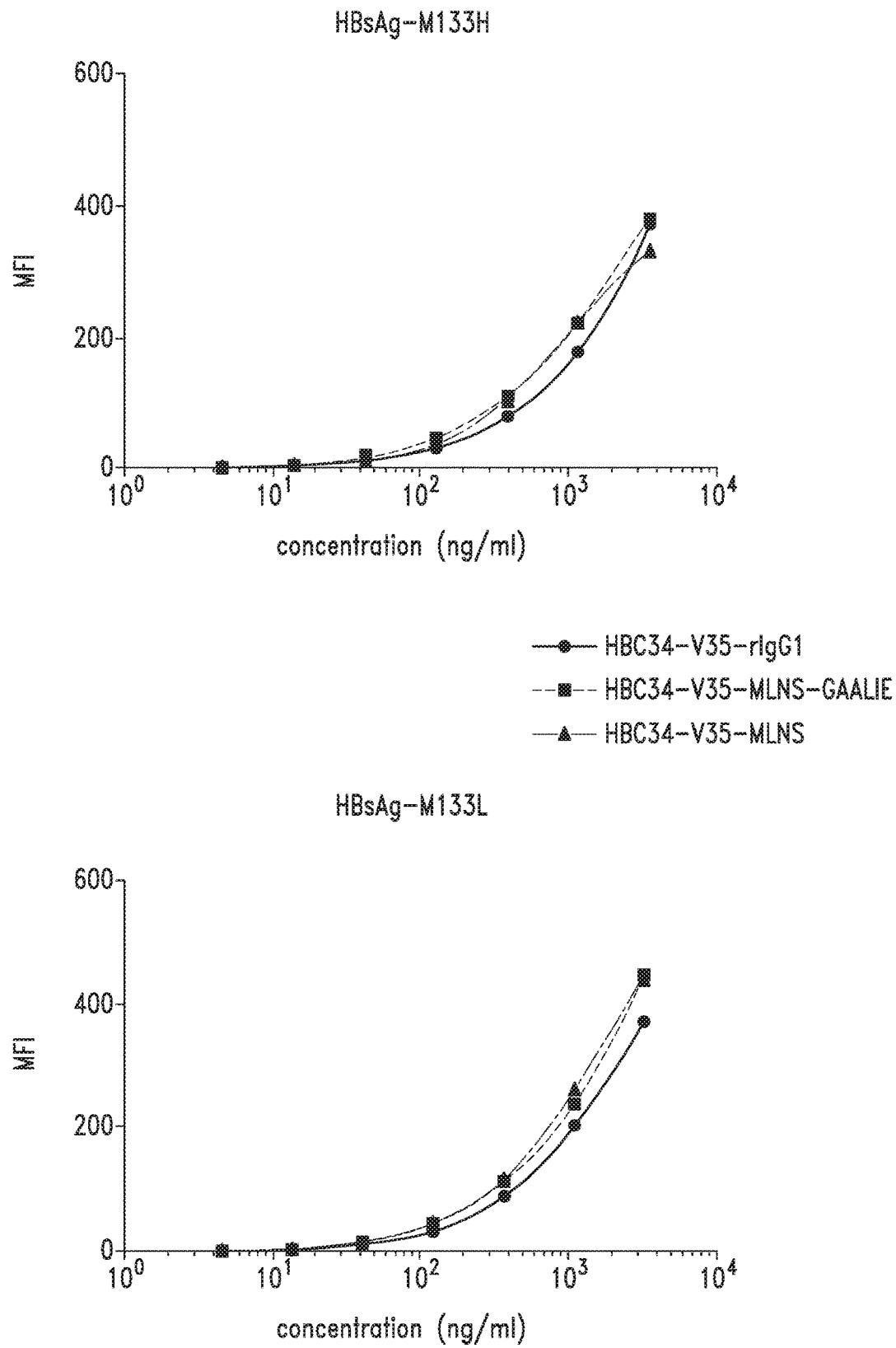
Figure 30:
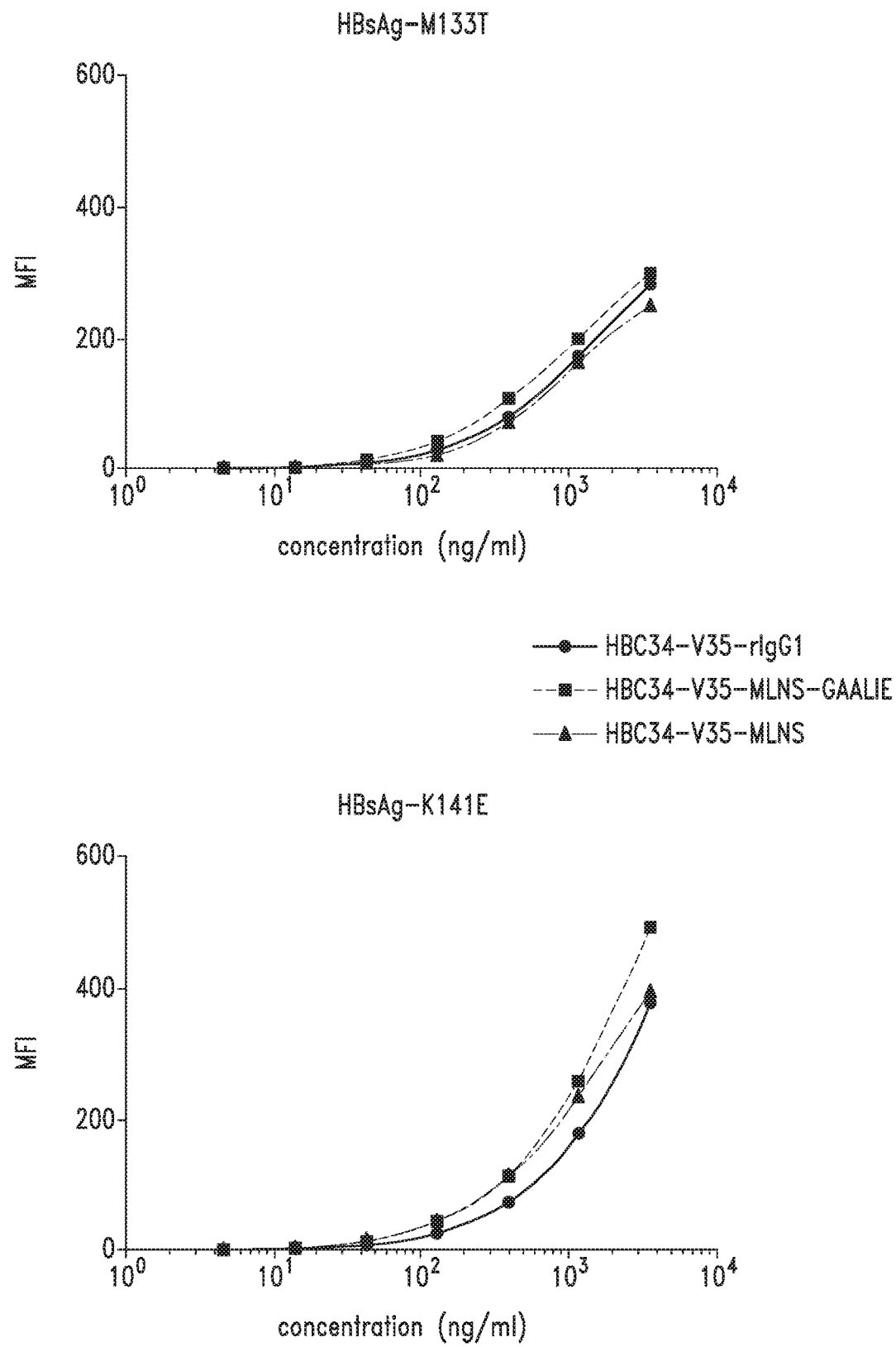
Figure 3Q:
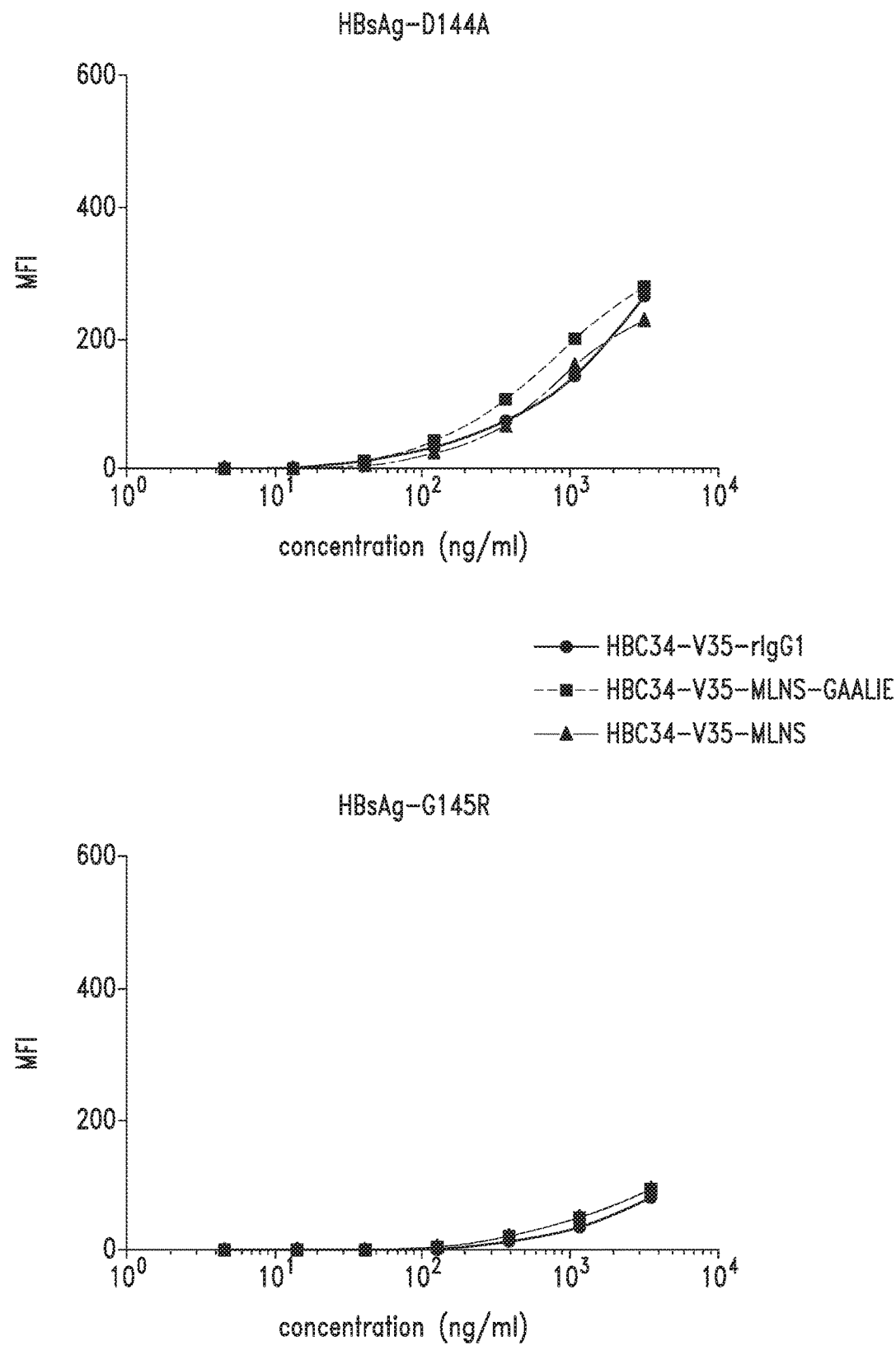
Figure 3R:
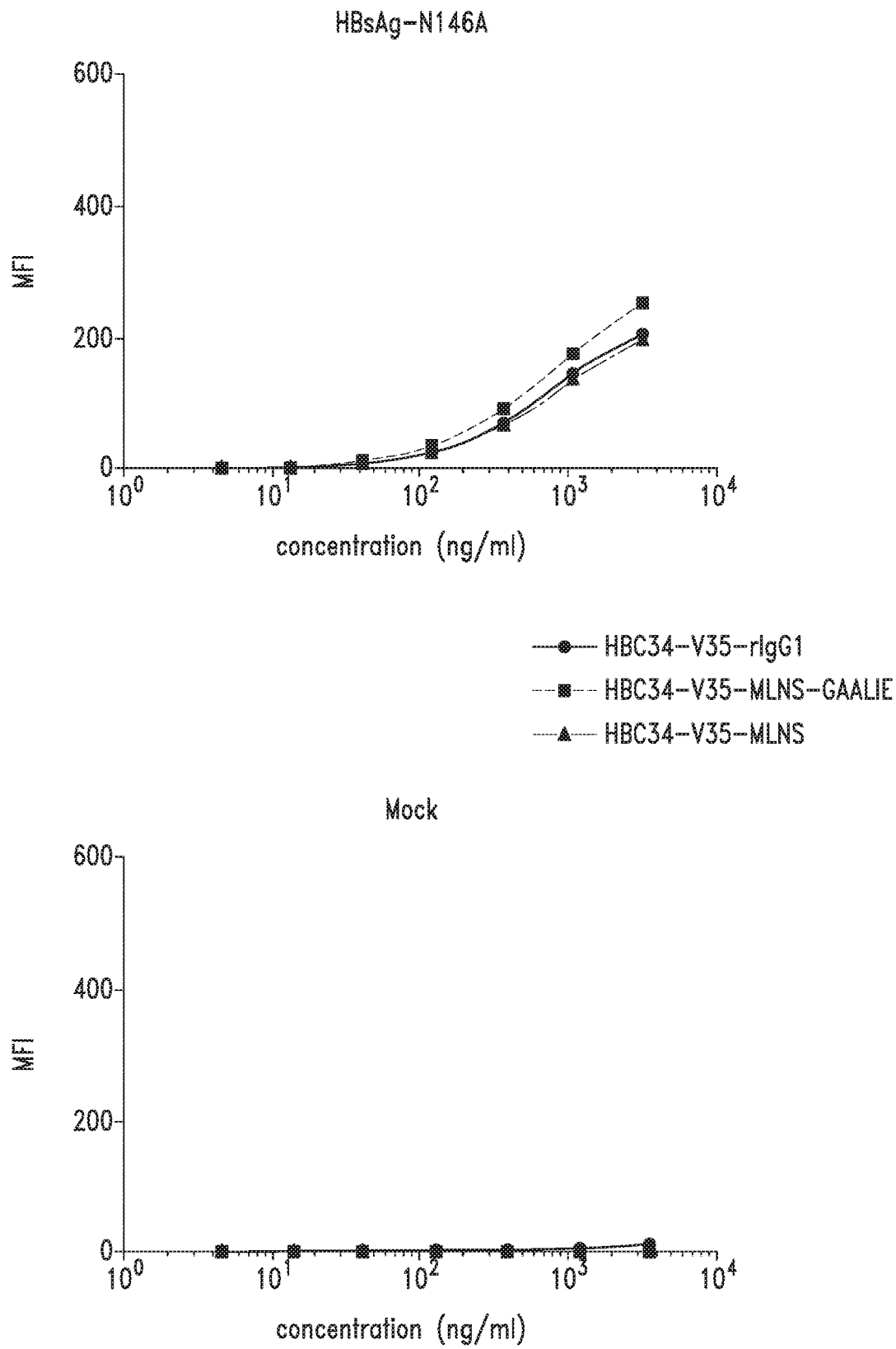
Figure 3S:
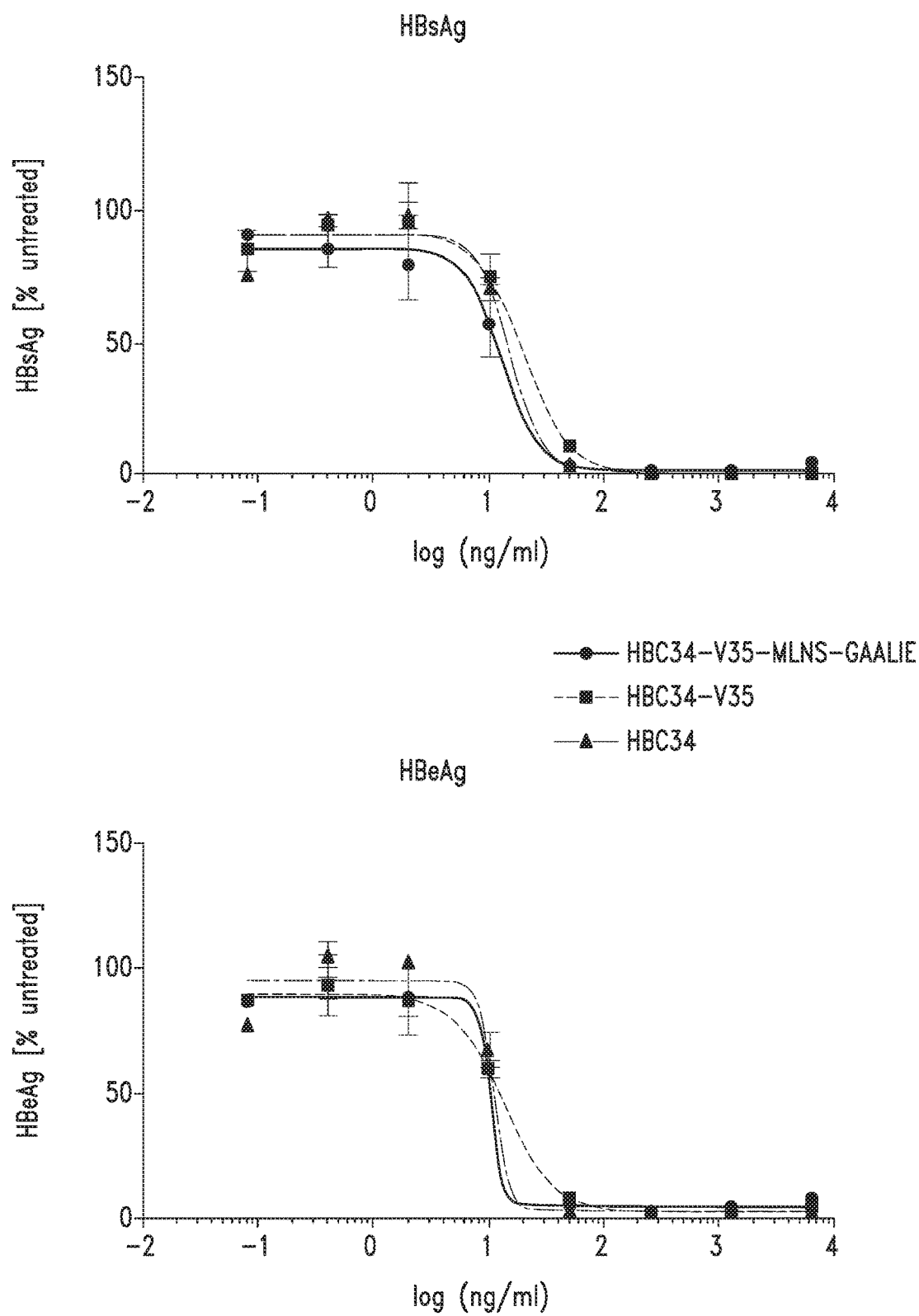
FIGS. 3S and 3U show neutralizing capacity of the indicated HBC antibodies against HBV genotype D as assessed by measuring levels of HBsAg (top) and HbeAg (bottom) in the cell culture supernatant of HBVD-infected HepG2 cells expressing NTCP. Data represent the means±SD from one of two independent experiments.
Figure 3U:
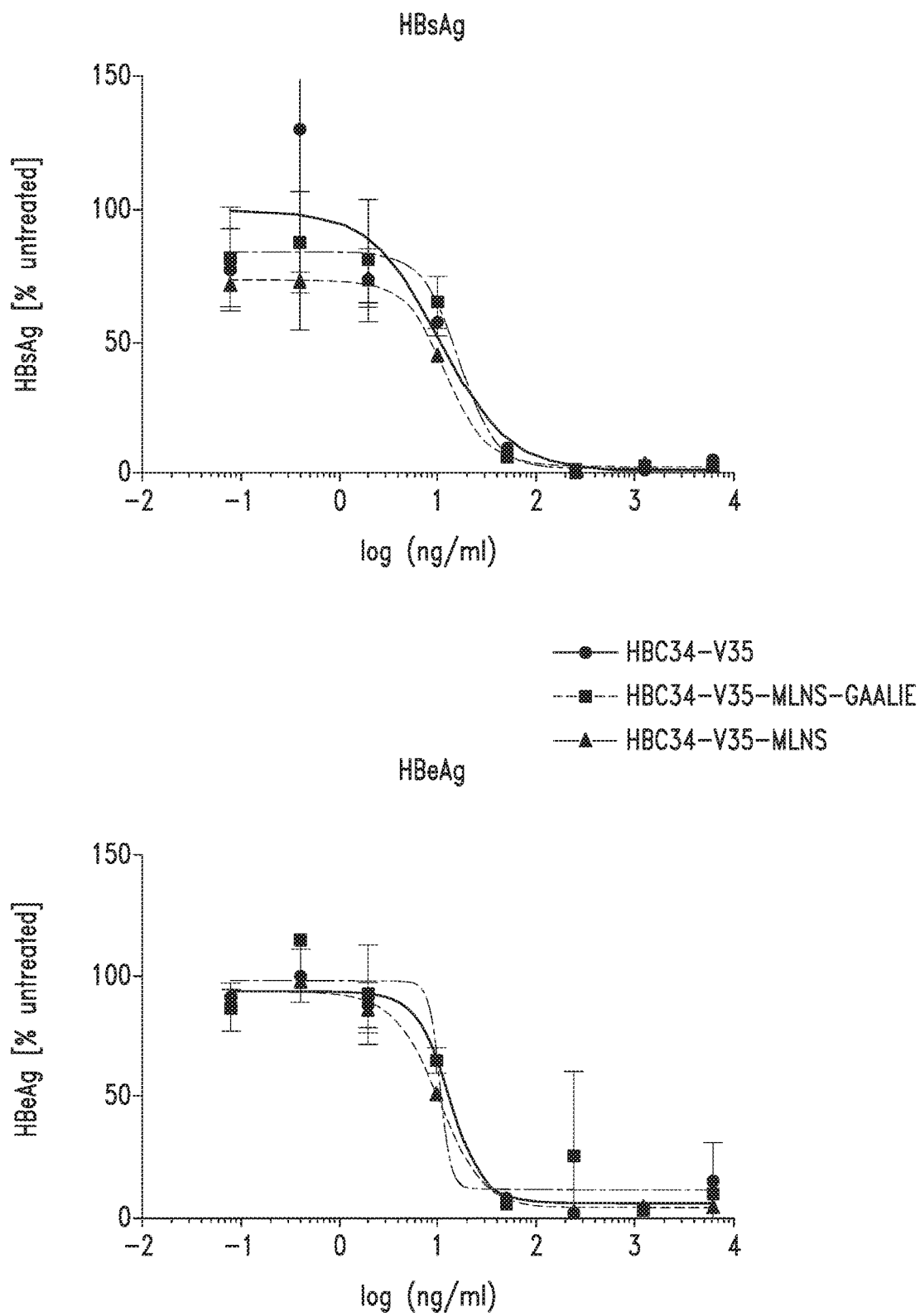
Figure 5:
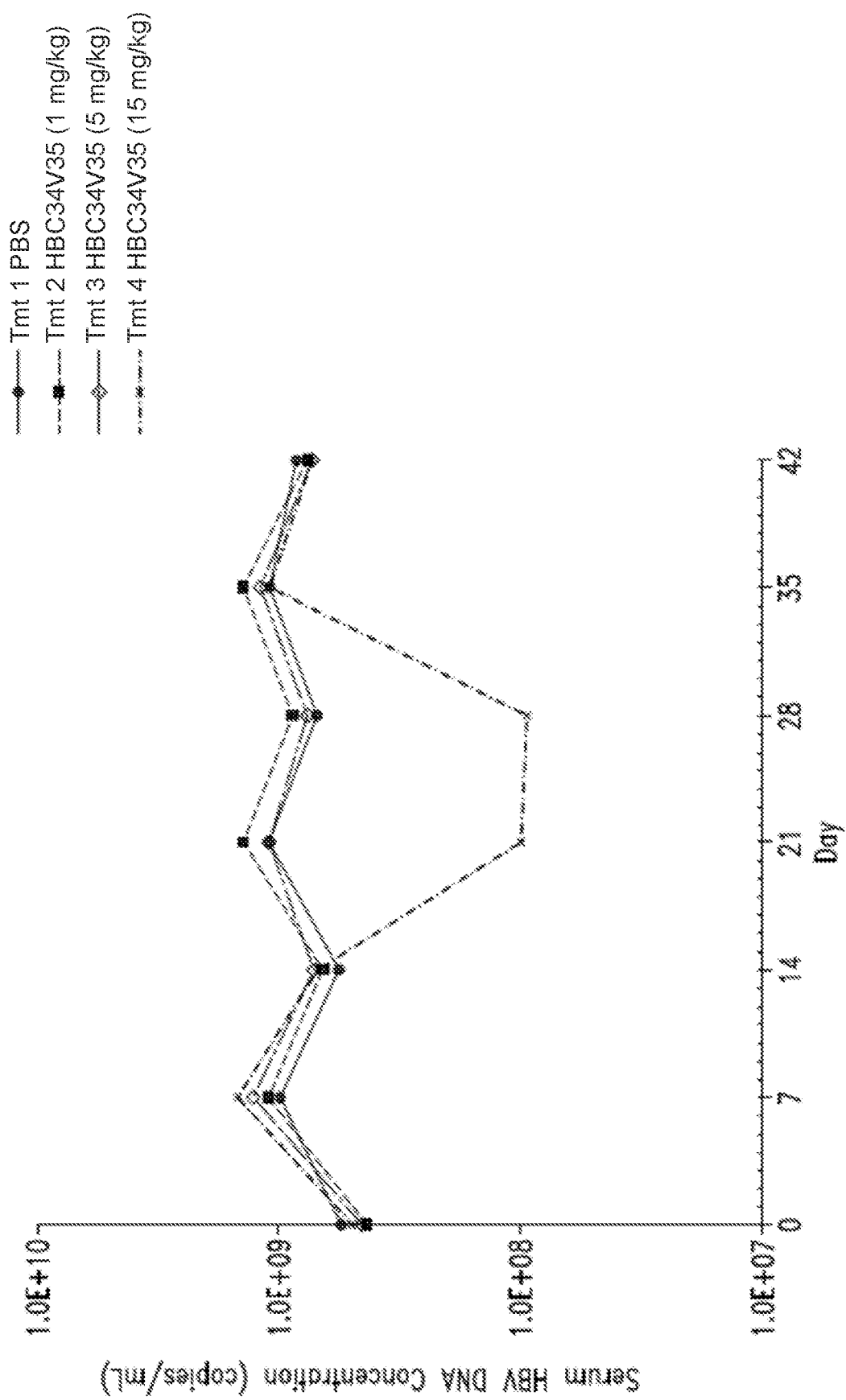
FIGS. 5-8 show the effect of HBC34-V35 on serum HBAg levels in an in vivo mouse model of HBV infection. HBV genotype C-infected SCID mice were transplanted with primary human hepatocytes and administered HBC34-V35 at 1, 5, or 15 mg/kg, or PBS (control), as described in Example 5.
Figure 6:
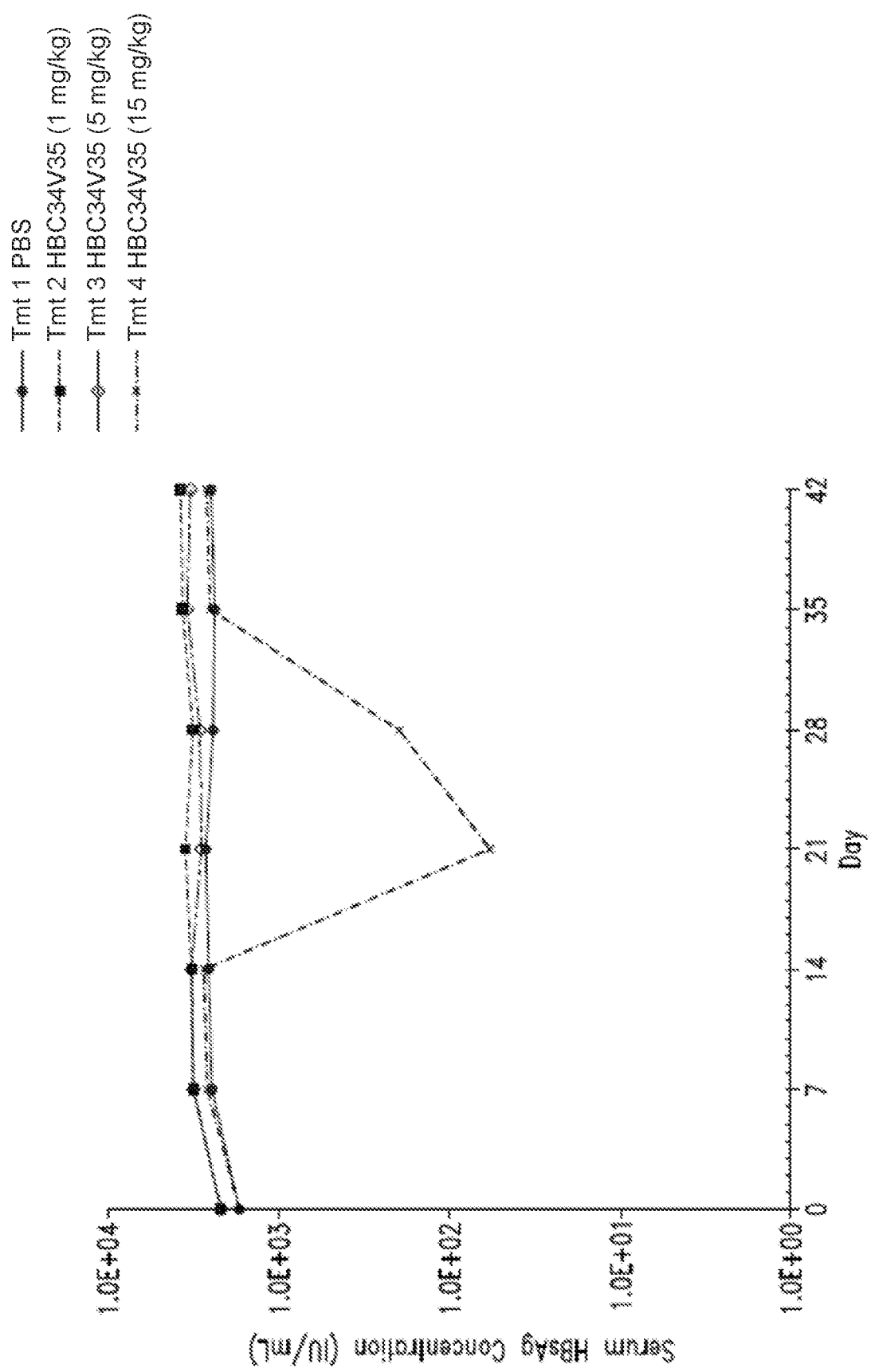
Figure 7:
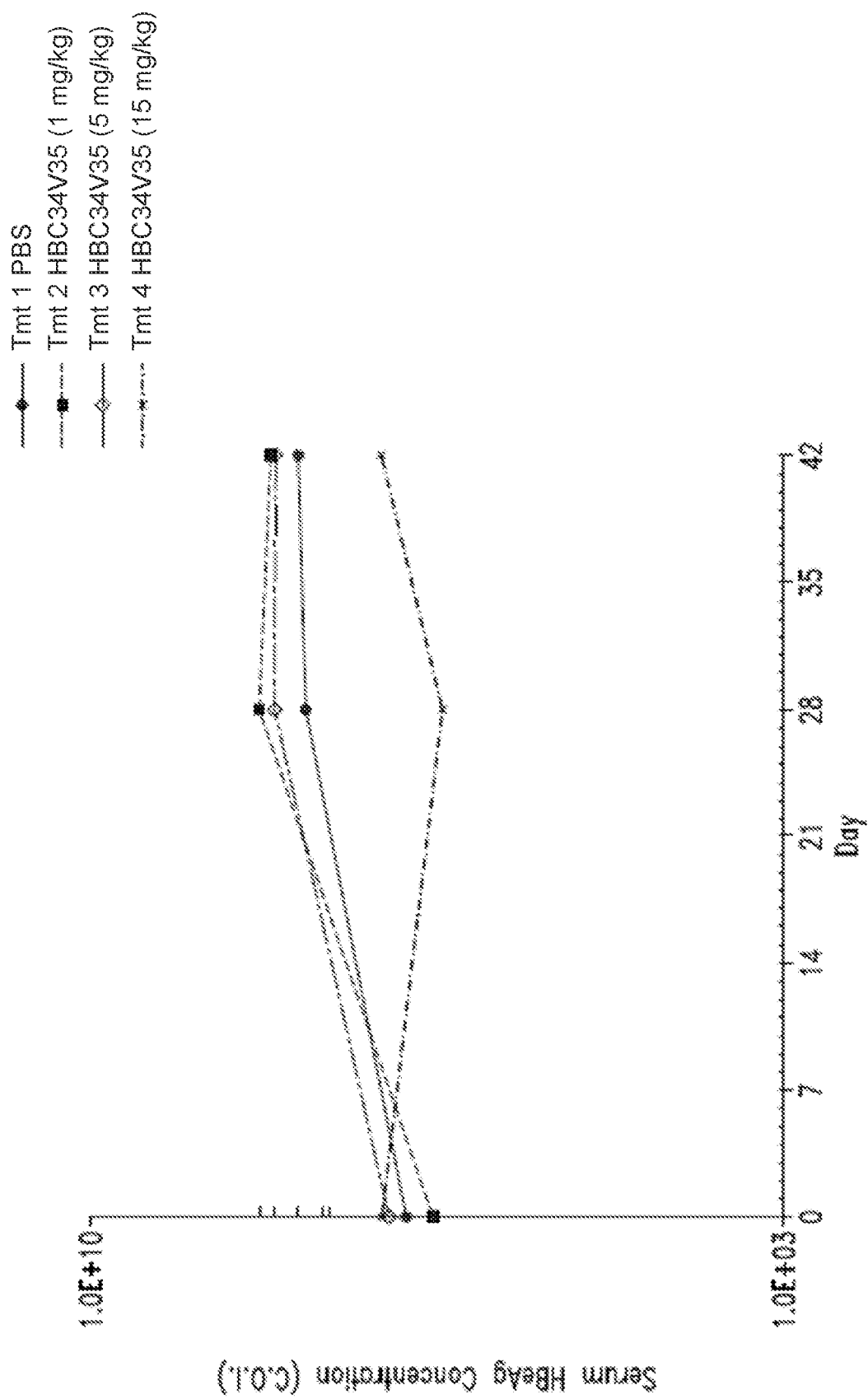
Figure 8:
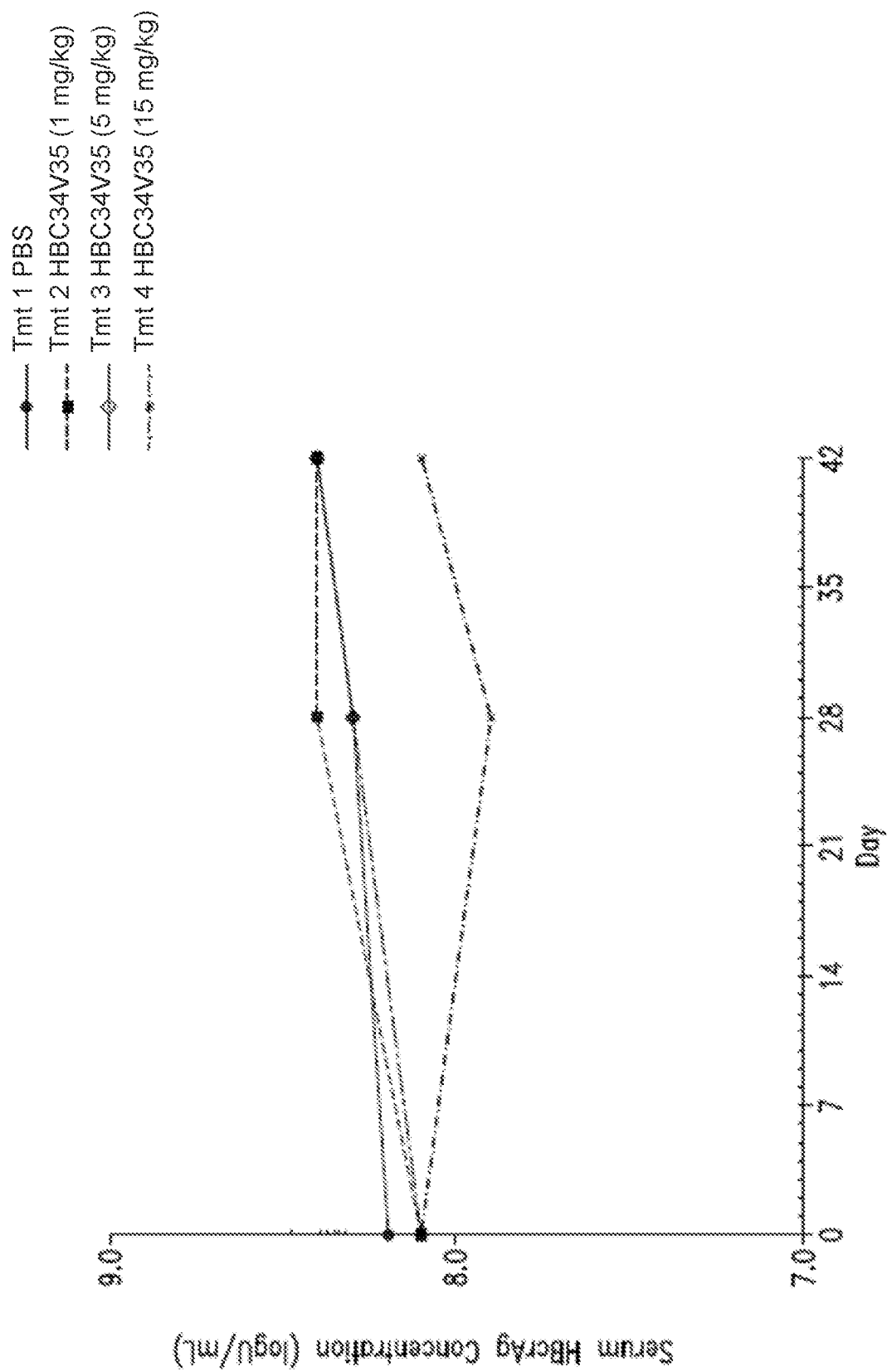

As shown in FIGS. 3A and 3B, the introduced Fc mutations did not affect antigen-binding activity of HBC34-V35. $EC_{50}$ values varied somewhat between the various constructs and the two experiments, and were generally low.

Binding of HBC34-V35 with MLNS or MLNS and GAALIE mutations to EXPI293 cells expressing HBsAg genotypes (A)-(J) or HBsAg variants was assessed. HBC34-V35 with wild-type IgG1 Fc was used as a comparator. Data showing binding to HBsAg genotypes are shown in FIGS. 3C-3H. Data showing binding to HBsAg variants are shown in FIGS. 3I-3R.

Example 3: In Vitro Neutralization Activity of Antibodies

The neutralizing capacity of HBC34, HBC34-V35, HBC34-V35-MLNS, and HBC34-V35-MLNS-GAALIE was compared by measuring the levels of HBsAg (A) and HBeAg (B) in the cell culture supernatant of HBV infected HepG2 cells expressing NTCP. Data are shown in FIGS. 3S-3V, and represent the means±SD from one of two independent experiments.

Example 4: Pan-Genotype Neutralization Capacity of HBC34-V35 MLNS-GAALIE Assessed in an HDV Pseudosystem To confirm the breadth of neutralization of HBC34-V35-MLNS-GAALIE against HBV virus, neutralization assays were conducted with HBC34-V35-MLNS-GAALIE against eight prevalent human HBV genotypes. An in vitro system that takes advantage of hepatitis D virus (HDV) engineered to express HBV HBsAg representing different genotypes was employed. Briefly, as both HBV and HDV share the same envelope proteins, their viral entry pathway via heparan sulfate proteoglycans and NTCP is identical, and HDV can be used as a model system to study HBsAg-mediated viral entry (Tu 2018; Lempp 2016). Further, HDV can be enveloped/pseudotyped with HBsAg of different HBV genotypes and subsequently be used in infection studies (Freitas 2014).

HBC34-V35-MLNS-GAALIE showed neutralizing capacity for all tested genotypes with similar $EC_{50}$ values, ranging from 0.92 ng/mL (genotype C) to 2.34 ng/mL (genotype A). These results show that HBC34-V35-MLNS-GAALIE is able to neutralize infectious virus carrying HBsAg from all eight HBV genotypes tested, supporting in vivo pan-genotypic neutralization activity of HBC34-V35-MLNS-GAALIE (FIG. 4).

Example 5: Clearance of HB Antigens and Viral Entry Inhibition in an In Vivo Model An immune-deficient mouse having transplanted human hepatocytes was used to test the effectiveness of anti-HBV antibodies of the present disclosure in clearing HBsAg. Briefly, primary human hepatocytes were transplanted into SCID mice for which mouse hepatocytes had previously been destroyed enzymatically. The mice were T- and B-cell deficient. This model is useful for studying HBV infection including entry, spreading, cccDNA regulation, hepatocyte-intrinsic immune responses, and viral integration into host genome.

Mice were inoculated via tail vein injection with HBV, genotype C, at $1.0 \times 10^7$ viral genomes per mouse at Day −28. Treatments at Day 0 following initial measurement of HBV. HBV-infected mice (n=4 per treatment group) were administered PBS (control) or HBC34-V35 (1, 5, or 15 mg/kg i.p., 2×/week). Antibodies were murinized with the exception of the antigen-binding Fab regions.

Plasma and serum samples were collected periodically throughout the study, and viral loads, HBV DNA (by PCR), and HB Ag (HBsAg, HBeAg, HBcrAg) were measured. Mice were sacrificed at week 6.

As shown in FIGS. 5-8, treatment with the highest tested dose of HBC34-V35 reduced viral load and viral entry into hepatocytes.

Example 6: In Vitro Effector Function Studies

In vitro studies were performed to examine the ability of HBC34 antibodies with modified Fc to: (1) bind to human FcRs and to complement; (2) activate FcγRIIa, FcγRIIb, and FcγRIIIa; and (3) promote ADCC and activate human Natural Killer (NK) cells. Test articles, cell lines, and reagents used were as described in Tables 5-7, below. The following abbreviations are used in this Example: GLP=Good Laboratory Practice; ADCC=Antibody-dependent cellular cytotoxicity; ADCP=Antibody-dependent cellular phagocytosis; Fc=Fragment crystallizable; HBsAg=Hepatitis B surface Antigen; mAb=Monoclonal antibody; PBS=Phosphate-buffered saline; UHPL-SEC=Ultra-high performance liquid size-exclusion chromatography; ATCC=American Type Culture Collection; FcγRs=Fc gamma receptor(s); CHO cells=Chinese hamster ovary cells; RLU=Relative luminescence units; BLI=Bio-layer interferometry.

TABLE 5

Test Articles.

| | |
|---|---|
| Test Article | HBC34-V35-MLNS |
| Isotype | IgG1λ |
| Relative molecular weight | ≈150 kDa |
| Concentration | 3.47 mg/ml |
| Source | In-house |
| Handling and storage conditions | 4° C. short term, −80° C. long term storage |
| Formulation buffer | PBS, pH 7.2 |
| Test Article | HBC34-V35-MLNS-GAALIE |
| Isotype | IgG1λ |
| Relative molecular weight | ≈150 kDa |
| Concentration | 2.1 mg/ml/0.86 mg/ml |
| Source | In-house |
| Handling and storage conditions | 4° C. short term, −80° C. long term storage |
| Formulation buffer | PBS, pH 7.2 |
| Test Article | HBC34-V35-LALA |
| Isotype | IgG1λ |
| Relative molecular weight | ≈150 kDa |
| Concentration | 1.2 mg/ml |
| Source | In-house |
| Handling and storage conditions | 4° C. short term, −80° C. long term storage |
| Formulation buffer | PBS, pH 7.2 |
| Test Article | mAb 17.1.41 |
| Isotype | IgG1κ |
| Relative molecular weight | ≈150 kDa |
| Concentration | 4.4 mg/ml |
| Source | In-house |
| Handling and storage conditions | 4° C. short term, −80° C. long term storage |
| Formulation buffer | PBS, pH 7.2 |

TABLE 6

Cell Lines

| | |
|---|---|
| Cell Line | PLC/PRF/5 |
| Catalogue number | #4325-FC-050 |
| Concentration | 100 µg/ml |
| Source | R&D Systems, mouse myeloma cell line, NS0-derived, with a C-terminal 6-His tag |
| Stability | Stable at −20 to 80° C. |
| Handling and storage conditions | Store at −80° C. until use, 1 month, 2 to 8° C. under sterile conditions after reconstitution |
| Formulation buffer | PBS |
| Cell Line | Jurkat-FcγRIIIA (F158) |
| Tissue origin | Immortalized line of human T lymphocyte cells; Jurkat cells stably expressing the FcγRIIIa receptor, F158 (low affinity) variant, and an NFAT response element driving expression of firefly luciferase as effector cells |
| Source | Promega (Cat. Nr.: G9798) |
| Assay media | RPMI1640 supplemented with 4% low IgG serum |
| Cell line | Jurkat-FcγRIIIA (V158) |
| Tissue origin | Immortalized line of human T lymphocyte cells; Jurkat cells stably expressing the FcγRIIIa receptor, V158 (high affinity) variant, and an NFAT response element driving expression of firefly luciferase as effector cells |
| Source | Promega (Cat. Nr.: G7018) |
| Assay media | RPMI1640 supplemented with 4% low IgG serum |
| Cell line | Jurkat-FcγRIIA (H131) |
| Tissue origin | Immortalized line of human T lymphocyte cells; Jurkat cells stably expressing the FcγRIIa receptor, H131 (high affinity) variant, and an NFAT response element driving expression of firefly luciferase as effector cells |
| Source | Promega (Cat. Nr.: G9995) |
| Assay media | RPMI1640 supplemented with 4% low IgG fetal bovine serum |
| Cell line | Jurkat-FcγRIIB |
| Tissue origin | Immortalized line of human T lymphocyte cells; Jurkat cells stably expressing the FcγRIIb receptor, and an NFAT response element driving expression of firefly luciferase as effector cells |
| Source | Promega (Cat. Nr.: CS1781E02) |
| Assay media | RPMI1640 supplemented with 4% low IgG fetal bovine serum |
| Cell line | Freshly isolated human NK cells |
| Tissue origin | Whole blood (EDTA) from donor HM_WB019 (genotyped for FcgRIIIa F/V), purified with MACSxpress ® NK Isolation Kit from Miltenyi Biotec (#130-098-185) |
| Source | In-house |
| Assay media | AIM-V |
| Growth media | RPMI1640 supplemented with 10% low IgG fetal bovine serum, Glutamax |
| Growth conditions | 37° C., 5% $CO_2$ |
| Cell line | Freshly isolated human NK cells |
| Tissue origin | Whole blood (EDTA) from donor HM_WB002 (genotyped for FcgRIIIa V/V), purified with MACSxpress ® NK Isolation Kit from Miltenyi Biotec (#130-098-185) |
| Source | In-house |
| Assay media | AIM-V |
| Growth media | RPMI1640 supplemented with 10% low IgG fetal bovine serum, Glutamax |
| Growth conditions | 37° C., 5% $CO_2$ |
| Cell line | Freshly isolated human NK cells |
| Tissue origin | Whole blood (EDTA) from donor HM_WB018 (genotyped for FcgRIIIa F/F), purified with MACSxpress ® NK Isolation Kit from Miltenyi Biotec (#130-098-185) |
| Source | In-house |
| Assay media | AIM-V |
| Growth media | RPMI1640 supplemented with 10% low IgG fetal bovine serum, Glutamax |
| Growth conditions | 37° C., 5% $CO_2$ |

TABLE 7

| Other Reagents | |
|---|---|
| Reagent | Recombinant human FcγRIIIa (V158) |
| Catalogue number | #4325-FC-050 |
| Concentration | 100 μg/ml |
| Source | R&D Systems, mouse myeloma cell line, NS0-derived, with a C-terminal 6-His tag |
| Stability | Stable at −20 to 80° C. |
| Handling and storage conditions | Store at −80° C. until use, 1 month, 2 to 8° C. under sterile conditions after reconstitution |
| Formulation buffer | PBS |
| Reagent | Recombinant human FcγRIIIa (F158) |
| Catalogue number | 10389-H08H |
| Concentration | 200 μg/ml (when reconstituted) |
| Source | Sino Biological, HEK293-derived, with a C-terminal 6-His tag |
| Stability | Stable at −20 to 80° C. |
| Handling and storage conditions | Store at −80° C. until use |
| Formulation buffer | PBS |
| Reagent | Recombinant human FcγRIIa (H131) |
| Catalogue number | 10374-H08C1 |
| Concentration | 200 μg/ml (when reconstituted) |
| Source | Sino Biological, CHO-derived, with a C-terminal 6-His tag |
| Stability | Stable at −20 to 80° C. |
| Handling and storage conditions | Store at −80° C. until use |
| Formulation buffer | PBS |
| Reagent | Recombinant human FcγRIIa (H131) |
| Catalogue number | 10374-H08B |
| Concentration | 200 μg/ml (when reconstituted) |
| Source | Sino Biological, insect cells-derived, with a C-terminal 6-His tag |
| Stability | Stable at −20 to 80° C. |
| Handling and storage conditions | Store at −80° C. until use |
| Formulation buffer | PBS |
| Reagent | Recombinant human FcγRIIb |
| Catalogue number | 10259-H08C |
| Concentration | 200 μg/ml (when reconstituted) |
| Source | Sino Biological, CHO-derived, with a C-terminal 6-His tag |
| Stability | Stable at −20 to 80° C. |
| Handling and storage conditions | Store at −80° C. until use |
| Reagent | Human complement component C1q |
| Catalogue number | 204873 |
| Concentration | 1.17 mg/ml |
| Source | Sigma-Aldrich, prepared from human serum |
| Stability | Stable at −80° C. |
| Handling and storage conditions | Store at −80° C. until use |
| Formulation buffer | 10 mM HEPES with 0.3M NaCl, pH 7.2 |
| Reagent | Source |
| PBS | Sigma-Aldrich Chemie GmbH, Switzerland |
| AIM-V media | Gibco |
| Ham's F-12K Medium | Gibco |
| MACSxpress ® NK Isolation Kit | Miltenyi Biotec GmbH, Germany |
| Cytotoxicity Detection Kit (LDH) | Roche Diagnostics GmbH, Switzerland |
| 96-well round bottom plates | Corning |
| white flat bottom 96-well plate | PerkinElmer |
| 384-well round bottom plates | Corning |
| 384-well flat bottom plates | Corning |
| Spectrophotometer | Bio-Tek |

TABLE 7-continued

| Other Reagents | |
|---|---|
| RMPI medium | Gibco |
| DMEM High Glucose with stable Glutamine | Bioconcept |
| FBS | GE Healthcare |
| Glutamax | Gibco |
| Trypsin-EDTA (0.05%), phenol red | Gibco |
| Prism7 Software Graph | Pad Software, Inc., La Jolla, CA |
| Triton X-100 | Sigma |
| ADCC Assay buffer | Promega |
| Bio-Glo-TM Luciferase Assay Reagent | Promega |
| ADCC Bioassay | Promega |
| Wash buffer | PBS, 1% FBS |
| Formaldehyde solution, conc. 37% | Sigma (Cat. Nr.: F1635-500ML) |
| Saponin | Sigma (Cat. Nr.: S7900-100G) |
| Permeabilization buffer | 0.5% saponin, PBS, 1% FBS |
| Alexa Fluor ® 647 secondary Ab | AffiniPure F(ab')2 Fragment Goat Anti-Human IgG, Fcγ Fragment Specific (Jackson ImmunoResearch, Cat. Nr.: 109-606-098) |
| Anti-CD107 PE secondary Ab | Anti-CD107 PE (BioLegend, Cat. Nr.: 328608, Clone H4A3, Mouse IgG1, kappa) |

EXPERIMENTAL PROCEDURES

Measurement of Binding to Human Fc-Receptors

Binding of HBC34-V35-MLNS and HBC34-V35-MLNS-GAALIE to human FcγRs was measured on an Octet® instrument (BLI, biolayer interferometry; FortéBio). Briefly, His-tagged human FcγRs (FcγRIIa allele H131, FcγRIIa allele R131, FcγRIIAa allele F158, FcγRIIIa allele V158 and FcγRIIb) at 2 µg/ml were captured onto anti-penta-His sensors for 6 minutes. FcγR-loaded sensors were then exposed for 4 minutes to a solution of kinetics buffer (pH 7.1) containing 2 µg/ml of each mAb in the presence 1 µg/ml of affiniPure F(ab')$_2$ Fragment Goat Anti-Human IgG, F(ab')$_2$ fragment-specific (to cross-link human mAbs through the Fab fragment), followed by a dissociation step in the same buffer for 4 additional minutes (right part of the plot). Association and dissociation profiles were measured in real time as change in the interference pattern using an Octet® RED96 (FortéBio). Binding of HBC34-V35-MLNS-GAALIE, HBC34-V35-MLNS, or HBC34-V35 in solution to immobilized human FcRn was measured by Octet in real time at pH=6.0 or pH=7.4.

Measurement of Binding to Human Complement Protein C1q

Binding of HBC34-V35-MLNS and HBC34-V35-MLNS-GAALIE to human complement was measured on an Octet® instrument (BLI, biolayer interferometry; FortéBio). Briefly, anti-human Fab (CH1-specific) sensors were used to capture, through the Fab fragment, the full IgG1 of HBC34-V35-MLNS and HBC34-V35-MLNS-GAALIE mAbs at 10 µg/ml for 10 minutes. IgG-loaded sensors were then exposed for 4 minutes to a solution of kinetics buffer (pH 7.1) containing 3 µg/ml of purified human C1q (left part of the plot), followed by a dissociation step in the same buffer for 4 additional minutes (right part of the plot). Association and dissociation profiles were measured in real time as change in the interference pattern using an Octet® RED96 (FortéBio).

Preparation of Human NK Cells from Whole Blood

NK cells were freshly isolated from whole EDTA blood using the MACSxpress® NK isolation Kit following the manufacturer's instruction. Briefly, anticoagulated blood was mixed in a 50 ml tube with 15 ml of the NK isolation cocktail and incubated for 5 minutes at room temperature using a rotator at approximately 12 rounds per minute. The tube was then placed in the magnetic field of the MACSxpress® Separator for 15 minutes. The magnetically labeled cells adhere to the wall of the tube while the aggregated erythrocytes sediment to the bottom. The target NK cells were then collected from the supernatant while the tube was still inside the MACSxpress® Separator. NK cells were centrifuged, treated with distilled water to remove residual erythrocytes, centrifuged again and finally resuspended in AIM-V medium.

Determination of Antibody-Dependent NK Cell Killing

MAbs were serially diluted 10-fold in AIM-V medium from 100 µg/ml to 0.001 µg/ml. Target cells (PLC/PRF/5; MacNab, et al., British Journal of Cancer, 34(5), 1976) were added in a round bottom 384-well plate at $7.5 \times 10^3$ cells/well in 23 µl, then serially diluted antibodies were added to each well (23 µl per well), and the antibody/cell mixture was incubated for 10 minutes at room temperature. Following incubation, human NK cells were added at a cell density of $7.5 \times 10^4$/well in 23 µl, yielding an effector to target ratio of 10:1. Control wells were also included that were used to measure maximal lysis (containing target cells with 23 µl of 3% Triton x-100) and spontaneous lysis (containing target cells and effector cells without antibody). Plates were incubated for 4 hours at 37° C. with 5% $CO_2$. Cell death was determined by measuring lactate dehydrogenase (LDH) release using a LDH detection kit according to the manufacturer's instructions. In brief, plates were centrifuged for 4 minutes at 400×g, and 35 µl of supernatant was transferred to a flat 384-well plate. LDH reagent was prepared and 35 µl were added to each well. Using a kinetic protocol, the absorbance at 490 nm and 650 nm was measured once every 2 minutes for 8 minutes. The percent specific lysis was determined by applying the following formula: (specific release−spontaneous release)/(maximum release−spontaneous release)×100.

Determination of Antibody-Dependent NK Cell Activation

Activation of primary NK cells was tested using freshly isolated cells from two donors that had been previously genotyped for expressing homozygous high (V158 allele) or low (F158 allele) affinity FcγRIIIa. Serial dilutions of mAbs (serially diluted 10-fold in AIM-V medium from 100 µg/ml to 0.0001 µg/ml) were incubated with NK cells for 4 hours. Activation of NK cell was measured by flow cytometry by staining NK cells with anti-CD107a mAb (anti-CD107 PE, BioLegend®, used diluted 1/35) as a functional marker for NK cell activity.

Determination of Antibody-Dependent Activation of Human FcγRIIIa

HBC34-V35-MLNS and HBC34-V35-MLNS-GAALIE were serially diluted 4-fold in ADCC Assay buffer from 5 µg/ml to 0.076 µg/ml. Target antigen (HBsAg from Engerix B, Glaxo SmithKline) was added in a white flat bottom 96-well plate at 0.6 µg/ml in 25 µl, then serially diluted antibodies were added to each well (25 µl per well), and the antibody/cell mixture was incubated for 10 minutes at room temperature. Effector cells for the ADCC Bioassay were thawed and added at a cell density of $7.5 \times 10^4$/well in 25 µl (final HBsAg concentration was 0.2 µg/ml). Control wells were also included that were used to measure antibody-independent activation (containing HBsAg and effector cells but no antibody) and spontaneous luminescence of the plate (wells containing the ADCC Assay buffer only). Plates were incubated for 24 hours at 37° C. with 5% $CO_2$. Activation of human FcγRIIIa (V158 or F158 variants) in this bioassay results in NFAT-mediated expression of the luciferase reporter gene. Luminescence was measured with a luminometer using the Bio-Glo-™ Luciferase Assay Reagent according to the manufacturer's instructions. The data (i.e., specific FcγRIIIa activation) are expressed as the average of relative luminescence units (RLU) over the background by applying the following formula: (RLU at concentration x of mAbs—RLU of background).

Determination of Antibody-Dependent Activation of Human FcγRIIa

HBC34-V35-MLNS and HBC34-V35-MLNS-GAALIE were serially diluted 5-fold in ADCP Assay buffer from 50 µg/ml to 0.00013 µg/ml. Target antigen (HBsAg from Engerix B) was added in a white flat-bottom 96-well plate at 0.6 or 6 µg/ml in 25 then serially diluted antibodies were added to each well (25 µl per well), and the antigen/antibody was incubated for 25 minutes at room temperature. Effector cells for the FcγRIIa activation bioassay were thawed and added at a cell density of $50.0 \times 10^4$/well in 25 µl (final HBsAg concentration was 0.2 or 2 µg/ml, respectively). Control wells were also included that were used to measure antibody-independent activation (containing HBsAg and effector cells but no antibody) and spontaneous luminescence of the plate (wells containing the ADCP Assay buffer only). Plates were incubated for 23 hours at 37° C. with 5% $CO_2$. Activation of human FcγRIIa (H131 variants) in this bioassay results in NFAT-mediated expression of the luciferase reporter gene. Luminescence was measured with a luminometer using the Bio-Glo-™ Luciferase Assay Reagent according to the manufacturer's instructions. The data (i.e., specific FcγRIIa activation) are expressed as the average of relative luminescence units (RLU) over the background by applying the following formula: (RLU at concentration [x] of mAbs—RLU of background).

Determination of Antibody-Dependent Activation of Human FcγRIM

HBC34-V35-MLNS and HBC34-V35-MLNS-GAALIE were serially diluted 5-fold in ADCP Assay buffer from 100 µg/ml to 0.00026 µg/ml. Target antigen (HBsAg from Engerix B) was added in a white flat bottom 96-well plate at 3 µg/ml in 25 then serially diluted antibodies were added to each well (25 µl per well), and the antigen/antibody was incubated for 15 minutes at room temperature. Effector cells for the FcγRIIb activation bioassay were thawed and added at a cell density of $75.0 \times 10^4$/well in 25 µl (the final HBsAg concentration was 1 µg/ml). Control wells were also included that were used to measure antibody-independent activation (containing HBsAg and effector cells but no antibody) and spontaneous luminescence of the plate (wells containing the ADCP Assay buffer only). Plates were incubated for 20 hours at 37° C. with 5% $CO_2$. Activation of human FcγRIIb in this bioassay results in NFAT-mediated expression of the luciferase reporter gene. Luminescence was measured with a luminometer using the Bio-Glo-™ Luciferase Assay Reagent according to the manufacturer's instructions. The data (i.e., specific FcγRIIb activation) are expressed as the average of relative luminescence units (RLU) over the background by applying the following formula: (RLU at concentration [x] of mAbs—RLU of background).

Determination of Antibody Binding to Human Hepatoma Cell Line PLC/PRF/5

PLC/PRF/5 cells were trypsinized for 5 min at 37° C., transferred in 7 ml growing medium, centrifugated at 400×g, 4 min, 4° C., and extensively washed at 4° C. in PBS. Some cells were fixed with 4% formaldehyde (20 minutes at 4° C.); others were fixed and then permeabilized with permeabilization buffer (20 minutes at 4° C.). The cellular pellet was resuspended in 2.64 ml of wash buffer (fixed cells) or permeabilization buffer (fix&perm cells) (Table 7) and dispensed at 200 µl/well into 96-well round bottom plates (corresponding to 100'000 cells/well). The plate was centrifugated at 400 g, 4 min, 4° C. Serial 1:5 5-points dilutions of the test antibodies starting from a final concentration of 10 µg/ml were added to cell-containing wells and incubated 30 minutes on ice. After 2 washes at 4° C., 400×g, 4 min in wash buffer (fix cells) or permeabilization buffer (fix&perm cells), 50 µl/well of Alexa Fluor® 647-labelled secondary antibody (Table 7) was added to cells and incubated for 20 min on ice. Cells were washed 2 more times with wash buffer (fix cells) or permeabilization buffer (fix&perm cells), resuspended in 200 µl/well of wash buffer (fix cells) or permeabilization buffer (fix&perm cells) and signal (MFI, mean fluorescence intensity) was quantified with a cytofluorimeter (BD FACSCanto™ II).

Results

Direct antiviral mechanisms are important for neutralizing HBV in vivo. Indirect, Fc-dependent mechanisms of action mediated by the interaction of the Fc region with Fc gamma receptors (FcγRs) on immune cells may also have important contributions to in vivo efficacy and to mediate endogenous immune responses. FcγR-dependent mechanisms can be assessed in vitro by measuring binding to FcγRs as well as in antibody-dependent activation of human FcγRs (Hsieh, Y.-T., et al., Journal of Immunological Methods, 441(C), 56-66. doi.org/10.1016/j.jim.2016.12.002). The ability of the antibody to bind to FcRn and to complement are other factors of interest.

In one set of experiments, HBC34-V35-MLNS and HBC34-V35-MLNS-GAALIE were compared side-by-side for their ability to bind to the full set of human FcγRs (FcγRIIIa V158 and F158 alleles, FcγRIIa H131 and R131 alleles, and FcγRIIb) using biolayer interferometry (BLI Octet® System, FortéBio). As shown in FIGS. 9A-9E, Fc bearing MLNS-GAALIE mutations have altered interactions with FcγRs; specifically, Fc bearing both of these mutations, as opposed to Fc bearing MLNS alone, have enhanced binding to FcγRIIIa and FcγRIIa, and reduced binding to FcγRIIb.

Figure 9A:
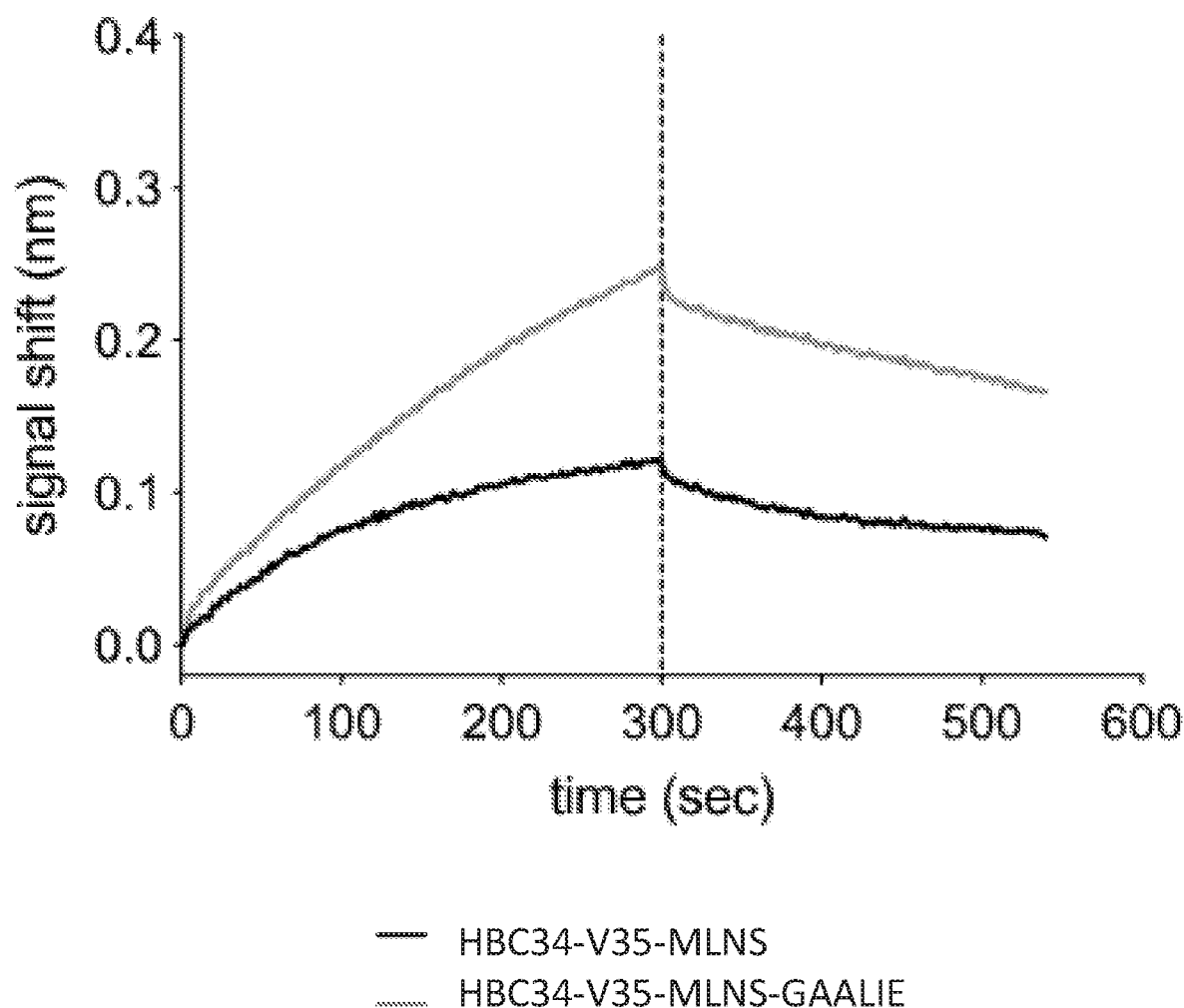
FIGS. 9A-9F show binding of HBC34-V35-MLNS and HBC34-V35-MLNS-GAALIE to human FcRs. (A)-(E) Binding to FcγRs, as assessed by biolayer interferometry (BLI). His-tagged human FcγRs ((A) FcγRIIa allele H131; (B) FcγRIIa allele R131; (C) FcγRIIIa allele F158; (D) FcγRIIIa allele V158; (E) FcγRIIb) at 2 μg/ml were captured onto anti-penta-His sensors for 6 minutes. FcγR-loaded sensors were then exposed for 5 minutes to a solution of kinetics buffer (pH 7.1) containing 2 μg/ml of each mAb (left part of the plot) in the presence 1 μg/ml of affiniPure F(ab')$_2$ Fragment Goat Anti-Human IgG, F(ab')$_2$ fragment specific (to cross-link human mAbs through the Fab fragment), followed by a dissociation step in the same buffer for additional 4 minutes (right part of the plot). Association and dissociation profiles were measured in real time as change in the interference pattern using an Octet® RED96 (FortéBio). (F) In vitro binding of HBC34 antibodies to FcRn at different pHs, as determined using Bio-Layer interferometry (BLI). The time point 0 seconds represents switch from base line buffer to buffer containing antibodies. Time point 300 seconds (dotted vertical line) represents switch to blank buffer at the corresponding pH. Curves indicate association and dissociation profiles of change in the interference patterns.
Figure 9B:
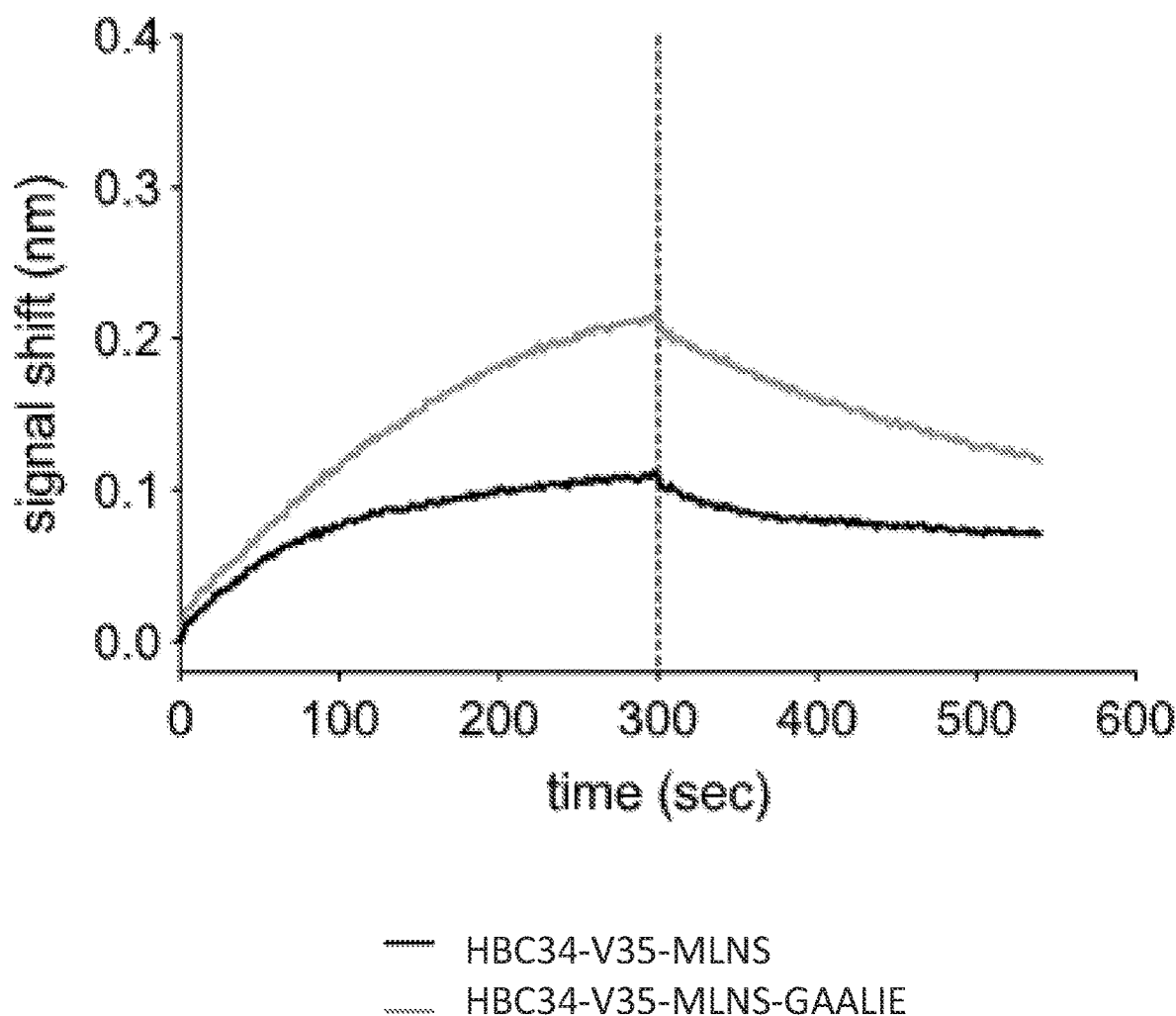
Figure 9C:
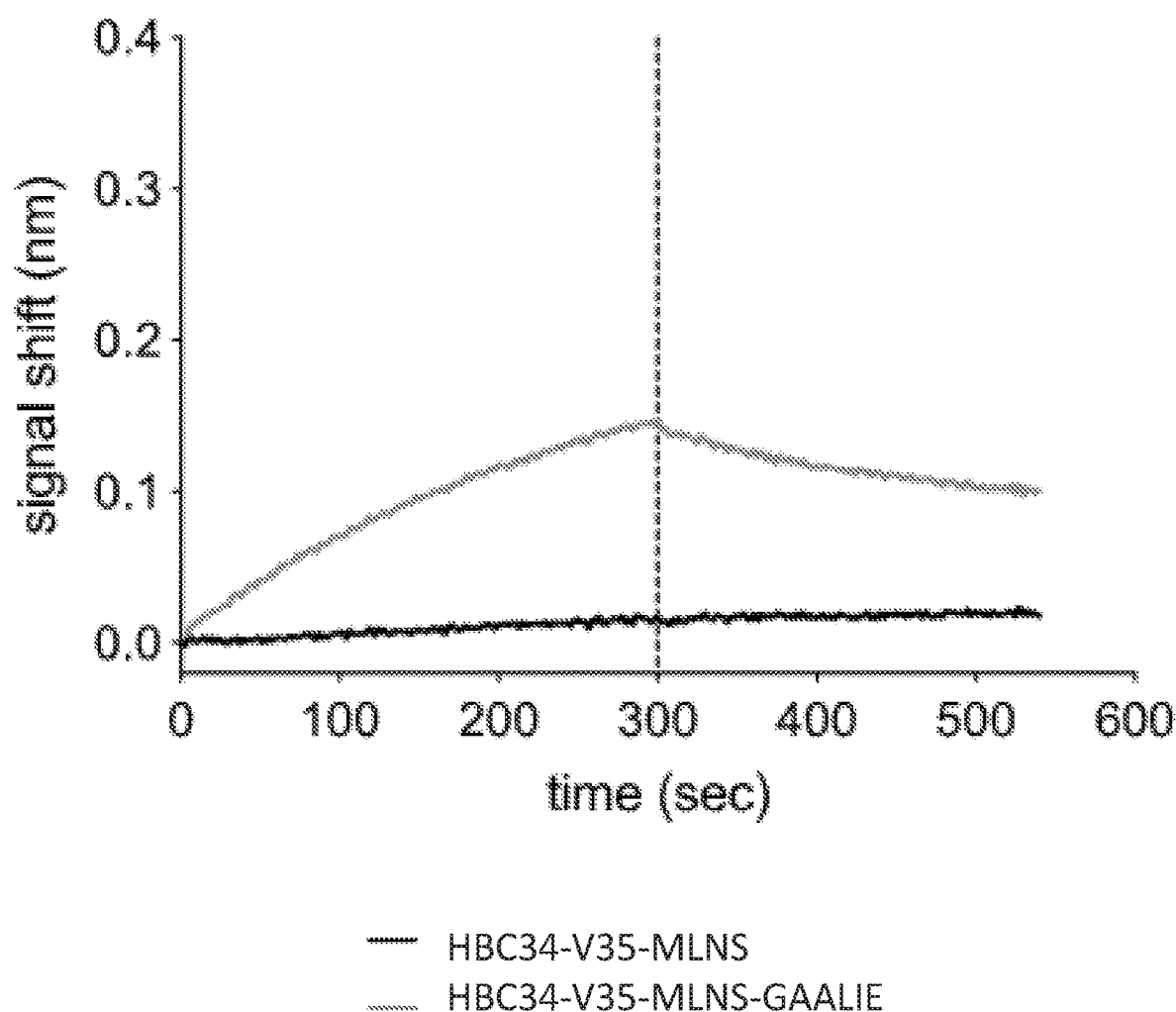
Figure 9D:
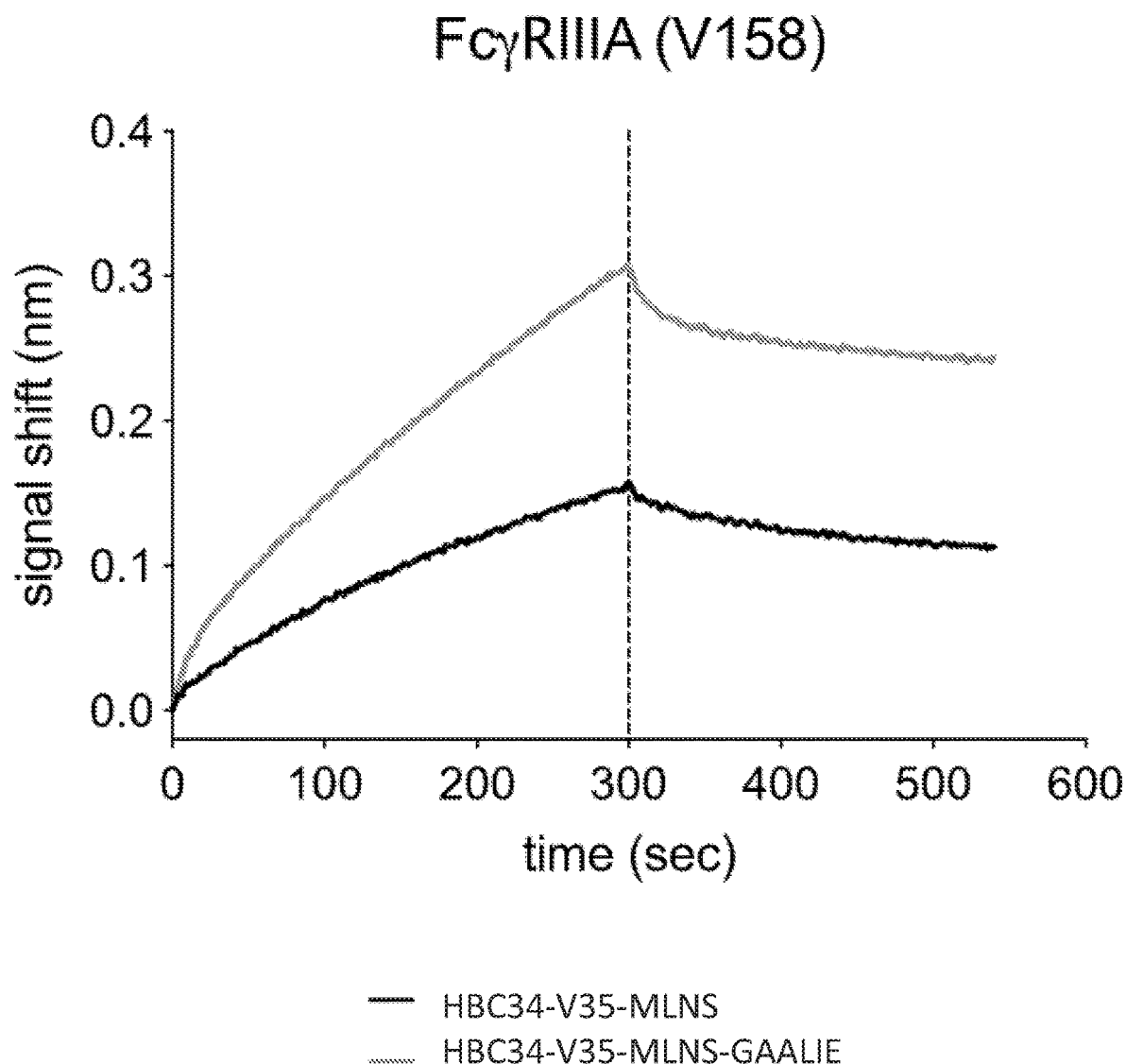
Figure 9E:
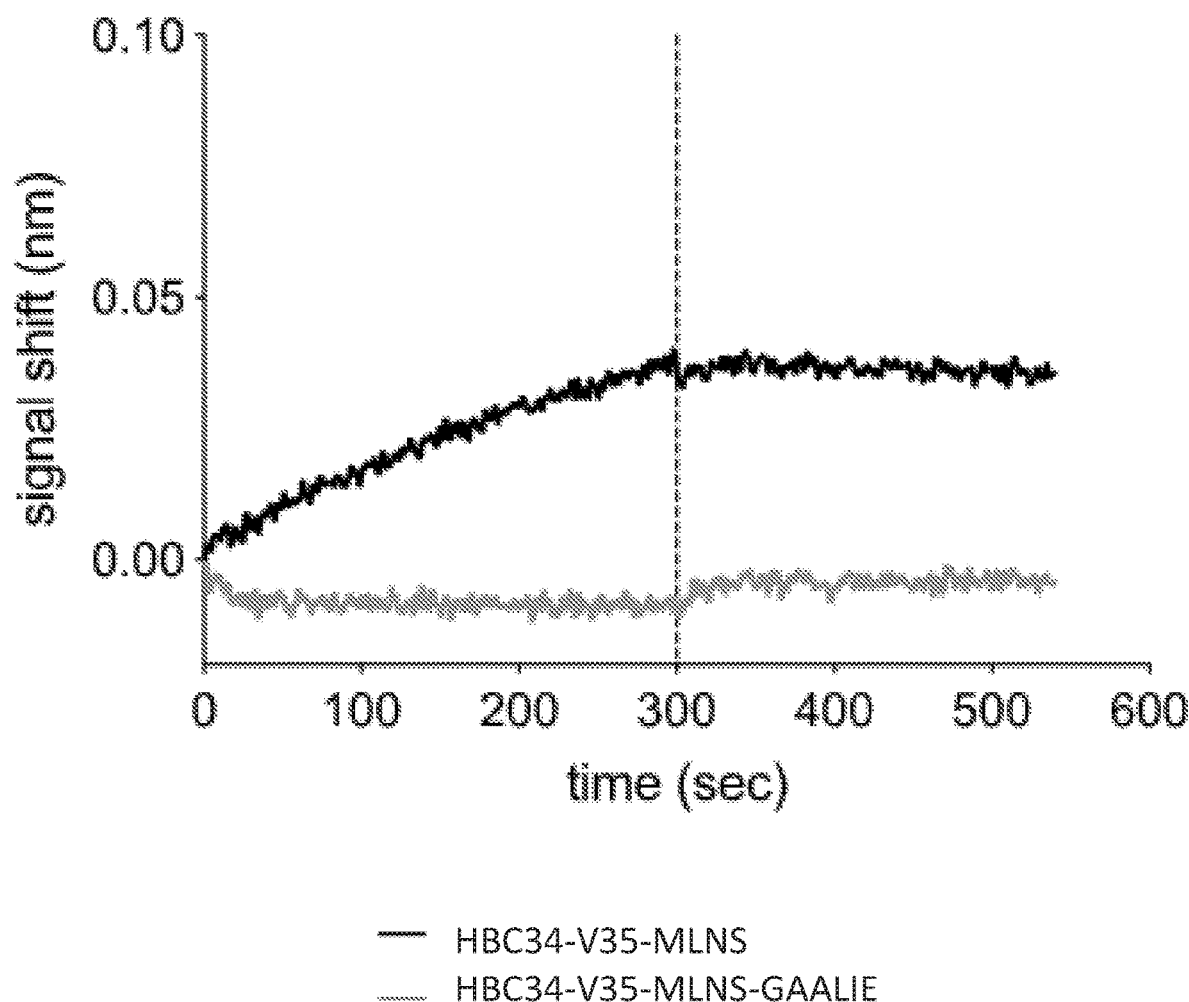
Figure 9F:
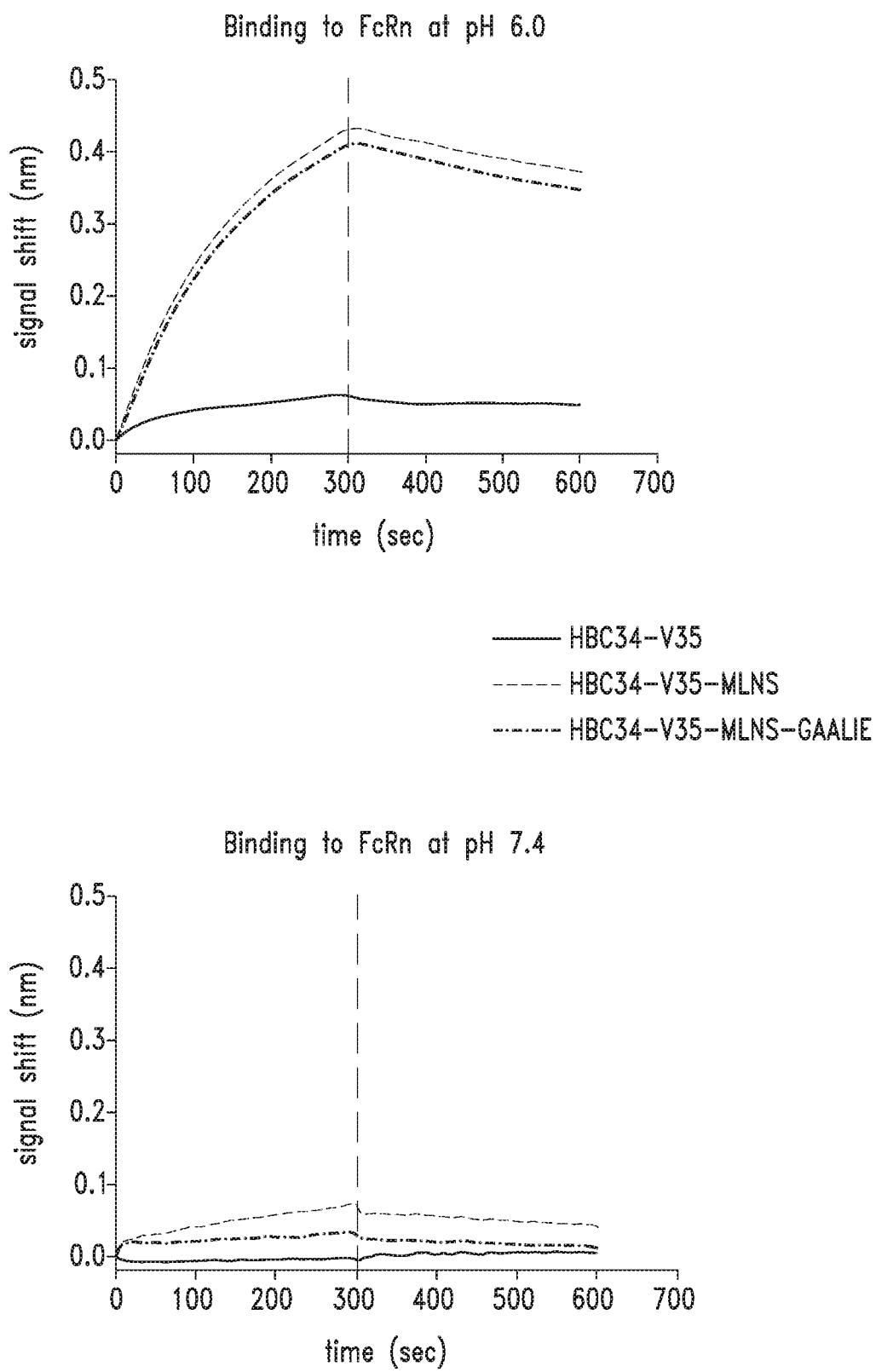

As shown in FIG. 9F, antibodies bearing the MLNS Fc mutation have increased binding to FcRn at pH 6.0 relative to antibody with wild-type Fc, but little to no measurable binding to FcRn at pH 7.4, which is comparable to antibody with wild-type Fc.

Figure 10:
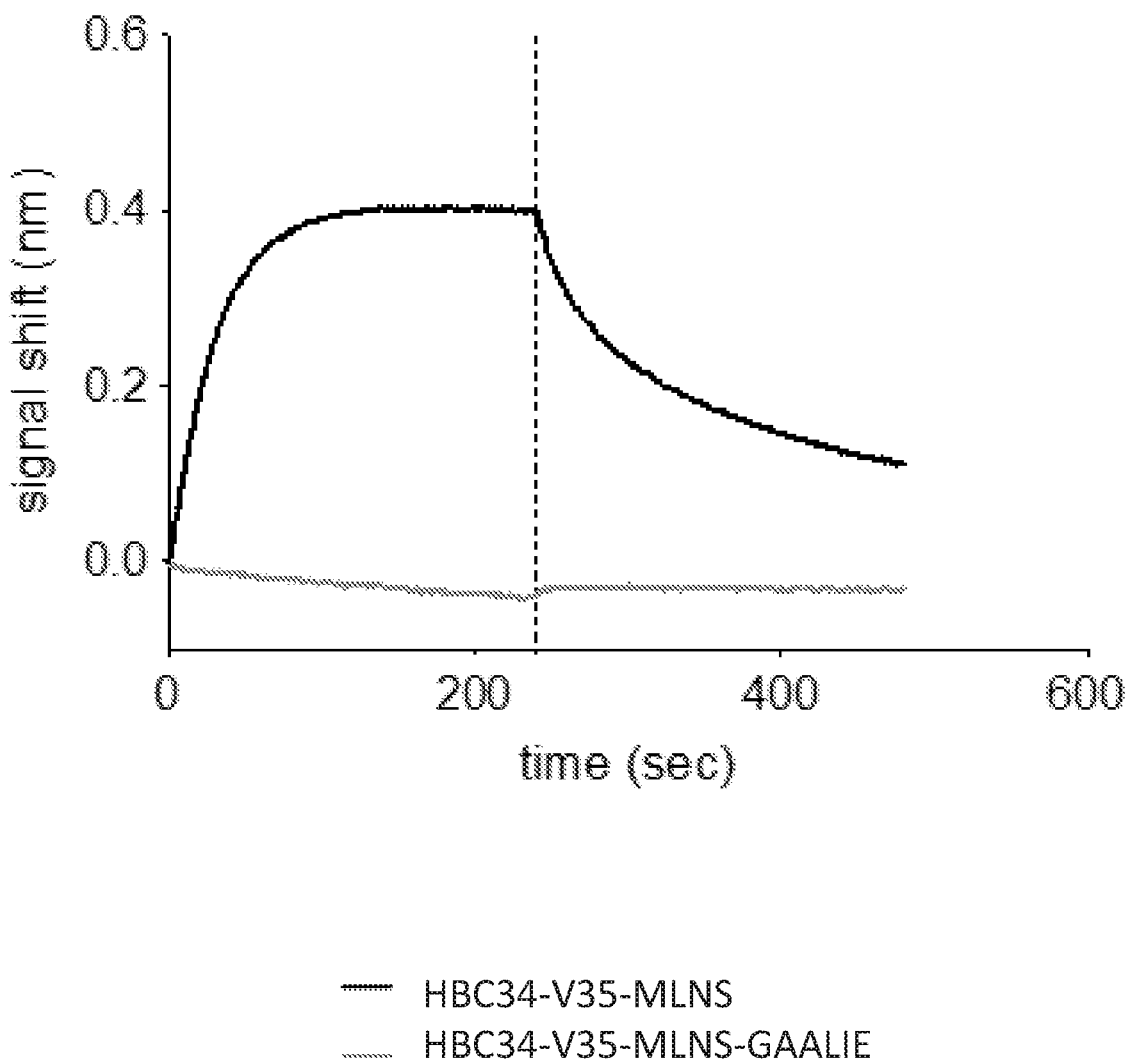
FIG. 10 shows binding of HBC34-V35-MLNS and HBC34-V35-MLNS-GAALIE to human C1q, as measured by Octet®. Anti-human Fab (CH1) sensors were used to capture, through the Fab fragment, the full IgG1 of HBC34v35-MLNS and HBC34-V35-MLNS-GAALIE mAbs at 10 μg/ml for 10 minutes. IgG-loaded sensors were then exposed for 4 minutes to a solution of kinetics buffer (pH 7.1) containing 3 μg/ml of purified human C1q (left part of the plot), followed by a dissociation step in the same buffer for additional 4 minutes (right part of the plot). Association and dissociation profiles were measured in real time as change in the interference pattern using an Octet® RED96 (FortéBio).
Figure 11A:
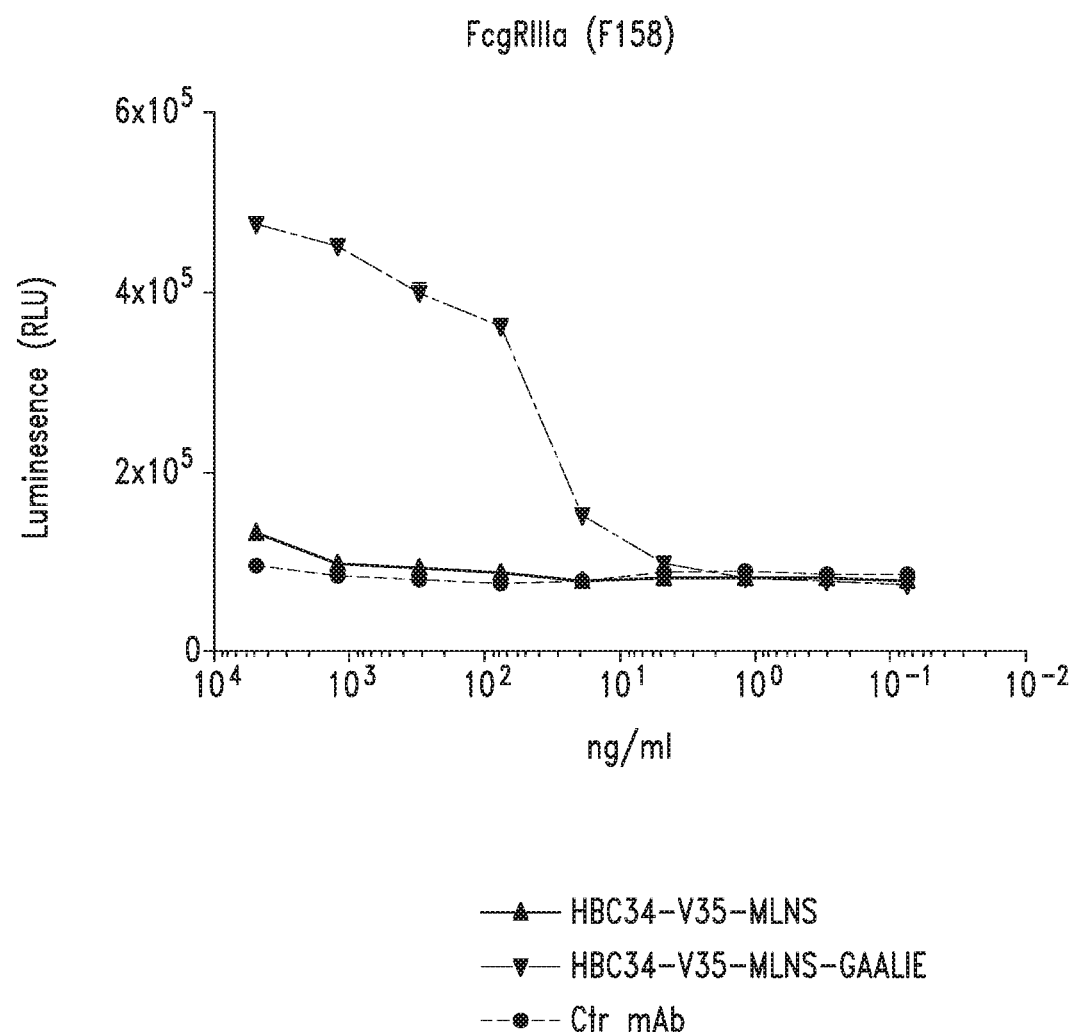
FIGS. 11A and 11B show in vitro activation of human FcγRIIIa using receptor-linked activation of a NFAT-mediated Luciferase reporter in engineered Jurkat cells. FcγRIIIa activation was tested using a validated, commercially available bioreporter assay in which recombinant HBsAg (Engerix B) is used as target antigen. Serial dilutions of HBC34-V35-MLNS and HBC34-V35-MLNS-GAALIE and a control (Ctr) mAb were incubated with 0.2 μg/ml of HBsAg at 37° C. for 25 min. Jurkat effector cells (Promega) expressing either FcγRIIIa low affinity allele F158 (A) or FcγRIIIa high affinity allele V158 (B) were resuspended in assay buffer and then added to assay plates. After incubation at 37° C. for 24 hours, Bio-Glo-™ Luciferase Assay Reagent (Promega) was added, and luminescence was quantified using luminometer (Bio-Tek).
Figure 11B:
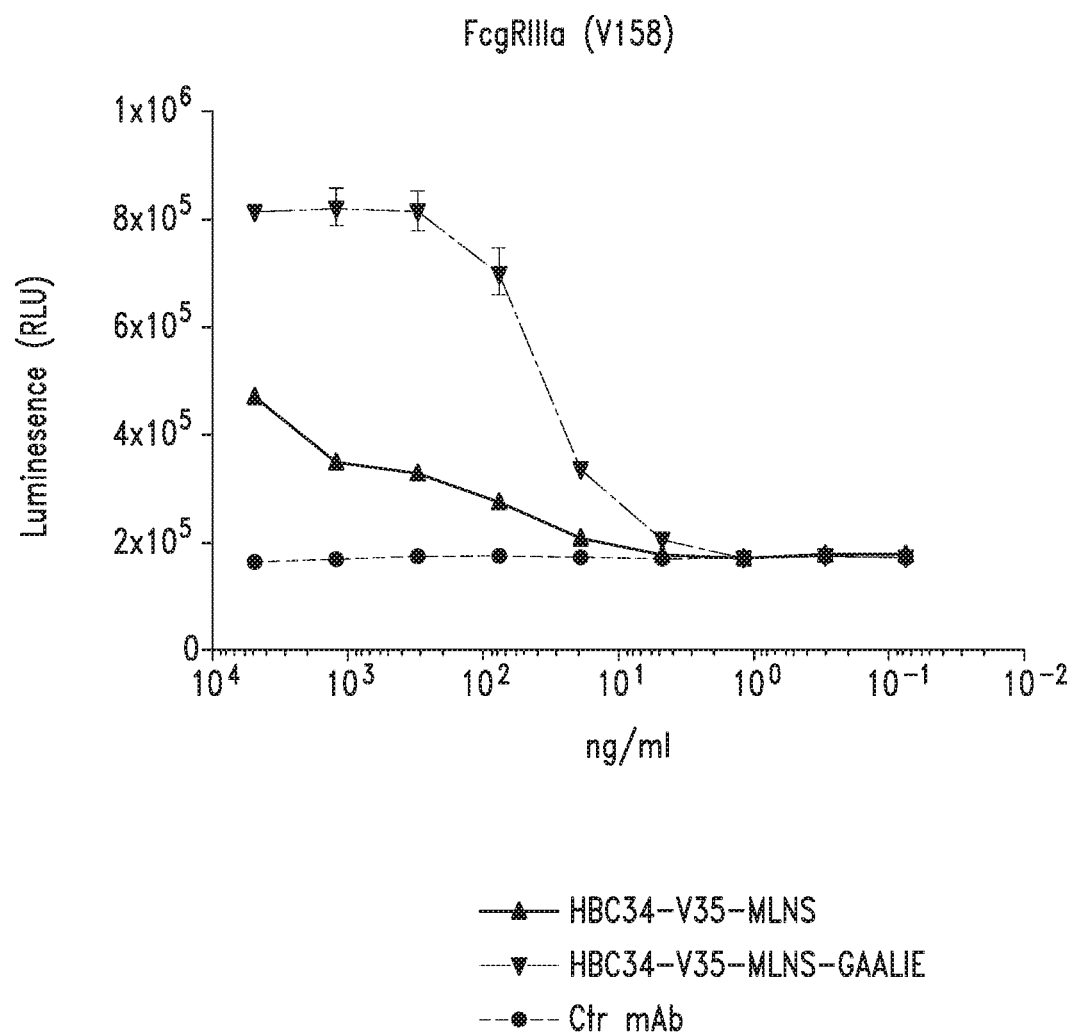
Figure 12A:
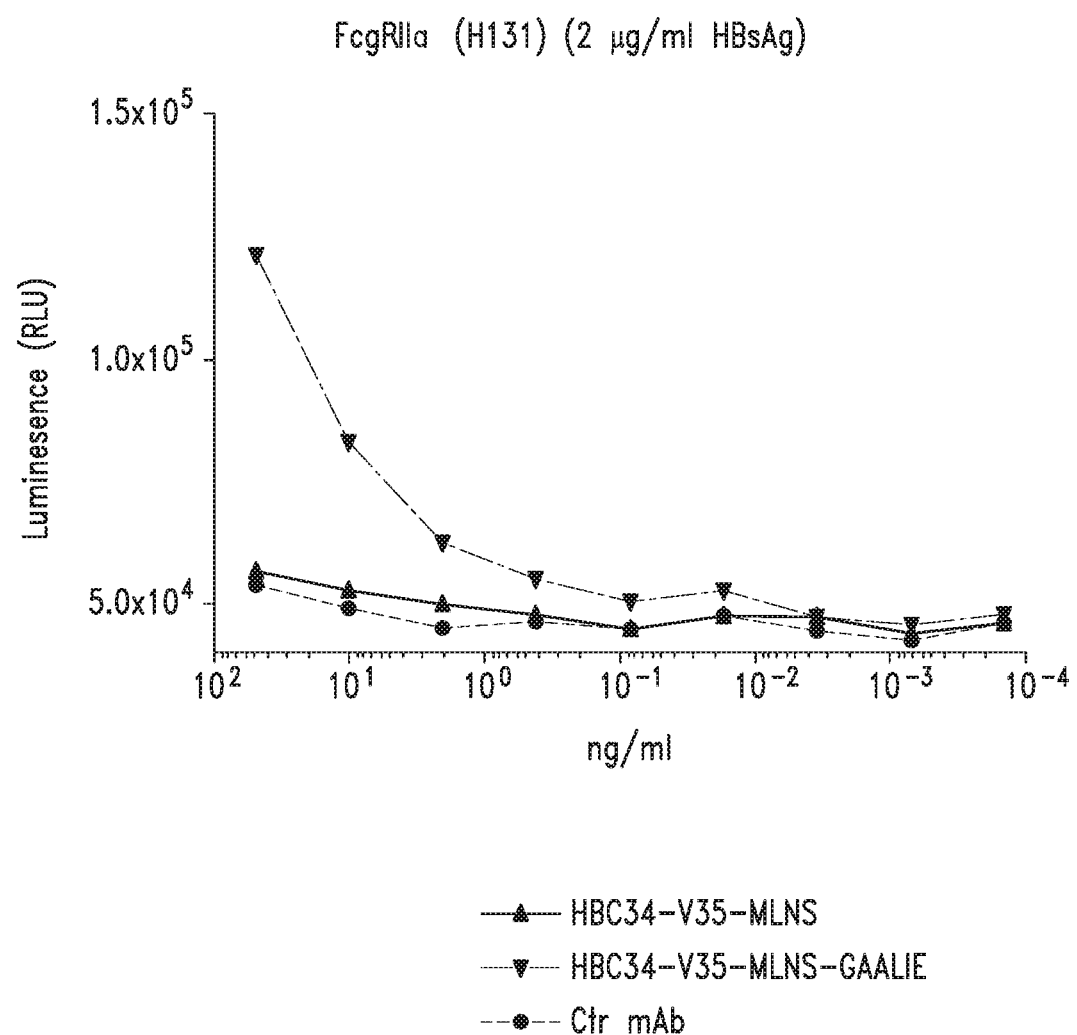
FIGS. 12A and 12B show in vitro activation of human FcγRIIa using receptor-linked activation of a NFAT-mediated luciferase reporter in engineered Jurkat cells. Activation of human FcγRIIa was determined using a validated, commercially available bioreporter assay in which recombinant HBsAg (Engerix B) was used as target antigen. Serial dilutions of HBC34v35-MLNS and HBC34-V35-MLNS-GAALIE and a control mAb (Ctr) were incubated with 2 μg/ml (A) or 0.2 μg/ml (B) of HBsAg at 37° C. for 25 min. Jurkat effector cells (Promega) expressing FcγRIIa high affinity allele H131 were resuspended in assay buffer and then added to assay plates. After incubation at 37° C. for 23 hours, Bio-Glo-™ Luciferase Assay Reagent (Promega) was added, and luminescence was quantified using luminometer (Bio-Tek).
Figure 12B:
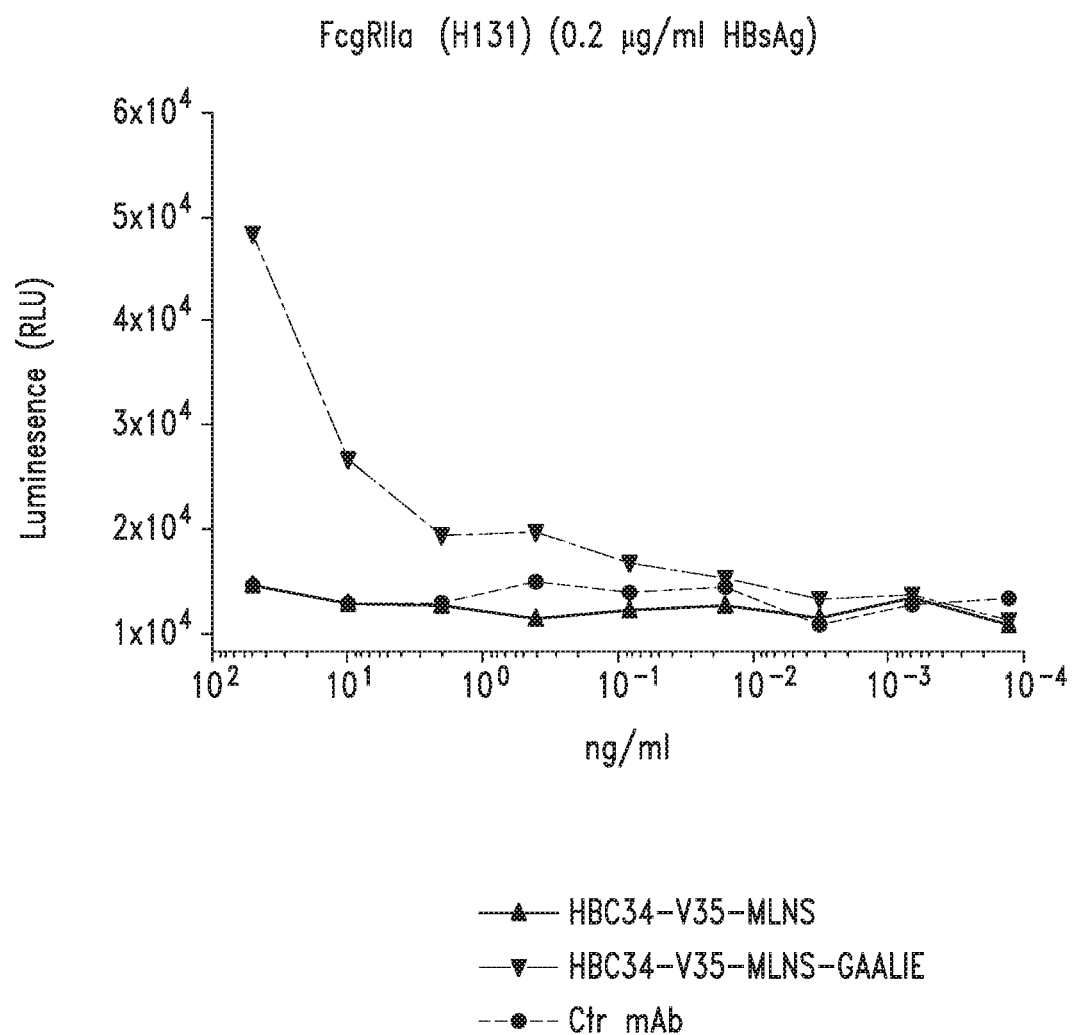

Also, binding of HBC34-V35-MLNS-GAALIE to C1q was abolished, as measured by biolayer interferometry (FIG. 10).

Figure 13A:
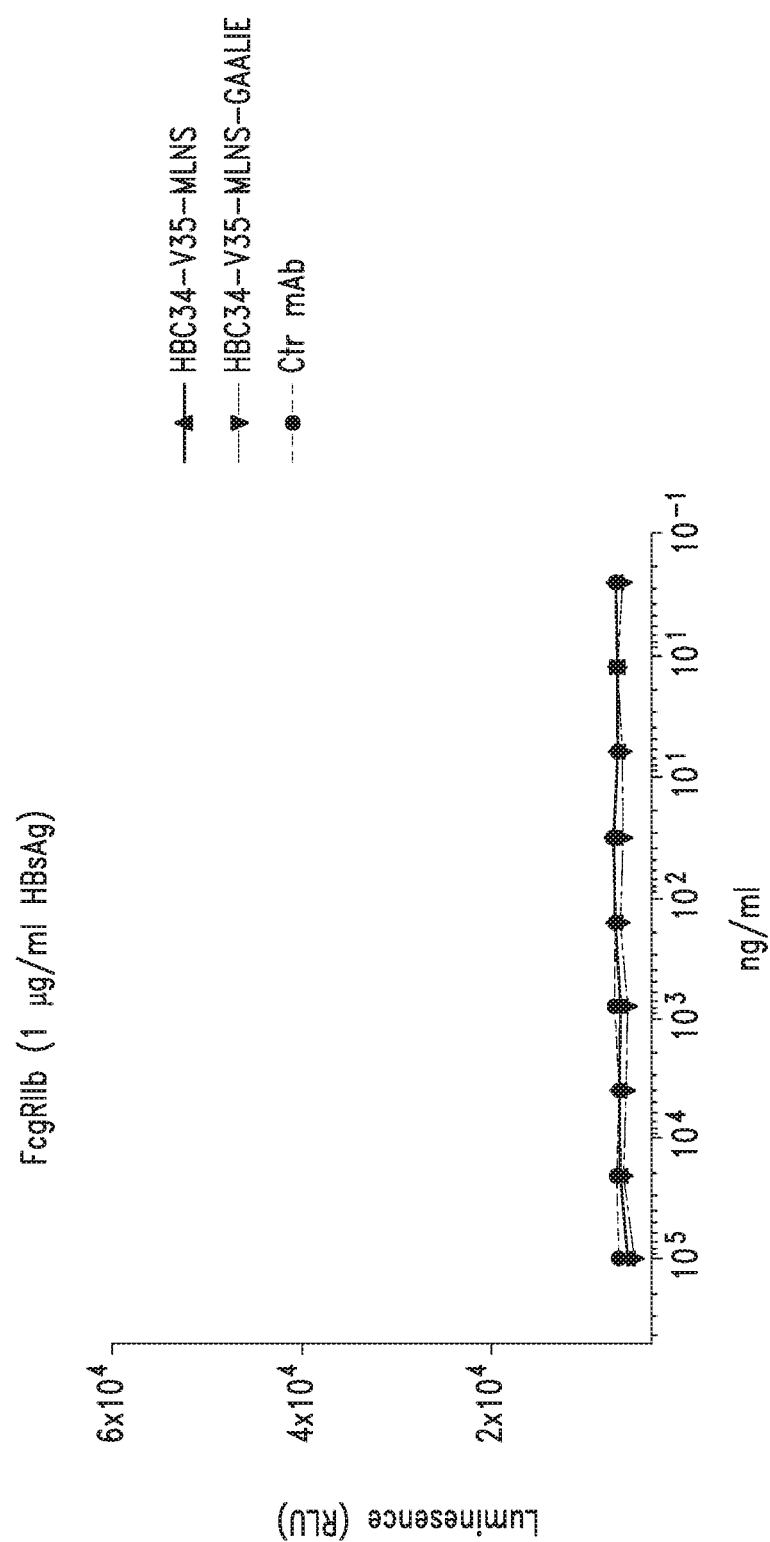
FIGS. 13A-13B show in vitro activation of human FcγRIIb using receptor-linked activation of a NFAT-mediated luciferase reporter in engineered Jurkat cells. Activation of human FcγRIIb was tested using a validated, commercially available bioreporter assay in which recombinant HBsAg (Engerix B) is used as target antigen. Serial dilutions of HBC34-V35-MLNS and HBC34-V35-MLNS-GAALIE and a control mAb (Ctr) were incubated with 1 µg/ml of HBsAg at 37° C. for 15 min. Jurkat effector cells (Promega) expressing FcγRIIb were resuspended in assay buffer and then added to assay plates. After incubation at 37° C. for 20 hours, Bio-Glo-™ Luciferase Assay Reagent (Promega) was added, and luminescence was quantified using luminometer (Bio-Tek).
Figure 13B:
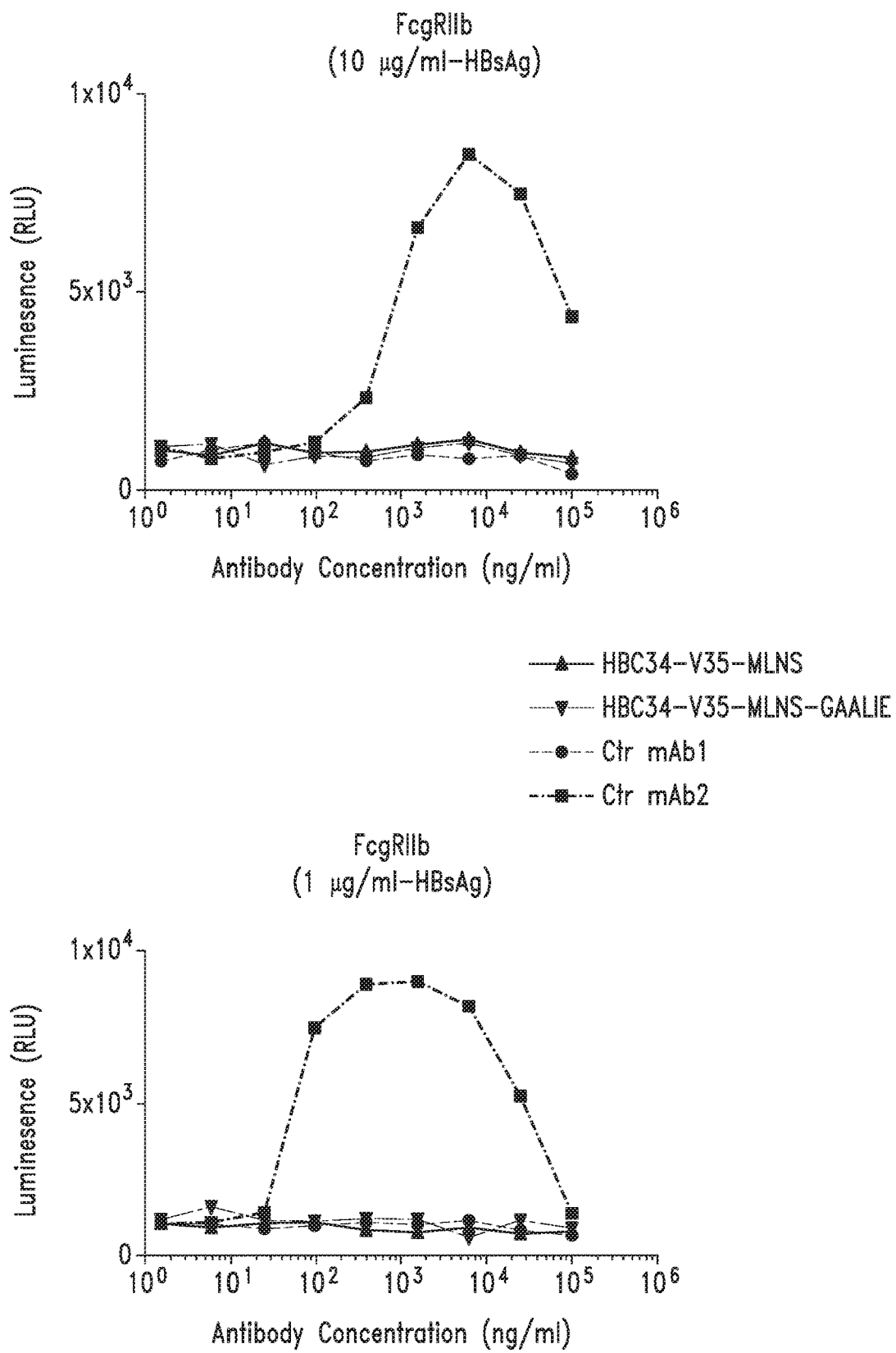

HBC34-V35-MLNS and HBC34-V35-MLNS-GAALIE were also tested for their ability to activate human FcγRIIIa and FcγRIIa using cell-based reporter bioassays. These assays utilize Jurkat cells engineered with a NFAT-mediated luciferase reporter to reflect activation of human FcγRs. While HBC34-V35-MLNS poorly activated or did not activate human FcγRIIIa and FcγRIIa in the presence of HBsAg, HBC34-V35-MLNS-GAALIE showed dose-dependent activation of all tested FcγRs (FIGS. 11A, 11B, 12A-12B). HBC34-V35-MLNS-GAALIE did not activate FcγRIIb, even when tested at 100 μg/ml (FIGS. 13A-13B).

Figure 14A:
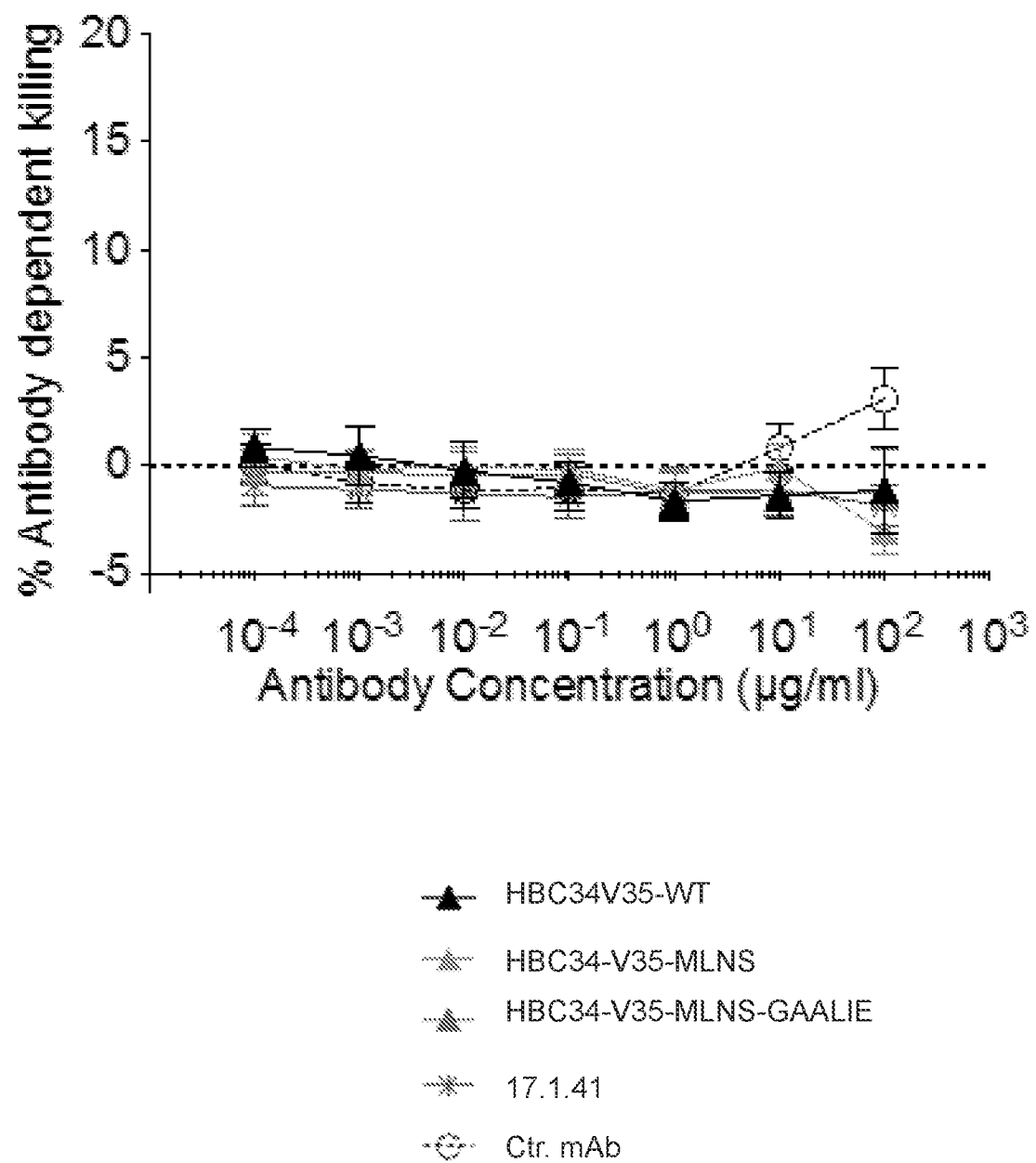
FIGS. 14A and 14B show in vitro killing of PLC/PRF/5 human hepatoma cells by human primary NK cells in the presence of HBC34-V35-MLNS and HBC34-V35-MLNS-GAALIE. (A) ADCC was tested using freshly isolated NK cells from one donor previously genotyped for expressing heterozygous high (V158) and low (F158) affinity FcγRIIIa (F/V). Serial dilutions of HBC34-V35, HBC34-V35-MLNS, HBC34-V35-MLNS-GAALIE, anti-HBV mAb 17.1.41, and a control mAb were added to the HBsAg-secreting hepatoma cell line PLC/PRF/5 (also referred to as Alexander cells). PLC/PRF/5 cells were incubated together with antibodies at room temperature for 10 min. NK cells were added to assay plates (effector cells to target cells ratio of 10:1) and incubated at 37° C. for 4 hours. Cell death was determined by measuring lactate dehydrogenase (LDH) release. (B) Staining of PLC/PRF/5 human hepatoma cells by HBC34-V35 and 17.1.41 mAbs as assessed by flow cytometry. Cells were extensively washed, fixed with formaldehyde (4%) or fixed and permeabilized (saponin 0.5%) before staining with different concentrations of HBC34-V35 and 17.1.41 mAbs. Binding of these human (in the case of HBC34-V35, engineered human) mAbs was detected by flow-cytometry using an Alexa Fluor® 647 AffiniPure F(ab')$_2$ Fragment Goat Anti-Human IgG, Fcγ Fragment Specific antibody.
Figure 14B:
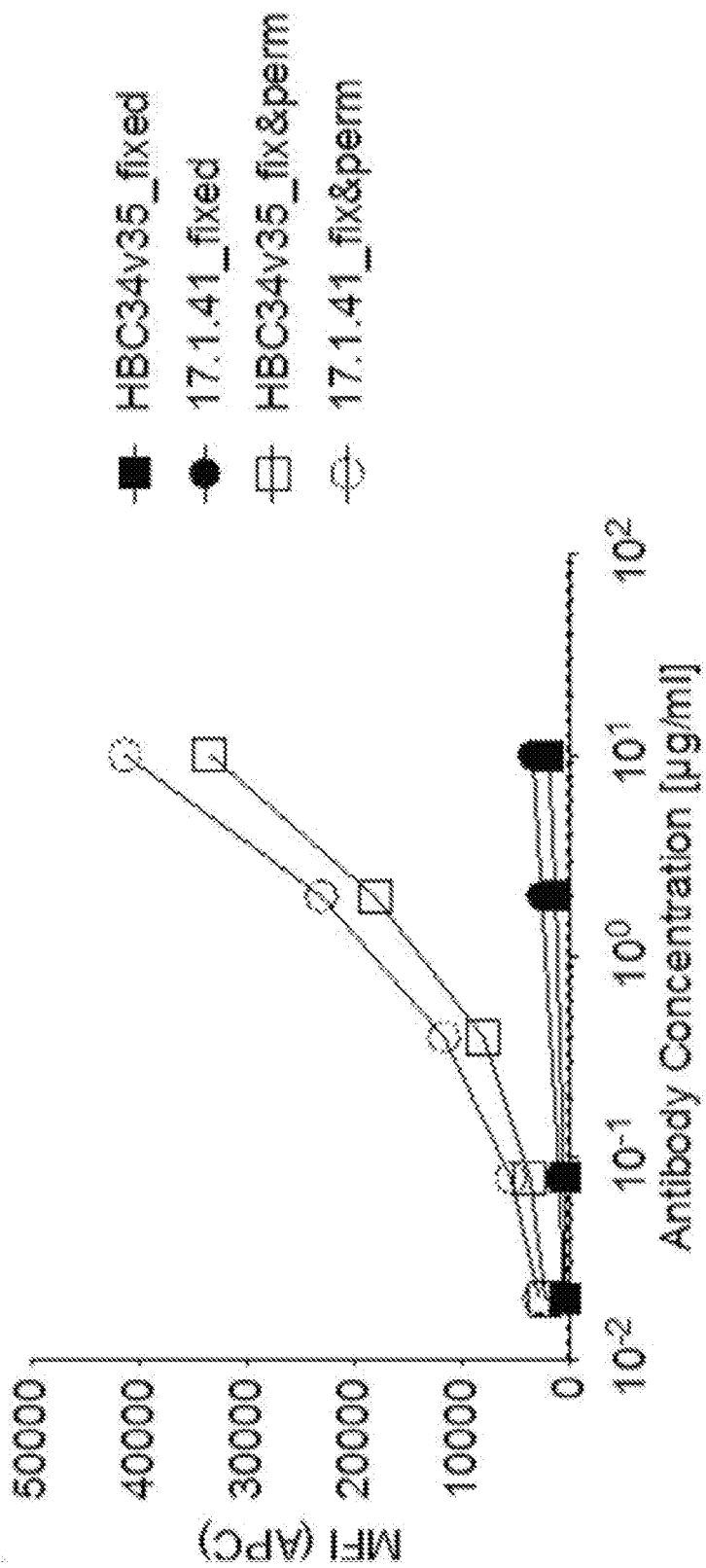

ADCC activity was also measured using natural killer cells (NK) isolated from human peripheral blood mononuclear cells of one donor who was previously genotyped for expressing heterozygous high (V158) and low (F158) affinity FcγRIIIa (FN). Isolated NK cells were used to measure the killing of the hepatoma cell line PLC/PR/5 upon exposure to HBC34-V35; HBC34-V35-MLNS; HBC34-V35-MLNS-GAALIE; or another mAb (17.1.41, targeting another epitope on the antigenic loop of the HBsAg; see Eren, R., et al., Hepatology, doi.org/10.1053/jhep.2000.9632; Galun, E., et al., Hepatology, doi.org/10.1053/jhep.2002.31867). Killing in the presence of the HBsAg-specific mAbs HBC34-V35, HBC34-V35-MLNS, HBC34-V35-MLNS-GAALIE and 17.1.41 was not observed (FIG. 14A). The observed lack of antibody-dependent killing of PLC/PR/5 cells might be related to the poor expression of HBsAg on the surface of these cells (FIG. 14B), which, without wishing to be bound by theory, may not be sufficient to trigger killing by NK cells. Conversely, high levels of HBsAg were detected with HBC34v35 and 17.1.41 when PLC/PR/5 cells were fixed and permeabilized, indicating that most of the HBsAg is found either intracellularly or in secreted forms (i.e. subviral particles) (FIG. 14B).

Figure 15A:
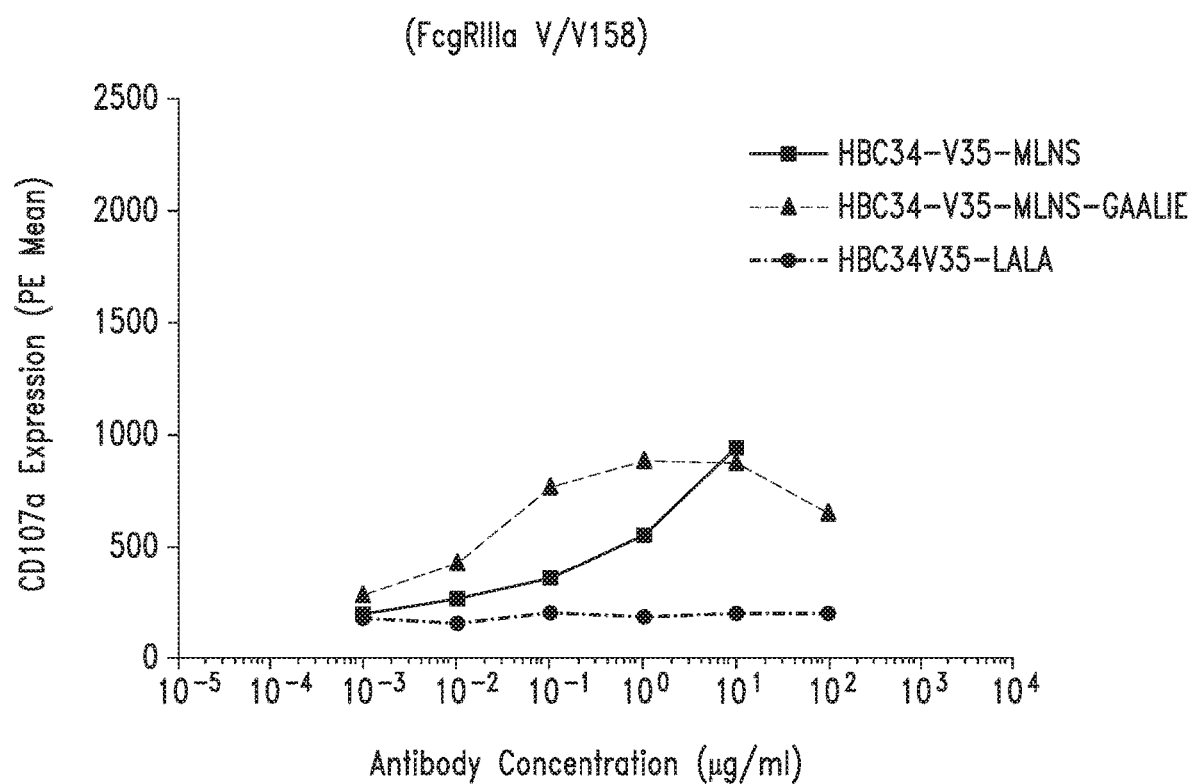
FIGS. 15A and 15B show in vitro activation of primary human NK cells in the presence of HBC34-V35-MLNS and HBC34-V35-MLNS-GAALIE and HBsAg. Activation of NK cells was tested using freshly isolated cells from two donors previously genotyped for expressing (A) homozygous high (V158) or (B) low (F158) affinity FcγRIIIa. Serial dilutions of HBC34-V35, HBC34-V35-MLNS-GAALIE, and HBC34v35-LALA mAbs were incubated with NK cells for 4 hours. Activation of NK cells was measured by flow cytometry by staining NK cells with anti-CD107a mAb, as a functional marker for the identification of NK cell activity. CD107a, also known as LAMP-1, is a marker for degranulation of NK cells.
Figure 15B:
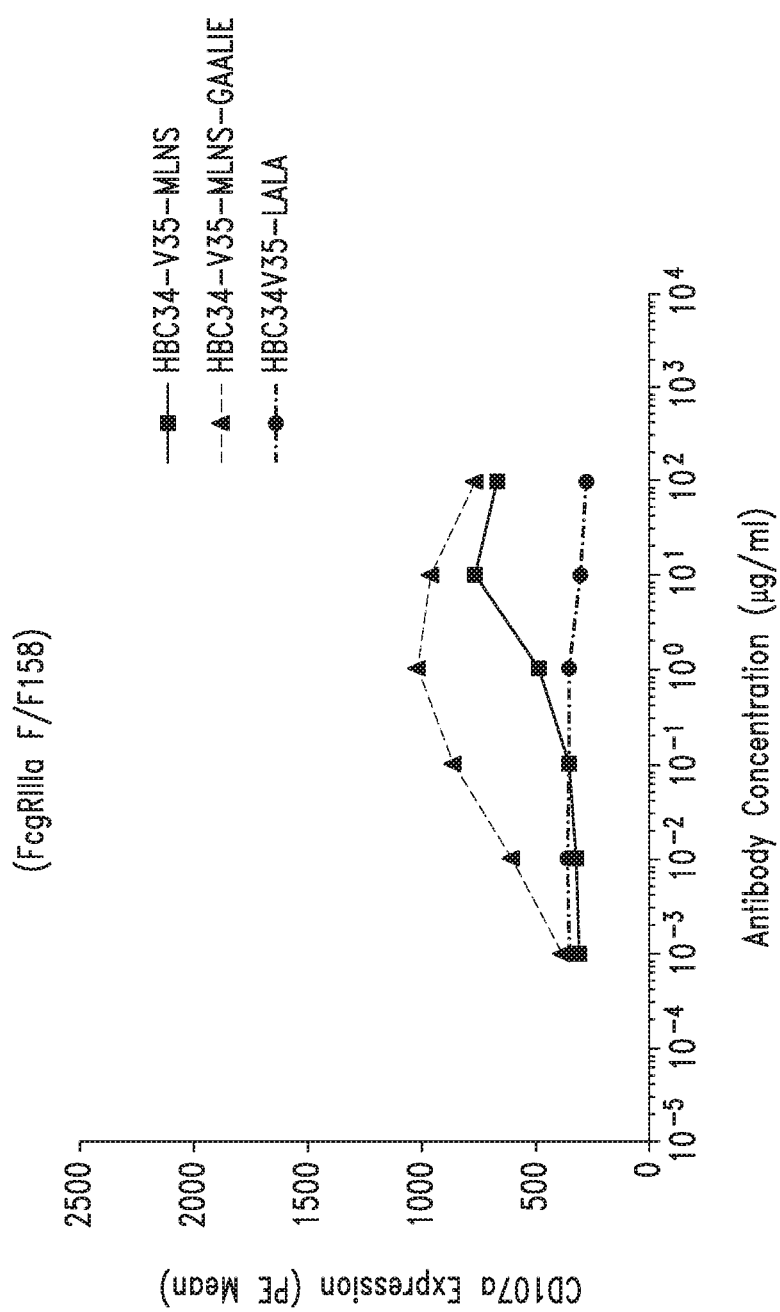

Activation of primary human NK cells (V/F) in the presence of HBC34v35-MLNS or HBC34-V35-MLNS-GAALIE and HBsAg was also examined using anti-CD107a mAb. Data are shown in FIGS. 15A and 15B.

These in vitro data show that HBV-specific binding proteins of the present disclosure bearing the GAALIE Fc mutation bind to and activate low affinity activating FcγRIIa and FcγRIIIa more effectively than the non-GAALIE Fc parental antibody. GAALIE-bearing binding proteins also do not bind to and or activate low affinity inhibitory FcγRIIb. GAALIE-bearing binding proteins also do not bind to C1q. Furthermore, GAALIE-bearing binding proteins do not promote ADCC on hepatoma cells, but activate human NK cells in the presence of soluble HBsAg. Introduction of MLNS mutation increases binding to FcRn at pH 6.0.

Example 7: In Vitro Study of Drug-Drug Interaction Between HBC34-V35-MLNS-GAALIE and a Pol/RT Inhibitor An in vitro study was conducted to identify possible combination effects of HBC34-V35-MLNS-GAALIE with the HBV pol/RT inhibitor Entecavir (ETV). In vitro combination effects were determined using HBC34-V35-MLNS-GAALIE and ETV in HepG2.2.15 cells in a checkerboard format. HBsAg and HBV DNA levels were used as read-outs and data were analyzed for combination effects using MacSynergy II (uab.edu/medicine/peds/macsynergy). For normalization, values obtained from untreated HepG2.2.15 cells were used as positive controls, while tissue culture medium was used as negative control. Synergy plots at 99% confidence were used for reporting. Data are shown in FIG. 16. The synergy plots for both readouts show an additive effect of HBC34-V35-MLNS-GAALIE with ETV in vitro. Notably, no antagonism was observed. These data support the use of nucleoside analogs in combination with HBC34-V35-MLNS-GAALIE in a clinical setting.

Example 8: Identification and Characterization of Human Monoclonal Antibody HBC24

An anti-HBV human monoclonal antibody was isolated in a similar manner as described in Traggiai E. et al., 2004, Nat Med 10(8): 871-5 from a human patient. The antibody was characterized by determining the nucleotide and amino acid sequences of its variable regions and the complementarity determining regions (CDRs) therein and termed "HBC24". Accordingly, HBC24 is an IgG1-type fully human monoclonal antibody having the CDR, $V_H$ and $V_L$ sequences as shown above in Table 3. Exemplary nucleotide sequences encoding the $V_H$ and $V_L$ of HBC24 are provided in Table 4.

Example 9: Generation of Germlined Variants of HBC24 and Functional Testing

HBC24 is analyzed for the presence of somatic mutations in the variable regions relative to germline sequence. Identified somatic mutations are reverted to germline sequence to produce HBC24 variants. HBC24 and variants are tested for binding (in vitro) and neutralization (in vitro; in vivo) of HBV and HBD serotypes using assays as described herein.

Example 10: Introduction of Fc Modifications to HBC24 and Variants

Further HBC24 variants are produced that contain the MLNS and GAALIE mutations in both Fc monomers. The HC amino acid sequences of selected variants are provided in SEQ ID NOs: 121 and 122. Variants are examined for: (1) in vitro binding to antigen; (2) in vitro neutralization of HBV serotypes using assays as described herein.

| TABLE OF SEQUENCES AND SEQ ID NUMBERS (SEQUENCE LISTING): | | |
|---|---|---|
| SEQ ID NO | Sequence | Remarks |
| 1 | $X_1$ $X_2$ $X_3$ TC $X_4$ $X_5$ $X_6$A $X_7$G<br>wherein $X_1$, $X_2$, $X_3$, $X_4$, $X_5$, $X_6$ and $X_7$ may be any amino | epitope |
| 2 | $X_1$ $X_2$ $X_3$ TC $X_4$ $X_5$ $X_6$A $X_7$G<br>wherein $X_1$ is P, T or S, | |

-continued

TABLE OF SEQUENCES AND SEQ ID NUMBERS (SEQUENCE LISTING):

| SEQ ID NO | Sequence | Remarks |
|---|---|---|
| | $X_2$ is C or S,<br>$X_3$ is R, K, D or I,<br>$X_4$ is M or T,<br>$X_5$ is T, A or I,<br>$X_6$ is T, P or L, and<br>$X_7$ is Q, H or L. | |
| 3 | MENITSGFLGPLLVLQAGFFLLTRILTIPQSLDSWWT<br>SLNFLGGTTVCLGQNSQSPTSNHSPTSCPPTCPGYR<br>WMCLRRFIIFLFILLLCLIFLLVLLDYQGMLPVCPLIP<br>GSSTTSTGPCRTCMTTAQGTSMYPSCCCTKPSDGNC<br>TCIPIPSSWAFGKFLWEWASARFSWLSLLVPFVQWF<br>VGLSPTVWLSVIWMMWYWGPSLYSILSPFLPLLPIFF<br>CLWVYI | S domain of HBsAg (GenBank acc. no. J02203) |
| 4 | MENVTSGFLGPLLVLQAGFFLLTRILTIPQSLDSWWT<br>SLNFLGGTTVCLGQNSQSPTSNHSPTSCPPTCPGYR<br>WMCLRRFIIFLFILLLCLIFLLVLLDYQGMLPVCPLIP<br>GSSTTGTGPCRTCTTPAQGTSMYPSCCCTKPSDGNC<br>TCIPIPSSWAFGKFLWEWASARFSWLSLLVPFVQWF<br>VGLSPTVWLSVIWMMWYWGPSLYSTLSPFLPLLPIF<br>FCLWVYI | S domain of HBsAg (GenBank acc. no. FJ899792) |
| 5 | QGMLPVCPLIPGSSTTSTGPCRTCMTTAQGTSMYPS<br>CCCTKPSDGNCTCIPIPSSWAFGKFLWEWASARFSW | J02203 (D, ayw3) |
| 6 | QGMLPVCPLIPGSSTTGTGPCRTCTTPAQGTSMYPSC<br>CCTKPSDGNCTCIPIPSSWAFGKFLWEWASARFSW | FJ899792 (D, adw2) |
| 7 | QGMLPVCPLIPGTTTTSTGPCKTCTTPAQGNSMFPSC<br>CCTKPSDGNCTCIPIPSSWAFAKYLWEWASVRFSW | AM282986 (A) |
| 8 | QGMLPVCPLIPGSSTTSTGPCKTCTTPAQGTSMFPSC<br>CCTKPTDGNCTCIPIPSSWAFAKYLWEWASVRFSW | D23678 (B1) |
| 9 | QGMLPVCPLLPGTSTTSTGPCKTCTIPAQGTSMFPSC<br>CCTKPSDGNCTCIPIPSSWAFARFLWEWASVRFSW | AB117758 (C1) |
| 10 | QGMLPVCPLIPGSSTTSTGPCRTCTTLAQGTSMFPSC<br>CCSKPSDGNCTCIPIPSSWAFGKFLWEWASARFSW | AB205192 (E) |
| 11 | QGMLPVCPLLPGSTTTSTGPCKTCTTLAQGTSMFPS<br>CCC SKPSDGNCITIPTPSSWALGKYT,WFWASARFSW | X69798 (F4) |
| 12 | QGMLPVCPLIPGSSTTSTGPCKTCTTPAQGNSMYPSC<br>CCTKPSDGNCTCIPIPSSWAFAKYLWEWASVRFSW | AF160501 (G) |
| 13 | QGMLPVCPLLPGSTTTSTGPCKTCTTLAQGTSMFPS<br>CCCTKPSDGNCTCIPIPSSWAFGKYLWEWASARFSW | AY090454 (H) |
| 14 | QGMLPVCPLIPGSSTTSTGPCKTCTTPAQGNSMYPSC<br>CCTKPSDGNCTCIPIPSSWAFAKYLWEWASARFSW | AF241409 (I) |
| 15 | QGMLPVCPLLPGSTTTSTGPCRTCTITAQGTSMFPSC<br>CCTKPSDGNCTCIPIPSSWAFAKFLWEWASVRFSW | AB486012 (J) |
| 16 | CQGMLPVCPLIPGSSTTGTGTCRTCTTPAQGTSMYPS<br>CCCTKPSDGNCTCIPIPSSWAFGKFLWEWASARFSW | HBsAg Y100C/P120T |
| 17 | QGMLPVCPLIPGSSTTGTGTCRTCTTPAQGTSMYPSC<br>CCTKPSDGNCTCIPIPSSWAFGKFLWEWASARFSW | HBsAg P120T |
| 18 | QGMLPVCPLIPGSSTTGTGTCRTCTTPAQGTSMYPSC<br>CCTKPLDGNCTCIPIPSSWAFGKFLWEWASARFSW | HBsAg P120T/S143L |
| 19 | QGMLPVCPLIPGSSTTGTGPSRTCTTPAQGTSMYPSC<br>CCTKPSDGNCTCIPIPSSWAFGKFLWEWASARFSW | HBsAg C121S |
| 20 | QGMLPVCPLIPGSSTTGTGPCDTCTTPAQGTSMYPSC<br>CCTKPSDGNCTCIPIPSSWAFGKFLWEWASARFSW | HBsAg R122D |
| 21 | QGMLPVCPLIPGSSTTGTGPCITCTTPAQGTSMYPSC<br>CCTKPSDGNCTCIPIPSSWAFGKFLWEWASARFSW | HBsAg R122I |

TABLE OF SEQUENCES AND SEQ ID NUMBERS (SEQUENCE LISTING):

| SEQ ID NO | Sequence | Remarks |
|---|---|---|
| 22 | QGMLPVCPLIPGSSTTGTGPCRNCTTPAQGTSMYPSCCCTKPSDGNCTCIPIPSSWAFGKFLWEWASARFSW | HBsAg T123N |
| 23 | QGMLPVCPLIPGSSTTGTGPCRTCTTPAHGTSMYPSCCCTKPSDGNCTCIPIPSSWAFGKFLWEWASARFSW | HBsAg Q129H |
| 24 | QGMLPVCPLIPGSSTTGTGPCRTCTTPALGTSMYPSCCCTKPSDGNCTCIPIPSSWAFGKFLWEWASARFSW | HBsAg Q129L |
| 25 | QGMLPVCPLIPGSSTTGT

TABLE OF SEQUENCES AND SEQ ID NUMBERS (SEQUENCE LISTING):

| SEQ ID NO | Sequence | Remarks |
|---|---|---|
| 49 | CAGACGTGGGACAGCACCACTGTGGTG | HBC34 CDRL3 nuc |
| 50 | GAACTGCAGCTGGTGGAGTCTGGGGGAGGCTGGG TCCAGCCGGGGGGGTCCCAGAGACTGTCCTGTGC AGCCTCTGGACGCATCTTTAGAAGTTTTTACATGA GCTGGGTCCGCCAGGCCCCAGGGAAGGGGCTGGA GTGGGTGGCCACTATAAACCAAGATGGAAGTGAG AAATTATATGTGGACTCTGTGAAGGGCCGATTCA CCATCTCCAGAGACAACGCCAAGAACTCACTATT TCTGCAAATGAACAACCTGAGAGTCGAGGACACG GCCGTTTATTACTGCGCGGCTTGGAGCGGCAATA GTGGGGGTATGGACGTCTGGGGCCAGGGGACCAC GGTCTCCGTCTCCTCA | HBC34 VH nuc |
| 51 | TCCTATGAGCTGACTCAGCCACCCTCAGTGTCCGT GTCCCCAGGACAGACAGTCAGCATCCCCTGCTCT GGAGATAAATTGGGGAATAAAAATGTTTGCTGGT TTCAGCATAAGCCAGGCCAGTCCCCTGTGTTGGTC ATCTATGAGGTTAAATACCGCCCCTCGGGGATTCC TGAGCGATTCTCTGGCTCCAACTCTGGGAACACA GCCACTCTGACCATCAGCGGGACCCAGGCTATGG ATGAGGCTGCCTATTTCTGTCAGACGTGGGACAG CACCACTGTGGTGTTCGGCGGAGGGACCAGGCTG ACCGTCCTA | HBC34 VL nuc |
| 52 | XGSSTTSTGPCRTCMTXPSDGNATAIPIPSSWX wherein the residues coded as X were substituted with Cysteines | peptide |
| 53 | TSTGPCRTCMTTAQG | peptide |
| 54 | GMLPVCPLIPGSSTTSTGPCRTCMTT | peptide |
| 55 | XSMYPSASATKPSDGNXTGPCRTCMTTAQGTSX wherein the residues coded as X were substituted with Cysteines | peptide |
| 56 | PCRTCMTTAQG | amino acids 120-130 of the S domain of HBsAg (HBV-D J02203 |
| 57 | PCX$_1$TCX$_2$X$_3$X$_4$AQG, wherein X$_1$ is R or K, X$_2$ is M or T, X$_3$ is T or I, and X$_4$ is T, P or L | epitope |
| 58 | QTFDSTTVV | HBC34-V7 CDRL3 and HBC34-V23 CDRL3 (aa) |
| 59 | SYELTQPPSVSVSPGQTVSIPCSGDKLGNKNVCWFQH KPGQSPVLVIYEVKYRPSGIPERFSGSNSGNTATLTIS GTQAMDEAAYFCQTFDSTTVVFGGGTRLTVL | HBC34-V7 VL |
| 60 | AAGCTGGGGAACAAAAAT | HBC34-V7 CDRL1 and HBC-V23 CDRL1 (nuc) |
| 61 | GAGGTGAAA | HBC34-V7 CDRL2 and HBC34v23 CDRL2 nuc |
| 62 | GTCATCTACGAGGTGAAATATCGGCCT | HBC34-V7 CDRL2 long and CDRL2 HBC34-V23 long |
| 63 | CAGACATTCGATTCCACCACAGTGGTC | CDRL3 HBC34-V7 and CDRL3 HBC34-V23 nuc |
| 64 | TCTTACGAGCTGACACAGCCACCTAGCGTGTCCGT CTCTCCAGGACAGACCGTGTCCATCCCTTGCTCTG | HBC34-V7, HBC34-V34, and |

TABLE OF SEQUENCES AND SEQ ID NUMBERS (SEQUENCE LISTING):

| SEQ ID NO | Sequence | Remarks |
|---|---|---|
|  | GCGACAAGCTGGGAACAAAAATGTCTGTTGGTTC CAGCACAAGCCAGGGCAGAGTCCCGTGCTGGTCAT CTACGAGGTGAAATATCGGCCTTCAGGAATTCCAG AACGGTTCAGCGGATCAAACAGCGGCAATACTGC AACCCTGACAATTAGCGGGACCCAGGCCATGGAC GAAGCCGCTTATTCTGCCAGACATTCGATTCCAC CACAGTGGTCTTTGGCGGGGGAACTAGGCTGACCG TGCTG | HBC34-V35 VL nuc |
| 65 | SYELTQPPSVSVSPGQTASITCSGDKLGNKNACWYQ QKPGQSPVLVIYEVKYRPSGIPERFSGSNSGNTATLTI SGTQAMDEADYYCQTFDSTTVVFGGGTKLTVL | HBC34-V23 VL aa |
| 66 | INQDGSEK | HBC34wt CDRH2 |
| 67 | EVQLVESGGGLVQPGGSLRLSCAASGRIFRSFYMSW VRQAPGKGLEWVANINQDGSEKLYVDSVKGRFTISR DNAKNSLFLQMNNLRVEDTAVYYCAAWSGNSGGM DVWGQGTTVTVSS | HBC34-V31, HBC34-V32 and HBC34-V33 VH |
| 68 | GAGGTGCAGCTGGTGGAATCCGGCGGGGGACTGG TGCAGCCTGGCGGCTCACTGAGACTGAGCTGTGCA GCTTCTGGAAGAATCTTCAGATCTTTTTACATGAGT TGGGTGAGACAGGCTCCTGGGAAGGGACTGGAGT GGGTCGCAAACATCAATCAGGACGGATCAGAAAA GCTGTATGTGGATAGCGTCAAAGGCAGGTTCACTA TTTCCCGCGACAACGCCAAAAATTCTCTGTTTCTGC AGATGAACAATCTGCGGGTGGAGGATACCGCTGTC TACTATTGTGCAGCCTGGTCTGGCAACAGTGGAGG CATGGACGTGTGGGGACAGGGAACCACAGTGACA GTCAGCTCC | HBC34-V31, HBC34-V32 and HBC34-V33 VH (nuc) |
| 69 | TCTTACGAGCTGACACAGCCCCCTAGCGTGTCCGT CTCTCCAGGCCAGACAGCATCCATCACTTGCTCTG GCGACAAGCTGGGGAACAAAAATGCCTGTTGGTA TCAGCAGAAGCCAGGGCAGAGTCCCGTGCTGGTC ATCTACGAGGTGAAATATCGGCCTTCAGGAATTCC AGAAAGATTCAGTGGATCAAACAGCGGCAATACT GCTACCCTGACAATTAGCGGGACCCAGGCCATGGA CGAAGCTGATTACTATTGCCAGACATTCGATTCCA CCACAGTGGTCTTTGGCGGGGGAACTAAGCTGACC GTGCTG | HBC34-V23 VL nuc |
| 70 | GAACTGCAGCTGGTCGAATCAGGAGGAGGGTGGG TCCAGCCCGGAGGGAGCCAGAGACTGTCTTGTGCC GCATCAGGGAGGATCTTCAGGAGCTTCTACATGTC CTGGGTGCGCCAGGCACCAGGCAAGGGACTGGAG TGGGTCGCACCATCAACCAGGACGGATCTGAAA AGCTGTATGTGGATAGTGTCAAAGGCCGGTTCACA ATTAGCAGAGACAACGCTAAAAATTCTCTGTTTCT GCAGATGAACAATCTGCGAGTGGAGGATACCGCC GTCTACTATTGCGCCGCTTGGTCTGGCAACAGCGG CGGGATGGATGTCTGGGGCAGGGCACAACAGTG AGCGTCTCTTCC | HBC34 wt VH codon optimized |
| 71 | TCATACGAACTGACTCAGCCTCCCTCCGTCTCCGTC TCACCTGGACAGACCGTCTCAATCCCCTGCTCCGG CGATAAACTGGGCAACAAGAACGTGTGCTGGTTCC AGCACAAACCCGGACAGAGTCCTGTGCTGGTCATC TACGAGGTCAAGTATCGGCCAAGCGGCATTCCCGA AAGATTCAGCGGCTCCAACTCTGGGAATACCGCAA CACTGACTATCTCTGGAACCCAGGCAATGGACGAG GCAGCTTACTTTTGCCAGACTTGGGATTCAACTAC TGTCGTGTTCGGCGGCGGAACTAGACTGACTGTCC TG | HBC34 wt VL codon optimized |
| 72 | GGGAGGATCTTCAGGAGCTTCTAC | HBC34 wt CDRH1 codon optimized |
| 73 | ATCAACCAGGACGGATCTGAAAAG | HBC34 wt CDRH2 codon optimized |
| 74 | GCCGCTTGGTCTGGCAACAGCGGCGGGATGGATGT C | HBC34 wt CDRH3 codon optimized |

-continued

TABLE OF SEQUENCES AND SEQ ID NUMBERS (SEQUENCE LISTING):

| SEQ ID NO | Sequence | Remarks |
|---|---|---|
| 75 | AAACTGGGCAACAAGAAC | HBC34 wt CDRL1 codon optimized |
| 76 | GAGGTCAAG | HBC34 wt CDRL2 codon optimized |
| 77 | GTCATCTACGAGGTCAAGTATCGGCCA | HBC34 wt CDRL2 long codon outimized |
| 78 | CAGACTTGGGATTCAACTACTGTCGTG | HBC34 wt CDRL3 codon optimized |
| 79 | GGSGG | linker |
| 80 | TGPCRTC | epitope |
| 81 | GNCTCIP | epitope |
| 82 | CCIPIPSSWAFGCSTTSTGPCRTCC<br>wherein in particular thy cysteines at positions 2, 21, and 24 are coupled to acetamidomethyl. | discontinuous epitope mimic |
| 83 | CGNCTCIPIPSSWAFCSTTSTGPCRTCC<br>wherein in particular thy cysteines at positions 4, 6, 24, and 27 are coupled to acetamidomethyl. | discontinuous epitope mimic |
| 84 | CGGGCSTTSTGPCRTCC<br>wherein in particular thy cysteines at positions 13 and 16 are coupled to acetamidomethyl. | looped epitope mimic |
| 85 | STTSTGPCRTC | epitope |
| 86 | GNCTCIPIPSSWAFC | epitope |
| 87 | GNCTCIPIPSSWAF | epitope |
| 88 | PCRXC | epitope |
| 89 | SYELTQPPSVSVSPGQTVSIPCSGDKLGNKNVAWFQH<br>KPGQSPVLVIYEVKYRPSGIPERFSGSNSGNTATLTIS<br>GTQAMDEAAYFCQTFDSTTVVFGGGTRLTVL | HBC34-V35 VL |
| 90 | SYELTQPPSVSVSPGQTVSIPCSGDKLGNKNVSWFQH<br>KPGQSPVLVIYEVKYRPSGIPERFSGSNSGNTATLTIS<br>GTQAMDEAAYFCQTFDSTTVVFGGGTRLTVL | HBC34-V34 VL |
| 91 | ELQLVESGGGWVQPGGSQRLSCAASGRIFRSFYMSW<br>VRQAPGKGLEWVATINQDGSEKLYVDSVKGRFTISR<br>DNAKNSLFLQMNNLRVEDTAVYYCAAWSGNSGGM<br>DVWGQGTTVSVSSASTKGPSVFPLAPSSKSTSGGTAA<br>LGCLVKDYFPEPVTVSWNSGALTSGVHTFPAVLQSS<br>GLYSLSSVVTVPSSSLGTQTYICNVNHKPSNTKVDKK<br>VEPKSCDKTHTCPPCPAPELLAGPSVFLFPPKPKDTL<br>MISRTPEVTCVVVDVSHEDPEVKFNWYVDGVEVHN<br>AKTKPREEQYNSTYRVVSVLTVLHQDWLNGKEYKC<br>KVSNKALPLPEEKTISKAKGQPREPQVYTLPPSRDEL<br>TKNQVSLTCLVKGFYPSDIAVEWESNGQPENNYKTT<br>PPVLDSDGSFFLYSKLTVDKSRWQQGNVFSCSVLHE<br>ALHSHYTQKSLSLSPGK | HC of HBC34-V35-MLNS-GAALIE and HBC34-V34-MLNS-GAALIE (g1M17, 1) |
| 92 | ELQLVESGGGWVQPGGSQRLSCAASGRIERSEYMSW<br>VRQAPGKGLEWVATINQDGSEKLYVDSVKGRFTISR<br>DNAKNSLFLQMNNLRVEDTAVYYCAAWSGNSGGM<br>DVWGQGTTVSVSSASTKGPSVFPLAPSSKSTSGGTAA<br>LGCLVKDYFPEPVTVSWNSGALTSGVHTFPAVLQSS<br>GLYSLSSVVTVPSSSLGTQTYICNVNHKPSNTKVDKK<br>VEPKSCDKTHTCPPCPAPELLGGPSVFLFPPKPKDTL<br>MISRTPEVTCVVVDVSHEDPEVKFNWYVDGVEVHN<br>AKTKPREEQYNSTYRVVSVLTVLHQDWLNGKEYKC<br>KVSNKALPAPIEKTISKAKGQPREPQVYTLPPSRDELT<br>KNQVSLTCLVKGFYPSDIAVEWESNGQPENNYKTTP | HC of HBC34-V35-MLNS and HBC34-V34-MLNS (g1M17, 1) |

TABLE OF SEQUENCES AND SEQ ID NUMBERS (SEQUENCE LISTING):

| SEQ ID NO | Sequence | Remarks |
|---|---|---|
| | PVLDSDGSFFLYSKLTVDKSRWQQGNVFSCSVLHEA<br>LHSHYTQKSLSLSPGK | |
| 93 | SYELTQPPSVSVSPGQTVSIPCSGDKLGNKNVAWFQH<br>KPGQSPVLVIYEVKYRPSGIPERFSGSNSGNTATLTIS<br>GTQAMDEAAYFCQTFDSTTVVFGGGTRLTVLGQPK<br>AAPSVTLFPPSSEELQANKATLVCLISDFYPGAVTVA<br>WKADSSPVKAGVETTTPSKQSNNKYAASSYLSLTPE<br>QWKSHRSYSCQVTHEGSTVEKTVAPTECS | LC of HBC34-V35 |
| 94 | SYELTQPPSVSVSPGQTVSIPCSGDKLGNKNVSWFQH<br>KPGQSPVLVIYEVKYRPSGIPERFSGSNSGNTATLTIS<br>GTQAMDEAAYFCQTFDSTTVVFGGGTRLTVLGQPK<br>AAPSVTLFPPSSEELQANKATLVCLISDFYPGAVTVA<br>WKADSSPVKAGVETTTPSKQSNNKYAASSYLSLTPE<br>QWKSHRSYSCQVTHEGSTVEKTVAPTECS | LC of HBC34-V34 |
| 95 | EVQLLESGGGLVQPGGSLRLSCAASGSTFTKYAMSW<br>VRQAPGKGLEWVASISGSVPGEGIDTYYADSVKGRE<br>TISRDTSKNTLYLQMNSLRAEDTALYYCAKDVGVIG<br>SYYYYAMDVWGQGTAVTVSS | HBC24 VH |
| 96 | EIVLTQSPGTLSLSPGERATLSCRASQGLSSSYLAWY<br>QQKPGQAPRLLIYSASTRATGIPDRFSGSGSGTDFTLT<br>ISRLEPEDFAVYYCQQYAYSPRWTEGQGTKVEIK | HBC24 VL |
| 97 | GSTFTKYA | CDRH1 of HBC24 |
| 98 | ISGSVPGF | CDRH2 of HBC24 |
| 99 | LYYCAKDVGVIGSYYYYAMDV | CDRH3 of HBC24 |
| 100 | QGLSSSY | CDRL1 of HBC24 |
| 101 | SAS | CDRL2 of HBC24 |
| 102 | QQYAYSPRWT | CDRL3 of HBC24 |
| 103 | gagctgcagctggtggagtccggcggcggctgggtgcagcctggcggctcccag<br>aggctgagctgtgccgcttctggcaggatcttccggtcttttacatgtcttgggtgcg<br>gcaggctccaggcaagggcctggagtgggtggctaccatcaaccaggacggctc<br>cgagaagctgtatgtggatagcgtgaagggcagattcacaatctctcgcgacaacg<br>ccaagaactccctgtttctgcagatgaacaatctgagggtggaggataccgccgtgt<br>actattgcgccgcttggtctgcaatagcggcggcatggacgtgtggggacaggg<br>caccaccgtgtccgtgtccagc | VH of HBC34-V7,<br>HBC34-V35, and<br>HBC34-V34 (codon optimized) |
| 104 | agctacgagctgacacagccccttccgtgtccgtgtccctggacagaccgtgtc<br>catcccatgcagcggcgacaagctgggcaacaagaacgtgtccggtttcagcata<br>agcctggccagtcccccgtgctggtcatctacgaggtgaagtataggcccagcgg<br>catccctgagcggttctctggctccaacagcggcaatacagccaccctgacaatctc<br>tggcacacaggctatggacgaggccgcttatttctgccagacctttgattccaccac<br>agtggtgttcggcggcggcaccagactgacagtgctg | HBC34-V34 VL (codon optimized) |
| 105 | agctacgagctgacacagccccttccgtgtccgtgtccctggacagaccgtgtc<br>catcccatgcagcggcgacaagctgggcaacaagaacgtggcctggtttcagcat<br>aagcctggccagtcccccgtgctggtcatctacgaggtgaagtataggcccagcg<br>gcatccctgagcggttctctggctccaacagcggcaatacagccaccctgacaatc<br>tctggcacacaggctatggacgaggccgcttatttctgccagacctttgattccacca<br>cagtggtgttcggcggcggcaccagactgacagtgctg | HBC34-V35 VL (codon optimized) |
| 106 | gaggtgcagttgttggagtctggggagggcttggtacagcctggggggtccctga<br>gactctcctgtgcagcctctGGATCCACTTTTACCAAATATGC<br>CatgagctgggtccgtcaggctccagggaaggggctggagtgggtcgcaagtA<br>TTAGTGGAAGTgttctggttttGGTATTGACACActactacgca<br>gactccgttaagggccggttcaccatctccagagacacttccaagaacaccctgtat<br>ctgcaaatgaacagcctgagagccgaggacacggccttatattactgtGCGAA<br>AGATGTCGGGGTTATCGGGTCATACTATTACTACG<br>CTATGGACGTCtggggtcaa | HBC24 VH (wild type) |
| 107 | aaattgtgttgacgcagtctccaggcaccctgtctttgtctccaggggaaagagcca<br>ccctctcctgcagggccagtCAGGGTCTTAGCAGCAGTTACtta<br>gcctggtaccagcagaaacctggccaggctcccaggctcctcatctatAGTGC<br>GTCCaccagggccactggcatcccagacaggttcagtggcagtgggtctggga<br>cagacttcactctcaccatcagcagactggagcctgaagattttgcagtgtattactgt | HBC24 VL (wild type) |

TABLE OF SEQUENCES AND SEQ ID NUMBERS (SEQUENCE LISTING):

| SEQ ID NO | Sequence | Remarks |
|---|---|---|
| | CAACAGTATGCTTACTCACCTCGGTGGACGttcggcca agggaccaaggtggagatcaaac | |
| 108 | GAGGTGCAGCTGCTGGAAAGCGGCGGCGGCCTGG TGCAGCCCGGCGGCTCCCTGAGGCTGTCTTGCGCC GCCTCTGGCAGCACCTTCACAAAGTATGCAATGTC TTGGGTGCGCCAGGCACCAGGCAAGGGCCTGGAG TGGGTGGCCTCCATCTCTGGCAGCGTGCCTGGCTT CGGCATCGACACCTACTATGCCGATTCCGTGAAGG GCCGGTTTACAATCAGCAGAGACACCTCCAAGAAC ACACTGTATCTGCAGATGAATTCTCTGCGGGCCGA GGACACCGCCCTGTACTATTGTGCCAAGGATGTGG GCGTGATCGGCAGCTACTATTACTATGCAATGGAC GTGTGGGGACAGGGAACAGCAGTGACAGTGAGCT CC | HBC24 VH (codon optimized) |
| 109 | GAGATCGTGCTGACCCAGTCTCCTGGCACACTGTC CCTGTCCCCTGGAGAGAGAGCCACCCTGTCCTGCA GAGCCTCTCAGGGCCTGAGCTCCTCTTACCTGGCC TGGTATCAGCAGAAGCCTGGACAGGCCCCTCGGCT GCTGATCTACTCTGCCTCCACCAGAGCAACAGGCA TTCCTGACCGCTTCTCCGGATCTGGAAGCGGCACA GACTTCACCCTGACAATCAGCCGGCTGGAGCCTGA GGACTTCGCCGTGTACTATTGTCAGCAGTACGCCT ATTCCCCAAGGTGGACCTTTGGCCAGGGCACAAAG GTGGAGATCAAG | HBC24 VL (codon optimized) |
| 110 | agctacgagctgacacagccccctttccgtgtccgtgtccctggacagaccgtgtc catcccatgcagcggcgacaagctgggcaacaagaacgtgtgctggtttcagcata agcctggccagtcccccgtgctggtcatctacgaggtgaagtataggcccagcgg catccctgagcggttctctggctccaacagcggcaatacagccaccctgacaatctc tggcacacaggctatggacgaggccgcttatttctgccagacctttgattccaccac agtggtgttcggcggcggcaccagactgacagtgctg | HBC34-V7 VL (codon optimized) |
| 111 | SYELTQPPSVSVSPGQTASITCSGDKLGNKNASWYQ QKPGQSPVLVIYEVKYRPSGIPERFSGSNSGNTATLTI SGTQAMDEADYYCQTFDSTTVVFGGGTKLTVL | HBC34-V23-L_C40S |
| 112 | SYELTQPPSVSVSPGQTASITCSGDKLGNKNAAWYQ QKPGQSPVLVIYEVKYRPSGIPERFSGSNSGNTATLTI SGTQAMDEADYYCQTFDSTTVVFGGGTKLTVL | HBC34-V23-L_C40A |
| 113 | SYELTQPPSVSVSPGQTVSIPCSGDKLGNKNVSWFQH KPGQSPVLVIYEVKYRPSGIPERFSGSNSGNTATLTIS GTQAMDEAAYFCQTWDSTTVVFGGGTRLTVL | HBC34-V31-L_C40S |
| 114 | SYELTQPPSVSVSPGQTVSIPCSGDKLGNKNVAWFQH KPGQSPVLVIYEVKYRPSGIPERFSGSNSGNTATLTIS GTQAMDEAAYFCQTWDSTTVVFGGGTRLTVL | HBC34-V31-L_C40A |
| 115 | SYELTQPPSVSVSPGQTVSIPCSGDKLGNKNVSWFQH KPGQSPVLVIYEVKYRPSGIPERFSGSNSGNTATLTIS GTQAMDEAAYFCQTFDSTTVVFGGGTRLTVL | HBC34-V32-L_C40S |
| 116 | SYELTQPPSVSVSPGQTVSIPCSGDKLGNKNVAWFQH KPGQSPVLVIYEVKYRPSGIPERFSGSNSGNTATLTIS GTQAMDEAAYFCQTWDSTTVVFGGGTRLTVL | HBC34-V32-L_C40A |
| 117 | SYELTQPPSVSVSPGQTASITCSGDKLGNKNASWYQ QKPGQSPVLVIYEVKYRPSGIPERFSGSNSGNTATLTI SGTQAMDEADYYCQTFDSTTVVFGGGTKLTVL | HBC34-V33-L_C40S |
| 118 | SYELTQPPSVSVSPGQTASITCSGDKLGNKNAAWYQ QKPGQSPVLVIYEVKYRPSGIPERFSGSNSGNTATLTI SGTQAMDEADYYCQTFDSTTVVFGGGTKLTVL | HBC34-V33-L_C40A |
| 119 | SYELTQPPSVSVSPGQTVSIPCSGDKLGNKNVSWFQH KPGQSPVLVIYEVKYRPSGIPERFSGSNSGNTATLTIS GTQAMDEAAYFCQTWDSTTVVFGGGTRLTVL | HBC34-L_C40S |
| 120 | SYELTQPPSVSVSPGQTVSIPCSGDKLGNKNVAWFQH KPGQSPVLVIYEVKYRPSGIPERFSGSNSGNTATLTIS GTQAMDEAAYFCQTWDSTTVVFGGGTRLTVL | HBC34-L_C40A |

TABLE OF SEQUENCES AND SEQ ID NUMBERS (SEQUENCE LISTING):

| SEQ ID NO | Sequence | Remarks |
|---|---|---|
| 121 | EVQLLESGGGLVQPGGSLRLSCAASGSTFTKYAMSWVRQAPGKGLEWVASISGSVPGEGIDTYYADSVKGRETISRDTSKNTLYLQMNSLRAEDTALYYCAKDVGVIGSYYYYAMDVWGQGTAVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK | HBC24-MLNS |
| 122 | EVQLLESGGGLVQPGGSLRLSCAASGSTFTKYAMSWVRQAPGKGLEWVASISGSVPGFGIDTYYADSVKGRFTISRDTSKNTLYLQMNSLRAEDTALYYCAKDVGVIGSYYYYAMDVWGQGTAVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLAGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPLPEEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK | HBC24-MLNS-GAALIE |
| 123 | ELQLVESGGGWVQPGGSQRLSCAASGRIFRSFYMSWVRQAPGKGLEWVATINQDGSEKLYVDSVKGRFTISRDNAKNSLFLQMNNLRVEDTAVYYCAAWSGNSGGMDVWGQGTTVSVSSAKTTAPSVYPLAPVCGDTTGSSVTLGCLVKGYFPEPVTLTWNSGSLSSGVHTFPAVLQSDLYTLSSSVTVTSSTWPSQSITCNVAHPASSTKVDKKIEPRGPTIKPCPPCKCPAPNLLGGPSVFIFPPKIKDVLMISLSPIVTCVVVDVSEDDPDVQISWFVNNVEVHTAQTQTHREDYNSTLRVVSALPIQHQDWMSGKEFKCKVNNKDLPAPIERTISKPKGSVRAPQVYVLPPPEEEMTKKQVTLTCMVTDFMPEDIYVEWTNNGKTELNYKNTEPVLDSDGSYFMYSKLRVEKKNWVERNSYSCSVVHEGLHNHHTTKSFSRTPGK | HBC34-V7-mu (IgG2a) HC |
| 124 | SYELTQPPSVSVSPGQTVSIPCSGDKLGNKNVCWFQHKPGQSPVLVIYEVKYRPSGIPERFSGSNSGNTATLTISGTQAMDEAAYFCQTFDSTTVVFGGGTRLTVLGQPKSSPSVTLFPPSSEELETNKATLVCTITDFYPGVVTVDWKVDGTPVTQGMETTQPSKQSNNKYMASSYLTLTARAWERHSSYSCQVTHEGHTVEKSLSRADCS | HBC34-V7-mu (IgG2a) LC |
| 125 | ELQLVESGGGWVQPGGSQRLSCAASGRIERSFYMSWVRQAPGKGLEWVATINQDGSEKLYVDSVKGRFTISRDNAKNSLFLQMNNLRVEDTAVYYCAAWSGNSGGMDVWGQGTTVSVSSAKTTAPSVYPLAPVCGDTTGSSVTLGCLVKGYFPEPVTLTWNSGSLSSGVHTFPAVLQSDLYTLSSSVTVTSSTWPSQSITCNVAHPASSTKVDKKIEPRGPTIKPCPPCKCPAPNLLGGPSVFIFPPKIKDVLMISLSPIVTCVVVDVSEDDPDVQISWFVNNVEVHTAQTQTHREDYNSTLRVVSALPIQHQDWMSGKEFKCKVNNKDLPAPIERTISKPKGSVRAPQVYVLPPPEEEMTKKQVTLTCMVTDFMPEDIYVEWTNNGKTELNYKNTEPVLDSDGSYFMYSKLRVEKKNWVERNSYSCSVVHEGLHNHHTTKSFSRTPGK | HBC34-V35-mu (IgG2a) HC |
| 126 | SYELTQPPSVSVSPGQTVSIPCSGDKLGNKNVAWFQHKPGQSPVLVIYEVKYRPSGIPERFSGSNSGNTATLTISGTQAMDEAAYFCQTFDSTTVVFGGGTRLTVLGQPKSSPSVTLFPPSSEELETNKATLVCTITDFYPGVVTVDWKVDGTPVTQGMETTQPSKQSNNKYMASSYLTLTARAWERHSSYSCQVTHEGHTVEKSLSRADCS | HBC34-V35-mu (IgG2a) LC |
| 127 | EVQLLESGGGLVQPGGSLRLSCAASGSTFTKYAMSWVRQAPGKGLEWVASISGSVPGFGIDTYYADSVKGRFTISRDTSKNTLYLQMNSLRAEDTALYYCAKDVGVIGSYYYYAMDVWGQGTAVTVSSAKTTAPSVYPLAPVC | HBC24-mu (IgG2a) HC |

TABLE OF SEQUENCES AND SEQ ID NUMBERS (SEQUENCE LISTING):

| SEQ ID NO | Sequence | Remarks |
|---|---|---|
| | GDTTGSSVTLGCLVKGYFPEPVTLTWNSGSLSSGVH TFPAVLQSDLYTLSSSVTVTSSTWPSQSITCNVAHPAS STKVDKKIEPRGPTIKPCPPCKCPAPNLLGGPSVFIFPP KIKDVLMISLSPIVTCVVVDVSEDDPDVQISWFVNNV EVHTAQTQTHREDYNSTLRVVSALPIQHQDWMSGK EFKCKVNNKDLPAPIERTISKPKGSVRAPQVYVLPPP EEEMTKKQVTLTCMVTDFMPEDIYVEWTNNGKTEL NYKNTEPVLDSDGSYFMYSKLRVEKKNWVERNSYS CSVVHEGLHNHHTTKSFSRTPGK | |
| 128 | EIVLTQSPGTLSLSPGERATLSCRASQGLSSSYLAWY QQKPGQAPRLLIYSASTRATGIPDRFSGSGSGTDFTLTLC ISRLEPEDFAVYYCQQYAYSPRWTFGQGTKVEIKAD AAPTVSIFPPSSEQLTSGGASVVCFLNNFYPKDINVK WKIDGSERQNGVLNSWTDQDSKDSTYSMSSTLTLTK DEYERHNSYTCEATHKTSTSPIVKSFNRNEC | HBC24-mu (IgG2a) |
| 129 | ELQLVESGGGWVQPGGSQRLSCAASGRIFRSFYMSW VRQAPGKGLEWVATINQDGSEKLYVDSVKGRFTISR DNAKNSLFLQMNNLRVEDTAVYYCAAWSGNSGGM DVWGQGTTVSVSSASTKGPSVFPLAPSSKSTSGGTAA LGCLVKDYFPEPVTVSWNSGALTSGVHTFPAVLQSS GLYSLSSVVTVPSSSLGTQTYICNVNHKPSNTKVDKK VEPKSCDKTHTCPPCPAPELLGGPSVFLFPPKPKDTL MISRTPEVTCVVVDVSHEDPEVKFNWYVDGVEVHN AKTKPREEQYNSTYRVVSVLTVLHQDWLNGKEYKC KVSNKALPAPIEKTISKAKGQPREPQVYTLPPSRDELT KNQVSLTCLVKGFYPSDIAVEWESNGQPENNYKTTP PVLDSDGSFFLYSKLTVDKSRWQQGNVFSCSVMHEA LHNHYTQKSLSLSPGK | HBC34-V7, HBC34-V34, HBC34-V35 Hc (wild-type) |
| 130 | GCCTCCACAAAGGGCCCAAGCGTGTTCCACTGGC TCCCTCTTCCAAGTCTACCTCCGGCGGCACAGCCG CTCTGGGATGTCTGGTGAAGGATTACTTCCCAGAG CCCGTGACCGTGTCTTGGAACTCCGGCGCCCTGAC CAGCGGAGTGCATACATTTCCAGCTGTGCTGCAGA GCTCTGGCCTGTACTCTCTGTCCAGCGTGGTGACC GTGCCCTCTTCCAGCCTGGGCACCCAGACATATAT CTGCAACGTGAATCACAAGCCAAGCAATACAAAG GTGGACAAGAAGGTGGAGCCCAAGTCTTGTGATA AGACCCATACATGCCCTCCATGTCCAGCTCCAGAG CTGCTGGGCGGCCCAAGCGTGTTCCTGTTTCCACC CAAGCCTAAGGATACCCTGATGATCTCCAGAACCC CCGAGGTGACATGCGTGGTGGTGGACGTGAGCCA CGAGGATCCTGAGGTGAAGTTCAACTGGTACGTGG ACGGCGTGGAGGTGCATAATGCTAAGACCAAGCC CAGGGAGGAGCAGTACAACTCTACCTATCGGGTG GTGTCCGTGCTGACAGTGCTGCACCAGGATTGGCT GAACGGCAAGGAGTATAAGTGCAAGGTGTCTAAT AAGGCCCTGCCCGCTCCTATCGAGAAGACCATCTC CAAGGCCAAGGGCCAGCCTAGAGAGCCACAGGTG TACACACTGCCTCCATCTCGCGATGAGCTGACCAA GAACCAGGTGTCCCTGACATGTCTGGTGAAGGGCT TCTATCCTTCCGACATCGCTGTGGAGTGGGAGAGC AATGGCCAGCCAGAGAACAATTACAAGACCACAC CCCCTGTGCTGGACAGCGATGGCTCTTTCTTTCTGT ATAGCAAGCTGACCGTGGACAAGTCTCGCTGGCAG CAGGGCAACGTGTTTAGCTGTTCTGTGATGCATGA GGCCCTGCACAATCATTATACACAGAAGTCCCTGA GCCTGTCTCCTGGCAAG | HBC34-V7, HBC34-V34, HBC34-V35 CH1-hinge-CH2-CH3 (codon-optimized) |
| 131 | GAGCTGCAGCTGGTGGAGTCCGGCGGCGGCTGGG TGCAGCCTGGCGGCTCCCAGAGGCTGAGCTGTGCC GCTTCTGGCAGGATCTTCCGGTCCTTTTACATGTCT TGGGTGCGGCAGGCTCCAGGCAAGGGCCTGGAGT GGGTGGCTACCATCAACCAGGACGGCTCCGAGAA GCTGTATGTGGATAGCGTGAAGGGCAGATTCACAA TCTCTCGCGACAACGCCAAGAACTCCCTGTTTCTG CAGATGAACAATCTGAGGGTGGAGGATACCGCCG TGTACTATTGCGCCGCTTGGTCTGGCAATAGCGGC GGCATGGACGTGTGGGGACAGGGCACCACCGTGT CCGTGTCCAGCGCCTCCACAAAGGGCCCAAGCGTG TTTCCACTGGCTCCCTCTTCCAAGTCTACCTCCGGC GGCACAGCCGCTCTGGGATGTCTGGTGAAGGATTA | HBC34-V7, HBC34-V34, HBC34-V35 VH-CH1-hinge-CH2-CH3 (codon-optimized) |

TABLE OF SEQUENCES AND SEQ ID NUMBERS (SEQUENCE LISTING):

| SEQ ID NO | Sequence | Remarks |
|---|---|---|
|  | CTTCCCAGAGCCCGTGACCGTGTCTTGGAACTCCG GCGCCCTGACCAGCGGAGTGCATACATTTCCAGCT GTGCTGCAGAGCTCTGGCCTGTACTCTCTGTCCAG CGTGGTGACCGTGCCCTCTTCCAGCCTGGGCACCC AGACATATATCTGCAACGTGAATCACAAGCCAAGC AATACAAAGGTGGACAAGAAGGTGGAGCCCAAGT CTTGTGATAAGACCCATACATGCCCTCCATGTCCA GCTCCAGAGCTGCTGGGCGGCCCAAGCGTGTTCCT GTTTCCACCCAAGCCTAAGGATACCCTGATGATCT CCAGAACCCCGAGGTGACATGCGTGGTGGTGGA CGTGAGCCACGAGGATCCTGAGGTGAAGTTCAACT GGTACGTGGACGGCGTGGAGGTGCATAATGCTAA GACCAAGCCCAGGGAGGAGCAGTACAACTCTACC TATCGGGTGGTGTCCGTGCTGACAGTGCTGCACCA GGATTGGCTGAACGGCAAGGAGTATAAGTGCAAG GTGTCTAATAAGGCCCTGCCCGCTCCTATCGAGAA GACCATCTCCAAGGCCAAGGGCCAGCCTAGAGAG CCACAGGTGTACACACTGCCTCCATCTCGCGATGA GCTGACCAAGAACCAGGTGTCCCTGACATGTCTGG TGAAGGGCTTCTATCCTTCCGACATCGCTGTGGAG TGGGAGAGCAATGGCCAGCCAGAGAACAATTACA AGACCACACCCCCTGTGCTGGACAGCGATGGCTCT TTCTTTCTGTATAGCAAGCTGACCGTGGACAAGTC TCGCTGGCAGCAGGGCAACGTGTTTAGCTGTTCTG TGATGCATGAGGCCCTGCACAATCATTATACACAG AAGTCCCTGAGCCTGTCTCCTGGCAAGTGATGAGG TACCGTGCGACGGCCGGCAAGCCCCCGCTCCCCGG GCTCTCGCGGTCGTACGAGGAAAGCTT |  |
| 132 | GGACAGCCAAAGGCTGCTCCATCTGTGACCCTGTT TCCACCCTCTTCCGAGGAGCTGCAGGCCAACAAGG CCACCCTGGTGTGCCTGATCTCTGACTTCTACCCTG GAGCTGTGACAGTGGCTTGGAAGGCTGATAGCTCT CCCGTGAAGGCTGGCGTGGAGACAACAACCCCTA GCAAGCAGTCTAACAATAAGTACGCCGCTTCCAGC TATCGTCTCTGACACCAGAGCAGTGGAAGTCCCA CCGCTCTTATTCCTGCCAGGTGACCCATGAGGGCA GCACCGTGGAGAAGACAGTGGCCCCCACCGAGTG TTCT | HBC34-V7 CL (codon-optimized) |
| 133 | AGCTACGAGCTGACACAGCCCCCTTCCGTGTCCGT GTCCCCTGGACAGACCGTGTCCATCCCATGCAGCG GCGACAAGCTGGGCAACAAGAACGTGTGCTGGTTT CAGCATAAGCCTGGCCAGTCCCCCGTGCTGGTCAT CTACGAGGTGAAGTATAGGCCCAGCGGCATCCCTG AGCGGTTCTCTGGCTCCAACAGCGGCAATACAGCC ACCCTGACAATCTCTGGCACACAGGCTATGACGA GGCCGCTTATTTCTGCCAGACCTTTGATTCCACCAC AGTGGTGTTCGGCGGCGGCACCAGACTGACAGTGC TGGGACAGCCAAAGGCTGCTCCATCTGTGACCCTG TTTCCACCCTCTTCCGAGGAGCTGCAGGCCAACAA GGCCACCCTGGTGTGCCTGATCTCTGACTTCTACCC TGGAGCTGTGACAGTGGCTTGGAAGGCTGATAGCT CTCCCGTGAAGGCTGGCGTGGAGACAACAACCCCT AGCAAGCAGTCTAACAATAAGTACGCCGCTTCCAG CTATCGTCTCTGACACCAGAGCAGTGGAAGTCCC ACCGCTCTTATTCCTGCCAGGTGACCCATGAGGGC AGCACCGTGGAGAAGACAGTGGCCCCCACCGAGT GTTCT | HBC34-V7 LC (VL-CL) (codon-optimized) |
| 134 | GGACAGCCAAAGGCTGCTCCATCTGTGACCCTGTT TCCACCCTCTTCCGAGGAGCTGCAGGCCAACAAGG CCACCCTGGTGTGCCTGATCTCTGACTTCTACCCTG GAGCTGTGACAGTGGCTTGGAAGGCTGATAGCTCT CCCGTGAAGGCTGGCGTGGAGACAACAACCCCTA GCAAGCAGTCTAACAATAAGTACGCCGCTTCCAGC TATCGTCTCTGACACCAGAGCAGTGGAAGTCCCA CCGCTCTTATTCCTGCCAGGTGACCCATGAGGGCA GCACCGTGGAGAAGACAGTGGCCCCCACCGAGTG | HBC34-V34, HBC34-V35 CL (codon-optimized) |
| 135 | AGCTACGAGCTGACACAGCCCCCTTCCGTGTCCGT GTCCCCTGGACAGACCGTGTCCATCCCATGCAGCG GCGACAAGCTGGGCAACAAGAACGTGTGCTGGTTT CAGCATAAGCCTGGCCAGTCCCCCGTGCTGGTCAT | HBC34-V34 LC (VL-CL) (codon-optimized) |

TABLE OF SEQUENCES AND SEQ ID NUMBERS (SEQUENCE LISTING):

| SEQ ID NO | Sequence | Remarks |
|---|---|---|
| | CTACGAGGTGAAGTATAGGCCCAGCGGCATCCCTG<br>AGCGGTTCTCTGGCTCCAACAGCGGCAATACAGCC<br>ACCCTGACAATCTCTGGCACACAGGCTATGGACGA<br>GGCCGCTTATTTCTGCCAGACCTTTGATTCCACCAC<br>AGTGGTGTTCGGCGGCGGCACCAGACTGACAGTGC<br>TGGGACAGCCAAAGGCTGCTCCATCTGTGACCCTG<br>TTTCCACCCTCTTCCGAGGAGCTGCAGGCCAACAA<br>GGCCACCCTGGTGTGCCTGATCTCTGACTTCTACCC<br>TGGAGCTGTGACAGTGGCTTGGAAGGCTGATAGCT<br>CTCCCGTGAAGGCTGGCGTGGAGACAACAACCCCT<br>AGCAAGCAGTCTAACAATAAGTACGCCGCTTCCAG<br>CTATCTGTCTCTGACACCAGAGCAGTGGAAGTCCC<br>ACCGCTCTTATTCCTGCCAGGTGACCCATGAGGGC<br>AGCACCGTGGAGAAGACAGTGGCCCCCACCGAGT<br>GTTCT | |
| 136 | AGCTACGAGCTGACACAGCCCCCTTCCGTGTCCGT<br>GTCCCCTGGACAGACCGTGTCCATCCCATGCAGCG<br>GCGACAAGCTGGGCAACAAGAACGTGGCCTGGTT<br>TCAGCATAAGCCTGGCCAGTCCCCCGTGCTGGTCA<br>TCTACGAGGTGAAGTATAGGCCCAGCGGCATCCCT<br>GAGCGGTTCTCTGGCTCCAACAGCGGCAATACAGC<br>CACCCTGACAATCTCTGGCACACAGGCTATGGACG<br>AGGCCGCTTATTTCTGCCAGACCTTTGATTCCACCA<br>CAGTGGTGTTCGGCGGCGGCACCAGACTGACAGTG<br>CTGGGACAGCCAAAGGCTGCTCCATCTGTGACCCT<br>GTTTCCACCCTCTTCCGAGGAGCTGCAGGCCAACA<br>AGGCCACCCTGGTGTGCCTGATCTCTGACTTCTAC<br>CCTGGAGCTGTGACAGTGGCTTGGAAGGCTGATAG<br>CTCTCCCGTGAAGGCTGGCGTGGAGACAACAACCC<br>CTAGCAAGCAGTCTAACAATAAGTACGCCGCTTCC<br>AGCTATCTGTCTCTGACACCAGAGCAGTGGAAGTC<br>CCACCGCTCTTATTCCTGCCAGGTGACCCATGAGG<br>GCAGCACCGTGGAGAAGACAGTGGCCCCCACCGA<br>GTGTTCT | HBC34-V35 LC<br>(VL-CL) (codon-<br>optimized) |
| 137 | APELLGGPSVFLFPPKPKDTLMISRTPEVTCVVVDVS<br>HEDPEVKFNWYVDGVEVHNAKTKPREEQYNSTYRV<br>VSVLTVLHQDWLNGKEYKCKVSNKALPAPIEKTISK<br>AKGQPREPQVYTLPPSRDELTKNQVSLTCLVKGFYPS<br>DIAVEWESNGQPENNYKTTPPVLDSDGSFFLYSKLTV<br>DKSRWQQGNVFSCSVMHEALHNHYTQKSLSLSPGK | WT hIgG1 Fc |
| 138 | ELQLVESGGGWVQPGGSQRLSCAASGRIFRSFYMSW<br>VRQAPGKGLEWVATINQDGSEKLYVDSVKGRFTISR<br>DNAKNSLFLQMNNLRVEDTAVYYCAAWSGNSGGM<br>DVWGQGTTVSVSSASTKGPSVFPLAPSSKSTSGGTAA<br>LGCLVKDYFPEPVTVSWNSGALTSGVHTFPAVLQSS<br>GLYSLSSVVTVPSSSLGTQTYICNVNHKPSNTKVDKK<br>VEPKSCDKTHTCPPCPAPELLAGPSVFLFPPKPKDTL<br>MISRTPEVTCVVVDVSHEDPEVKFNWYVDGVEVHN<br>AKTKPREEQYNSTYRVVSVLTVLHQDWLNGKEYKC<br>KVSNKALPLPEEKTISKAKGQPREPQVYTLPPSRDEL<br>TKNQVSLTCLVKGFYPSDIAVEWESNGQPENNYKTT<br>PPVLDSDGSFFLYSKLTVDKSRWQQGNVFSCSVMHE<br>ALHNHYTQKSLSLSPGK | HBC34,<br>HBC34-V7,<br>HBC34-V23,<br>HBC34-V34,<br>HBC34-V35,<br>HBC34_C40S,<br>HBC34_C40A,<br>HBC34-V23_C40S,<br>HBC34-V23_C40A<br>HC with GAALIE<br>mutation in hIgG1<br>Fc |
| 139 | ESKYGPPCPPCPAPPVAGP | Chimeric hinge sequence |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

U.S. Provisional Application 62/782,274, filed Dec. 19, 2018 and U.S. Provisional Application 62/860,085, filed Jun. 11, 2019 are incorporated herein by reference, in their entirety.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An isolated antibody that binds HBsAg comprising:
   (i) a heavy chain (HC) comprising the amino acid sequence according to SEQ ID NO: 91; and
   (ii) a light chain (LC) comprising the amino acid sequence according to SEQ ID NO: 93.

2. The antibody of claim 1, wherein the antibody is capable of binding an HBsAg of a genotype selected from the HBsAg genotypes A, B, C, D, E, F, G, H, I, and J, or any combination thereof.

3. The antibody of claim 1, wherein the antibody is capable of reducing a serum concentration of hepatitis B virus (HBV) DNA in a mammal having an HBV infection.

4. The antibody of claim 1, wherein the antibody is capable of reducing a serum concentration of HBsAg in a mammal having an HBV infection.

5. The antibody of claim 1, wherein the antibody is capable of reducing a serum concentration of HBeAg in a mammal having an HBV infection.

6. The antibody of claim 1, wherein the antibody is capable of reducing a serum concentration of HBcrAg in a mammal having an HBV infection.

7. An isolated polynucleotide comprising a nucleotide sequence that encodes the antibody of claim 1.

8. The polynucleotide of claim 7, wherein the nucleotide sequence that encodes the antibody is codon optimized for expression in a host cell.

9. The polynucleotide of claim 7, comprising a nucleotide sequence having at least 80% identity to the nucleotide sequence according to any one of SEQ ID NO: 103 and SEQ ID NO:105.

10. A polynucleotide that encodes an antibody, comprising a $V_H$-encoding nucleotide sequence according to SEQ ID NO: 103, and a $V_L$-encoding nucleotide sequence according to SEQ ID NO: 105.

11. A vector comprising the polynucleotide of claim 9.

12. The vector of claim 11, wherein the vector comprises a retroviral vector.

13. A host cell comprising a heterologous polynucleotide of claim 9.

14. A pharmaceutical composition comprising the antibody of claim 1 and a pharmaceutically acceptable excipient, diluent or carrier.

15. A kit comprising:
   (a) the antibody of claim 1; and
   (b) instructions for using the component to attenuate a hepatitis B virus infection and/or a hepatitis D virus infection.

16. The kit of claim 15, further comprising:
   (i) a polymerase inhibitor, wherein the polymerase inhibitor optionally comprises Lamivudine, Adefovir, Entecavir, Telbivudine, Tenofovir, or any combination thereof;
   (ii) an interferon, wherein the interferon optionally comprises IFNbeta and/or IFNalpha;
   (iii) a checkpoint inhibitor, wherein the checkpoint inhibitor optionally comprises an anti-PD-1 antibody or antigen binding fragment thereof, an anti-PD-L1 antibody or antigen binding fragment thereof, and/or an anti-CTLA4 antibody or antigen binding fragment thereof;
   (iv) an agonist of a stimulatory immune checkpoint molecule; or
   (v) any combination of (i)-(iv).

17. The kit of claim 16, wherein the polymerase inhibitor comprises Lamivudine.

18. A method of producing an antibody, comprising culturing the host cell of claim 13 under conditions and for a time sufficient to produce the antibody, wherein the antibody comprises:
   (i) a heavy chain (HC) comprising the amino acid sequence according to SEQ ID NO: 91; and
   (ii) a light chain (LC) comprising the amino acid sequence according to SEQ ID NO: 93.

19. A method of attenuating a hepatitis B infection and/or hepatitis D infection in a subject, comprising administering to the subject an effective amount of an antibody comprising:
   (i) a heavy chain (HC) comprising the amino acid sequence according to SEQ ID NO: 91; and
   (ii) a light chain (LC) comprising the amino acid sequence according to SEQ ID NO:93.

20. The method of claim 19, further comprising administering to the subject one or more of:
   (i) a polymerase inhibitor, wherein the polymerase inhibitor optionally comprises Lamivudine, Adefovir, Entecavir, Telbivudine, Tenofovir, or any combination thereof;
   (ii) an interferon, wherein the interferon optionally comprises IFNbeta and/or IFNalpha;
   (iii) a checkpoint inhibitor, wherein the checkpoint inhibitor optionally comprises an anti-PD-1 antibody or antigen binding fragment thereof, an anti-PD-L1 antibody or antigen binding fragment thereof, and/or an anti-CTLA4 antibody or antigen binding fragment thereof;
   (iv) an agonist of a stimulatory immune checkpoint molecule; or
   (v) any combination of (i)-(iv).

21. The method of claim 19, wherein the hepatitis B virus infection is a chronic hepatitis B virus infection.

22. The method of claim 19, wherein the subject has received a liver transplant.

23. The method of claim 19, wherein the subject is non-immunized against hepatitis B virus.

24. The method of claim 19, wherein the subject is a newborn.

25. The method of claim 19, wherein the subject is undergoing or has undergone hemodialysis.

26. A method for in vitro diagnosis of a hepatitis B infection, the method comprising:
   (i) contacting a sample from a subject with an antibody of claim 1; and (ii) detecting a complex comprising an antigen and the antibody.

27. The method of claim 26, wherein the sample comprises blood isolated from the subject.

28. A method for detecting the presence or absence of an epitope in a correct conformation in an anti-hepatitis-B vaccine, the method comprising:
  (i) contacting the vaccine with an antibody of claim 1; and
  (ii) determining whether a complex comprising an antigen and the antibody, has been formed.

* * * * *